(12) United States Patent
Brunner et al.

(10) Patent No.: US 9,616,053 B2
(45) Date of Patent: Apr. 11, 2017

(54) INDOLIN-2-ONE OR PYRROLO-PYRIDIN/PYRIMIDIN-2-ONE DERIVATIVES

(71) Applicant: Hoffmann-La Roche Inc., Little Falls, NJ (US)

(72) Inventors: Daniela Brunner, Riverdale, NY (US); Hans Hilpert, Muenchenstein (CH); Sabine Kolczewski, Loerrach (DE); Anja Limberg, Basel (CH); Jessica Malberg, Dobbs Ferry, NY (US); Eric Prinssen, Guebwiller (FR); Claus Riemer, Freiburg (DE); Bavani G. Shankar, Nanuet, NY (US); Theodor Stoll, Binningen (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 14/971,120

(22) Filed: Dec. 16, 2015

(65) Prior Publication Data
US 2016/0095844 A1 Apr. 7, 2016

Related U.S. Application Data

(63) Continuation of application No. PCT/EP2014/062491, filed on Jun. 16, 2014.

(30) Foreign Application Priority Data

Jun. 19, 2013 (EP) ..................................... 13172663

(51) Int. Cl.
| | | |
|---|---|---|
| A61K 31/404 | (2006.01) |
| C07D 401/04 | (2006.01) |
| C07D 403/04 | (2006.01) |
| C07D 403/14 | (2006.01) |
| A61K 31/4439 | (2006.01) |
| C07D 405/14 | (2006.01) |
| C07D 413/14 | (2006.01) |
| C07D 413/04 | (2006.01) |
| C07H 19/044 | (2006.01) |
| C07D 417/04 | (2006.01) |
| C07D 471/04 | (2006.01) |
| C07D 487/04 | (2006.01) |
| C07D 498/04 | (2006.01) |
| A61K 31/19 | (2006.01) |
| A61K 31/4178 | (2006.01) |
| A61K 31/422 | (2006.01) |
| A61K 31/4245 | (2006.01) |
| A61K 31/433 | (2006.01) |
| A61K 31/437 | (2006.01) |
| A61K 31/438 | (2006.01) |
| A61K 31/496 | (2006.01) |
| A61K 31/497 | (2006.01) |
| A61K 31/501 | (2006.01) |
| A61K 31/506 | (2006.01) |
| A61K 31/519 | (2006.01) |
| A61K 31/5377 | (2006.01) |
| A61K 31/5383 | (2006.01) |
| A61K 31/55 | (2006.01) |

(Continued)

(52) U.S. Cl.
CPC .......... *A61K 31/4439* (2013.01); *A61K 31/19* (2013.01); *A61K 31/4178* (2013.01); *A61K 31/422* (2013.01); *A61K 31/4245* (2013.01); *A61K 31/433* (2013.01); *A61K 31/437* (2013.01); *A61K 31/438* (2013.01); *A61K 31/496* (2013.01); *A61K 31/497* (2013.01); *A61K 31/501* (2013.01); *A61K 31/506* (2013.01); *A61K 31/519* (2013.01); *A61K 31/5377* (2013.01); *A61K 31/5383* (2013.01); *A61K 31/55* (2013.01); *A61K 31/7064* (2013.01); *A61K 45/06* (2013.01); *C07C 53/06* (2013.01); *C07D 401/04* (2013.01); *C07D 403/04* (2013.01); *C07D 403/14* (2013.01); *C07D 405/14* (2013.01); *C07D 413/04* (2013.01); *C07D 413/14* (2013.01); *C07D 417/04* (2013.01); *C07D 471/04* (2013.01); *C07D 471/10* (2013.01); *C07D 487/04* (2013.01); *C07D 498/04* (2013.01); *C07H 19/044* (2013.01)

(58) Field of Classification Search
CPC ... C07D 401/04; C07D 403/04; C07D 403/14
See application file for complete search history.

(56) References Cited

FOREIGN PATENT DOCUMENTS

| EP | 2 113 503 A1 | 11/2009 |
| WO | 91/04974 A1 | 4/1991 |

(Continued)

OTHER PUBLICATIONS

ISR for PCT/EP2014/062491.

*Primary Examiner* — Brian McDowell

(57) ABSTRACT

The present invention is concerned with 2-oxo-2,3-dihydroindoles of general formula (I)

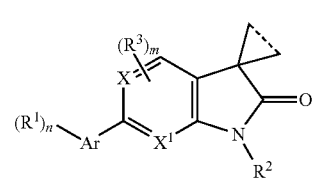

wherein Ar, X, $X^1$, $R^1$, $R^2$, $R^3$, m, n and the dotted line are as defined herein which compounds are useful for treating certain central nervous system disorders as described herein.

7 Claims, 1 Drawing Sheet

(51) Int. Cl.
*A61K 31/7064* (2006.01)
*A61K 45/06* (2006.01)
*C07C 53/06* (2006.01)
*C07D 471/10* (2006.01)

(56) References Cited

FOREIGN PATENT DOCUMENTS

| WO | 2006/113875 A2 | 10/2006 |
| WO | 2007/098214 A1 | 8/2007 |
| WO | 2012/143510 A1 | 10/2012 |
| WO | 2012/152629 A1 | 11/2012 |

INDOLIN-2-ONE OR PYRROLO-PYRIDIN/PYRIMIDIN-2-ONE DERIVATIVES

CROSS REFERENCE TO RELATED APPLICATIONS

This application is a continuation of International Application No. PCT/EP2014/062941 having an international filing date of Jun. 16, 2014 and which claims benefit under 35 U.S.C. §119 to European Patent Application No. 13172663.0 filed Jun. 19, 2013. The entire contents of both are incorporated herein by reference.

FIELD OF THE INVENTION

The present invention relates to novel compounds of formula I, wherein $R^1$, $R^3$, $R^2$, Ar, X, $X^1$, m and n are as described herein, having pharmaceutical activity, their manufacture, pharmaceutical compositions containing them and their potential use as medicaments.

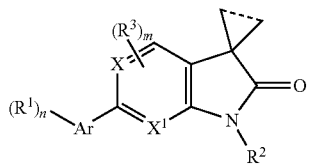

BACKGROUND OF THE INVENTION

Schizophrenia is a complex mental disorder typically appearing in late adolescence or early adulthood with a world-wide prevalence of approximately 1% of the adult population, which has enormous social and economic impact. The criteria of the Association of European Psychiatrists (ICD) and the American Psychiatric Association (DSM) for the diagnosis of schizophrenia require two or more characteristic symptoms to be present: delusions, hallucinations, disorganized speech, grossly disorganized or catatonic behavior (positive symptoms), or negative symptoms (alogia, affective flattening, lack of motivation, anhedonia). As a group, people with schizophrenia have functional impairments that may begin in childhood, continue throughout adult life and make most patients unable to maintain normal employment or otherwise have normal social function. They also have a shortened lifespan compared to the general population, and suffer from an increased prevalence of a wide variety of other neuropsychiatric syndromes, including substance abuse, obsessive-compulsive symptoms and abnormal involuntary movements prior to antipsychotic treatment. Schizophrenia is also associated with a wide range of cognitive impairments, bipolar disorders, major depression and anxiety disorders, the severity of which limits the functioning of patients, even when psychotic symptoms are well controlled. The primary treatment of schizophrenia is antipsychotic medications. Antipsychotics, for example risperidone, olanzapine, however, fail to significantly ameliorate the negative symptoms and cognitive dysfunction. Antipsychotic drugs have shown clinical efficacy for the treatment of the following diseases:

Fibromyalgia, which is a syndrome characterized by chronic generalized pain associated with different somatic symptoms, such as sleep disturbances, fatigue, stiffness, balance problems, hypersensitivity to physical and psychological environmental stimuli, depression and anxiety (*CNS Drugs*, 2012, 26(2): 135-53);

Schizoaffective disorders: includes psychotic and affective symptoms, this disorder falls on a spectrum between bipolar disorders (with depressive and manic episodes, alcohol and drug addiction, substance abuse) and schizophrenia. *J Clin. Psychiatry*, 2010, 71, Suppl. 2, 14-9, *Pediatr. Drugs* 2011, 13 (5), 291-302;

Major depression: *BMC Psychiatry* 2011, 11, 86;

Treatment resistant depression: *Journal of Psychopharmacology*, 0(0) 1-16;

Anxiety: *European Neuropsychopharmacology*, 2011, 21, 429-449;

Bipolar disorders: *Encephale, International J. of Neuropsychopharmacology*, 2011, 14, 1029-104, *International J. of Neuropsychopharmacology*, 2012, pages 1-12, *J. of Neuropsychopharmacology*, 2011, 0(0), 1-15;

Mood disorders: *J. Psychopharmacol.* 2012, January 11, *CNS Drugs*, 2010, February 24(2), 131-61;

Autism: *Current opinion in pediatrics*, 2011, 23:621-627; J. Clin. Psychiatry, 2011, 72(9), 1270-1276;

Alzheimer's disease: *J. Clin. Psychiatry*, 2012, 73(1), 121-128;

Parkinson's disease: *Movement Disorders*, Vol. 26, No. 6, 2011;

Chronic fatigue syndrome: *European Neuropsychopharmacology*, 2011, 21, 282-286;

Borderline Personality disorder: *J. Clin. Psychiatry*, 2011, 72 (10), 1363-1365, *J. Clin. Psychiatry*, 2011, 72 (10), 1353-1362;

Anti-inflammatory effects in arthritis: *European J. of Pharmacology*, 678, 2012, 55-60.

Now it has been found that the compounds of formula I may be used for the treatment of CNS diseases. The described compounds have been shown to reverse the L-687,414 ((3R,4R)-3 amino-1-hydroxy-4-methyl-pyrrolidin-2-one, a NMDA glycine site antagonist) induced hyperlocomotion, a behavioral pharmacodynamic mouse model for schizophrenia, described by D. Alberati et al. in *Pharmacology, Biochemistry and Behavior*, 97 (2010), 185-191. The authors described that hyperlocomotion induced by L-687,414 was inhibited by a series of known antipsychotic drugs. The compounds of formula I demonstrate marked activity in this model. The results are shown in Table 1. These findings predict antipsychotic activity for the present compounds, making them useful for the treatment of positive (psychosis) and negative symptoms of schizophrenia, substance abuse, alcohol and drug addiction, obsessive-compulsive disorders, cognitive impairment, bipolar disorders, mood disorders, major depression, resistant depression, anxiety disorders, Alzheimer's disease, autism, Parkinson's disease, chronic pain, borderline personality disorder, sleep disturbances, chronic fatigue syndrome, stiffness, antiinflammatory effects in arthritis and balance problems.

In addition to the reversal of L-687,414 induced hyperlocomotion experiment as described above, some compounds of the present invention have been tested in Smart-Cube®, an automated system in which the behaviors of compound-treated mice in response to multiple challenges are captured by digital video and analyzed with computer algorithms (Roberds et al., Frontiers in Neuroscience, 2011, Vol. 5, Art. 103, 1-4). In this way, the neuro-pharmacological effects of a test compound can be predicted by similarity to major classes of compounds, such as antipsychotics, anxiolytics and antidepressants. Examples 13, 54, 58, 71 show similarity to atypical antipsychotics. The results are shown in Table 2.

WO9106545 describes a very close structure containing a phenyl substituted imidazole moiety for Ar for prevention of clumping of both erythrocytes and thrombocytes. EP2108641 and WO2008046083 disclose a very broad scope of similar compounds which are inhibitors of the p38 nitrogen activated protein kinase for the treatment of inflammation diseases and benign prostatic hyperplasia, respectively.

BRIEF SUMMARY OF THE INVENTIONS

The present invention is concerned with indolin-2-one or pyrrolo-pyridin/pyrimidin-2-one derivatives of general formula

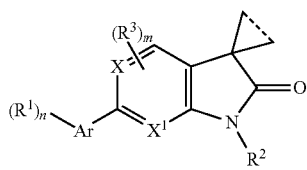

I wherein
Ar is a heteroaryl group, containing one, two or three heteroatoms, selected from N, S or O;
$R^1$ is hydrogen, lower alkyl, halogen, amino, dimethylamino, cyano, lower alkyl substituted by halogen, lower alkyl substituted by hydroxy, $CH(OH)CF_3$, $(CH_2)_o$-lower alkoxy, cycloalkyl optionally substituted by $CF_3$, or heterocycloalkyl optionally substituted by lower alkyl;
$R^2$ is hydrogen, lower alkyl, $(CH_2)_o$-cycloalkyl, $(CH_2)_o$—O-cycloalkyl, $(CH_2)_o$-lower alkoxy, $CH_2)_o$-lower alkoxy substituted by halogen, $(CH_2)_o$-heterocycloalkyl optionally substituted by lower alkyl, $(CH_2)_o$—$S(O)_2$-cycloalkyl, lower alkyl substituted by one or two hydroxy, lower alkyl substituted by one or two lower alkoxy, $(CH_2)_o$—$S(O)_2$-lower alkyl, lower alkyl substituted by halogen or $CH_2CH(OH)CF_3$;
$R^3$ is halogen or lower alkyl;
X is CH or N;
$X^1$ is CH or N;
n is 1 or 2;
o is 0, 1, 2 or 3;
m is 0, 1 or 2;
and the dotted line is a bond or not;
as well as with a pharmaceutically acceptable salts thereof, with a racemic mixture, or with its corresponding enantiomer and/or optical isomer and/or stereoisomer thereof.

DETAILED DESCRIPTION OF THE INVENTION

Figure 1:
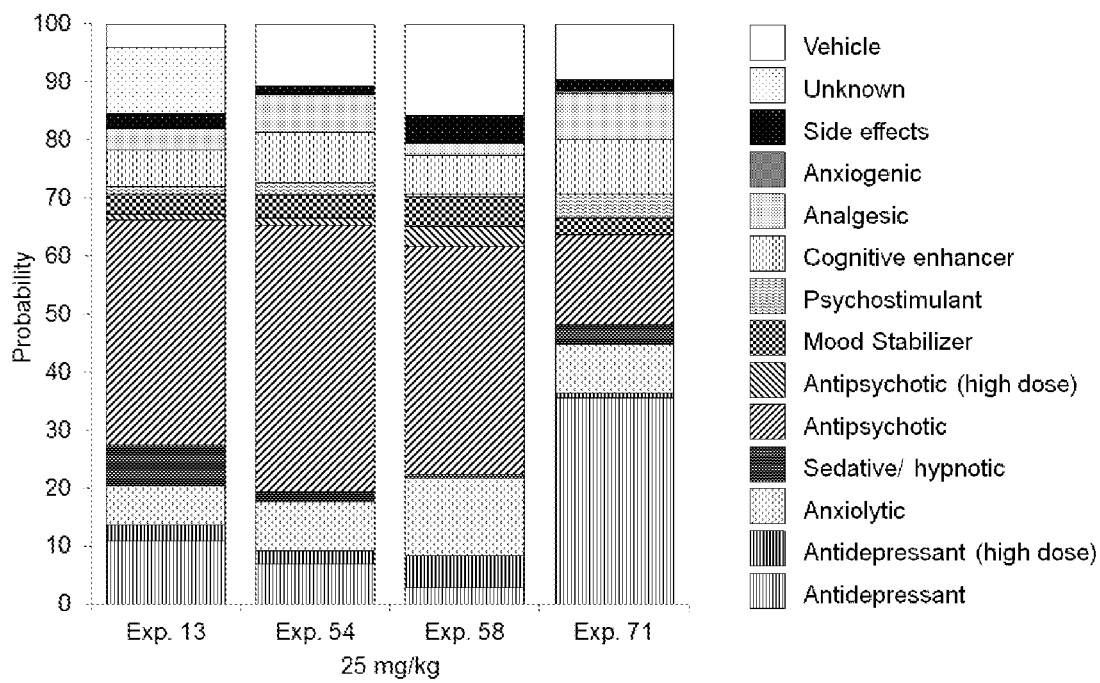
FIG. 1 is a bar chart exhibiting the SmartCube® behavioral signature of example compounds 13, 54, 58 and 71 at a dose of 25 mg/kg compared to the behavioral signature of a test compound to a database of behavioral signatures obtained from a large set of clinically approved reference drugs, grouped per indications.

Objects of the present invention are novel compounds of formula I and the use of compounds of formula I and their pharmaceutically acceptable salts for the treatment of CNS diseases related to positive (psychosis) and negative symptoms of schizophrenia, substance abuse, alcohol and drug addiction, obsessive-compulsive disorders, cognitive impairment, bipolar disorders, mood disorders, major depression, resistant depression, anxiety disorders, Alzheimer's disease, autism, Parkinson's disease, chronic pain, borderline personality disorder, sleep disturbances, chronic fatigue syndrome, stiffness, antiinflammatory effects in arthritis and balance problems. Further objects of the present invention are medicaments containing such novel compounds as well as methods for preparation of compounds of formula I, a combination of compounds of formula I with marketed antipsychotics, antidepressants, anxiolytics or mood stabilizers, and methods for the treatment of CNS disorders as mentioned above.

Encompassed by the present invention are corresponding prodrugs of compounds of formula I.

A common antipsychotic drug for the treatment of schizophrenia is olanzapine. Olanzapine (ZYPREXA) belongs to a drug class known as atypical antipsychotics. Other members of this class include for example clozapine (CLOZARIL), risperidone (RISPERDAL), aripiprazole (ABILIFY) and ziprasidone (GEODON).

Olanzapine is approved for the treatment of psychotic disorders, long term treatment of bipolar disorders and in combination with fluoxetine for the treatment of depressive episodes associated with bipolar disorders and for the treatment of resistant depression. The compounds of the present invention may be combined with antipsychotic drugs like olanzapine (ZYPREXA), clozapine (CLOZARIL), risperidone (RISPERDAL), aripiprazole (ABILIFY), amisulpride (SOLIAN), asenapine (SAPHRIS), blonanserin (LONASEN), clotiapine (ENTUMINE), iloperidone (FANAPT), lurasidone (LATUDA), mosapramine (CREMIN), paliperidone (INVEGA), perospirone (LULLAN), quetiapine (SEROQUEL), remoxipride (ROXIAM), sertindole (SERDOLECT), sulpiride (SULPIRID, EGLONYL), ziprasidone (GEODON, ZELDOX), zotepine (NIPOLEPT), haloperidol (HALDOL, SERENACE), droperidol (DROLEPTAN), chlorpromazine (THORAZINE, LARGACTIL), fluphenazine (PROLIXIN), perphenazine (TRILAFON), prochlorperazine (COMPAZINE), thioridazine (MELLARIL, MELLERIL), trifluoperazine (STELAZINE), triflupromazine (VESPRIN), levomepromazine (NOZINAN), promethazine (PHENERGAN), pimozide (ORAP) and cyamemazine (TERCIAN).

One preferred embodiment of the invention is a combination, wherein the marketed antipsychotic drug is olanzapine (ZYPREXA), clozapine (CLOZARIL), risperidone (RISPERDAL), aripiprazole (ABILIFY) or ziprasidone.

Furthermore, the compounds of the present invention can be combined with antidepressants such as selective serotonin reuptake inhibitors [Citalopram (CELEXA), Escitalopram (LEXAPRO, CIPRALEX), Paroxetine (PAXIL, SEROXAT), Fluoxetine (PROZAC), Fluvoxamine (LUVOX), Sertraline (ZOLOFT, LUSTRAL)], serotonin-norepinephrine reuptake inhibitors [Duloxetine (CYMBALTA), Milnacipran (IXEL, SAVELLA), Venlafaxine (EFFEXOR), Desvenlafaxine (PRISTIQ), Tramadol (TRAMAL, ULTRAM), Sibutramine (MERIDIA, REDUCTIL)], serotonin antagonist and reuptake inhibitors [Etoperidone (AXI- OMIN, ETONIN), Lubazodone (YM-992, YM-35,995), Nefazodone (SERZONE, NEFADAR), Trazodone (DESYREL)], norepinephrine reuptake inhibitors [Reboxetine (EDRONAX), Viloxazine (VIVALAN), Atomoxetine (STRATTERA)], norepinephrine-dopamine reuptake inhibitors [Bupropion (WELLBUTRIN, ZYBAN), Dexmethylphenidate (FOCALIN), Methylphenidate (RITALIN, CONCERTA)], norepinephrine-dopamine releasing agents [Amphetamine (ADDERALL), Dextroamphetamine (DEXEDRINE), Dextromethamphetamine (DESOXYN), Lisdexamfetamine (VYVANSE)], tricyclic antidepressants [Amitriptyline (ELAVIL, ENDEP), Clomipramine (ANAFRANIL), Desipramine (NORPRAMIN, PERTOFRANE), Dosulepin [Dothiepin](PROTHIADEN), Doxepin (ADAPIN, SINEQUAN), Imipramine (TOFRANIL), Lofepramine (FEPRAPAX, GAMANIL, LOMONT), Nortriptyline (Pamelor), Protriptyline (Vivactil), Trimipramine (Surmontil)], tetracyclic antidepressants [Amoxapine (ASENDIN), Maprotiline (LUDIOMIL), Mianserin (BOLVIDON, NORVAL, TOLVON), Mirtazapine (REMERON)], monoamine oxidase inhibitors [Isocarboxazid (MARPLAN), Moclobemide (AURORIX, MANERIX), Phenelzine (NARDIL), Selegiline [L-Deprenyl](ELDEPRYL, ZELAPAR, EMSAM), Tranylcypromine (PARNATE), Pirlindole (PIRAZIDOL)], 5-HT1A Receptor Agonists [Buspirone (BUSPAR), Tandospirone (SEDIEL), Vilazodone (VIIBRYD)], 5-HT2 Receptor Antagonists [Agomelatine (VALDOXAN), Nefazodone (NEFADAR, SERZONE), selective Serotonin Reuptake Enhancers [TIANEPTINE].

A preferred embodiment of this invention is a combination, wherein the marketed anti-depressive drug is citalopram (CELEXA), escitalopram (LEXAPRO, CIPRALEX), paroxetine (PAXIL, SEROXAT), fluoxetine (PROZAC), sertraline (ZOLOFT, LUSTRAL) duloxetine (CYMBALTA), milnacipran (IXEL, SAVELLA), venlafaxine (EFFEXOR), or mirtazapine (REMERON).

Compounds can also be combined with anxiolytics such as Alprazolam (HELEX, XANAX, XANOR, ONAX, ALPROX, RESTYL, TAFIL, PAXAL), Bretazenil, Bromazepam (LECTOPAM, LEXOTANIL, LEXOTAN, BROMAM), Brotizolam (LENDORMIN, DORMEX, SINTONAL, NOCTILAN), Chlordiazepoxide (LIBRIUM, RISOLID, ELENIUM), Cinolazepam (GERODORM), Clonazepam (RIVOTRIL, KLONOPIN, IKTORIVIL, PAXAM), Clorazepate (TRANXENE, TRANXILIUM), Clotiazepam (VERATRAN, CLOZAN, RIZE), Cloxazolam (SEPAZON, OLCADIL), Delorazepam (DADUMIR), Diazepam (ANTENEX, APAURIN, APZEPAM, APOZEPAM, HEXALID, PAX, STESOLID, STEDON, VALIUM, VIVAL, VALAXONA), Estazolam (PROSOM), Etizolam (ETILAAM, PASADEN, DEPAS), Flunitrazepam (ROHYPNOL, FLUSCAND, FLUNIPAM, RONAL, ROHYDORM), Flurazepam (DALMADORM, DALMANE), Flutoprazepam (RESTAS), Halazepam (PAXIPAM), Ketazolam (ANXON), Loprazolam (DORMONOCT), Lorazepam (ATIVAN, TEMESTA, TAVOR, LORABENZ), Lormetazepam (LORAMET, NOCTAMID, PRONOCTAN), Medazepam (NOBRIUM), Midazolam (DORMICUM, VERSED, HYPNOVEL, DORMONID), Nimetazepam (ERIMIN), Nitrazepam (MOGADON, ALODORM, PACISYN, DUMOLID, NITRAZADON), Nordazepam (MADAR, STILNY), Oxazepam (SERESTA, SERAX, SERENID, SEREPAX, SOBRIL, OXABENZ, OXAPAX), Phenazepam (PHENAZEPAM), Pinazepam (DOMAR), Prazepam (LYSANXIA, CENTRAX), Premazepam, Quazepam (DORAL), Temazepam (RESTORIL, NORMISON, EUHYPNOS, TEMAZE, TENOX), Tetrazepam (MYLOSTAN), Triazolam (HALCION, RILAMIR), Clobazam (FRISIUM, URBANOL), Eszopiclone (LUNESTA), Zaleplon (SONATA, STARNOC), Zolpidem (AMBIEN, NYTAMEL, STILNOCT, STILNOX, ZOLDEM, ZOLNOD), Zopiclone (IMOVANE, RHOVANE, XIMOVAN; ZILEZE; ZIMOCLONE; ZIMOVANE; ZOPITAN; ZORCLONE), Pregabalin (LYRICA) and Gabapentin (FANATREX, GABARONE, GRALISE, NEURONTIN, NUPENTIN).

One preferred embodiment of the invention is a combination, wherein the marketed anxiolytic drug is alprazolam (HELEX, XANAX, XANOR, ONAX, ALPROX, RESTYL, TAFIL, PAXAL), chlordiazepoxide (LIBRIUM, RISOLID, ELENIUM), clonazepam (RIVOTRIL, KLONOPIN, IKTORIVIL, PAXAM), diazepam (ANTENEX, APAURIN, APZEPAM, APOZEPAM, HEXALID, PAX, STESOLID, STEDON, VALIUM, VIVAL, VALAXONA), Estazolam (PROSOM), eszopiclone (LUNESTA), zaleplon (SONATA, STARNOC), zolpidem (AMBIEN, NYTAMEL, STILNOCT, STILNOX, ZOLDEM, ZOLNOD), pregabalin (LYRICA) or gabapentin (FANATREX, GABARONE, GRALISE, NEURONTIN, NUPENTIN).

A further object of the invention is a combination with mood stabilizers such as Carbamazepine (TEGRETOL), Lamotrigine (LAMICTAL), Lithium (ESKALITH, LITHANE, LITHOBID), and Valproic Acid (DEPAKOTE).

Compounds can also be combined with procognitive compounds such as donepezil (ARICEPT), galantamine (RAZADYNE), rivastigmine (EXELON) and memantine (NAMENDA).

The preferred indications using the compounds of the present invention are psychotic diseases like schizophrenia.

As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkoxy" denotes an alkyl group as defined above, which alkyl group is bonded via an O atom.

As used herein, the term "lower alkyl substituted by halogen" denotes a group wherein the alkyl residue is as defined above, wherein at least one hydrogen atom is replaced by a halogen atom.

As used herein, the term "lower alkoxy substituted by halogen" denotes a group wherein the alkoxy residue is as defined above, wherein at least one hydrogen atom is replaced by a halogen atom.

As used herein, the term "lower alkyl substituted by hydroxy" denotes a group wherein the alkyl residue is as defined above, wherein at least one hydrogen atom is replaced by a hydroxy group.

The term "cycloalkyl" denotes an alkyl ring with 3-6 carbon ring atoms.

The term "halogen" denotes chlorine, iodine, fluorine and bromine.

The term "heteroaryl, containing one, two or three heteroatoms, selected from N, S or O" denotes a 6 membered heteroaryl group, containing one or two N-atoms, selected from the groups pyridinyl, pyrimidinyl, pyridazinyl, a bicyclic ring system, containing from 1 to 3 heteroatoms, selected from the groups of cyclopenta[b]pyridinyl, 2,3-dihydro-1H-pyrido[2,3-b][1,4]oxazinyl, 6,7-dihydro-5H-pyrrolo[3,4-b]pyridinyl, imidazole[1,2-a]pyridinyl, or a 5 membered heteroaryl group, containing from 1 to 3 heteroatoms, selected from N, S or O, which groups are imidazolyl, 1,2,4-oxadiazolyl, 1,3,4-oxadiazolyl, isoxazolyl, oxazolyl, 1,3,4-thiadiazolyl or pyrazolyl.

The term "heterocycloalkyl" denotes a saturated 4, 5 or 6 membered carbon ring, wherein at least one carbon atom is replaced by N or O, for example pyrrolidinyl, morpholinyl, thiomorpholinyl, piperidinyl, piperazinyl, tetrahydro-pyran-4-yl, tetrahydro-furan-3-yl or oxetanyl.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

One embodiment of the invention are compounds of formula I, wherein Ar is a 6 membered heteroaryl group, containing one or two N-atoms and $R^2$ is hydrogen, and the other substituents are as described above, for example the following compounds:
3,3-Dimethyl-6-(pyridin-3-yl)indolin-2-one
3,3-Dimethyl-6-(pyridin-4-yl)indolin-2-one
3,3-Dimethyl-6-(pyrimidin-5-yl)indolin-2-one
6-(2-Aminopyrimidin-5-yl)-3,3-dimethylindolin-2-one
3,3-Dimethyl-6-(pyridazin-4-yl)indolin-2-one
6-(6-Aminopyridin-3-yl)-3,3-dimethylindolin-2-one
3,3-Dimethyl-6-(2-methylpyridin-3-yl)indolin-2-one
3,3-Dimethyl-6-(3-methylpyridin-4-yl)indolin-2-one
3,3-Dimethyl-6-(2-methylpyrimidin-5-yl)indolin-2-one
3,3-Dimethyl-6-(2-methylpyridin-4-yl)indolin-2-one
5-(3,3-Dimethyl-2-oxoindolin-6-yl)nicotinonitrile
6-(2,4-Dimethyl-pyridin-3-yl)-3,3-dimethyl-1,3-dihydro-indol-2-one
3,3-Dimethyl-6-(2-methylpyrimidin-4-yl)indolin-2-one
6-(2-Cyclopropylpyrimidin-5-yl)-3,3-dimethyl-indolin-2-one
3,3-Dimethyl-6-(2-methylpyrimidin-5-yl)-1H-pyrrolo[3,2-c]pyridin-2-one
3,3-Dimethyl-6-(6-methylpyrimidin-4-yl)indolin-2-one
3,3-Dimethyl-6-(3-methylpyridin-4-yl)-1H-pyrrolo[3,2-c]pyridin-2(3H)-one
3,3-Dimethyl-6-(6-methyl-3-pyridyl)-1H-pyrrolo[3,2-c]pyridin-2-one
3,3-Dimethyl-6-(6-methylpyridin-3-yl)indolin-2-one
6-(4-Fluoropyridin-3-yl)-3,3-dimethylindolin-2-one
3,3-Dimethyl-6-(5-methylpyrazin-2-yl)indolin-2-one
6-(2,6-Dimethylpyrimidin-4-yl)-3,3-dimethylindolin-2-one or
3,3-Dimethyl-6-(6-methylpyridazin-3-yl)indolin-2-one.

One embodiment of the invention are further compounds of formula I, wherein Ar is a six membered heteroaryl group, containing one or two N-atoms and $R^2$ is lower alkyl and the other substituents are as described above, for example the following compounds:
1,3,3-Trimethyl-6-(pyridin-4-yl)indolin-2-one
1,3,3-Trimethyl-6-(2-methylpyridin-4-yl)indolin-2-one
1,3,3-Trimethyl-6-(pyridin-3-yl)indolin-2-one
1,3,3-Trimethyl-6-(pyrimidin-5-yl)indolin-2-one
1,3,3-Trimethyl-6-(pyridin-2-yl)indolin-2-one
1,3,3-Trimethyl-6-(2-(pyrrolidin-1-yl)pyrimidin-5-yl)indolin-2-one
6-(2-Aminopyrimidin-5-yl)-1,3,3-trimethylindolin-2-one
6-(2-(Dimethylamino)pyrimidin-5-yl)-1,3,3-trimethylindolin-2-one
1,3,3-Trimethyl-6-(2-methylpyrimidin-5-yl)indolin-2-one
1,3,3-Trimethyl-6-(pyridazin-3-yl)indolin-2-one
6-(4-Ethylpyrimidin-5-yl)-1,3,3-trimethylindolin-2-one
6-(6-Aminopyridin-3-yl)-1,3,3-trimethylindolin-2-one
1,3,3-Trimethyl-6-(6-methylpyridazin-3-yl)indolin-2-one
6-(5-Aminopyridin-3-yl)-1,3,3-trimethylindolin-2-one
6-(3,5-Dimethyl-pyridin-4-yl)-1,3,3-trimethyl-1,3-dihydro-indol-2-one
6-(4,6-Dimethyl-pyrimidin-5-yl)-1,3,3-trimethyl-1,3-dihydro-indol-2-one
6-(2,4-Dimethyl-pyridin-3-yl)-1,3,3-trimethyl-1,3-dihydro-indol-2-one
7-Fluoro-1,3,3-trimethyl-6-(pyridin-3-yl)indolin-2-one
1,3,3,7-Tetramethyl-6-(pyridin-3-yl)indolin-2-one
5-Fluoro-1,3,3-trimethyl-6-(pyridin-3-yl)indolin-2-one
5-Fluoro-1,3,3-trimethyl-6-(pyridin-4-yl)indolin-2-one
7-Fluoro-1,3,3-trimethyl-6-pyridin-4-yl-1,3-dihydro-indol-2-one
5-Fluoro-1,3,3-trimethyl-6-(2-methylpyridin-4-yl)indolin-2-one
1-Isopropyl-3,3-dimethyl-6-(2-methylpyrimidin-5-yl)indolin-2-one
5,7-Difluoro-1,3,3-trimethyl-6-pyridin-3-yl-1,3-dihydro-indol-2-one
5,7-Difluoro-1,3,3-trimethyl-6-pyrimidin-5-yl-1,3-dihydro-indol-2-one
1,3,3,5-Tetramethyl-6-(2-methyl-pyridin-4-yl)-1,3-dihydro-indol-2-one
5,7-Difluoro-1,3,3-trimethyl-6-(2-methyl-pyrimidin-5-yl)-1,3-dihydro-indol-2-one
6-(2-Cyclopropylpyrimidin-5-yl)-1,3,3-trimethyl-indolin-2-one
6-(6-Cyclopropylpyridazin-3-yl)-1,3,3-trimethyl-indolin-2-one
1,3,3-Trimethyl-6-(2-methyl-4-pyridyl)pyrrolo[3,2-c]pyridin-2-one
3,3-Dimethyl-6-(2-methyl-4-pyridyl)-1H-pyrrolo[3,2-c]pyridin-2-one
1,3,3-Trimethyl-6-(6-morpholinopyridin-3-yl)indolin-2-one
1,3,3-Trimethyl-6-(2-methylpyrimidin-5-yl)pyrrolo[3,2-c]pyridin-2-one
1-Ethyl-3,3-dimethyl-6-(2-methylpyrimidin-5-yl)indolin-2-one
1,3,3-Trimethyl-6-(3-methyl-4-pyridyl)pyrrolo[3,2-c]pyridin-2-one
1,3,3-Trimethyl-6-(6-methyl-3-pyridyl)pyrrolo[3,2-c]pyridin-2-one
6-(2-Fluoro-4-pyridyl)-1,3,3-trimethyl-pyrrolo[3,2-c]pyridin-2-one
1'-Methyl-6'-(2-methylpyridin-4-yl)spiro[cyclopropane-1,3'-pyrrolo[3,2-c]pyridin]-2'(1'H)-one
1'-Methyl-6'-(pyridin-3-yl)spiro[cyclopropane-1,3'-pyrrolo[3,2-c]pyridin]-2'(1'H)-one or
1,3,3-Trimethyl-6-pyridazin-4-yl-pyrrolo[3,2-c]pyridin-2-one.

One embodiment of the invention are compounds of formula I, wherein Ar is a 6 membered heteroaryl group, containing one or two N-atoms and $R^2$ is $(CH_2)_o$-cycloalkyl, $(CH_2)_o$—O-cycloalkyl, $(CH_2)_o$-lower alkoxy, $CH_2)_o$-lower alkoxy substituted by halogen, $(CH_2)_o$-heterocycloalkyl optionally substituted by lower alkyl, $(CH_2)_o$—$S(O)_2$-cycloalkyl, lower alkyl substituted by one or two hydroxy, lower alkyl substituted by one or two lower alkoxy, $(CH_2)_o$—$S(O)_2$-lower alkyl, lower alkyl substituted by halogen or $CH_2CH(OH)CF_3$ and the other substituents are as described above, for example the following compounds:
1-Cyclopropyl-5-fluoro-3,3-dimethyl-6-(2-methylpyrimidin-5-yl)indolin-2-one
1-(Cyclopropylmethyl)-3,3-dimethyl-6-(2-methylpyrimidin-5-yl)indolin-2-one
1-(Cyclobutylmethyl)-3,3-dimethyl-6-(2-methylpyrimidin-5-yl)indolin-2-one 3,3-Dimethyl-6-(2-methyl-pyrimidin-5-yl)-1-oxetan-3-yl-1,3-dihydro-indol-2-one
1-(3-Cyclopropoxypropyl)-3,3-dimethyl-6-(2-methylpyrimidin-5-yl)indolin-2-one
3,3-Dimethyl-6-(2-methylpyridin-4-yl)-1-(oxetan-3-yl)indolin-2-one
3,3-Dimethyl-1-(oxetan-3-yl)-6-(pyridin-3-yl)indolin-2-one
3,3-Dimethyl-6-(6-methyl-pyridazin-3-yl)-1-oxetan-3-yl-1,3-dihydro-indol-2-one
1-(3-(Cyclopropyl sulfonyl)propyl)-3,3-dimethyl-6-(2-methylpyrimidin-5-yl)indolin-2-one
1-(2-Hydroxyethyl)-3,3-dimethyl-6-(2-methylpyrimidin-5-yl)indolin-2-one
1-(3-Hydroxypropyl)-3,3-dimethyl-6-(2-methylpyrimidin-5-yl)indolin-2-one
3,3-Dimethyl-6-(2-methylpyrimidin-5-yl)-1-(2-(methylsulfonyl)ethyl)indolin-2-one
1-Cyclopropyl-6-(2-cyclopropylpyrimidin-5-yl)-3,3-dimethyl-indolin-2-one
1-Cyclopropyl-6-(6-cyclopropylpyridazin-3-yl)-3,3-dimethyl-indolin-2-one
6-(6-Cyclopropylpyridazin-3-yl)-3,3-dimethyl-1-(oxetan-3-yl)indolin-2-one
1-Cyclopropyl-3,3-dimethyl-6-(2-methyl-4-pyridyl)pyrrolo[3,2-c]pyridin-2-one
7-Cyclopropyl-5,5-dimethyl-2-(2-methylpyridin-4-yl)-5H-pyrrolo[2,3-d]pyrimidin-6(7H)-one
1-Cyclopropyl-3,3-dimethyl-6-(6-methyl-3-pyridyl)pyrrolo[3,2-c]pyridin-2-one
1-Cyclopropyl-3,3-dimethyl-6-(3-methyl-4-pyridyl)pyrrolo[3,2-c]pyridin-2-one
1-Cyclopropyl-3,3-dimethyl-6-(2-methylpyrimidin-5-yl)-1H-pyrrolo[3,2-c]pyridin-2(3H)-one
1-(2-Methoxyethyl)-3,3-dimethyl-6-(2-methylpyrimidin-5-yl)indolin-2-one
3,3-Dimethyl-6-(2-methylpyrimidin-5-yl)-1-(2,2,2-trifluoroethyl)indolin-2-one
3,3-Dimethyl-6-(2-methylpyrimidin-5-yl)-1-(2-(trifluoromethoxy)ethyl)indolin-2-one
3,3-Dimethyl-6-(2-methylpyrimidin-5-yl)-1-(oxetan-3-ylmethyl)indolin-2-one
3,3-Dimethyl-6-(2-methylpyrimidin-5-yl)-1-(3,3,3-trifluoro-2-hydroxypropyl)indolin-2-one
1-(3-Fluoropropyl)-3,3-dimethyl-6-(2-methylpyrimidin-5-yl)indolin-2-one
1-(2-Fluoroethyl)-3,3-dimethyl-6-(2-methylpyrimidin-5-yl)indolin-2-one
1'-Cyclopropyl-6'-(2-methylpyridin-4-yl)spiro[cyclopropane-1,3'-pyrrolo[3,2-c]pyridin]-2'(1'H) one
1'-Cyclopropyl-6'-(pyridin-3-yl)spiro[cyclopropane-1,3'-pyrrolo[3,2-c]pyridin]-2'(1'H)-one
1-(2,3-Dihydroxypropyl)-3,3-dimethyl-6-(2-methylpyrimidin-5-yl)indolin-2-one
1-((4S,5R)-4-Hydroxy-5-(hydroxymethyl)tetrahydrofuran-2-yl)-3,3-dimethyl-6-(2-ethylpyrimidin-5-yl)indolin-2-one
1-(2,3-dimethoxypropyl)-3,3-dimethyl-6-(2-methylpyrimidin-5-yl)indolin-2-one or
3,3-dimethyl-6-(2-methylpyrimidin-5-yl)-1-(tetrahydrofuran-3-yl)indolin-2-one.

One embodiment of the invention are further compounds of formula I, wherein Ar is a bi-cyclic ring system, containing from 1 to 3 heteroatoms, and the other substituents are as described above, for example the following compounds:
6-(6,7-Dihydro-5H-cyclopenta[b]pyridin-3-yl)-1,3,3-trimethylindolin-2-one 6-(2,3-Dihydro-1H-pyrido[2,3-b][1,4]oxazin-7-yl)-1,3,3-trimethylindolin-2-one
6-(6,7-Dihydro-5H-pyrrolo[3,4-b]pyridin-3-yl)-1,3,3-trimethylindolin-2-one
6-(Imidazo[1,2-a]pyridin-7-yl)-1,3,3-trimethylindolin-2-one or
6-(Imidazo[1,2-a]pyridin-6-yl)-1,3,3-trimethylindolin-2-one.

One embodiment of the invention are compounds of formula I, wherein $R^1$ is a 5 membered heteroaryl group, containing from 1 to 3 heteroatoms, selected from N, S or O, and $R^2$ is hydrogen and the other substituents are as described above, for example the following compounds:
6-Imidazol-1-yl-3,3-dimethyl-1,3-dihydro-indol-2-one
3,3-Dimethyl-6-(3-methyl-1,2,4-oxadiazol-5-yl)indolin-2-one
3,3-Dimethyl-6-(4-methyl-1H-imidazol-1-yl)indolin-2-one
3,3-Dimethyl-6-(1-methyl-1H-pyrazol-4-yl)indolin-2-one
6-(5-Cyclopropyl-1,3,4-oxadiazol-2-yl)-3,3-dimethylindolin-2-one
6-(4-Cyclopropyl-1H-imidazol-1-yl)-3,3-dimethylindolin-2-one
3,3-Dimethyl-6-(5-methyl-1,3,4-oxadiazol-2-yl)indolin-2-one
6-(1-Cyclopropyl-1H-pyrazol-4-yl)-3,3-dimethylindolin-2-one
6-(1-Cyclopropyl-1H-imidazol-4-yl)-3,3-dimethylindolin-2-one
6-(4-Isopropyl-1H-imidazol-1-yl)-3,3-dimethylindolin-2-one
3,3-Dimethyl-6-[5-[1-(trifluoromethyl)cyclopropyl]-1,3,4-oxadiazol-2-yl]indolin-2-one
6-(5-Ethyl-1,3,4-oxadiazol-2-yl)-3,3-dimethyl-indolin-2-one
3,3-Dimethyl-6-(1-methyl-1H-imidazol-4-yl)indolin-2-one
3,3-Dimethyl-6-[5-(oxetan-3-yl)-1,3,4-oxadiazol-2-yl]indolin-2-one
3,3-Dimethyl-6-(2-methyloxazol-5-yl)indolin-2-one
6-(4-Ethylimidazol-1-yl)-3,3-dimethyl-indolin-2-one
6-(1,3-Dimethyl-1H-pyrazol-5-yl)-3,3-dimethylindolin-2-one
3,3-Dimethyl-6-(1-methyl-1H-pyrazol-3-yl)indolin-2-one
6-(5-(Hydroxymethyl)-1,3,4-oxadiazol-2-yl)-3,3-dimethyl-indolin-2-one
3,3-Dimethyl-6-[4-(trifluoromethyl)imidazol-1-yl]indolin-2-one
3,3-Dimethyl-6-[4-(2,2,2-trifluoro-1-hydroxy-ethyl)imidazol-1-yl]indolin-2-one or
6-[4-(1-Hydroxyethyl)imidazol-1-yl]-3,3-dimethyl-indolin-2-one.

One embodiment of the invention are compounds of formula I, wherein Ar is a 5 membered heteroaryl group, containing from 1 to 3 heteroatoms, selected from N, S or O, and $R^2$ is lower alkyl and the other substituents are as described above, for example the following compounds:
1,3,3-Trimethyl-6-(3-methyl-1,2,4-oxadiazol-5-yl)indolin-2-one
6-(1H-Imidazol-1-yl)-1,3,3-trimethylindolin-2-one
1,3,3-Trimethyl-6-(3-(trifluoromethyl)-1,2,4-oxadiazol-5-yl)indolin-2-one
1,3,3-Trimethyl-6-(4-methyl-1H-imidazol-1-yl)indolin-2-one
1,3,3-Trimethyl-6-(5-methyl-1H-imidazol-1-yl)indolin-2-one
6-(1,5-Dimethyl-1H-imidazol-2-yl)-1,3,3-trimethylindolin-2-one 1,3,3-Trimethyl-6-(2-methyl-1H-imidazol-5-yl)indolin-2-one
6-(1H-Imidazol-4-yl)-1,3,3-trimethylindolin-2-one
1,3,3-Trimethyl-6-(oxazol-5-yl)indolin-2-one
1,3,3-Trimethyl-6-(oxazol-4-yl)indolin-2-one
1,3,3-Trimethyl-6-(2-methyloxazol-5-yl)indolin-2-one
1,3,3-Trimethyl-6-(5-methyl-1,3,4-thiadiazol-2-yl)indolin-2-one
1,3,3-Trimethyl-6-(1,3,4-thiadiazol-2-yl)indolin-2-one
6-(2-Cyclopropyloxazol-5-yl)-1,3,3-trimethylindolin-2-one
1,3,3-Trimethyl-6-(2-(4-methylpiperazin-1-yl)oxazol-5-yl)indolin-2-one
1,3,3-Trimethyl-6-(2-methyloxazol-4-yl)indolin-2-one
1,3,3-Trimethyl-6-(1-methyl-1H-pyrazol-4-yl)indolin-2-one
1,3,3-Trimethyl-6-(5-methyl-1,3,4-oxadiazol-2-yl)indolin-2-one
6-(5-Cyclopropyl-1,3,4-oxadiazol-2-yl)-1,3,3-trimethylindolin-2-one
6-(4-Cyclopropyl-1H-imidazol-1-yl)-1,3,3-trimethylindolin-2-one
6-(5-Cyclopropyl-1H-imidazol-1-yl)-1,3,3-trimethylindolin-2-one
6-(1-Cyclopropyl-1H-pyrazol-4-yl)-1,3,3-trimethylindolin-2-one
6-(1-Cyclopropyl-1H-imidazol-4-yl)-1,3,3-trimethylindolin-2-one
1,3,3-Trimethyl-6-(1-methyl-1H-imidazol-4-yl)indolin-2-one
6-(4-Isopropyl-1H-imidazol-1-yl)-1,3,3-trimethylindolin-2-one
6-(1-Ethyl-1H-imidazol-4-yl)-1,3,3-trimethylindolin-2-one
1,3,3-Trimethyl-6-(1-(2,2,2-trifluoroethyl)-1H-imidazol-4-yl)indolin-2-one
6-(5-Ethyl-1,3,4-oxadiazol-2-yl)-1,3,3-trimethyl-indolin-2-one
6-(3-Cyclopropylisoxazol-5-yl)-1,3,3-trimethylindolin-2-one
1,3,3-Trimethyl-6-(3-methylisoxazol-5-yl)indolin-2-one
6-(3-(Methoxymethyl)isoxazol-5-yl)-1,3,3-trimethylindolin-2-one
1,3,3-Trimethyl-6-(2-(tetrahydro-2H-pyran-4-yl)oxazol-5-yl)indolin-2-one
1,3,3-Trimethyl-6-[5-(oxetan-3-yl)-1,3,4-oxadiazol-2-yl]indolin-2-one
1,3,3-Trimethyl-6-[4-(trifluoromethyl)imidazol-1-yl]indolin-2-one
6-(4-Ethyl-1H-imidazol-1-yl)-1,3,3-trimethylindolin-2-one
6-(2-(Hydroxymethyl)oxazol-5-yl)-1,3,3-trimethylindolin-2-one
6-[4-(1-Hydroxyethyl)imidazol-1-yl]-1,3,3-trimethyl-indolin-2-one One embodiment of the invention are compounds of formula I, wherein Ar is a 5 membered heteroaryl group, containing from 1 to 3 heteroatoms, selected from N, S or O, and $R^2$ is $(CH_2)_o$-cycloalkyl, $(CH_2)_o$—O-cycloalkyl, $(CH_2)_o$-lower alkoxy, $CH_2)_o$-lower alkoxy substituted by halogen, $(CH_2)_o$-heterocycloalkyl optionally substituted by lower alkyl, $(CH_2)_o$—S(O)-cycloalkyl, lower alkyl substituted by one or two hydroxy, lower alkyl substituted by one or two lower alkoxy, $(CH_2)_o$—S(O)$_2$-lower alkyl, lower alkyl substituted by halogen or $CH_2CH(OH)CF_3$, and the other substituents are as described above, for example the following compounds:

1-Cyclopropyl-3,3-dimethyl-6-(1-methyl-1H-pyrazol-4-yl)indolin-2-one
1-Cyclopropyl-3,3-dimethyl-6-(4-methyl-1-H-imidazol-1-yl)indolin-2-one
1-Cyclopropyl-3,3-dimethyl-6-(5-methyl-1H-imidazol-1-yl)indolin-2-one
1-Cyclopropyl-6-(4-cyclopropyl-1H-imidazol-1-yl)-3,3-dimethylindolin-2-one
1-Cyclopropyl-6-(5-cyclopropyl-1H-imidazol-1-yl)-3,3-dimethylindolin-2-one
1-Cyclopropyl-6-(5-cyclopropyl-1,3,4-oxadiazol-2-yl)-3,3-dimethylindolin-2-one
1-Cyclopropyl-3,3-dimethyl-6-(5-methyl-1,3,4-oxadiazol-2-yl)indolin-2-one
1-Cyclopropyl-6-(1-cyclopropyl-1H-pyrazol-4-yl)-3,3-dimethylindolin-2-one
1-Cyclopropyl-3,3-dimethyl-6-(1-methyl-1H-imidazol-4-yl)indolin-2-one
1-Cyclopropyl-6-(1H-imidazol-4-yl)-3,3-dimethyl-1H-pyrrolo[3,2-c]pyridin-2(3H)-one
1-Cyclopropyl-3,3-dimethyl-6-[5-(trifluoromethyl)-1,3,4-oxadiazol-2-yl]indolin-2-one
1-Cyclopropyl-3,3-dimethyl-6-[4-(trifluoromethyl)imidazol-1-yl]indolin-2-one
1-Cyclopropyl-3,3-dimethyl-6-[5-(oxetan-3-yl)-1,3,4-oxadiazol-2-yl]indolin-2-one
1-Cyclopropyl-6-[4-(1-hydroxyethyl)imidazol-1-yl]-3,3-dimethyl-indolin-2-one or
1-Cyclopropyl-3,3-dimethyl-6-[4-(2,2,2-trifluoro-1-hydroxy-ethyl)imidazol-1-yl]indolin-2-one.

One further embodiment of the invention are compounds of formula I, wherein X is N and $X^1$ is CH and the other substituents are as described above, for example the following compounds 1,3,3-Trimethyl-6-(2-methyl-4-pyridyl)pyrrolo[3,2-c]pyridin-2-one
3,3-Dimethyl-6-(2-methyl-4-pyridyl)-1H-pyrrolo[3,2-c]pyridin-2-one
1-Cyclopropyl-3,3-dimethyl-6-(2-methyl-4-pyridyl)pyrrolo[3,2-c]pyridin-2-one
3,3-Dimethyl-6-(2-methylpyrimidin-5-yl)-1H-pyrrolo[3,2-c]pyridin-2-one
1,3,3-Trimethyl-6-(2-methylpyrimidin-5-yl)pyrrolo[3,2-c]pyridin-2-one
1-Cyclopropyl-6-(1H-imidazol-4-yl)-3,3-dimethyl-1H-pyrrolo[3,2-c]pyridin-2(3H)-one
3,3-Dimethyl-6-(3-methylpyridin-4-yl)-1H-pyrrolo[3,2-c]pyridin-2(3H)-one
1-Cyclopropyl-3,3-dimethyl-6-(6-methyl-3-pyridyl)pyrrolo[3,2-c]pyridin-2-one
3,3-Dimethyl-6-(6-methyl-3-pyridyl)-1H-pyrrolo[3,2-c]pyridin-2-one
1-Cyclopropyl-3,3-dimethyl-6-(3-methyl-4-pyridyl)pyrrolo[3,2-c]pyridin-2-one
1,3,3-Trimethyl-6-(3-methyl-4-pyridyl)pyrrolo[3,2-c]pyridin-2-one
1,3,3-Trimethyl-6-(6-methyl-3-pyridyl)pyrrolo[3,2-c]pyridin-2-one
1-Cyclopropyl-3,3-dimethyl-6-(2-methylpyrimidin-5-yl)-1H-pyrrolo[3,2-c]pyridin-2(3H)-one
6-(2-Fluoro-4-pyridyl)-1,3,3-trimethyl-pyrrolo[3,2-c]pyridin-2-one
1'-Methyl-6'-(2-methylpyridin-4-yl)spiro[cyclopropane-1,3'-pyrrolo[3,2-c]pyridin]-2'(1'H)-one
1'-Methyl-6'-(pyridin-3-yl)spiro[cyclopropane-1,3'-pyrrolo[3,2-c]pyridin]-2'(1'H)-one 1'-Cyclopropyl-6'-(2-methylpyridin-4-yl)spiro[cyclopropane-1,3'-pyrrolo[3,2-c]pyridin]-2'(1'H)-one 1'-Cyclopropyl-6'-(pyridin-3-yl)spiro[cyclopropane-1,3'-pyrrolo[3,2-c]pyridin]-2'(1'H)-one or 1,3,3-Trimethyl-6-pyridazin-4-yl-pyrrolo[3,2-c]pyridin-2-one.

One further embodiment of the invention are compounds of formula I, wherein X is N and $X^1$ is N and the other substituents are as described above, for example the following compound 7-Cyclopropyl-5,5-dimethyl-2-(2-methylpyridin-4-yl)-5H-pyrrolo[2,3-d]pyrimidin-6(7H)-one.

One further embodiment of the invention are compounds of formula I, wherein the dotted line is a bond and the other substituents are as described above, for example the following compounds 1'-Methyl-6'-(2-methylpyridin-4-yl)spiro[cyclopropane-1,3'-pyrrolo[3,2-c]pyridin]-2'(1'H)-one 1'-M ethyl-6'-(pyridin-3-yl)spiro[cyclopropane-1,3'-pyrrolo[3,2-c]pyridin]-2'(1'H)-one 1'-Cyclopropyl-6'-(2-methylpyridin-4-yl)spiro[cyclopropane-1,3'-pyrrolo[3,2-c]pyridin]-2(1'H)-one or 1'-Cyclopropyl-6'-(pyridin-3-yl)spiro[cyclopropane-1,3'-pyrrolo[3,2-c]pyridin]-2'(1'H)-one.

The present compounds of formula I and their pharmaceutically acceptable salts can be prepared by methods known in the art, for example, by processes described below, which processes comprise a) reacting a compound of formula

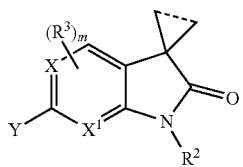

2 with a compound of formula

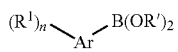

3 to a compound of formula

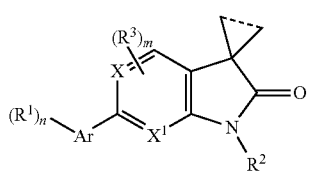

I wherein Y is halide (like e.g. bromine or iodine), R' is hydrogen or lower alkyl, (—B(OR')$_2$ representing for example boronic acid or boronic acid pinacol ester) and the further groups have the meaning as described above and, if desired, converting the compounds obtained into pharmaceutically acceptable acid addition salts;

or b) converting a suitable precursor of formula

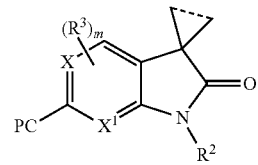

4 by applying standard reaction sequences for the formation of the heteroaryl substituent to a compound of formula

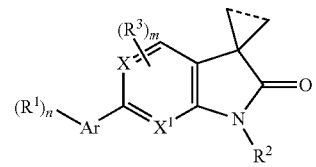

I wherein PC is —CO$_2$R', —CO$_2$H, —CHO, —CH$_2$OH or —(CO)R' with R'=lower alkyl and the further groups have the meaning as described above and, if desired, converting the compounds obtained into pharmaceutically acceptable acid addition salts.

The preparation of compounds of formula I of the present invention may be carried out in sequential or convergent synthetic routes. Syntheses of the compounds of the invention are shown in the following schemes. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in the examples, or by methods known in the art.

Scheme 1

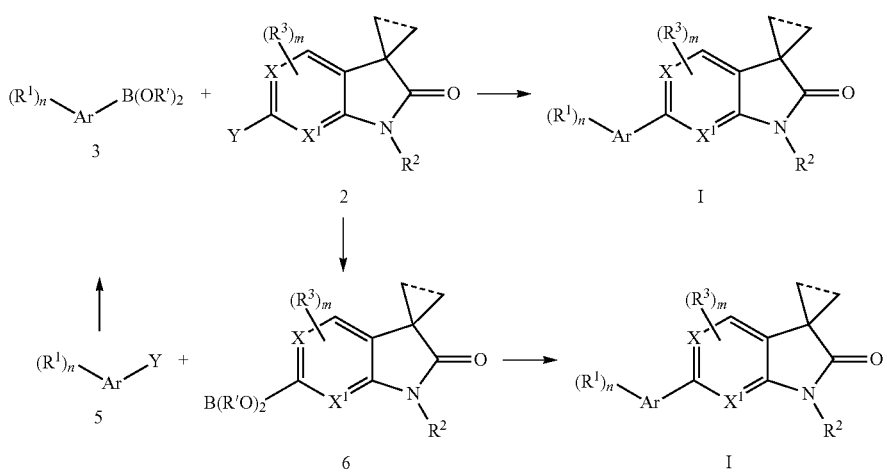

wherein Y is halide (like e.g. bromine or iodine), R' is hydrogen or lower alkyl (—B(OR')$_2$ representing for example boronic acid or boronic acid pinacol ester)

The present compounds of formula I and their pharmaceutically acceptable salts can be prepared by Suzuki coupling of the corresponding heteroaryl boronic acids or esters 3 with halides 2 or by Suzuki coupling of boronic acids or esters 6 with heteroaryl halides 5 (see Scheme 1).

Heteroarylboronic acids and esters 3 are either commercially available or can be prepared from corresponding halides 5 by generally known procedures, e.g. treatment of halides 5 with bis(pinacolato)diboron in the presence of a palladium catalyst. Boronic acids and esters 6 can be prepared from corresponding halides 2 by generally known procedures, e.g. treatment with bis(pinacolato)diboron in the presence of a palladium catalyst.

In case R$^2$=H this position can be modified using for example alkyl halides or heterocycloalkyl halides in the presence of an appropriate base. R$^2$ may be modified by appropriate reactions, like a dihydroxylation when R$^2$=allyl with osmium tetroxide in the presence of 4-methylmorpholine n-oxide monohydrate and a reductive workup, which can be further alkylated with alkyl halides like MeI in the presence of an appropriate base like NaH. Or, where R$^2$ is a protecting group like for example 4-methoxybenzyl or 2-trimethylsilylethoxymethyl, it may be removed by generally known procedures leading to R$^2$ is hydrogen.

Scheme 2

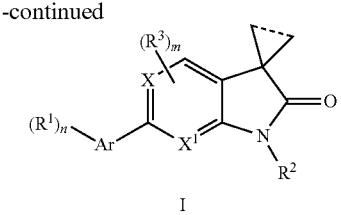

-continued

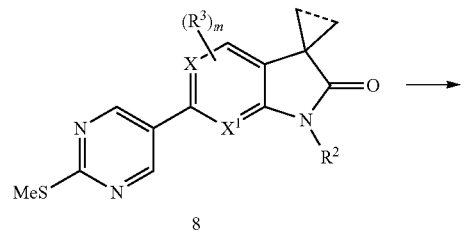

wherein Y is halide (like e.g. bromine or iodine), R' is lower alkyl (e.g. butyl).

Alternatively compounds of formula I and their pharmaceutically acceptable salts can be prepared by palladium catalyzed Stille coupling of heteroaryl stannanes 7 with halides 2 (see Scheme 2).

Scheme 3

-continued

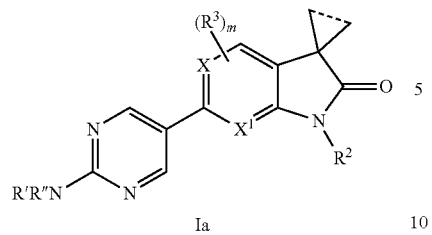

Ia

-continued

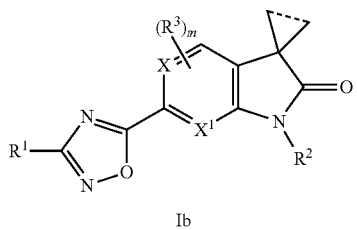

Ib

Compound of formula Ia (see Scheme 3) with R¹=pyrimidyl and substituted by R'R"N (R' and R" represent independent from each other hydrogen or lower alkyl) can be obtained from compounds 8 (prepared according to Scheme 1) by oxidation of the methyl thioether with e.g. mCPBA followed by substitution of the methyl sulfone with amines R'R"NH.

1,2,4-Oxadiazoles of formula Ib can be prepared by condensation of acids 11 with N-hydroxy amidines R¹C(=NOH)NH₂ e.g. in the presence of CDI (see Scheme 5).

Scheme 6

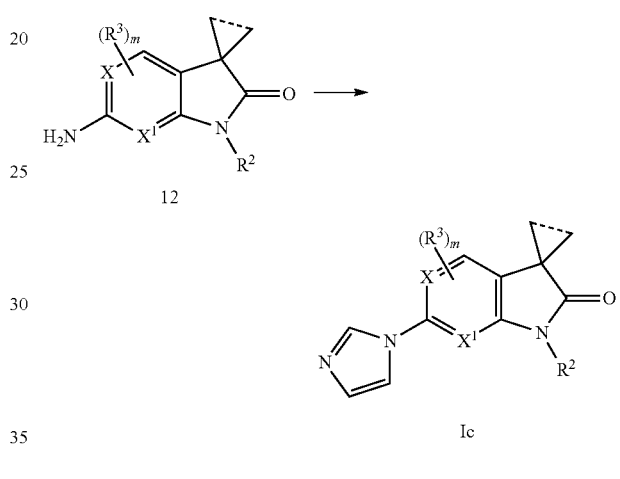

Scheme 4

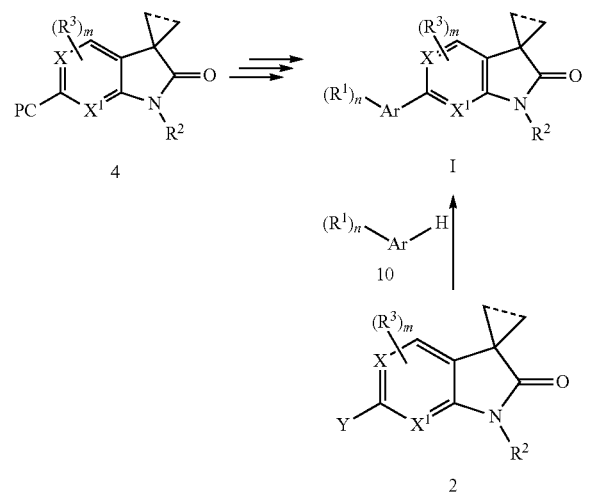

Alternatively the present compounds of formula I and their pharmaceutically acceptable salts can be prepared from suitable precursors 4 (PC is —CO₂R', —CO₂H, —CHO, —CH₂OH or —(CO)R' with R'=lower alkyl) by applying standard reaction sequences for the formation of the heteroaryl substituent (see Scheme 4) and as exemplified in the following schemes. Alternatively compounds of formula I can be prepared by a displacement reaction of a halide 2 (Y is halide, like e.g. bromine or iodine) with a heteroaryl compound 10 (like e.g. 1H-imidazoles) e.g. under catalytic conditions (like palladium or copper catalysis).

Imidazoles of formula Ic can be prepared by condensation of glyoxal, formaldehyde and ammonium acetate with anilines 12 (see Scheme 6).

Scheme 7

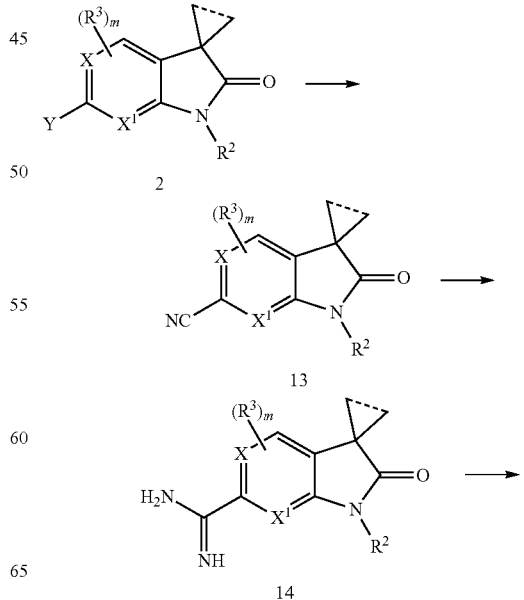

Scheme 5

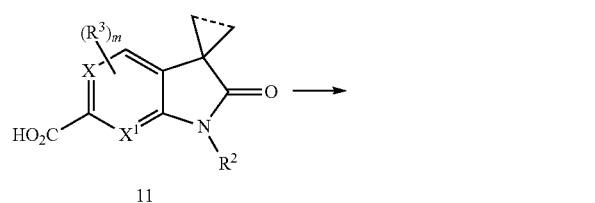

11

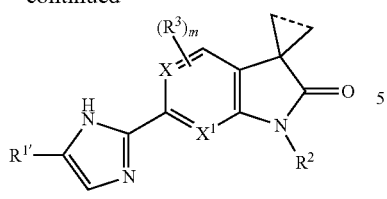

Id

Imidazoles of formula Id can be prepared starting with substitution of halides 2 with cyanide e.g. with zinc cyanide in the presence of a palladium catalyst. Addition of LiHMDS to the nitrile followed by acidic hydrolysis provides amidines 14, which can be condensed with α-halomethylketones $R^{1'}$—C(=O)CH$_2$Y (Y is halogen, like bromine, chlorine and $R^{1'}$ is lower alkyl, lower alkyl substituted by halogen, cycloalkyl or heterocycloalkyl) in the presence of a base to provide imidazoles Id (see Scheme 7).

Scheme 8

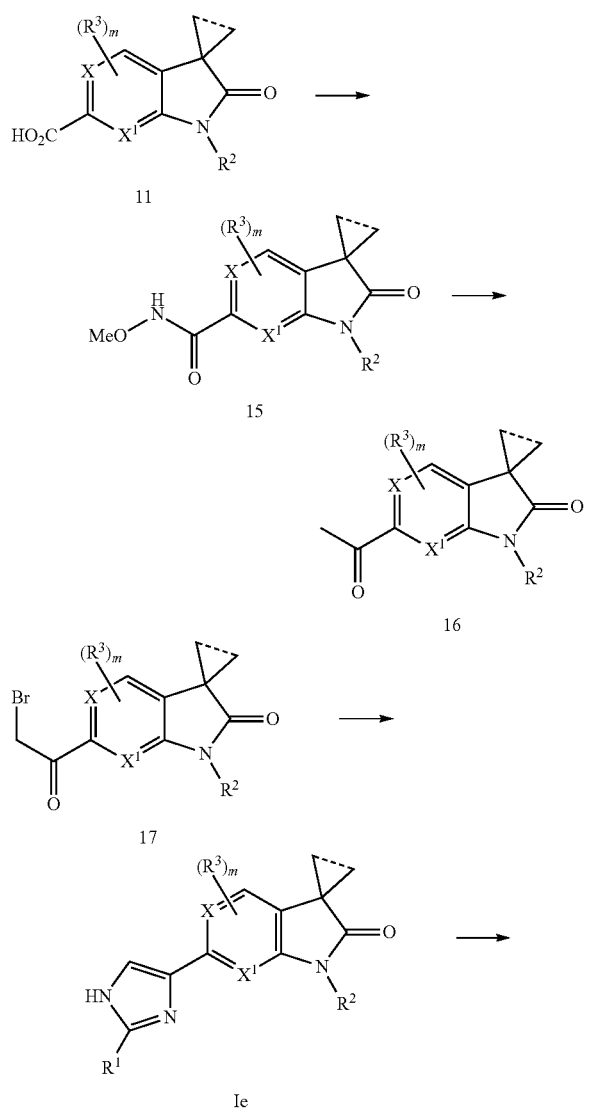

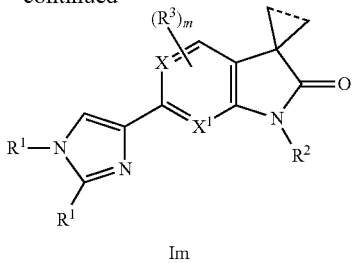

Im

Imidazoles of formula Ie can be prepared starting from carboxylic acids 11. Conversion to Weinreb amides 15 and reaction with methyl Grignard reagent provides methyl ketones 16 which can be brominated with e.g. tetra-n-butylammonium tribromide. Condensation with amidines $R^{1'}$—C(=NH)NH$_2$ yields imidazoles Ie (R is lower alkyl, lower alkyl substituted by halogen, cycloalkyl or heterocycloalkyl), Compounds 17 can also be condensed with amides like formamide to give imidazoles where $R^1$ is hydrogen or lower alkyl. Ie can be further transferred to imidazoles of formula Im where $R^1$ is lower alkyl by for example using alky-halides in the presence of an appropriate base or a boronic acid and a copper (II) source under Chan Lam conditions, see Scheme 8.

Scheme 9

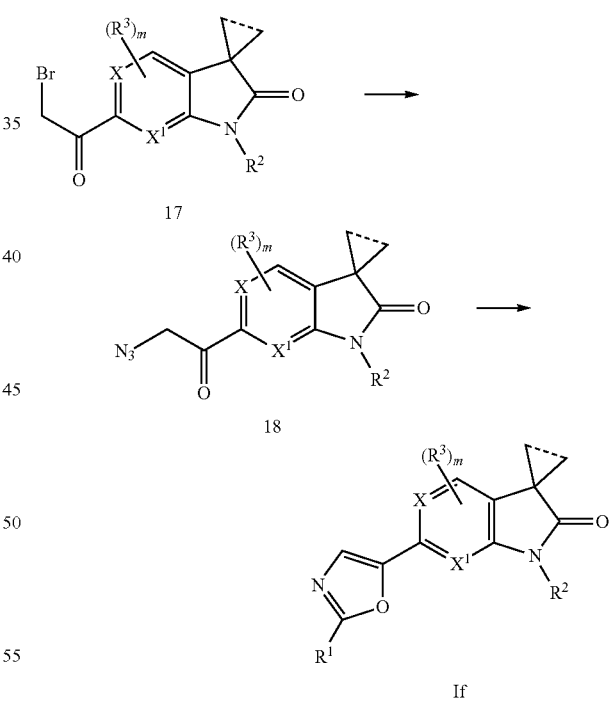

Oxazoles of formula If can be prepared by substitution of bromides 17 with sodium azide followed by reaction with acid chlorides $R^1$C(=O)Cl in the presence of triphenylphosphine, ($R^1$ is lower alkyl, lower alkyl substituted by halogen, cycloalkyl or heterocycloalkyl). In cases where $R^1$ is a lower alkyl substituted by acetoxy it can be further modified by cleaving the present ester using generally known methods leading to $R^1$ being lower alkyl substituted by hydroxy, see Scheme 9.

Scheme 10

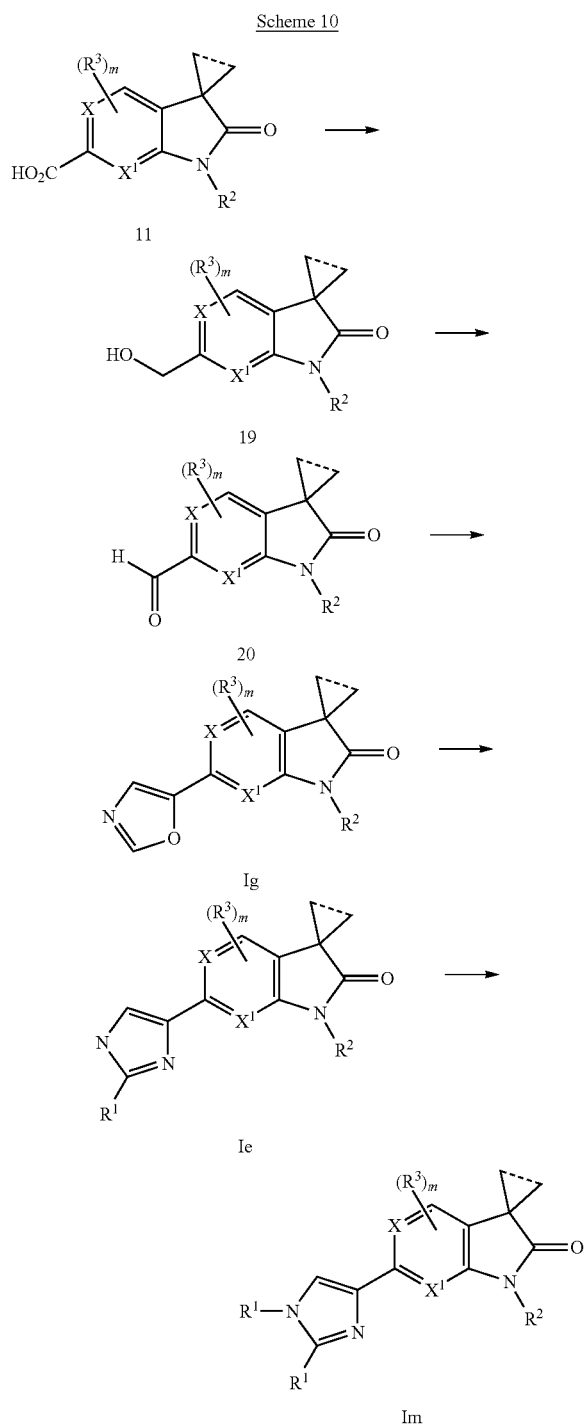

Scheme 11

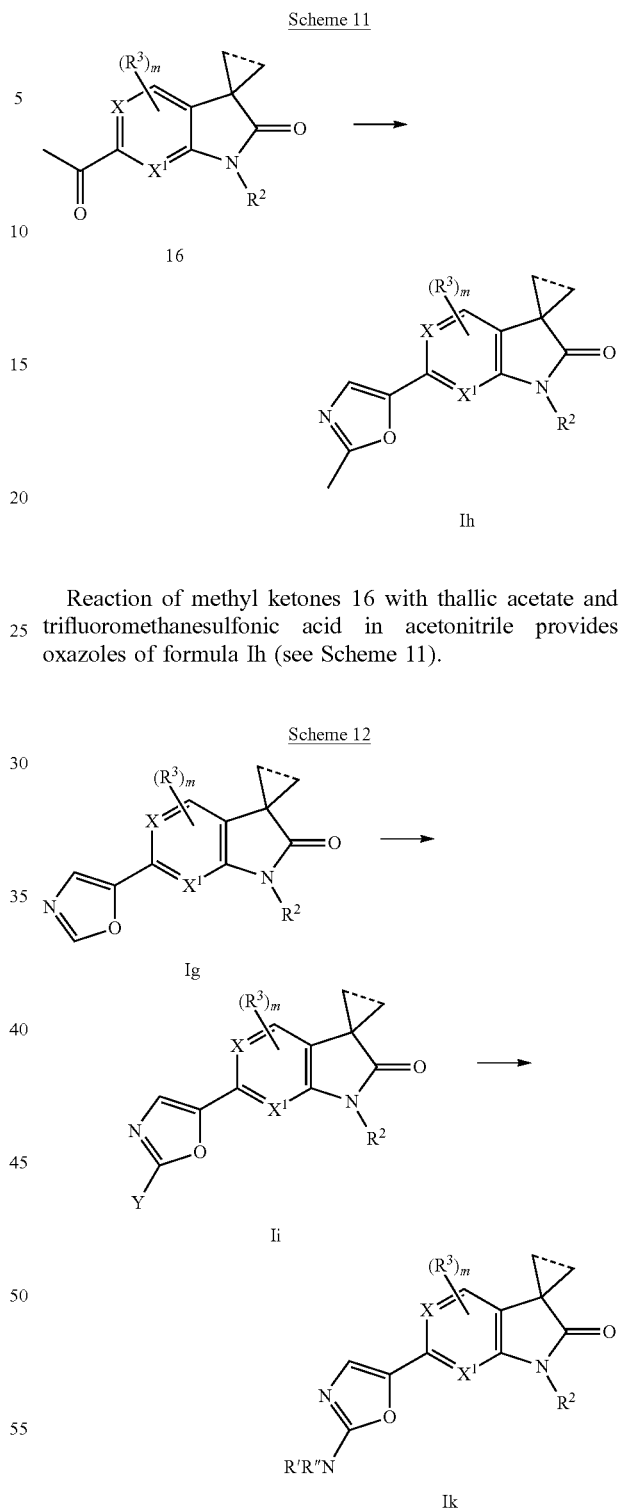

Reaction of methyl ketones 16 with thallic acetate and trifluoromethanesulfonic acid in acetonitrile provides oxazoles of formula Ih (see Scheme 11).

Scheme 12

Oxazoles of formula Ig can be prepared by conversion of carboxylic acids 11 into aldehydes 20 in a reduction (e.g. with borane tetrahydrofuran complex)—oxidation (e.g. with manganese dioxide) sequence. Reaction of the aldehyde with TOSMIC (tosylmethyl isocyanide) yields oxazoles Ig. These compounds may be transferred to compounds of formula Ie where $R^1$ is hydrogen or lower alkyl by reacting with amides like formamide and subsequently to compounds of formula Im like already described in Scheme 8, see Scheme 10.

Compounds of formula Ik with Ar=oxazolyl, substituted by R'R''N (R' and R'' represent independent from each other hydrogen or lower alkyl) can be prepared by halogenation of oxazoles Ig (Y=halogen) with e.g. hexachloroethane after deprotonation with a base like LiHMDS, followed by substitution with amine R'R''NH with heating under conventional or microwave conditions (see Scheme 12).

Scheme 13

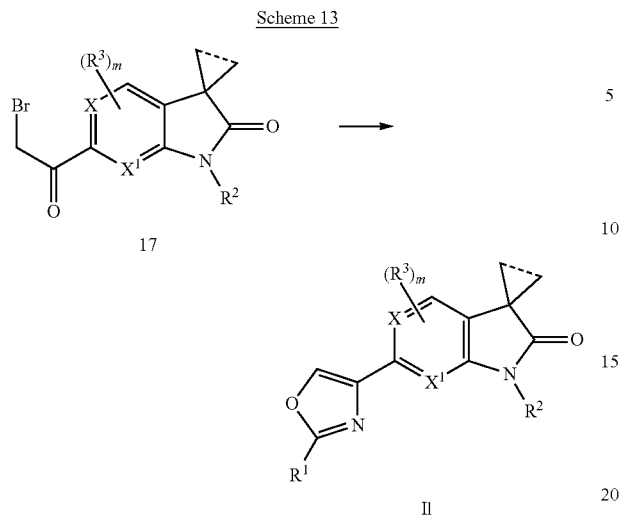

Oxazoles of formula Il can be prepared by condensation of α-bromoketones 17 with amides $R^1C(=O)NH_2$ ($R^1$ is lower alkyl, lower alkyl substituted by halogen, cycloalkyl or heterocycloalkyl), see Scheme 13.

Scheme 14

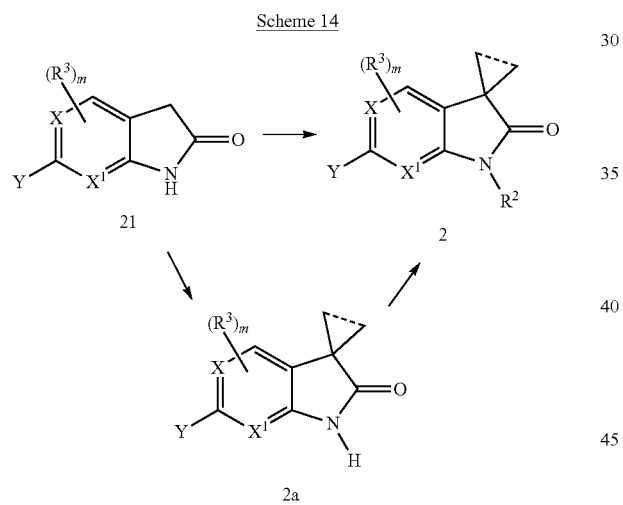

For $R^2$=methyl compounds of general formula 2 can e.g. be prepared by trimethylation of 6-halo-oxindoles 21 with Me-LG with LG being a leaving group like iodide, bromide, chloride, tosylate in the presence of a base like sodium hydride (see Scheme 14), and wherein Y is halogen.

For $R^2 \neq$ methyl compounds of general formula 2 can e.g. be prepared by dimethylation of 6-halo-oxindoles 21 with Me-LG (LG being a leaving group like iodide, bromide, chloride, tosylate) in the presence of a base like potassium tert-butoxide and in the presence of copper (I) bromide-dimethylsulfide complex. The dialkylated product 2a can then be converted to compounds 2 by alkylation with $R^2$-LG in the presence of a base like sodium hydride or cesium carbonate or by coupling of boronic acids $R^2$—$B(OH)_2$ or esters $R^2$—$B(OR')_2$ (e.g. $R^2$-4,4,5,5-tetramethyl-[1,3,2]di-oxaborolane) under metal catalysis (like e.g. palladium(0) or copper(II) catalysis) in the presence of a base like e.g. sodium bis(trimethylsilyl)amide or sodium carbonate.

For $R^2$=3-(cyclopropylthio)propyl and LG=bromide $R^2$-LG can be prepared by reaction of 3-mercaptopropan-1-ol with bromocyclopropane in the presence of a base followed by conversion of the alcohol into the bromide with e.g. tetrabromo-methane and triphenyl phosphine.

Scheme 15

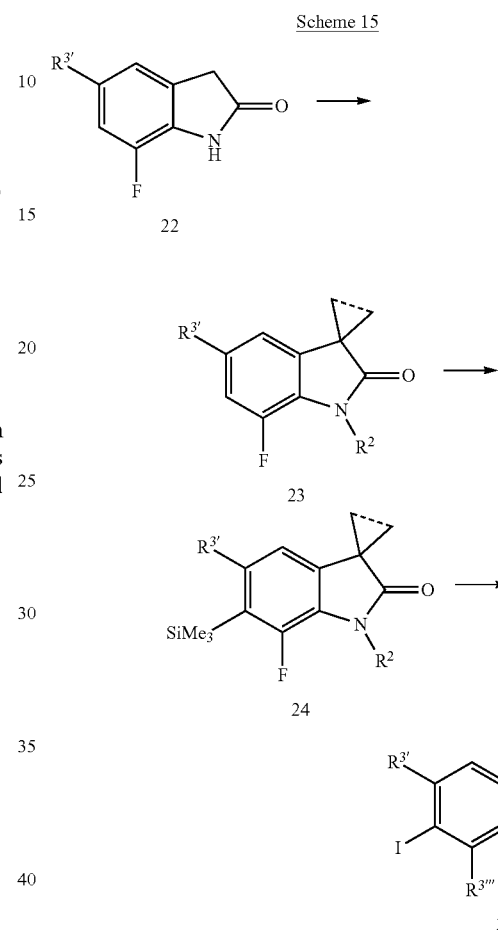

For Y=I, $R^{3'}$=H or F and $R^{3'''}$=F compounds of general formula 2b can e.g. be prepared by alkylation of oxindole 22 in analogy to Scheme 14, followed by ortho silylation by treatment with LDA and trimethylsilyl chloride and then exchange of the silyl group with iodide with iodine monochloride (see Scheme 15).

Scheme 16

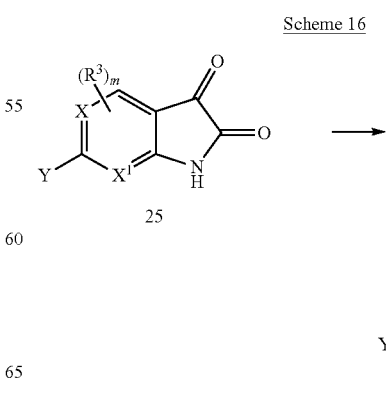

25

Compounds of general formula 21 can e.g. be prepared by reduction of isatin derivatives 25 with e.g. hydrazine, wherein Y is halogen (see Scheme 16).

Scheme 17

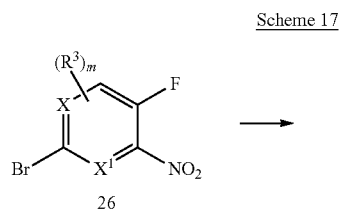

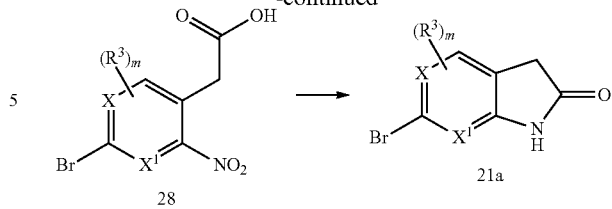

Alternatively compounds of general formula 21a with Y=Br can e.g. be prepared starting from 4-bromo-1-fluoro-2-nitro-benzene derivatives 26 by nucleophilic substitution of the fluoride with malonate ester in the presence of a base like e.g. sodium hydride (see Scheme 17). Ester hydrolysis and decarboxylation can e.g. be accomplished by heating in the presence hydrochloric acid to provide acid 28. Nitro reduction with e.g. iron in acetic acid is followed by cyclization to lactam 21a.

Scheme 18

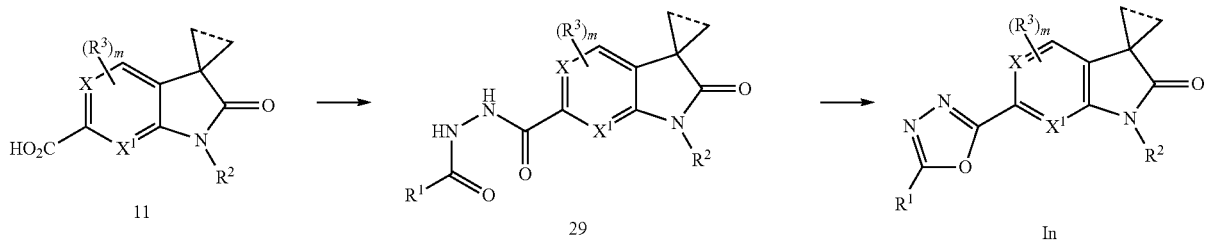

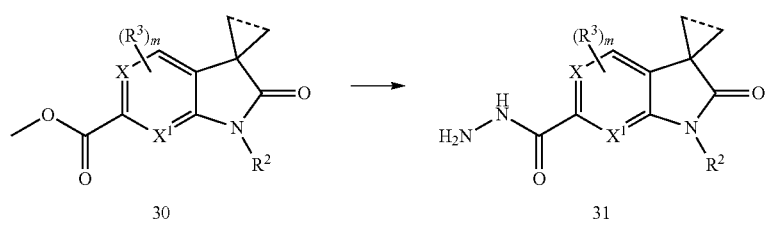

Intermediate hydrazides 29 can be prepared from ester 30. Either via transformation to the hydrazides 31 with hydrazine hydrate in methanol and then to the hydrazides 29 by reacting with R¹—COOH by methods like a TBTU coupling. Or by saponification of compound 30 to the acids 11 and then by reacting with R¹-hydrazides by methods like a HOBt/EDCI coupling.

Subsequently the intermediates 29 can be transformed to compounds of formula In by reacting for example with p-toluenesulfonyl chloride in the presence of a base like triethylamine, see Scheme 18.

Scheme 19

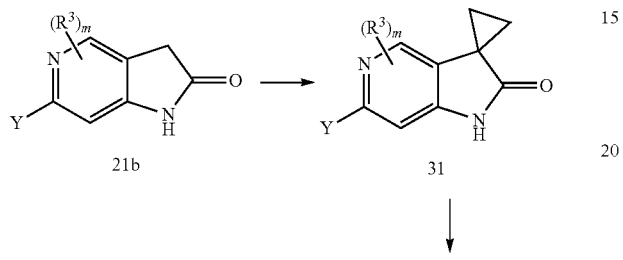

21b → 31 →

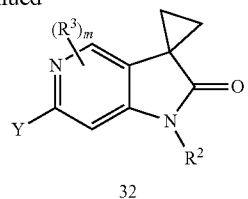

32

Compounds of formula 21b can be transformed to the spirocyclic intermediates 31 by reaction with ethylenedibromide in the presence of a strong base. These compounds may be further modified like described in Scheme 14 to get the intermediates 32 which can be used like compounds of formula 2, see Scheme 19. Y is halide, like e.g. bromine or iodine.

Scheme 20

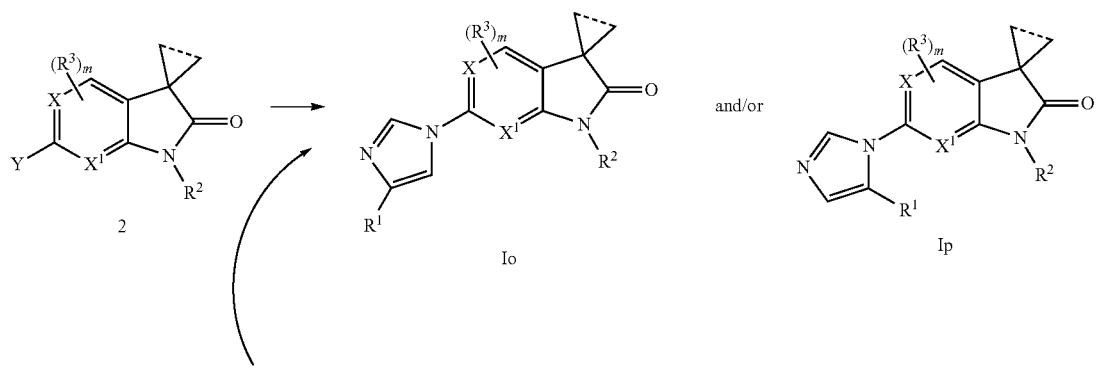

2 → Io and/or Ip

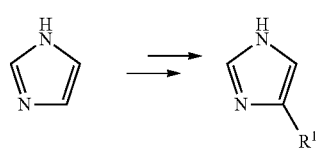

33

Compounds of formula Io and Ip, where $R^1$ is lower alkyl, haloalkyl, hydroxyalkyl or a combination of these can be prepared by reacting intermediates of formula 2 with imidazoles of formula 33 under Ullmann conditions, where the position $R^1$ for example with TBMDS protected hydroxy groups may be deprotected thereafter to give $R^1$. Compounds of formula 33 are either commercially available or can be prepared from imidazole, for example by reacting with trifluoroacetaldehyde methyl hemiacetal and subsequent protection of the hydroxy functionality with TBDMS-Cl in the presence of a base like triethylamine, see Scheme 20.

Scheme 21

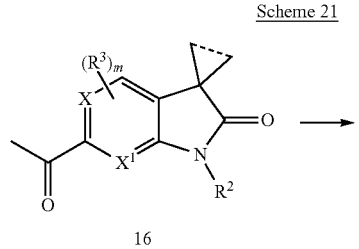

16

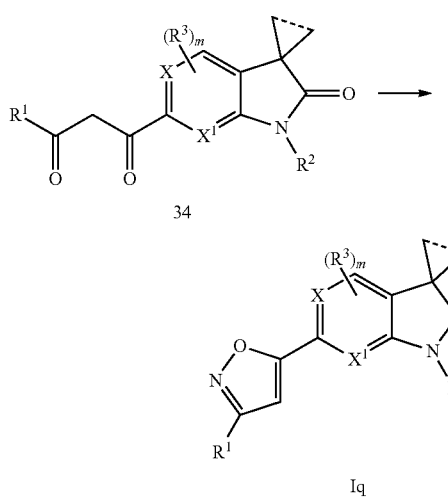

Compounds of formula Iq where $R^1$=lower alkyl or alkoxyalkyl can be prepared by reacting ketones 16 with $R^1$-esters in the presence of a strong base like sodium hydride to give the 1,3-diketones 34, which can subsequently be cyclized with hydroxylamine hydrochloride, see Scheme 21.

Scheme 22

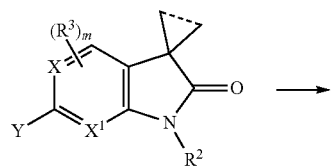

2

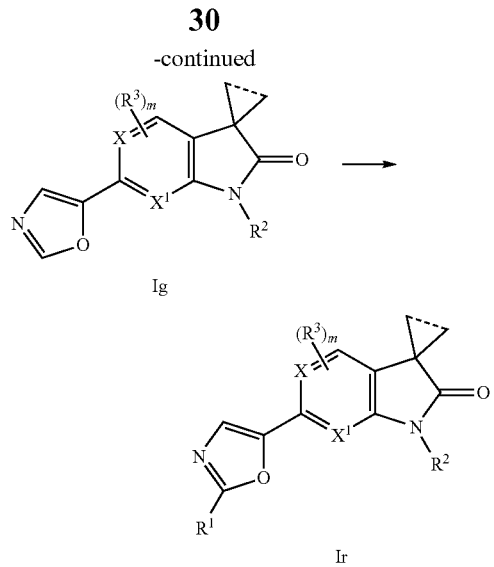

Compounds of formula Ig can alternatively to Scheme 10 be prepared by reacting halides 2 with oxazole in the presence of palladium (II) acetate, 2-di-t-butylphosphino-3,4,5,6-tetramethyl-2',4',6'-tri-i-propylbiphenyl, pivalic acid and potassium carbonate. These can be further transformed to compounds with formula Ir, where $R^1$ is lower alkyl, by reaction with alkyl halides in the presence of borane tetrahydrofuran complex and a strong base like n-butyl lithium, see Scheme 22.

Scheme 23

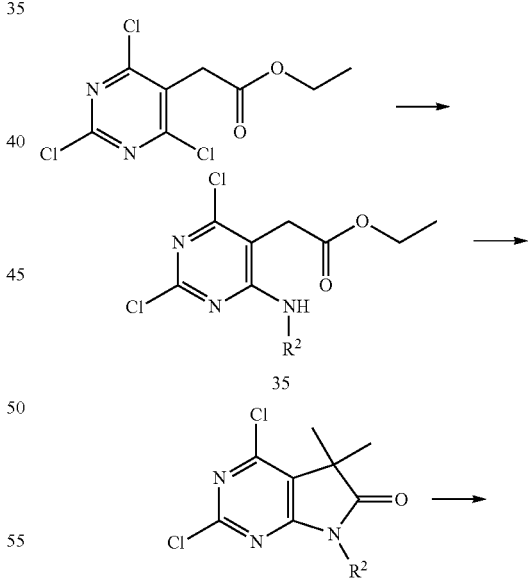

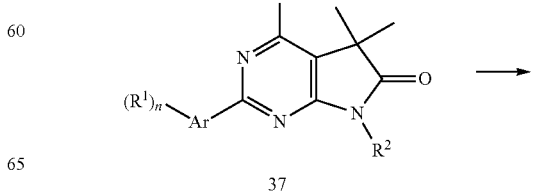

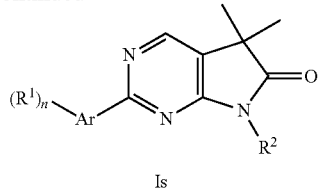

Is

Compounds of formula Is can be prepared as follows. Reacting ethyl 2-(2,4,6-trichloropyrimidin-5-yl)acetate with $R^2$—$NH_2$ in the presence of a base like diisopropylethylamine to give intermediates of structure 35. These may be dimethylated and cyclized to compounds 36 by reaction with methyl iodide in the presence of a base like cesium carbonate. These compounds can be further functionalized to compounds 37 by means already described in Schema 1. Finally compounds of formula Is are obtained by hydrogenating in the presence of palladium on charcoal, see Scheme 23.

EXPERIMENTAL PART

The following examples are provided for illustration of the invention. They should not be considered as limiting the scope of the invention, but merely as being representative thereof.

ABBREVIATIONS

Brettphos, 2-(dicyclohexylphosphino)-3,6-dimethoxy-2'-4'-6'-tri-i-propyl-1,1'-biphenyl;
$CBr_4$, tetrabromomethane;
$CDCl_3$, deutero chloroform;
CDI, 1,1'-carbonyldiimidazole;
$CH_2Cl_2$, dichloromethane;
CO, carbon monoxide;
$Cs_2CO_3$, cesium carbonate;
CuI, copper (I) iodide;
DIPEA, diisopropyl ethyl amine;
DMA, N,N-dimethylacetamide;
DMAP, 4-dimethylaminopyridine;
DMF, N,N-dimethylformamide;
DMSO, dimethylsulfoxide;
EDCI, N1-((ethylimino)methylene)-N3,N3-dimethylpropane-1,3-diamine hydrochloride;
ESI, ion spray ionization;
EtOAc, ethyl acetate;
$H_2O$, water;
HATU, O-(7-azabenzotriazol-1-yl)-N,N,N',N'-tetramethyluronium hexafluorophosphate;
HCl, hydrochloric acid;
HOBt, 1H-benzo[d][1,2,3]triazol-1-ol;
HPLC, high performance liquid chromatography;
KOH, potassium hydroxide;
$LiBH_4$, lithium borohydride;
LiHMDS, lithium hexamethyldisilazide;
mCPBA, 3-chloroperbenzoic acid;
MeI, methyl iodide;
MeOH, methanol;
MS, mass spectrum;
$Na_2CO_3$, sodium carbonate;
$Na_2SO_4$, sodium sulfate;
NaH, sodium hydride;
$NaHCO_3$, sodium bicarbonate;
NaOH, sodium hydroxide;
NaOtBu, sodium tert.-butoxide;
$NH_4Cl$, ammonium chloride;
NMP, 1-methyl-2-pyrrolidone;
NMR, nuclear magnetic resonance spectrum;
Pd(dppf)$Cl_2$, [1,1'-bis(diphenylphosphino)ferrocene]dichloropalladium(II);
Pd(PPh$_3$)$_4$, tetrakis(triphenylphosphine)palladium (0);
Pd$_2$dba$_3$.CHCl$_3$, tris(dibenzylideneacetone)dipalladium(0) chloroform complex;
SFC, supercritical fluid chromatography;
TBAF, tetrabutylammonium fluoride;
TBDMS-Cl, tert-butyldimethylchlorosilane;
TBME, tert.-butyl methyl ether;
TBTU, 2-(1H-benzotriazole-1-yl)-1,1,3,3-tetramethyluronium tetrafluoroborate;
t-BuOH, tert-butanol;
TFA, trifluoroacetic acid;
THF, tetrahydrofurane;
TPPO, triphenylphosphine oxide;
xantphos, 4,5-bis(diphenylphosphino)-9,9-dimethylxanthene;

General:

Silica gel chromatography was either performed using prepacked cartridges like for example SiliCycle® SiliaSep™ OT silica gel 40-63 m or SiliCycle® SiliaSep™ OT Amine silica gel 40-63 m on a system like Teledyne Isco CombiFlash® Rf 200 or self packed glass columns with silica gel 60 40-63 μm. MS were measured on a device like the Waters ACQUITY-SQD. NMR spectras were measured on a device like Bruker Avance I 300.

Example 1

1,3,3-Trimethyl-6-(pyridin-4-yl)indolin-2-one

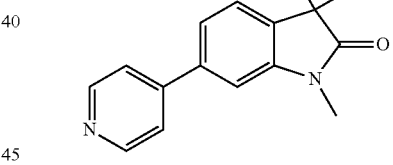

a) 6-Bromo-1,3,3-trimethylindolin-2-one

Under an argon atmosphere NaH (60% on mineral oil, 7.32 g, 183 mmol) was suspended in dry THF (45 ml). A suspension of 6-bromoindolin-2-one (10 g, 45.7 mmol) in dry THF (108 ml) was added in portions during 10 minutes while temperature was kept below 27° C. The reaction mixture was warmed to 25° C. and MeI (11.4 ml, 183 mmol) was added dropwise during 1 hour while the internal temperature was carefully kept between 24 and 27° C. The reaction mixture was stirred at room temperature for 18 hours. Saturated aqueous $NH_4Cl$ solution (20 ml) was carefully added at 10-15° C. The mixture was diluted with EtOAc, $H_2O$ and saturated aqueous $NaHCO_3$ solution. The aqueous phase was extracted with EtOAc, the organic layers were washed with saturated aqueous $NaHCO_3$ solution, combined and dried with $Na_2SO_4$. The solvent was evaporated and the residue was purified by silica gel chromatography using heptane/ethyl acetate as eluent. The title compound was obtained as light red solid (7.0 g). Mixed fractions were purified again by preparative HPLC yielding further 3.1 g of the title compound.

MS ESI (m/z): 254.1, 256.2 [(M+H)+].

$^1$H NMR (CDCl$_3$, 300 MHz): δ=7.19 (dd, J=1.5, 7.8 Hz, 1H), 7.06 (d, J=7.9 Hz, 1H), 6.99 (d, J=1.6 Hz, 1H), 3.19 (s, 3H), 1.35 (s, 6H).

b) 1,3,3-Trimethyl-6-(pyridin-4-yl)indolin-2-one

To a solution of 6-bromo-1,3,3-trimethylindolin-2-one (250 mg, 984 μmol) and pyridine-4-boronic acid (121 mg, 984 μmol) in dioxane (3.17 ml) was added a 2M aqueous solution of Na$_2$CO$_3$ (1.06 ml). The reaction vessel was evacuated and flushed with argon four times and [1,1'-bis(diphenylphosphino)ferrocene]dichloropalladium(II) (36.0 mg, 49.2 μmol) was added. The reaction mixture was then heated to reflux for 24 hours. The reaction mixture was diluted with water and the aqueous phase was extracted with ethyl acetate. The combined organic layers were washed with 1M aqueous Na$_2$CO$_3$ solution and dried over Na$_2$SO$_4$. The solvent was evaporated and the residue was purified by flash chromatography on silica gel using EtOAc/dichloromethane as eluent. The title compound was obtained as a yellow solid (138 mg).

MS ESI (m/z): 253.2 [(M+H)+].

$^1$H NMR (DMSO-d$_6$, 300 MHz) δ=8.64 (d, J=6.1 Hz, 2H), 7.75 (d, J=5.9 Hz, 2H), 7.55-7.39 (m, 3H), 3.22 (s, 3H), 1.31 (s, 6H).

Example 2

1,3,3-Trimethyl-6-(2-methylpyridin-4-yl)indolin-2-one

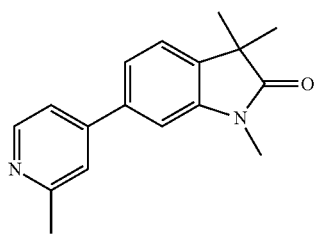

Prepared in analogy to example 1b from 6-bromo-1,3,3-trimethylindolin-2-one (example 1a) and 2-methylpyridine-4-boronic acid. The title compound was obtained as brown oil.

MS ESI (m/z): 267.2 [(M+H)+].

$^1$H NMR (CDCl$_3$, 300 MHz): δ=8.56 (d, J=5.2 Hz, 1H), 7.41-7.28 (m, 4H), 7.05 (s, 1H), 3.36-3.23 (m, 3H), 2.64 (s, 3H), 1.42 (s, 6H).

Example 3

1,3,3-Trimethyl-6-(pyridin-3-yl)indolin-2-one

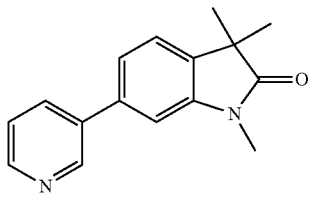

Prepared in analogy to example 1b from 6-bromo-1,3,3-trimethylindolin-2-one (example 1a) and pyridine-3-boronic acid. The title compound was obtained as light yellow solid.

MS ESI (m/z): 253.1 [(M+H)+].

$^1$H NMR (CDCl$_3$, 300 MHz): δ=8.86 (d, J=2.2 Hz, 1H), 8.62 (dd, J=1.4, 4.6 Hz, 1H), 7.88 (td, J=1.9, 7.9 Hz, 1H), 7.38 (dd, J=4.8, 7.9 Hz, 1H), 7.31 (d, J=7.5 Hz, 1H), 7.26 (dd, J=1.4, 7.5 Hz, 1H), 7.02 (d, J=1.2 Hz, 1H), 3.28 (s, 3H), 1.42 (s, 6H).

Example 4

1,3,3-Trimethyl-6-(pyrimidin-5-yl)indolin-2-one

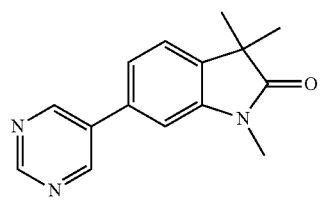 [SMILES: CN1C(=O)C(C)(C)c2ccc(-c3cncnc3)cc21]

Prepared in analogy to example 1b from 6-bromo-1,3,3-trimethylindolin-2-one (example 1a) and pyrimidin-5-ylboronic acid. The title compound was obtained as light red solid.

MS ESI (m/z): 254.2 [(M+H)+].

$^1$H NMR (CDCl$_3$, 300 MHz): δ=9.23 (s, 1H), 8.96 (s, 2H), 7.35 (d, J=7.7 Hz, 1H), 7.26 (dd, J=1.4, 7.5 Hz, 1H), 7.00 (d, J=1.2 Hz, 1H), 3.29 (s, 3H), 1.43 (s, 6H).

Example 5

1,3,3-Trimethyl-6-(pyridin-2-yl)indolin-2-one

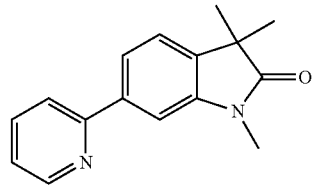 [SMILES: CN1C(=O)C(C)(C)c2ccc(-c3ccccn3)cc21]

A solution of 6-bromo-1,3,3-trimethylindolin-2-one (example 1a, 150 mg, 590 μmol) in THF (3 ml) was evacuated 3 times and flushed with argon. 2-(Tributylstannyl)pyridine (266 mg, 231 μl, 649 μmol), bis(triphenylphosphine)palladium(II) dichloride (21.1 mg, 29.5 μmol) and copper(I) iodide (5.62 mg, 29.5 μmol) were added and the mixture heated to reflux. After 3 hours again 2-(tributylstannyl)pyridine (266 mg, 231 μl, 649 μmol), bis(triphenylphosphine)palladium(II) dichloride (21.1 mg, 29.5 μmol) und copper(I) iodide (5.62 mg, 29.5 μmol) were added and the mixture stirred 60 hours at reflux. The mixture was filtered through a pad of silica gel, washed with EtOAc and the obtained solution concentrated in vacuo. The crude material was purified by silica gel chromatography using heptane/ethyl acetate as eluent. The title compound was obtained as light yellow solid (38 mg).

MS ESI (m/z): 253.1 [(M+H)+].
¹H NMR (CDCl₃, 300 MHz): δ=8.70 (d, J=4.6 Hz, 1H), 7.83-7.70 (m, 2H), 7.62 (dd, J=1.4, 7.7 Hz, 1H), 7.57 (s, 1H), 7.32-7.22 (m, 2H), 3.31 (s, 3H), 1.41 (s, 6H).

Example 6

3,3-Dimethyl-6-(pyridin-3-yl)indolin-2-one

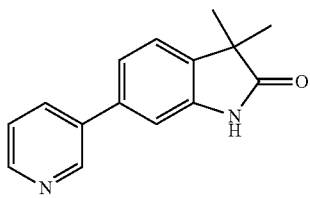 [SMILES: CC1(C)C(=O)Nc2cc(-c3cccnc3)ccc21]

Prepared in analogy to example 1b from 6-bromo-3,3-dimethyl-indolin-2-one (example 24a) and pyridine-3-boronic acid. The title compound was obtained as light brown solid.
MS ESI (m/z): 239.1 [(M+H)+].
¹H NMR (CDCl₃, 300 MHz): δ=8.92 (br s, 1H), 8.84 (d, J=2.2 Hz, 1H), 8.61 (dd, J=1.4, 4.6 Hz, 1H), 7.86 (td, J=1.9, 7.9 Hz, 1H), 7.37 (dd, J=4.8, 7.9 Hz, 1H), 7.30 (d, J=7.7 Hz, 1H), 7.25 (dd, J=1.4, 8.1 Hz, 1H), 7.16 (d, J=1.2 Hz, 1H), 1.46 (s, 6H).

Example 7

3,3-Dimethyl-6-(pyridin-4-yl)indolin-2-one

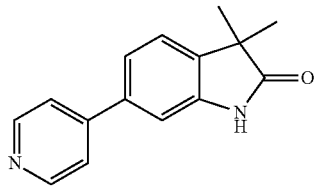 [SMILES: CC1(C)C(=O)Nc2cc(-c3ccncc3)ccc21]

Prepared in analogy to example 1b from 6-bromo-3,3-dimethyl-indolin-2-one (example 24a) and pyridine-4-boronic acid. The title compound was obtained as light brown solid.
MS ESI (m/z): 239.1 [(M+H)+].
¹H NMR (CDCl₃, 300 MHz): δ=8.72-8.63 (m, 2H), 8.41 (br. s., 1H), 7.53-7.44 (m, 2H), 7.36-7.28 (m, 2H), 7.18 (s, 1H), 1.46 (s, 6H).

Example 8

3,3-Dimethyl-6-(pyrimidin-5-yl)indolin-2-one

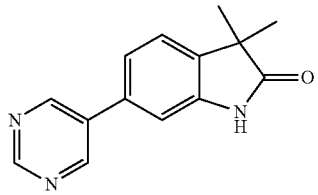

Prepared in analogy to example 1b from 6-bromo-3,3-dimethyl-indolin-2-one (example 24a) and pyrimidin-5-yl-boronic acid. The title compound was obtained as light brown solid.
MS ESI (m/z): 240.3 [(M+H)+].
1H NMR (CDCl3, 300 MHz): δ=9.22 (s, 1H), 8.94 (s, 2H), 8.61 (br. s, 1H), 7.35 (d, J=7.7 Hz, 1H), 7.25 (dd, J=1.6, 7.7 Hz, 1H), 7.14 (d, J=1.4 Hz, 1H), 1.51-1.40 (s, 6H).

Example 9

1,3,3-Trimethyl-6-(2-(pyrrolidin-1-yl)pyrimidin-5-yl)indolin-2-one

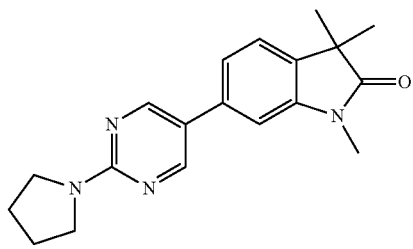 [SMILES: CN1C(=O)C(C)(C)c2ccc(-c3cnc(N4CCCC4)nc3)cc21]

a) 1,3,3-Trimethyl-6-(2-(methylthio)pyrimidin-5-indolin-2-one

To a suspension of 6-bromo-1,3,3-trimethylindolin-2-one (example 1a, 0.15 g, 590 μmol) and 2-(methylthio)pyrimidine-5-boronic acid (155 mg, 885 μmol) in dioxane (1.9 ml) was added 2M aqueous Na₂CO₃ solution (633 μl). The reaction vessel was evacuated four times and purged with argon. [1,1'-Bis(diphenylphosphino)ferrocene]dichloropalladium(II) (21.6 mg, 29.5 μmol) was added, evacuation and purging was repeated and the mixture heated to reflux for 15 hours. The reaction mixture was diluted with EtOAc and MeOH, two spoons silicagel were added and the suspension was concentrated in vacuo. The crude material was purified by silica gel chromatography using heptane/ethyl acetate as eluent. The title compound was isolated as light yellow solid (158 mg).
MS ESI (m/z): 300.4 [(M+H)+].
¹H NMR (CDCl₃, 300 MHz): δ=8.80 (s, 2H), 7.32 (d, J=7.7 Hz, 1H), 7.21 (dd, J=1.6, 7.5 Hz, 1H), 6.95 (d, J=1.4 Hz, 1H), 3.28 (s, 3H), 2.63 (s, 3H), 1.41 (s, 6H).

b) 1,3,3-Trimethyl-6((2-methylsulfonyl)pyrimidin-5-yl)indolin-2-one

To a solution of 1,3,3-trimethyl-6-(2-(methylthio)pyrimidin-5-yl)indolin-2-one (0.09 g, 301 μmol) in dichloromethane (3.01 ml) was added mCPBA (168 mg, 752 μmol) and the reaction mixture was stirred 4 hours at room temperature. The mixture was diluted with CH₂Cl₂, H₂O and 1M aqueous Na₂CO₃ solution. The mixture was extracted with CH₂Cl₂ and the organic layer was washed with 1M aqueous Na₂CO₃ solution. The combined organic layers were dried with Na₂SO₄, filtered and concentrated in vacuo. The title compound was obtained as yellow solid (109 mg, 92% purity) and used for the next step without further purification.

MS ESI (m/z): 332.1 [(M+H)+].

¹H NMR (CDCl₃, 300 MHz): δ=9.11 (s, 2H), 7.39 (d, J=7.7 Hz, 1H), 7.32-7.27 (m, 1H), 7.01 (d, J=1.0 Hz, 1H), 3.42 (s, 3H), 3.31 (s, 3H), 1.43 (s, 6H).

c) 1,3,3-Trimethyl-6-(2-(pyrrolidin-1-yl)pyrimidin-5-yl)indolin-2-one

A suspension of 1,3,3-trimethyl-6-(2-(methylsulfonyl)pyrimidin-5-yl)indolin-2-one (0.107 g, 297 μmol, 92% purity) in pyrrolidine (860 mg, 1 ml, 12.0 mmol) was heated to reflux. After 30 minutes the mixture was diluted with ethyl acetate and water. The aqueous layer was extracted with EtOAc and the organic layers were washed with 1M aqueous Na₂CO₃ solution. The combined organic layers were dried with Na₂SO₄, filtered and concentrated in vacuo. The crude material was purified by silica gel chromatography using heptane/ethyl acetate as eluent. The title compound was obtained as yellow solid (81 mg).

MS ESI (m/z): 323.3 [(M+H)+].

¹H NMR (CDCl₃, 300 MHz): δ=8.56 (s, 2H), 7.26 (d, J=7.5 Hz, 1H), 7.15 (dd, J=1.5, 7.6 Hz, 1H), 6.90 (d, J=1.4 Hz, 1H), 3.69-3.58 (m, 4H), 3.26 (s, 3H), 2.09-1.98 (m, 4H), 1.40 (s, 6H).

Example 10

6-(2-Aminopyrimidin-5-yl)-1,3,3-trimethylindolin-2-one

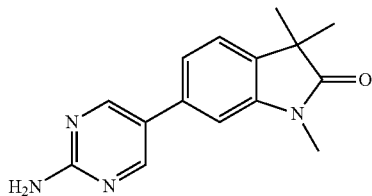 [SMILES: CN1C(=O)C(C)(C)c2ccc(-c3cnc(N)nc3)cc21]

Prepared in analogy to example 9c from 1,3,3-trimethyl-6-(2-(methylsulfonyl)pyrimidin-5-yl)indolin-2-one (example 9b) and ammonium hydroxide. The title compound was obtained as white solid.

MS ESI (m/z): 269.4 [(M+H)+].

¹H NMR (CDCl₃, 300 MHz): δ=8.54 (s, 2H), 7.28 (d, J=7.6 Hz, 1H), 7.16 (dd, J=1.5, 7.6 Hz, 1H), 6.91 (d, J=1.4 Hz, 1H), 5.12 (br s, 2H), 3.27 (s, 3H), 1.40 (s, 6H).

Example 11

6-(2-(Dimethylamino)pyrimidin-5-yl)-1,3,3-trimethylindolin-2-one

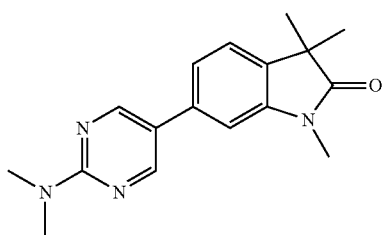 [SMILES: CN(C)c1ncc(-c2ccc3c(c2)N(C)C(=O)C3(C)C)cn1]

Prepared in analogy to example 9c from 1,3,3-trimethyl-6-(2-(methylsulfonyl)pyrimidin-5-yl)indolin-2-one (example 9b) and dimethylamine in ethanol. The title compound was obtained as light yellow solid.

MS ESI (m/z): 297.4 [(M+H)+].

¹H NMR (CDCl₃, 300 MHz): δ=8.56 (s, 2H), 7.26 (d, J=7.5 Hz, 1H), 7.15 (dd, J=1.4, 7.3 Hz, 1H), 6.90 (d, J=1.2 Hz, 1H), 3.28-3.22 (m, 9H), 1.40 (s, 6H).

Example 12

1,3,3-Trimethyl-6-(2-methylpyrimidin-5-yl)indolin-2-one

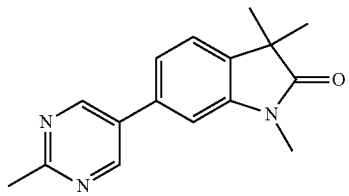

A suspension of 1,3,3-trimethyl-6-(2-(methyl sulfonyl)pyrimidin-5-yl)indolin-2-one (example 9b, 0.15 g, 430 μmol) in dry tetrahydrofurane (2.2 ml) was cooled to 0° C. A solution of methylmagnesium chloride in THF (3M, 287 μl, 860 μmol) was added dropwise, the cooling bath was removed and the reaction mixture stirred 15 hours at room temperature. The mixture was diluted with CH₂Cl₂, H₂O and 1M aqueous Na₂CO₃ solution and the aqueous layer was extracted with CH₂Cl₂. The combined organic layers were washed with 1M aqueous Na₂CO₃ solution, dried with sodium sulfate, filtered and concentrated in vacuo. The crude material was purified by silica gel chromatography using dichlormethane/ethyl acetate as eluent. The obtained material was purified by preparative HPLC through a Chiralpak AD column using heptane/ethanol as eluent. The title compound was obtained as light red solid (52 mg).

MS ESI (m/z): 268.3 [(M+H)+].

¹H NMR (CDCl₃, 300 MHz): δ=8.85 (s, 2H), 7.33 (d, J=7.7 Hz, 1H), 7.23 (dd, J=1.4, 7.5 Hz, 1H), 6.98 (d, J=1.4 Hz, 1H), 3.29 (s, 3H), 2.81 (s, 3H), 1.42 (s, 6H).

Example 13

1,3,3-Trimethyl-6-(pyridazin-3-yl)indolin-2-one

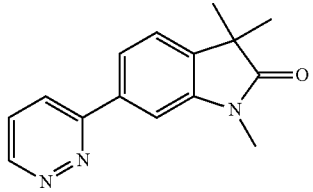 [SMILES: CN1C(=O)C(C)(C)c2ccc(-c3cccnn3)cc21]

A suspension of 1,3,3-trimethyl-6-(4,4,5,5-tetramethyl-1,3,2-dioxaborolan-2-yl)indolin-2-one (example 29a, 297 mg, 779 μmol), 3-bromo-pyridazine hydrobromide (286 mg, 1.17 mmol) in dioxane (3.9 ml) and 2M aqueous Na₂CO₃ solution (1.3 ml) was evacuated three times and flushed with argon. Then [1,1'-bis(diphenylphosphino)ferrocene]dichloropalladium(II) (28.5 mg, 39.0 µmol) was added, the mixture was heated to reflux for 15 hours. The reaction mixture was diluted with MeOH, silica gel was added and the mixture concentrated in vacuo. The crude material was purified by silica gel chromatography using dichloromethane/methanol as eluent. The obtained material was again purified by preparative HPLC on a Gemini NX 3u C18 110A column using water/formic acid/methanol as eluent. The title compound was obtained as white solid (136 mg).

MS ESI (m/z): 254.2 [(M+H)+].

¹H NMR (CDCl₃, 300 MHz): δ=9.18 (d, J=3.8 Hz, 1H), 7.89 (dd, J=1.4, 8.7 Hz, 1H), 7.79 (d, J=1.0 Hz, 1H), 7.63 (dd, J=1.3, 7.8 Hz, 1H), 7.56 (dd, J=4.8, 8.5 Hz, 1H), 7.34 (d, J=7.5 Hz, 1H), 3.32 (s, 3H), 1.43 (s, 6H).

Example 14

6-(4-Ethylpyrimidin-5-yl)-1,3,3-trimethylindolin-2-one

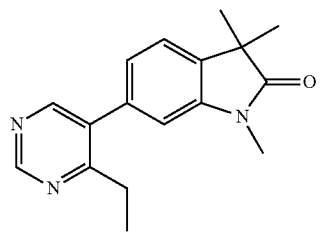 [SMILES: CCc1ncncc1-c1ccc2c(c1)N(C)C(=O)C2(C)C]

Prepared in analogy to example 13 from 1,3,3-trimethyl-6-(4,4,5,5-tetramethyl-1,3,2-dioxaborolan-2-yl)indolin-2-one (example 29a) and 5-bromo-4-ethylpyrimidine. The title compound was obtained as colorless oil.

MS ESI (m/z): 282.2 [(M+H)+].

¹H NMR (CDCl₃, 300 MHz): δ=9.14 (s, 1H), 8.54 (s, 1H), 7.29 (d, J=7.5 Hz, 1H), 6.99 (d, J=7.5 Hz, 1H), 6.76 (s, 1H), 3.24 (s, 3H), 2.81 (q, J=7.5 Hz, 2H), 1.43 (s, 6H), 1.27 (t, J=7.5 Hz, 3H).

Example 15

6-(6-Aminopyridin-3-yl)-1,3,3-trimethylindolin-2-one

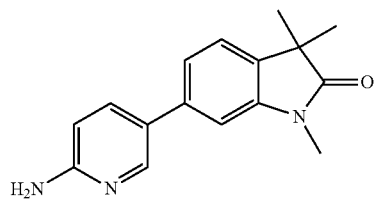 [SMILES: CN1C(=O)C(C)(C)c2ccc(-c3ccc(N)nc3)cc21]

Prepared in analogy to example 13 from 1,3,3-trimethyl-6-(4,4,5,5-tetramethyl-1,3,2-dioxaborolan-2-yl)indolin-2-one (example 29a) and 2-amino-5-bromopyridine. The title compound was obtained as light yellow solid.

MS ESI (m/z): 268.3 [(M+H)+].

¹H NMR (CDCl₃, 300 MHz): δ=8.32 (d, J=2.4 Hz, 1H), 7.68 (dd, J=2.3, 8.6 Hz, 1H), 7.25 (d, J=7.4 Hz, 1H), 7.18 (dd, J=1.4, 7.7 Hz, 1H), 6.94 (d, J=1.4 Hz, 1H), 6.60 (d, J=8.5 Hz, 1H), 4.55 (br s, 2H), 3.27 (s, 3H), 1.40 (s, 6H).

Example 16

6-(2-Aminopyrimidin-5-yl)-3,3-dimethylindolin-2-one

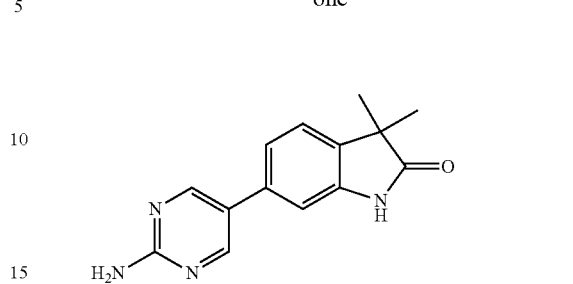

Prepared in analogy to example 24b from 6-bromo-3,3-dimethyl-indolin-2-one (example 24a) and 2-aminopyrimidine-5-boronic acid, pinacol ester. The title compound was obtained as light brown solid.

MS ESI (m/z): 255.3 [(M+H)+].

¹H NMR (DMSO-d₆, 300 MHz) δ=10.40 (s, 1H), 8.49 (s, 2H), 7.33 (d, J=7.9 Hz, 1H), 7.22-7.11 (m, 1H), 6.98 (s, 1H), 6.75 (s, 2H), 1.26 (s, 6H).

Example 17

3,3-Dimethyl-6-(pyridazin-4-yl)indolin-2-one

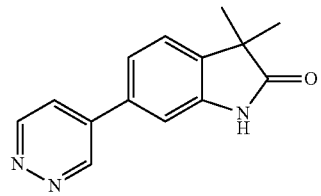 [SMILES: CC1(C)C(=O)Nc2cc(-c3ccnnc3)ccc21]

a) 3,3-Dimethyl-6-(4,4,5,5-tetramethyl-1,3,2-dioxaborolan-2-yl)indolin-2-one

Prepared in analogy to example 29a from 6-bromo-3,3-dimethyl-indolin-2-one (example 24a). The title compound was obtained as light yellow solid.

MS ESI (m/z): 288.2 [(M+H)+].

¹H NMR (CDCl₃, 300 MHz): δ=7.94 (br s, 1H), 7.53 (d, J=7.5 Hz, 1H), 7.35 (s, 1H), 7.21 (d, J=7.3 Hz, 1H), 1.40 (s, 6H), 1.34 (s, 12H)

b) 3,3-Dimethyl-6-(pyridazin-4-yl)indolin-2-one

Prepared in analogy to example 29b from 3,3-dimethyl-6-(4,4,5,5-tetramethyl-1,3,2-dioxaborolan-2-yl)indolin-2-one and 4-bromopyridazine hydrobromide. The title compound was obtained as brown solid.

MS ESI (m/z): 240.2 [(M+H)+].

¹H NMR (CDCl₃, 300 MHz): δ=9.46 (d, J=1.2 Hz, 1H), 9.25 (d, J=5.4 Hz, 1H), 8.52 (br s, 1H), 7.64 (dd, J=2.4, 5.4 Hz, 1H), 7.36 (s, 2H), 7.23 (s, 1H), 1.47 (s, 6H)

Example 18

6-(6-Aminopyridin-3-yl)-3,3-dimethylindolin-2-one

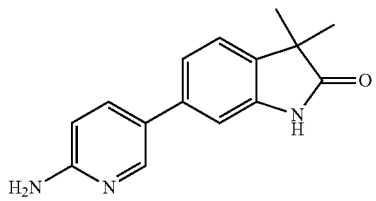 [SMILES: CC1(C)C(=O)Nc2cc(-c3ccc(N)nc3)ccc21]

Prepared in analogy to example 29b from 3,3-dimethyl-6-(4,4,5,5-tetramethyl-1,3,2-dioxaborolan-2-yl)indolin-2-one (example 17a) and 2-amino-5-bromopyridine. The title compound was obtained as light brown solid.

MS ESI (m/z): 254.2 [(M+H)$^+$].
$^1$H NMR (DMSO-d$_6$, 300 MHz) δ=10.35 (s, 1H), 8.16 (d, J=2.4 Hz, 1H), 7.62 (dd, J=2.5, 8.6 Hz, 1H), 7.30 (d, J=7.7 Hz, 1H), 7.12 (dd, J=1.2, 7.7 Hz, 1H), 6.94 (d, J=1.2 Hz, 1H), 6.51 (d, J=8.5 Hz, 1H), 6.05 (br. s, 2H), 1.26 (s, 6H)

Example 19

3,3-Dimethyl-6-(2-methylpyridin-3-yl)indolin-2-one

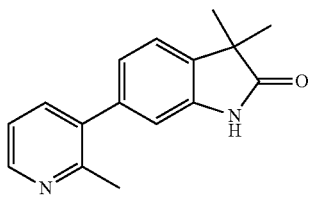 [SMILES: Cc1ncccc1-c1ccc2c(c1)NC(=O)C2(C)C]

Prepared in analogy to example 24b from 6-bromo-3,3-dimethyl-indolin-2-one (example 24a) and 2-methylpyridin-3-ylboronic acid. The title compound was obtained as off-white solid.

MS ESI (m/z): 253.2 [(M+H)$^+$].
$^1$H NMR (CDCl$_3$, 300 MHz): δ=8.51 (dd, J=1.7, 4.7 Hz, 1H), 7.94 (br s, 1H), 7.51 (dd, J=1.7, 7.6 Hz, 1H), 7.25 (d, J=7.6 Hz, 1H), 7.19 (dd, J=4.8, 7.7 Hz, 1H), 6.98 (dd, J=1.2, 7.7 Hz, 1H), 6.86 (d, J=1.2 Hz, 1H), 2.53 (s, 3H), 1.46 (s, 6H).

Example 20

3,3-Dimethyl-6-(3-methylpyridin-4-yl)indolin-2-one

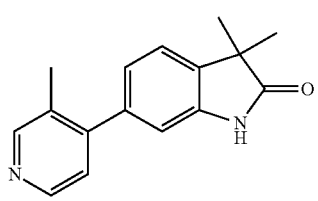

Prepared in analogy to example 24b from 6-bromo-3,3-dimethyl-indolin-2-one (example 24a) and 3-methylpyridin-4-ylboronic acid. The title compound was obtained as light brown solid.

MS ESI (m/z): 253.2 [(M+H)$^+$].
$^1$H NMR (CDCl$_3$, 300 MHz): δ=8.51 (s, 1H), 8.47 (d, J=5.0 Hz, 1H), 8.06 (br s, 1H), 7.26 (d, J=7.5 Hz, 1H), 7.14 (d, J=4.8 Hz, 1H), 6.99 (dd, J=1.4, 7.7 Hz, 1H), 6.86 (d, J=1.4 Hz, 1H), 2.30 (s, 3H), 1.46 (s, 6H).

Example 21

3,3-Dimethyl-6-(2-methylpyrimidin-5-yl)indolin-2-one

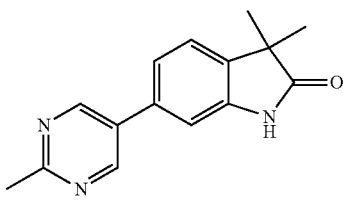 [SMILES: Cc1ncc(-c2ccc3c(c2)NC(=O)C3(C)C)cn1]

Prepared in analogy to example 24b from 6-bromo-3,3-dimethyl-indolin-2-one (example 24a) and 2-methylpyrimidin-5-ylboronic acid. The title compound was obtained as brown solid.

MS ESI (m/z): 254.2 [(M+H)$^+$].
$^1$H NMR (CDCl$_3$, 300 MHz): δ=8.83 (s, 2H), 8.27 (br s, 1H), 7.32 (d, J=8.1 Hz, 1H), 7.23 (dd, J=1.4, 7.7 Hz, 1H), 7.10 (d, J=1.2 Hz, 1H), 2.80 (s, 3H), 1.45 (s, 6H).

Example 22

1,3,3-Trimethyl-6-(6-methylpyridazin-3-yl)indolin-2-one

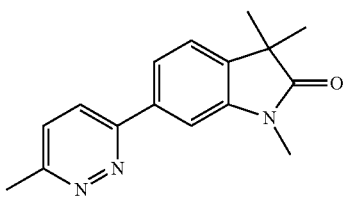 [SMILES: Cc1ccc(-c2ccc3c(c2)N(C)C(=O)C3(C)C)nn1]

Prepared in analogy to example 29b from 1,3,3-trimethyl-6-(4,4,5,5-tetramethyl-1,3,2-dioxaborolan-2-yl)indolin-2-one (example 29a) and 3-bromo-6-methylpyridazine. The title compound was obtained as brown solid.

MS ESI (m/z): 268.2 [(M+H)$^+$].
$^1$H NMR (CDCl$_3$, 300 MHz): δ=7.82-7.74 (m, 2H), 7.61 (dd, J=1.6, 7.9 Hz, 1H), 7.41 (d, J=8.7 Hz, 1H), 7.33 (d, J=7.7 Hz, 1H), 3.31 (s, 3H), 2.78 (s, 3H), 1.42 (s, 6H).

Example 23

6-(6,7-Dihydro-5H-cyclopenta[b]pyridin-3-yl)-1,3,3-trimethylindolin-2-one

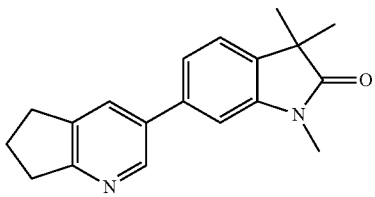 [SMILES: CN1C(=O)C(C)(C)c2ccc(-c3cnc4c(c3)CCC4)cc21]

Prepared in analogy to example 29b from 1,3,3-trimethyl-6-(4,4,5,5-tetramethyl-1,3,2-dioxaborolan-2-yl)indolin-2-one (example 29a) and 3-bromo-6,7-dihydro-5H-cyclopenta[b]pyridine. The title compound was obtained as light red solid.

MS ESI (m/z): 293.1 [(M+H)+].

$^1$H NMR (CDCl$_3$, 300 MHz): δ=8.57 (s, 1H), 7.69 (s, 1H), 7.31-7.20 (m, 2H), 6.99 (s, 1H), 3.28 (s, 3H), 3.13-2.96 (m, 4H), 2.20 (quin, J=7.6 Hz, 2H), 1.41 (s, 6H).

Example 24

3,3-Dimethyl-6-(2-methylpyridin-4-yl)indolin-2-one

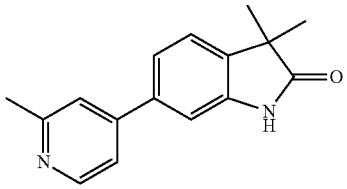 [SMILES: Cc1cc(-c2ccc3c(c2)NC(=O)C3(C)C)ccn1]

a) 6-Bromo-3,3-dimethyl-indolin-2-one

To a suspension of potassium tert-butylate (12.8 g, 114 mmol) in dry THF (80 ml) at 0° C. under an argon atmosphere was added portionwise 6-bromoindolin-2-one (5.0 g, 22.9 mmol) followed by copper(I) bromide-dimethylsulfide complex (470 mg, 2.29 mmol). MeI (6.82 g, 3.00 ml, 48.0 mmol) was added dropwise within 45 minutes, keeping internal temperature below 8° C. The reaction mixture was warmed to room temperature and kept at this temperature for 16 hours. The reaction mixture was cooled to 0° C. again and saturated aqueous ammonium chloride solution was cautiously added. The mixture was diluted with tert-butyl methyl ether and water. The aqueous phase was extracted with tert-butyl methyl ether, the combined organic phases were dried over sodium sulfate, the solvent was evaporated and the residue was purified by silica gel chromatography using ethyl acetate/heptane as eluent. The title compound was obtained as light yellow solid (5.17 g).

MS ESI (m/z): 240.0/242.1 [(M+H)+].

$^1$H NMR (CDCl$_3$, 400 MHz): δ (ppm)=8.12 (m, 1H), 7.20-7.16 (m, 1H), 7.09-7.08 (m, 1H), 7.06-7.04 (m, 1H), 1.39 (s, 6H).

b) 3,3-Dimethyl-6-(2-methylpyridin-4-yl)indolin-2-one

To a suspension of 6-bromo-3,3-dimethylindolin-2-one (120 mg, 500 μmol) and 2-methylpyridin-4-ylboronic acid (105 mg, 750 μmol) in dioxane (2 ml) and an aqueous solution of sodium carbonate (2M, 667 μl) [1,1'-bis(diphenylphosphino)ferrocene]dichloropalladium(II) (18.3 mg, 25.0 μmol) was added under an argon atmosphere. The reaction mixture was heated to reflux and stirred at this temperature under an argon atmosphere for 12 hours.

The mixture was diluted with ethyl acetate and 2M aqueous solution of sodium carbonate. The aqueous phase was extracted with ethyl acetate, the combined organic phases were washed with brine, dried over sodium sulfate, the solvent was evaporated and the residue was purified by silica gel chromatography using ethyl acetate/heptane as eluent. The title compound was obtained as off-white foam (60 mg).

MS ESI (m/z): 253.1 [(M+H)+].

$^1$H NMR (CDCl$_3$, 400 MHz): δ (ppm)=8.55 (d, J=5.2 Hz, 1H), 8.33 (br s, 1H), 7.40-7.27 (m, 4H), 7.20-7.13 (m, 1H), 2.63 (s, 3H), 1.45 (s, 6H).

Example 25

6-(2,3-Dihydro-1H-pyrido[2,3-b][1,4]oxazin-7-yl)-1,3,3-trimethylindolin-2-one

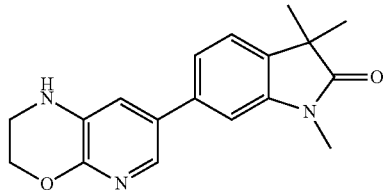 [SMILES: CN1C(=O)C(C)(C)c2ccc(-c3cnc4c(c3)NCCO4)cc21]

Prepared in analogy to example 29b from 1,3,3-trimethyl-6-(4,4,5,5-tetramethyl-1,3,2-dioxaborolan-2-yl)indolin-2-one (example 29a) and 7-bromo-2,3-dihydro-1H-pyrido[2,3-b][1,4]oxazine. The title compound was obtained as light yellow solid.

MS ESI (m/z): 310.2 [(M+H)+].

$^1$H NMR (CDCl$_3$, 300 MHz): δ=7.84 (d, J=2.0 Hz, 1H), 7.24 (d, J=8.1 Hz, 1H), 7.18 (dd, J=1.2, 7.7 Hz, 1H), 7.06 (d, J=2.2 Hz, 1H), 6.97-6.91 (m, 1H), 4.50-4.42 (m, 2H), 3.96 (br s, 1H), 3.52-3.42 (m, 2H), 3.26 (s, 3H), 1.40 (s, 6H).

Example 26

6-(6,7-Dihydro-5H-pyrrolo[3,4-b]pyridin-3-yl)-1,3,3-trimethylindolin-2-one

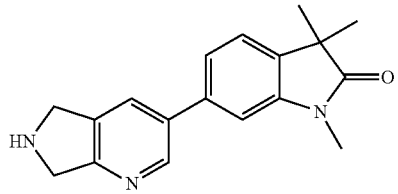 [SMILES: CN1C(=O)C(C)(C)c2ccc(-c3cnc4c(c3)CNC4)cc21]

Prepared in analogy to example 29b from 1,3,3-trimethyl-6-(4,4,5,5-tetramethyl-1,3,2-dioxaborolan-2-yl)indolin-2-one (example 29a) and 3-bromo-6,7-dihydro-5H-pyrrolo[3,4-b]pyridine. The title compound was obtained as light brown solid.

MS ESI (m/z): 294.2 [(M+H)+].

1H NMR (CDCl3, 300 MHz): δ=8.65 (s, 1H), 7.73 (s, 1H), 7.34-7.20 (m, 2H), 7.00 (d, J=1.2 Hz, 1H), 4.44-4.30 (m, 4H), 3.28 (s, 3H), 2.56 (br s, 1H), 1.42 (s, 6H).

Example 27

6-(5-Aminopyridin-3-yl)-1,3,3-trimethylindolin-2-one

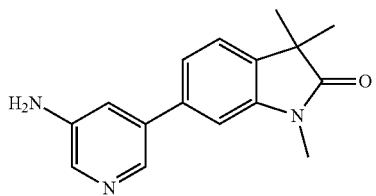 [SMILES: CN1C(=O)C(C)(C)c2ccc(-c3cncc(N)c3)cc21]

Prepared in analogy to example 29b from 1,3,3-trimethyl-6-(4,4,5,5-tetramethyl-1,3,2-dioxaborolan-2-yl)indolin-2-one (example 29a) and 5-bromopyridin-3-amine. The title compound was obtained as light yellow solid.

MS ESI (m/z): 268.2 [(M+H)+].

1H NMR (CDCl3, 300 MHz): δ=8.26 (d, J=1.8 Hz, 1H), 8.10 (d, J=2.6 Hz, 1H), 7.28 (d, J=7.7 Hz, 1H), 7.23 (dd, J=1.6, 7.7 Hz, 1H), 7.17-7.13 (m, 1H), 6.99 (d, J=1.2 Hz, 1H), 3.79 (br s, 2H), 3.27 (s, 3H), 1.41 (s, 6H).

Example 28

6-(3,5-Dimethyl-pyridin-4-yl)-1,3,3-trimethyl-1,3-dihydro-indol-2-one formate

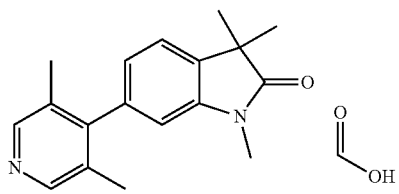

A solution of 4-bromo-3,5-dimethylpyridine (500 mg, 2.69 mmol) in dry THF (20 ml) was evacuated and purged with argon. Cesium carbonate (1051 mg, 3.22 mmol) was added followed by 1,3,3-trimethyl-6-(4,4,5,5-tetramethyl-1,3,2-dioxaborolan-2-yl)indolin-2-one (example 29a, 972 mg, 3.22 mmol). After 15 minutes of purging with argon tetrakis(triphenylphosphine)palladium(0) (249 mg, 0.21 mmol) was added. Again the vessel was purged for 15 minutes with argon and the reaction mixture was heated to reflux for 15 hours. The reaction mixture was diluted with ethyl acetate, filtered through a bed of celite, washed with more ethyl acetate and the obtained solution was concentrated in vacuo. The crude material was purified by silica gel chromatography. The obtained material was finally purified by preparative HPLC to get the title compound as an off white solid (344 mg).

MS ESI (m/z): 281 [(M+H)+].

Example 29

6-(Imidazo[1,2-a]pyridin-7-yl)-1,3,3-trimethylindolin-2-one

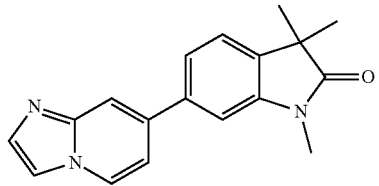 [SMILES: CN1C(=O)C(C)(C)c2ccc(-c3ccn4ccnc4c3)cc21]

a) 1,3,3-Trimethyl-6-(4,4,5,5-tetramethyl-1,3,2-dioxaborolan-2-yl)indolin-2-one

Through a suspension of 6-bromo-1,3,3-trimethylindolin-2-one (example 1a, 500 mg, 1.97 mmol), bis(pinacolato)diboron (757 mg, 2.95 mmol) and potassium acetate (390 mg, 3.94 mmol) in DMSO (10 ml) was bubbled argon for 5 minutes. [1,1'-Bis(diphenylphosphino)ferrocene]dichloropalladium(II) (72 mg, 98.4 μmol) was added and argon was bubbled through again for 5 minutes. The reaction mixture was heated to 110° C. for 5 hours. Water was added and the aqueous phase was extracted with ethyl acetate. The combined organic layers were dried over sodium sulfate, the solvent was evaporated and the residue was purified by silica gel chromatography using ethyl acetate/heptane as eluent. The title compound was obtained as white solid (607 mg).

MS ESI (m/z): 302.3 [(M+H)+].

1H NMR (CDCl3, 300 MHz): δ=7.57 (dd, J=0.8, 7.3 Hz, 1H), 7.27 (s, 1H), 7.23 (d, J=7.3 Hz, 1H), 3.24 (s, 3H), 1.37 (s, 6H), 1.36 (s, 12H)

b) 6-(Imidazo[1,2-a]pyridin-7-yl)-1,3,3-trimethylindolin-2-one

Through a suspension of 1,3,3-trimethyl-6-(4,4,5,5-tetramethyl-1,3,2-dioxaborolan-2-yl)indolin-2-one (300 mg, 896 μmol), 7-bromoimidazo[1,2-a]pyridine (F. P. Marmsäter et al., WO2008/121687; 212 mg, 1.08 mmol) and Na2CO3 (2M, 896 μl, 1.79 mmol) in dioxane (4 ml) was bubbled argon for 5 minutes. [1,1'-Bis(diphenylphosphino)ferrocene]dichloropalladium(II) (32.8 mg, 44.8 μmol) was added and argon was bubbled through again for 5 minutes. The reaction mixture was heated to 110° C. for 12 hours. The solvent was evaporated and the residue was purified by silica gel chromatography using ethyl acetate/heptane and dichloromethane/methanol/ammonia as eluent. The title compound was obtained as light red solid (244 mg).

MS ESI (m/z): 292.2 [(M+H)+].

1H NMR (CDCl3, 300 MHz): δ=8.20 (dd, J=0.8, 7.1 Hz, 1H), 7.87-7.80 (m, 1H), 7.69 (d, J=1.2 Hz, 1H), 7.62 (s, 1H), 7.38-7.28 (m, 2H), 7.14-7.04 (m, 2H), 3.29 (s, 3H), 1.42 (s, 6H).

Example 30

6-(Imidazo[1,2-a]pyridin-6-yl)-1,3,3-trimethylindolin-2-one

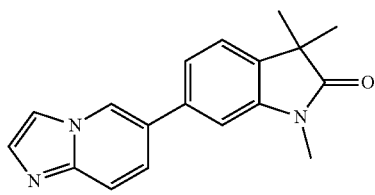 [SMILES: CN1C(=O)C(C)(C)c2ccc(-c3ccc4nccn4c3)cc21]

Prepared in analogy to example 29 from 6-bromoimidazo[1,2-a]pyridine (M. Yamanaka et al., Chem. Pharm. Bull. 1991, 39(6), 1556-1567). The title compound was obtained as light red solid.
MS ESI (m/z): 292.1 [(M+H)$^+$].
$^1$H NMR (CDCl$_3$, 300 MHz): δ=8.33 (dd, J=1.0, 1.8 Hz, 1H), 7.74-7.62 (m, 3H), 7.43 (dd, J=1.8, 9.5 Hz, 1H), 7.33-7.28 (m, 1H), 7.26-7.21 (m, 1H), 7.00 (d, J=1.2 Hz, 1H), 3.29 (s, 3H), 1.42 (s, 6H).

Example 31

6-(4,6-Dimethyl-pyrimidin-5-yl)-1,3,3-trimethyl-1,3-dihydro-indol-2-one

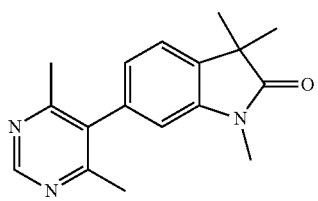 [SMILES: Cc1ncnc(C)c1-c1ccc2c(c1)N(C)C(=O)C2(C)C]

Prepared in analogy to example 29b from 1,3,3-trimethyl-6-(4,4,5,5-tetramethyl-1,3,2-dioxaborolan-2-yl)indolin-2-one (example 29a) and 5-bromo-4,6-dimethylpyrimidine. The title compound was obtained as off white solid.
MS ESI (m/z): 282 [(M+H)$^+$].

Example 32

6-(2,4-Dimethyl-pyridin-3-yl)-1,3,3-trimethyl-1,3-dihydro-indol-2-one

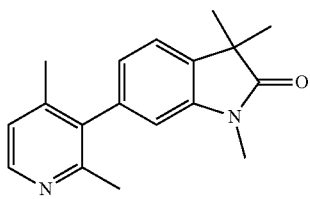

Prepared in analogy to example 29b from 1,3,3-trimethyl-6-(4,4,5,5-tetramethyl-1,3,2-dioxaborolan-2-yl)indolin-2-one (example 29a) and 3-bromo-2,4-dimethylpyrimidine. The title compound was obtained as off white solid.
MS ESI (m/z): 281 [(M+H)$^+$].

Example 33

5-(3,3-Dimethyl-2-oxoindolin-6-yl)nicotinonitrile

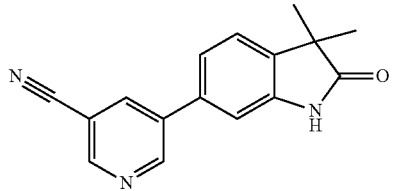 [SMILES: CC1(C)C(=O)Nc2cc(-c3cncc(C#N)c3)ccc21]

Prepared in analogy to example 29b from 3,3-dimethyl-6-(4,4,5,5-tetramethyl-1,3,2-dioxaborolan-2-yl)indolin-2-one (example 17a) and 5-bromonicotinonitrile. The title compound was obtained as white solid.
MS ESI (m/z): 264.1 [(M+H)$^+$].
$^1$H NMR (CDCl$_3$, 300 MHz): δ=9.02 (d, J=2.4 Hz, 1H), 8.87 (d, J=1.8 Hz, 1H), 8.53 (br. s, 1H), 8.11 (t, J=2.1 Hz, 1H), 7.35 (d, J=7.3 Hz, 1H), 7.24 (dd, J=1.6, 7.7 Hz, 1H), 7.13 (d, J=1.2 Hz, 1H), 1.46 (s, 6H).

Example 34

7-Fluoro-1,3,3-trimethyl-6-(pyridin-3-yl)indolin-2-one

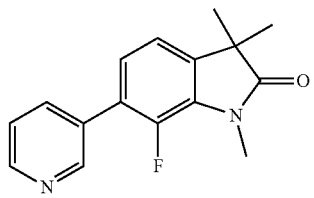

a) 7-Fluoro-1,3,3-trimethylindolin-2-one

To a suspension of NaH (8.79 g, 220 mmol) in tetrahydrofuran (100 ml) was added 7-fluoroindolin-2-one (8.30 g, 54.9 mmol) portionwise within 20 minutes. The reaction mixture was stirred for 30 minutes. MeI (31.2 g, 13.7 ml, 220 mmol) was added dropwise at 24-27° C. within 1.5 hours. The reaction mixture was stirred at room temperature for 3 hours. The reaction mixture was very carefully quenched with 20 ml saturated aqueous ammonium chloride solution at 10-15° C., then diluted with tert-butyl methyl ether and water. The aqueous phase was extracted with tert-butyl methyl ether, the combined organic phases were washed with brine and dried over sodium sulfate. The solvent was evaporated and the residue purified by silica gel chromatography using ethyl acetate/heptane as eluent. The title compound was obtained as orange crystals (9.91 g).
MS ESI (m/z): 194.3 [(M+H)$^+$].
$^1$H NMR (CDCl$_3$, 400 MHz): δ (ppm)=6.99-6.97 (m, 3H), 3.43 (d, J=2.62 Hz, 3H), 1.37 (s, 6H).

b) 7-Fluoro-1,3,3-trimethyl-6-(trimethylsilyl)indolin-2-one

A solution of diisopropylamine (5.4 g, 7.6 ml, 52.8 mmol) in dry tetrahydrofuran (23 ml) under an argon atmosphere was cooled to −40° C. and a solution of n-BuLi (1.6 M in hexane, 31.6 ml, 50.5 mmol) was added dropwise. The mixture was stirred at −40° C. for 30 minutes and then added to a solution of 7-fluoro-1,3,3-trimethylindolin-2-one (8.875 g, 45.9 mmol) and trimethylsilyl chloride (5.49 g, 6.46 ml, 50.5 mmol) in dry tetrahydrofuran (69 ml) at −75° C. The reaction mixture was warmed to room temperature within 16 hours. The reaction mixture was carefully quenched with water (2 ml) and diluted with ethyl acetate and water. The aqueous phase was extracted with ethyl acetate, the combined organic layers were washed with brine and dried over sodium sulfate. The solvent was evaporated in vacuo and the residue purified by silica gel chromatography using ethyl acetate/heptane as eluent. The title compound was obtained as light yellow oil (8.55 g).

MS ESI (m/z): 266.2 [(M+H)⁺].

$^1$H NMR (CDCl$_3$, 400 MHz): δ (ppm)=7.06-7.02 (m, 1H), 6.99-6.96 (m, 1H), 3.44 (d, J=3.03 Hz, 3H), 1.36 (s, 6H), 0.33 (s, 9H).

c) 7-Fluoro-6-iodo-1,3,3-trimethylindolin-2-one

To a solution of 7-fluoro-1,3,3-trimethyl-6-(trimethylsilyl)indolin-2-one (9.9 g, 37.3 mmol) in dichloromethane (500 ml) at 0° C. was added iodine monochloride (1M in CH$_2$Cl$_2$, 37.3 ml, 37.3 mmol). The reaction mixture was warmed to room temperature and stirred for 16 hours. A saturated aqueous solution of sodium thiosulfate was added to the reaction mixture and the aqueous phase was extracted with dichloromethane. The combined organic layers were dried over sodium sulfate. The solvent was evaporated and the residue purified by silica gel chromatography using ethyl acetate/heptane as eluent. The title compound was obtained as off-white crystals (9.82 g).

MS ESI (m/z): 320.0 [(M+H)⁺].

$^1$H NMR (CDCl$_3$, 400 MHz): δ (ppm)=7.43-7.39 (m, 1H), 6.77-6.75 (m, 1H), 3.42 (d, J=3.23 Hz, 3H), 1.36 (s, 6H).

d) 7-Fluoro-1,3,3-trimethyl-6-(pyridin-3-yl)indolin-2-one

Prepared in analogy to example 1b from 7-fluoro-6-iodo-1,3,3-trimethylindolin-2-one and pyridin-3-ylboronic acid. The title compound was obtained as yellow solid.

MS ESI (m/z): 271.2 [(M+H)⁺].

$^1$H NMR (CDCl$_3$, 300 MHz): δ=8.81-8.74 (m, 1H), 8.63 (dd, J=1.6, 4.8 Hz, 1H), 7.85 (qd, J=2.0, 7.9 Hz, 1H), 7.39 (ddd, J=0.9, 4.9, 7.9 Hz, 1H), 7.12-7.03 (m, 2H), 3.48 (d, J=3.2 Hz, 3H), 1.42 (s, 6H).

Example 35

6-(2,4-Dimethyl-pyridin-3-yl)-3,3-dimethyl-1,3-dihydro-indol-2-one

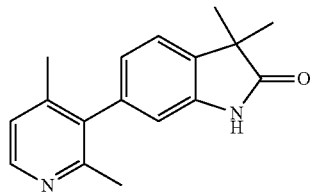 [SMILES: Cc1ccnc(C)c1-c1ccc2c(c1)NC(=O)C2(C)C]

Prepared in analogy to example 29b from 3,3-dimethyl-6-(4,4,5,5-tetramethyl-1,3,2-dioxaborolan-2-yl)indolin-2-one (example 17a) and 3-bromo-2,4-dimethylpyridine. The title compound was obtained as off white solid.

MS ESI (m/z): 267 [(M+H)⁺].

Example 36

1,3,3,7-Tetramethyl-6-(pyridin-3-yl)indolin-2-one

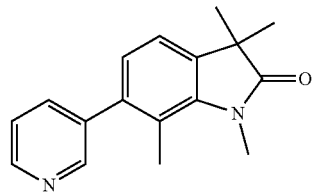 [SMILES: Cc1c(-c2cccnc2)ccc2c1N(C)C(=O)C2(C)C]

a) 6-Bromo-7-methyl-1,3-dihydro-indol-2-one

A mixture of 6-bromo-7-methylindoline-2,3-dione (G. W. Rewcastle et al., J. Med. Chem. 1991, 34(1), 217-222; 7.65 g, 31.9 mmol) and hydrazine monohydrate (35.9 g, 35 ml, 718 mmol) was heated to 130° C. for 3 hours and then cooled to 10° C. 37% HCl (72.2 g, 60.2 ml, 733 mmol) was added slowly. The precipitate was filtered through sintered glass, washed excessively with water, then with little heptane and dried under high vacuum. The title compound was obtained as yellow crystals and used for the next reaction without further purification.

b) 6-Bromo-1,3,3,7-tetramethylindolin-2-one

Prepared in analogy to example 1a from 6-bromo-7-methyl-1,3-dihydro-indol-2-one. The title compound was obtained as light brown solid.

MS ESI (m/z): 268.1, 270.4 [(M+H)⁺].

$^1$H NMR (CDCl$_3$, 300 MHz): δ=7.29 (d, J=7.9 Hz, 1H), 6.89 (d, J=8.0 Hz, 1H), 3.51 (s, 3H), 2.67 (s, 3H), 1.33 (s, 6H).

c) 1,3,3,7-Tetramethyl-6-(4,4,5,5-tetramethyl-1,3,2-dioxaborolan-2-yl)indolin-2-one Prepared in analogy to example 29a from 6-bromo-1,3,3,7-tetramethylindolin-2-one. The title compound was obtained as white solid.

MS ESI (m/z): 316.2 [(M+H)⁺].

$^1$H NMR (CDCl$_3$, 300 MHz): δ=7.49 (d, J=7.5 Hz, 1H), 7.04 (d, J=7.3 Hz, 1H), 3.53 (s, 3H), 2.78 (s, 3H), 1.35 (s, 12H), 1.33 (s, 6H).

d) 1,3,3,7-Tetramethyl-6-(pyridin-3-yl)indolin-2-one

Prepared in analogy to example 29b from 1,3,3,7-tetramethyl-6-(4,4,5,5-tetramethyl-1,3,2-dioxaborolan-2-yl)indolin-2-one and 3-bromopyridine. The title compound was obtained as viscous brown oil.

MS ESI (m/z): 267.2 [(M+H)⁺].

$^1$H NMR (CDCl$_3$, 300 MHz): δ=8.61 (dd, J=1.6, 4.8 Hz, 1H), 8.57 (d, J=1.6 Hz, 1H), 7.66-7.59 (m, 1H), 7.36 (ddd, J=0.9, 4.8, 7.8 Hz, 1H), 7.11 (d, J=7.5 Hz, 1H), 6.92 (d, J=7.5 Hz, 1H), 3.56 (s, 3H), 2.44 (s, 3H), 1.40 (s, 6H)

Example 37

5-Fluoro-1,3,3-trimethyl-6-(pyridin-3-yl)indolin-2-one

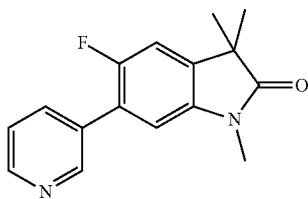 [SMILES: CN1C(=O)C(C)(C)c2cc(F)c(-c3cccnc3)cc21]

a) 2-(4-Bromo-5-fluoro-2-nitro-phenyl)-malonic acid dimethyl ester/2-(2-Bromo-5-fluoro-4-nitro-phenyl)-malonic acid dimethyl ester A suspension of NaH (60% in mineral oil, 20.2 g, 504 mmol) in dioxane (233 ml) was cooled to 11° C. A solution of 1-bromo-2,4-difluoro-5-nitrobenzene (50 g, 26.5 ml, 210 mmol) and dimethyl malonate (33.3 g, 28.9 ml, 242 mmol) in dioxane (467 ml) was carefully added at 11-14° C. within 45 minutes (gas evolution). After completion of the addition the reaction mixture was kept at 12° C. for another hour and then warmed to room temperature. After 16 hours the reaction mixture was cooled to 10° C. and 100 ml saturated aqueous ammonium chloride solution was added. The reaction mixture was diluted with tert-butyl methyl ether, water and saturated aqueous ammonium chloride solution. The aqueous phase was extracted with tert-butyl methyl ether, the combined organic phases were washed with saturated aqueous ammonium chloride solution and brine and dried over sodium sulfate. The solvent was evaporated and the residue purified by silica gel chromatography using ethyl acetate/heptane as eluent. The title compounds were obtained as yellow liquid (53.7 g) as a 2.6:1 mixture and used for the next reaction without further purification.

MS ESI (m/z): 348.1/350.3 [(M−H)$^-$].

$^1$H NMR (CDCl$_3$, 400 MHz) of 2-(4-Bromo-5-fluoro-2-nitro-phenyl)-malonic acid dimethyl ester: δ (ppm)=8.37-8.35 (m, 1H), 7.36-7.33 (m, 1H), 5.36 (s, 1H), 3.82 (s, 6H).

$^1$H NMR (CDCl$_3$, 400 MHz) of 2-(2-Bromo-5-fluoro-4-nitro-phenyl)-malonic acid dimethyl ester: δ (ppm)=8.33-8.30 (m, 1H), 7.60-7.56 (m, 1H), 5.27 (s, 1H), 3.76 (s, 6H).

b) (4-Bromo-5-fluoro-2-nitrophenyl)-acetic acid/2-Bromo-5-fluoro-4-nitro-phenyl)-acetic acid A mixture of 2-(4-bromo-5-fluoro-2-nitro-phenyl)-malonic acid dimethyl ester/2-(2-bromo-5-fluoro-4-nitro-phenyl)-malonic acid dimethyl ester (2.6:1 mixture, 53.7 g, 153 mmol) and 6 M aqueous hydrochloric acid (767 ml) was heated to reflux for 7 hours and then cooled to 5° C. The precipitate was filtered, washed with water and with n-pentane and then coevaporated 3 times with toluene to give 25.9 g of a mixture of the title compounds as white solid. The mother liquor was extracted with ethyl acetate and the combined organic phases dried over sodium sulfate. The solvent was evaporated and the residue triturated with n-pentane and then coevaporated with toluene to give 11.42 g of a mixture of the title compounds as an off-white solid. This material was combined with the first crop to give a total of 37.32 g of the title compounds as a 2.6:1 mixture which was used for the next reaction without further purification.

MS ESI (m/z): 232.0/233.9 [(M-CO$_2$—H)$^-$].

$^1$H NMR (DMSO-D$_6$, 400 MHz) of 2-(4-Bromo-5-fluoro-2-nitrophenyl)acetic acid: δ (ppm)=8.50-8.47 (m, 1H), 7.70-7.67 (m, 1H), 4.00 (s, 2H).

$^1$H NMR (DMSO-D$_6$, 400 MHz) of (2-Bromo-5-fluoro-4-nitro-phenyl)-acetic acid: δ (ppm)=8.40-8.37 (m, 1H), 7.78-7.74 (m, 1H), 3.87 (s, 2H).

c) 6-Bromo-5-fluoroindolin-2-one

A suspension of (4-bromo-5-fluoro-2-nitrophenyl)-acetic acid/(2-bromo-5-fluoro-4-nitro-phenyl)-acetic acid (2.6:1 mixture, 37.3 g, 134 mmol) and iron (30.0 g, 537 mmol) in acetic acid (671 ml) was heated to 100° C. for 7 hours and then cooled to room temperature. Remaining elemental iron was removed with a magnetic rod. Ice water (900 ml) was added to the reaction mixture. The precipitate was filtered off, washed four times with water and then suspended in an ice-cold aqueous solution of 25% HCl (300 ml) and conc. HCl (50 ml). After stirring for 10 minutes the precipitate was filtered off and washed four times with water.

The precipitate was suspended in a mixture of 1 M aqueous Na$_2$CO$_3$ (400 ml) solution and 0.1 M NaOH (100 ml) and stirred for 40 minutes. The precipitate was filtered off and washed four times with 0.1 M aqueous NaOH, three times with water and once with diisopropylether to give title compound as light grey solid (20.5 g).

MS ESI (m/z): 228.0/230.0 [(M−H)$^-$].

$^1$H NMR (DMSO-D$_6$, 400 MHz): δ (ppm)=10.47 (bs, 1H), 7.31-7.28 (m, 1H), 7.01-6.99 (m, 1H), 3.49 (s, 2H).

d) 6-Bromo-5-fluoro-1,3,3-trimethylindolin-2-one

To a suspension of NaH (5.04 g, 126 mmol) in tetrahydrofuran (105 ml) 6-bromo-5-fluoroindolin-2-one (7.24 g, 31.5 mmol) was added portionwise under an argon atmosphere. After gas evolution had ceased methyl iodide (17.9 g, 7.88 ml, 126 mmol) was added dropwise within 50 minutes by means of a syringe pump (exothermic reaction), keeping the temperature of the reaction mixture between 24° C. and 26° C. The reaction mixture was kept at room temperature for 4 hours and then carefully quenched with aqueous ammonium chloride solution. The reaction mixture was diluted with tert-butyl methyl ether, water and saturated aqueous ammonium chloride solution. The aqueous phase was extracted with tert-butyl methyl ether, the combined organic phases were washed with saturated aqueous ammonium chloride and dried over sodium sulfate. The solvent was evaporated and the residue was triturated with heptane to give the title compound as light brown solid (7.87 g).

MS ESI (m/z): 272.1, 274.1 [(M+H)$^+$].

$^1$H NMR (CDCl$_3$, 400 MHz): δ (ppm)=7.02-6.97 (m, 2H), 3.19 (s, 3H), 1.36 (s, 6H).

e) 5-fluoro-1,3,3-trimethyl-6-(pyridin-3-yl)indolin-2-one

Prepared in analogy to example 1b from 6-bromo-5-fluoro-1,3,3-trimethylindolin-2-one and pyridin-3-ylboronic acid. The title compound was obtained as light brown solid.

MS ESI (m/z): 271.3 [(M+H)$^+$].

$^1$H NMR (CDCl$_3$, 300 MHz): δ=8.80 (s, 1H), 8.63 (d, J=3.6 Hz, 1H), 7.88 (qd, J=1.8, 7.9 Hz, 1H), 7.40 (dd, J=4.8, 7.9 Hz, 1H), 7.08 (d, J=9.5 Hz, 1H), 6.83 (d, J=5.9 Hz, 1H), 3.25 (s, 3H), 1.42 (s, 6H).

Example 38

5-Fluoro-1,3,3-trimethyl-6-(pyridin-4-yl)indolin-2-one

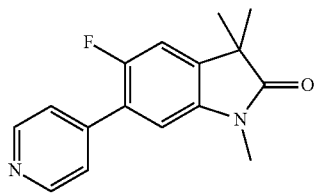 [SMILES: CN1C(=O)C(C)(C)c2cc(F)c(-c3ccncc3)cc21]

Prepared in analogy to example 1b from 6-bromo-5-fluoro-1,3,3-trimethylindolin-2-one (example 37d) and pyridin-4-ylboronic acid. The title compound was obtained as light brown foam.

MS ESI (m/z): 271.3 [(M+H)$^+$].

$^1$H NMR (CDCl$_3$, 300 MHz): δ=8.71 (d, J=5.0 Hz, 2H), 7.49 (d, J=5.0 Hz, 2H), 7.08 (d, J=9.7 Hz, 1H), 6.85 (d, J=5.9 Hz, 1H), 3.25 (s, 3H), 1.42 (s, 6H).

Example 39

7-Fluoro-1,3,3-trimethyl-6-pyridin-4-yl-1,3-dihydro-indol-2-one

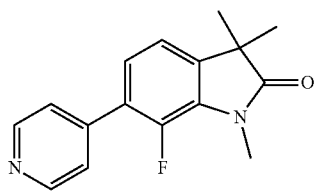 [SMILES: CN1C(=O)C(C)(C)c2ccc(-c3ccncc3)c(F)c21]

Prepared in analogy to example 1b from 7-fluoro-6-iodo-1,3,3-trimethylindolin-2-one (example 34c) and pyridin-4-ylboronic acid. The title compound was obtained as brown solid.

MS ESI (m/z): 271 [(M+H)$^+$].

Example 40

5-Fluoro-1,3,3-trimethyl-6-(2-methylpyridin-4-yl)indolin-2-one

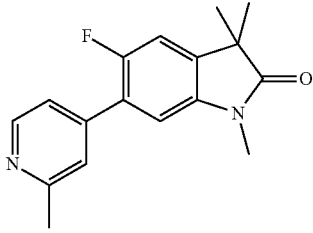 [SMILES: Cc1cc(-c2cc3c(cc2F)C(C)(C)C(=O)N3C)ccn1]

Prepared in analogy to example 1b from 6-bromo-5-fluoro-1,3,3-trimethylindolin-2-one (example 37d) and 2-methylpyridin-4-ylboronic acid. The title compound was obtained as yellow solid.

MS ESI (m/z): 285.1 [(M+H)$^+$].

$^1$H NMR (CDCl$_3$, 300 MHz): δ=8.58 (d, J=5.2 Hz, 1H), 7.34 (s, 1H), 7.31-7.27 (m, 1H), 7.07 (d, J=9.5 Hz, 1H), 6.84 (d, J=5.9 Hz, 1H), 3.30-3.21 (m, 3H), 2.64 (s, 3H), 1.41 (s, 6H).

Example 41

1-Isopropyl-3,3-dimethyl-6-(2-methylpyrimidin-5-yl)indolin-2-one

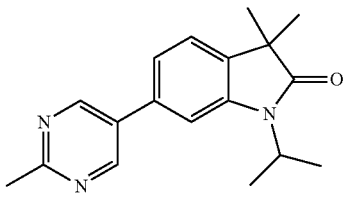 [SMILES: Cc1ncc(-c2ccc3c(c2)N(C(C)C)C(=O)C3(C)C)cn1]

a) 6-Bromo-1-isopropyl-3,3-dimethyl-1,3-dihydro-indol-2-one

To a suspension of 6-bromo-3,3-dimethylindolin-2-one (example 24a, 1.0 g, 4.16 mmol) in DMF (18 ml) were added 2-bromopropane (1.28 g, 978 μl, 10.4 mmol) and cesium carbonate (2.99 g, 9.16 mmol). The reaction mixture was heated to 80° C. for 18 hours. The reaction mixture was treated with 1 M aqueous HCl solution and the aqueous phase was extracted with EtOAc. The combined organic layers were dried over Na$_2$SO$_4$ and the solvent was evaporated. The residue was purified by silica gel chromatography using ethyl acetate/heptane as eluent. The title compound was obtained as orange solid (824 mg).

MS ESI (m/z): 281.1/282.9 [(M+H)$^+$].

$^1$H NMR (CDCl$_3$, 300 MHz): δ=7.20-7.11 (m, 2H), 7.09-7.02 (m, 1H), 4.60 (spt, J=7.1 Hz, 1H), 1.47 (d, J=7.1 Hz, 6H), 1.33 (s, 6H)

b) 1-Isopropyl-3,3-dimethyl-6-(4,4,5,5-tetramethyl-1,3,2-dioxaborolan-2-yl)indolin-2 one Through a suspension of 6-bromo-1-isopropyl-3,3-dimethylindolin-2-one (400 mg, 1.42 mmol), bis(pinacolato)

diboron (720 mg, 2.84 mmol) and potassium acetate (348 mg, 3.54 mmol) in DMSO (6.5 ml) was bubbled argon for 5 minutes. [1,1'-Bis(diphenylphosphino)ferrocene]dichloropalladium(II), complex with dichloromethane (1:1) (57.9 mg, 70.9 µmol) was added and argon was bubbled through again for 5 minutes. The reaction mixture was heated to 110° C. for 22 hours. The reaction mixture was treated with water and the aqueous phase was extracted with EtOAc. The organic layers were combined, dried over $Na_2SO_4$, the solvent was evaporated and the residue was purified by silica gel chromatography using EtOAc/heptane as eluent. The title compound was obtained as light yellow solid (660 mg, 65% purity) which was used for the next step without further purification.

MS ESI (m/z): 330.2 [(M+H)$^+$].

$^1$H NMR (CDCl$_3$, 300 MHz): δ=7.53 (dd, J=0.8, 7.3 Hz, 1H), 7.40 (s, 1H), 7.23 (d, J=7.3 Hz, 1H), 4.61 (spt, J=7.0 Hz, 1H), 1.51 (d, J=7.1 Hz, 6H), 1.35 (s, 12H), 1.34 (s, 6H).

c) 1-Isopropyl-3,3-dimethyl-6-(2-methylpyrimidin-5-yl)indolin-2-one

Through a suspension of 1-isopropyl-3,3-dimethyl-6-(4,4,5,5-tetramethyl-1,3,2-dioxaborolan-2-yl)indolin-2-one (220 mg, 668 µmol), 5-bromo-2-methylpyrimidine (139 mg, 802 µmol) and 2M aqueous $Na_2CO_3$ solution (668 µl, 1.34 mmol) in dioxane (3.0 ml) was bubbled argon for 5 minutes. [1,1'-Bis(diphenylphosphino)ferrocene]dichloropalladium (II), complex with dichloromethane (1:1) (27.3 mg, 33.4 µmol) was added and argon was bubbled through again for 5 minutes. The reaction mixture was heated to 110° C. for 20 hours. The solvent was evaporated and the residue was purified by silica gel chromatography using EtOAc/heptane as eluent followed by amino silica gel chromatography using EtOAc/heptane as eluent. The title compound was obtained as off-white solid (115 mg).

MS ESI (m/z): 296.3 [(M+H)$^+$].

$^1$H NMR (CDCl$_3$, 300 MHz): δ=8.83 (s, 2H), 7.32 (d, J=7.7 Hz, 1H), 7.23-7.15 (m, 1H), 7.12 (d, J=1.4 Hz, 1H), 4.69 (spt, J=7.1 Hz, 1H), 2.81 (s, 3H), 1.52 (d, J=7.1 Hz, 6H), 1.39 (s, 6H).

Example 42

5,7-Difluoro-1,3,3-trimethyl-6-pyridin-3-yl-1,3-dihydro-indol-2-one

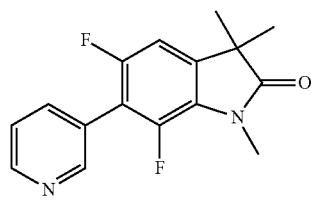 [SMILES: CN1C(=O)C(C)(C)c2cc(F)c(-c3cccnc3)c(F)c21]

a) 5,7-Difluoro-6-iodo-1,3-trimethyl-1,3-dihydro-indol-2-one

Prepared in analogy to example 34a-c from 5,7-difluoro-1,3-dihydro-indol-2-one. The title compound was obtained as off white solid.

MS ESI (m/z): 338 [(M+H)$^+$].

b) 5,7-Difluoro-1,3,3-trimethyl-6-pyridin-3-yl-1,3-dihydro-indol-2-one

Prepared in analogy to example 1b from 5,7-difluoro-6-iodo-1,3,3-trimethyl-1,3-dihydro-indol-2-one and pyridin-3-ylboronic acid. The title compound was obtained as brown solid.

MS ESI (m/z): 289.2 [(M+H)$^+$].

Example 43

5,7-Difluoro-1,3,3-trimethyl-6-pyrimidin-5-yl-1,3-dihydro-indol-2-one

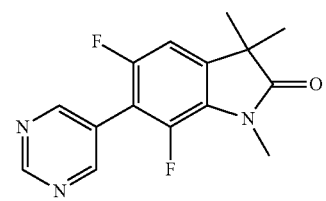 [SMILES: CN1C(=O)C(C)(C)c2cc(F)c(-c3cncnc3)c(F)c21]

Prepared in analogy to example 1b from 5,7-difluoro-6-iodo-1,3,3-trimethyl-1,3-dihydro-indol-2-one (example 42a) and pyrimidine-5-yl boronic acid. The title compound was obtained as brown solid.

MS ESI (m/z): 290.0 [(M+H)$^+$].

Example 44

1,3,3,5-Tetramethyl-6-(2-methyl-pyridin-4-yl)-1,3-dihydro-indol-2-one

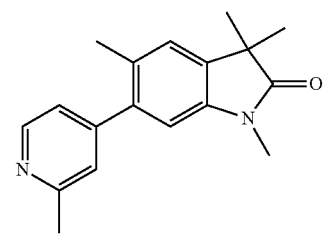 [SMILES: Cc1cc(-c2cc3c(cc2C)C(C)(C)C(=O)N3C)ccn1]

Prepared in analogy to example 37a-e from 1-bromo-4-fluoro-2-methyl-5-nitrobenzene and 2-methylpyridin-4-yl boronic acid. The title compound was obtained as light yellow solid.

MS ESI (m/z): 289 [(M+H)$^+$].

Example 45

1-Cyclopropyl-5-fluoro-3,3-dimethyl-6-(2-methyl-pyrimidin-5-yl)indolin-2-one

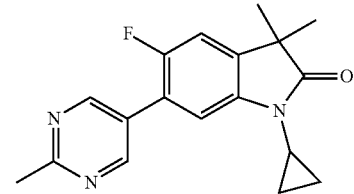 [SMILES: Cc1ncc(-c2cc3c(cc2F)C(C)(C)C(=O)N3C2CC2)cn1]

a) 6-Bromo-5-fluoro-3,3-dimethylindolin-2-one

Prepared in analogy to example 24a from 6-bromo-5-fluoroindolin-2-one (example 37c). The title compound was obtained as brown solid.

MS ESI (m/z): 258.0, 259.9 [(M+H)$^+$].

$^1$H NMR (CDCl$_3$, 300 MHz): δ=8.52 (br s, 1H), 7.11 (d, J=5.4 Hz, 1H), 6.99 (d, J=7.7 Hz, 1H), 1.40 (s, 6H).

b) 6-Bromo-1-cyclopropyl-5-fluoro-3,3-dimethylindolin-2-one

To a suspension of 6-bromo-5-fluoro-3,3-dimethylindolin-2-one (10.5 g, 40.7 mmol), cyclopropylboronic acid (6.99 g, 81.4 mmol), DMAP (14.9 g, 122 mmol) and copper (II) acetate (11.1 g, 61.0 mmol) in tetrahydrofuran (810 ml) was added sodium bis(trimethylsilyl)amide (40% in THF, 21.3 ml, 42.7 mmol). While bubbling dry air through the mixture the reaction was heated to 60° C. for 15 hours. The reaction mixture was diluted with TBME and water, then 400 ml 1 M aqueous HCl were added. The aqueous phase was extracted with TBME. The combined organic phases were washed with 1 M aqueous HCl and brine, dried with sodium sulfate, filtered and the obtained solution was concentrated in vacuo. The crude material was purified by silica gel chromatography using heptane/ethyl acetate as eluent.

The title compound was isolated as yellow solid (8.84 g).

MS ESI (m/z): 298.1, 300.0 [(M+H)$^+$].

$^1$H NMR (CDCl$_3$, 300 MHz): δ=7.23 (d, J=5.7 Hz, 1H), 6.97 (d, J=7.7 Hz, 1H), 2.67-2.57 (m, 1H), 1.32 (s, 6H), 1.13-1.02 (m, 2H), 0.94-0.84 (m, 2H).

c) 1-Cyclopropyl-5-fluoro-3,3-dimethyl-6-(4,4,5,5-tetramethyl-1,3,2-dioxaborolan-2-yl)indolin-2-one Prepared in analogy to example 29a from 6-bromo-1-cyclopropyl-5-fluoro-3,3-dimethylindolin-2-one. The title compound was obtained as light yellow solid.

$^1$H NMR (CDCl$_3$, 300 MHz): δ=7.34 (d, J=4.4 Hz, 1H), 6.90 (d, J=8.3 Hz, 1H), 2.72-2.61 (m, 1H), 1.38 (s, 12H), 1.32 (s, 6H), 1.14-1.03 (m, 2H), 0.96-0.86 (m, 2H).

d) 1-Cyclopropyl-5-fluoro-3,3-dimethyl-6-(2-methylpyrimidin-5-yl)indolin-2-one Prepared in analogy to example 29b from 1-cyclopropyl-5-fluoro-3,3-dimethyl-6-(4,4,5,5-tetramethyl-1,3,2-dioxaborolan-2-yl)indolin-2-one and 5-bromo-2-methylpyrimidine. The title compound was obtained as light yellow solid.

$^1$H NMR (CDCl$_3$, 300 MHz): δ=8.84 (d, J=1.4 Hz, 2H), 7.07 (d, J=1.8 Hz, 1H), 7.05 (d, J=1.0 Hz, 1H), 2.82 (s, 3H), 2.74-2.62 (m, 1H), 1.38 (s, 6H), 1.14-1.04 (m, 2H), 0.96-0.87 (m, 2H).

Example 46

5,7-Difluoro-1,3,3-trimethyl-6-(2-methyl-pyrimidin-5-yl)-1,3-dihydro-indol-2-one

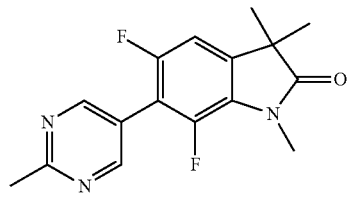 [SMILES: Cc1ncc(-c2c(F)cc3c(c2F)N(C)C(=O)C3(C)C)cn1]

To a solution of 5-bromo-2-methyl-pyrimidine (247 mg, 1.42 mmol) in dry DMSO (5 ml) was added bis(pinacolato)diborane (452 mg, 1.78 mmol) and potassium acetate (233 mg, 2.37 mmol). The reaction mixture was then stirred in the ultra sonic bath while bubbling argon through it for 1 hour. Then [1,1'-bis(diphenylphosphino)ferrocene]dichloropalladium (II) (44 mg, 0.059 mmol) was added, purged with argon for another 15 minutes and then 5,7-difluoro-6-iodo-1,3,3-trimethyl-1,3-dihydro-indol-2-one (example 42a, 400 mg, 1.18 mmol) was added and the reaction mixture stirred at 110° C. over night. The mixture was diluted with ethyl acetate, 0.1M aqueous hydrochloric acid solution and water, filtered through a bed of celite and washed with EtOAc. The organic layer was separated and washed with brine, dried over sodium sulfate and concentrated in vacuo. The obtained material was purified by amino silica gel chromatography. The title compound was obtained as yellow solid (72 mg).

MS ESI (m/z): 304.2 [(M+H)$^+$].

Example 47

1-(Cyclopropylmethyl)-3,3-dimethyl-6-(2-methylpyrimidin-5-yl)indolin-2-one

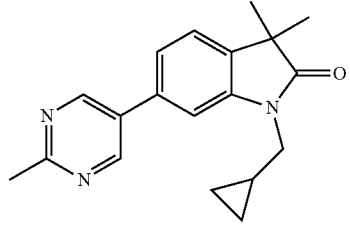 [SMILES: Cc1ncc(-c2ccc3c(c2)N(CC2CC2)C(=O)C3(C)C)cn1]

Prepared in analogy to example 48 employing (bromomethyl)cyclopropane. The title compound was obtained as white solid.

MS ESI (m/z): 308.5 [(M+H)$^+$].

$^1$H NMR (CDCl$_3$, 300 MHz): δ=8.85 (s, 2H), 7.33 (d, J=7.7 Hz, 1H), 7.22 (dd, J=1.5, 7.7 Hz, 1H), 7.06 (d, J=1.4 Hz, 1H), 3.67 (d, J=6.9 Hz, 2H), 2.81 (s, 3H), 1.42 (s, 6H), 1.23-1.07 (m, 1H), 0.61-0.32 (m, 4H).

Example 48

1-(Cyclobutylmethyl)-3,3-dimethyl-6-(2-methylpyrimidin-5-yl)indolin-2-one

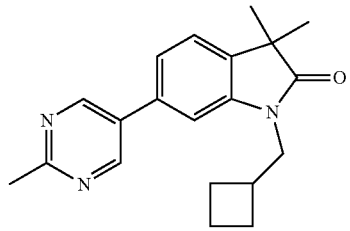 [SMILES: Cc1ncc(-c2ccc3c(c2)N(CC2CCC2)C(=O)C3(C)C)cn1]

a) 6-Bromo-1-(cyclobutylmethyl)-3,3-dimethylindolin-2-one

To a solution of 6-bromo-3,3-dimethylindolin-2-one (example 24a, 500 mg, 2.08 mmol) in DMF (17 ml) was added (bromomethyl)cyclobutane (621 mg, 468 μl, 4.16 mmol) and cesium carbonate (1.36 g, 4.16 mmol). The reaction mixture was heated to 80° C. for 1 hour and then treated with 1 M aqueous HCl solution. The aqueous phase was extracted with EtOAc, the combined organic layers were dried over $Na_2SO_4$, the solvent was evaporated and the residue was purified by flash chromatography on silica gel using EtOAc/heptane as eluent.

MS ESI (m/z): 308.4/310.4 [(M+H)+].

$^1$H NMR (CDCl$_3$, 300 MHz): δ=7.16 (dd, J=1.6, 7.7 Hz, 1H), 7.04 (d, J=7.7 Hz, 1H), 6.98 (d, J=1.6 Hz, 1H), 3.71 (d, J=7.3 Hz, 2H), 2.74 (quin, J=7.7 Hz, 1H), 2.10-1.71 (m, 6H), 1.34 (s, 6H).

b) 1-(Cyclobutylmethyl)-3,3-dimethyl-6-(4,4,5,5-tetramethyl-1,3,2-dioxaborolan-2-yl)indolin-2-one Through a solution of 6-bromo-1-(cyclobutylmethyl)-3,3-dimethylindolin-2-one (145 mg, 470 μmol), bis(pinacolato)diboron (239 mg, 941 μmol) and potassium acetate (115 mg, 1.18 mmol) in DMSO (4 ml) was bubbled argon for 5 minutes and [1,1'-bis(diphenylphosphino)ferrocene]dichloropalladium(II), complex with dichloromethane (19.2 mg, 23.5 μmol) was added. The reaction mixture was heated to 120° C. for 5 hours. Water was added, the aqueous phase was extracted with EtOAc and the combined organic layers were dried over $Na_2SO_4$. The solvent was evaporated and the residue was purified by silica gel chromatography using heptane/ethyl acetate as eluent. The title compound was obtained as light yellow solid (200 mg, ~80% purity) and was used for next reaction without further purification.

MS ESI (m/z): 356.6 [(M+H)+].

c) 1-(Cyclobutylmethyl)-3,3-dimethyl-6-(2-methyl-pyrimidin-5-yl)indolin-2-one

Through a mixture of 1-(cyclobutylmethyl)-3,3-dimethyl-6-(4,4,5,5-tetramethyl-1,3,2-dioxaborolan-2-yl)indolin-2-one (200 mg, 563 μmol), 5-bromo-2-methylpyrimidine (146 mg, 844 μmol), a 2M aqueous solution of $Na_2CO_3$ (563 μl, 1.13 mmol) and dioxane (5 ml) was bubbled argon for 5 minutes and [1,1'-bis(diphenylphosphino)ferrocene]dichloro palladium(II), complex with dichloromethane (1:1) (25.5 mg, 28.1 mol) was added. The reaction mixture was heated to 120° C. for 4 hours and then treated with saturated aqueous NaHCO$_3$ solution. The aqueous phase was extracted with EtOAc, the combined organic layers were dried over $Na_2SO_4$ and the solvent was evaporated. The residue was purified by silica gel chromatography using heptane/ethyl acetate as eluent, followed by NH$_2$-silica gel chromatography using heptane/ethyl acetate as eluent. The title compound was obtained as light yellow solid (105 mg).

MS ESI (m/z): 322.5 [(M+H)+].

$^1$H NMR (CDCl$_3$, 300 MHz): δ=8.83 (s, 2H), 7.35-7.28 (m, 1H), 7.23-7.15 (m, 1H), 6.96 (d, J=1.4 Hz, 1H), 3.81 (d, J=7.3 Hz, 2H), 2.87-2.70 (m, 1H), 2.80 (s, 3H), 2.13-1.78 (m, 6H), 1.40 (s, 6H).

Example 49

3,3-Dimethyl-6-(2-methyl-pyrimidin-5-yl)-1-oxetan-3-yl-1,3-dihydro-indol-2-one

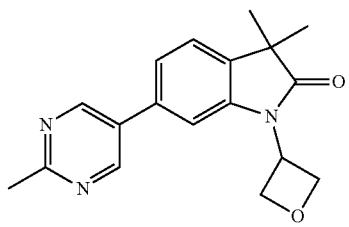 [SMILES: Cc1ncc(-c2ccc3c(c2)N(C2COC2)C(=O)C3(C)C)cn1]

a) 6-Bromo-3,3-dimethyl-1-(oxetan-3-yl)indolin-2-one

To a solution of 6-bromo-3,3-dimethylindolin-2-one (example 24a, 500 mg, 2.08 mmol) in DMF (6.6 ml) under an argon atmosphere was added 3-bromooxetane (535 mg, 298 μl, 3.75 mmol) and cesium carbonate (1.36 g, 4.16 mmol). The reaction mixture was heated to 60° C. for 18 h and then treated with 1M aqueous ammonium chloride solution. The aqueous phase was extracted with EtOAc, the combined organic layers were dried over $Na_2SO_4$ and the solvent was evaporated. The residue was purified by silica gel chromatography using EtOAc/heptane as eluent. The title compound was obtained as orange oil (545 mg).

MS ESI (m/z): 296.5/298.5 [(M+H)+].

$^1$H NMR (CDCl$_3$, 300 MHz): δ=7.71 (d, J=1.6 Hz, 1H), 7.27 (dd, =1.8, 7.9 Hz, 2H), 7.12 (d, J=7.9 Hz, 1H), 5.56 (tt, J=6.0, 7.8 Hz, 1H), 5.12-5.03 (m, 4H), 1.36 (s, 6H).

b) 3,3-Dimethyl-6-(2-methyl-pyrimidin-5-yl)-1-oxetan-3-yl-1,3-dihydro-indol-2-one Prepared in analogy to example 48b-c from 6-bromo-3,3-dimethyl-1-(oxetan-3-yl)indolin-2-one.

The title compound was obtained as white solid.

MS ESI (m/z): 310.5 [(M+H)+].

$^1$H NMR (CDCl$_3$, 300 MHz): δ=8.87 (s, 2H), 7.75 (d, J=1.2 Hz, 1H), 7.39 (d, J=7.6 Hz, 1H), 7.30 (dd, J=1.4, 7.5 Hz, 1H), 5.63 (tt, J=5.8, 7.9 Hz, 1H), 5.20-5.03 (m, 4H), 2.81 (s, 3H), 1.42 (s, 6H).

Example 50

1-(3-Cyclopropoxypropyl)-3,3-dimethyl-6-(2-methylpyrimidin-5-yl)indolin-2-one

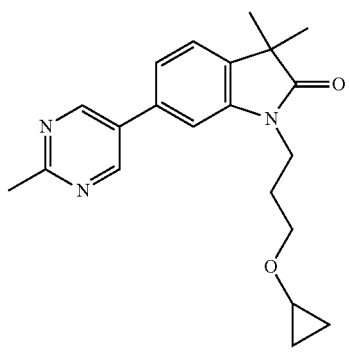 [SMILES: Cc1ncc(-c2ccc3c(c2)N(CCCOC2CC2)C(=O)C3(C)C)cn1]

a) 6-Bromo-1-(3-cyclopropoxypropyl)-3,3-dimethyl-indolin-2-one

To a suspension of 6-bromo-3,3-dimethylindolin-2-one (example 24a, 1.34 g, 5.58 mmol) and Cs₂CO₃ (3.64 g, 11.2 mmol) in DMF (10 ml) was added a solution of (3-bromopropoxy)cyclopropane (2.00 g, 11.2 mmol) in DMF (2.5 ml). The reaction mixture was heated to 70° C. and stirred at this temperature for 15 hours. The reaction mixture was filtered and the obtained solution concentrated in vacuo. The crude material was purified by silica gel chromatography using heptane/ethyl acetate as eluent. The title compound was obtained as yellow oil (1.44 g).

MS ESI (m/z): 338.4, 340.4 [(M+H)⁺].

¹H NMR (CDCl₃, 300 MHz): δ=7.17 (dd, J=1.8, 7.7 Hz, 1H), 7.08-7.02 (m, 2H), 3.75 (t, J=6.8 Hz, 2H), 3.49 (t, J=6.0 Hz, 2H), 3.29-3.20 (m, 1H), 1.92 (quin, J=6.4 Hz, 2H), 1.35 (s, 6H), 0.61-0.40 (m, 4H).

b) 1-(3-Cyclopropoxypropyl)-3,3-dimethyl-6-(4,4,5,5-tetramethyl-1,3,2-dioxaborolan-2-yl)indolin-2-one Prepared in analogy to example 29a from 6-bromo-1-(3-cyclopropoxypropyl)-3,3-dimethylindolin-2-one. The title compound was obtained as yellow viscous oil.

MS ESI (m/z): 386.6 [(M+H)⁺].

¹H NMR (CDCl₃, 300 MHz): δ=7.54 (dd, J=0.8, 7.3 Hz, 1H), 7.31 (s, 1H), 7.22 (d, J=7.3 Hz, 1H), 3.81 (t, J=6.7 Hz, 2H), 3.50 (t, J=6.2 Hz, 2H), 3.30-3.22 (m, 1H), 1.96 (quin, J=6.5 Hz, 2H), 1.36 (s, 6H), 1.35 (s, 12H), 0.62-0.52 (m, 2H), 0.47-0.37 (m, 2H).

c) 1-(3-Cyclopropoxypropyl)-3,3-dimethyl-6-(2-methylpyrimidin-5-yl)indolin-2-one Prepared in analogy to example 29b from 1-(3-cyclopropoxypropyl)-3,3-dimethyl-6-(4,4,5,5-tetramethyl-1,3,2-dioxaborolan-2-yl)indolin-2-one and 5-bromo-2-methylpyrimidine. The title compound was obtained as light yellow oil.

MS ESI (m/z): 352.5 [(M+H)⁺].

¹H NMR (CDCl₃, 300 MHz): δ=8.85 (s, 2H), 7.32 (d, J=7.5 Hz, 1H), 7.22 (dd, =1.6, 7.7 Hz, 1H), 7.07 (d, J=1.2 Hz, 1H), 3.85 (t, J=6.9 Hz, 2H), 3.52 (t, J=6.0 Hz, 2H), 3.26-3.16 (m, 1H), 2.80 (s, 3H), 1.96 (quin, J=6.4 Hz, 2H), 1.41 (s, 6H), 0.58-0.36 (m, 4H).

Example 51

3,3-Dimethyl-6-(2-methylpyridin-4-yl)-1-(oxetan-3-yl)indolin-2-one

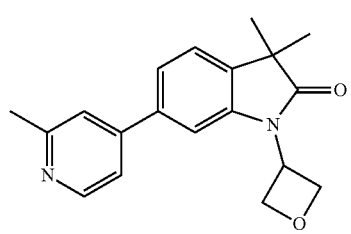 [SMILES: Cc1cc(-c2ccc3c(c2)N(C2COC2)C(=O)C3(C)C)ccn1]

Through a suspension of 6-bromo-3,3-dimethyl-1-(oxetan-3-yl)indolin-2-one (example 49a, 130 mg, 439 µmol) and 2-methyl-4-(4,4,5,5-tetramethyl-1,3,2-dioxaborolan-2-yl)pyridine (118 mg, 527 µmol) in dioxane (3.8 ml) and 2M aqueous solution of sodium carbonate (219 µl, 439 µmol) was bubbled argon for 5 minutes. [1,1'-Bis(diphenylphosphino)ferrocene]dichloropalladium(II), complex with dichloromethane (1:1) (17.9 mg, 21.9 µmol) was added and argon was bubbled through again for 5 minutes. The reaction mixture was heated to 110° C. for 2 hours. The solvent was evaporated and the residue was purified by silica gel chromatography using dichloromethane/methanol with 1% ammonia as eluent followed by preparative HPLC. The title compound was obtained as white solid (75 mg).

MS ESI (m/z): 309.5 [(M+H)⁺].

¹H NMR (CDCl₃, 300 MHz): δ=8.56 (d, J=5.0 Hz, 1H), 7.83 (d, J=0.8 Hz, 1H), 7.43-7.31 (m, 4H), 5.65 (tt, J=5.9, 8.0 Hz, 1H), 5.24-5.05 (m, 4H), 2.64 (s, 3H), 1.42 (s, 6H).

Example 52

3,3-Dimethyl-1-(oxetan-3-yl)-6-(pyridin-3-yl)indolin-2-one

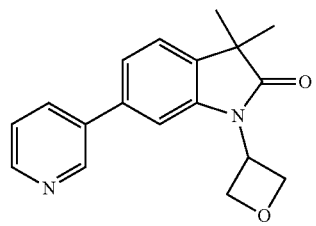 [SMILES: CC1(C)C(=O)N(C2COC2)c2cc(-c3cccnc3)ccc21]

Prepared in analogy to example 51 employing 3-(4,4,5,5-tetramethyl-1,3,2-dioxaborolan-2-yl)pyridine. The title compound was obtained as off-white solid.

MS ESI (m/z): 295.4 [(M+H)⁺].

¹H NMR (CDCl₃, 300 MHz): δ=8.88 (d, J=2.0 Hz, 1H), 8.63 (dd, J=1.4, 4.8 Hz, 1H), 7.96-7.85 (m, 1H), 7.81-7.73 (m, 1H), 7.45-7.29 (m, 3H), 5.64 (tt, =5.8, 8.0 Hz, 1H), 5.25-5.03 (m, 4H), 1.43 (s, 6H).

Example 53

3,3-Dimethyl-6-(6-methyl-pyridazin-3-yl)-1-oxetan-3-yl-1,3-dihydro-indol-2-one

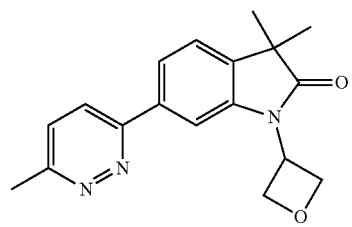 [SMILES: Cc1ccc(-c2ccc3c(c2)N(C2COC2)C(=O)C3(C)C)nn1]

Prepared in analogy to example 49 employing 3-chloro-6-methylpyridazine. The title compound was obtained as white solid.

MS ESI (m/z): 310.5 [(M+H)⁺].

¹H NMR (CDCl₃, 300 MHz): δ=8.16 (d, J=1.2 Hz, 1H), 7.82 (dd, J=1.4, 7.7 Hz, 1H), 7.78 (d, J=8.7 Hz, 1H), 7.44-7.37 (m, 2H), 5.60 (tt, J=6.1, 7.9 Hz, 1H), 5.28-5.02 (m, 4H), 2.78 (s, 3H), 1.43 (s, 6H).

Example 54

1-(3-(Cyclopropylsulfonyl)propyl)-3,3-dimethyl-6-(2-methylpyrimidin-5-yl)indolin-2-one

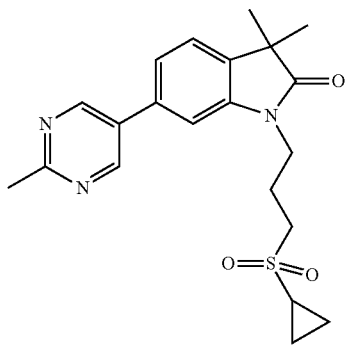 [SMILES: Cc1ncc(-c2ccc3c(c2)N(CCCS(=O)(=O)C2CC2)C(=O)C3(C)C)cn1]

a) 3-(Cyclopropylthio)propan-1-ol

A solution of 3-mercaptopropan-1-ol (1.15 g, 1.08 ml, 12.5 mmol), potassium tert-butoxide (1.4 g, 12.5 mmol) and bromocyclopropane (1.51 g, 1 ml, 12.5 mmol) in DMSO (30 ml) was heated to 80° C. for 15 hours. The reaction mixture was poured into 75 mL saturated aqueous NaHCO$_3$ solution and extracted with diethyl ether and washed with water. The combined organic layers were dried with sodium sulfate, filtered and the obtained solution concentrated in vacuo. The title compound was obtained as red liquid (1.24 g) and was used without further purification.

$^1$H NMR (CDCl$_3$, 300 MHz): δ=3.78 (q, J=5.9 Hz, 2H), 2.70 (t, J=7.1 Hz, 2H), 2.00-1.81 (m, 3H), 0.95-0.75 (m, 2H), 0.61-0.47 (m, 2H).

b) (3-Bromopropyl cyclopropyl)sulfane

To a suspension of 3-(cyclopropylthio)propan-1-ol (1.68 g, 12.7 mmol) and CBr$_4$ (5.06 g, 15.2 mmol) in pentane (13 ml) was added triphenylphosphine (4.00 g, 15.2 mmol) portionwise under icecooling. To the very thick suspension dichloromethane (7 ml) was added and the suspension was stirred 4 hours. The reaction mixture was filtered and washed with pentane. The obtained solution was concentrated in vacuo. The title compound was obtained as a mixture with TPPO as brown semisolid (6.66 g). The material was used without further purification.

c) 6-Bromo-1-(3-(cyclopropylthio)propyl)-3,3-dimethylindolin-2-one

Prepared in analogy to example 50a from 6-bromo-3,3-dimethylindolin-2-one (example 24a) and (3-bromopropyl)(cyclopropyl)sulfane. The title compound was obtained as yellow viscous oil.

MS ESI (m/z): 354.4, 356.4 [(M+H)$^+$].

$^1$H NMR (CDCl$_3$, 300 MHz): δ=7.18 (dd, J=1.8, 7.9 Hz, 1H), 7.10-7.01 (m, 2H), 3.79 (t, J=7.2 Hz, 2H), 2.61 (t, J=7.3 Hz, 2H), 2.09-1.95 (m, 2H), 1.95-1.83 (m, 1H), 1.35 (s, 6H), 0.93-0.78 (m, 2H), 0.59-0.50 (m, 2H).

d) 1-(3-(Cyclopropylthio)propyl)-3,3-dimethyl-6-(4,4,5,5-tetramethyl-1,3,2-dioxaborolan-2-yl)indolin-2-one Prepared in analogy to example 29a from 6-bromo-1-(3-(cyclopropylthio)propyl)-3,3-dimethylindolin-2-one. The title compound was obtained as light yellow viscous oil.

MS ESI (m/z): 402.6 [(M+H)$^+$].

$^1$H NMR (CDCl$_3$, 300 MHz): δ=7.55 (dd, J=0.9, 7.4 Hz, 1H), 7.30 (s, 1H), 7.23 (d, J=7.7 Hz, 1H), 3.85 (t, J=7.1 Hz, 2H), 2.62 (t, J=7.5 Hz, 2H), 2.05 (quin, J=7.3 Hz, 2H), 1.90 (tt, J=4.4, 7.4 Hz, 1H), 1.36 (s, 6H), 1.35 (s, 12H), 0.89-0.77 (m, 2H), 0.59-0.51 (m, 2H).

e) 1-(3-(Cyclopropylthio)propyl)-3,3-dimethyl-6-(2-methylpyrimidin-5-yl)indolin-2-one Prepared in analogy to example 29b from 1-(3-(cyclopropylthio)propyl)-3,3-dimethyl-6-(4,4,5,5-tetramethyl-1,3,2-dioxaborolan-2-yl)indolin-2-one and 5-bromo-2-methylpyrimidine. The title compound was obtained as red viscous oil.

MS ESI (m/z): 368.6 [(M+H)$^+$].

$^1$H NMR (CDCl$_3$, 300 MHz): δ=8.85 (s, 2H), 7.33 (d, J=7.5 Hz, 1H), 7.23 (d, J=7.7 Hz, 1H), 7.09 (s, 1H), 3.90 (t, J=7.0 Hz, 2H), 2.81 (s, 3H), 2.63 (t, J=7.0 Hz, 2H), 2.13-2.00 (m, 2H), 1.95-1.81 (m, 1H), 1.41 (s, 6H), 0.91-0.75 (m, 2H), 0.61-0.43 (m, 2H).

f) 1-(3-(Cyclopropylsulfonyl)propyl)-3,3-dimethyl-6-(2-methylpyrimidin-5-yl)indolin-2-one To a solution of 1-(3-(cyclopropylthio)propyl)-3,3-dimethyl-6-(2-methylpyrimidin-5-yl)indolin-2-one (147 mg, 340 µmol) in methanol (1.5 ml) was added a solution of oxone (314 mg, 510 µmol) in water (1.5 ml) and the mixture was stirred for 2 hours. The reaction mixture was poured into 20 mL 2M aqueous sodium carbonate solution and extracted with ethyl acetate. The organic layers were dried with sodium sulfate, filtered and the obtained solution was concentrated in vacuo. The crude material was purified by silica gel chromatography using ethyl acetate/methanol as eluent. The title compound was obtained as light yellow solid (35 mg).

MS ESI (m/z): 400.6 [(M+H)$^+$].

$^1$H NMR (CDCl$_3$, 300 MHz): δ=8.86 (s, 2H), 7.34 (d, J=7.7 Hz, 1H), 7.26-7.23 (m, 1H), 7.11 (d, J=1.4 Hz, 1H), 3.98 (t, J=7.0 Hz, 2H), 3.18-3.07 (m, 2H), 2.80 (s, 3H), 2.46-2.25 (m, 3H), 1.42 (s, 6H), 1.29-1.22 (m, 2H), 1.12-0.99 (m, 2H).

Example 55

1-(2-Hydroxyethyl)-3,3-dimethyl-6-(2-methylpyrimidin-5-yl)indolin-2-one

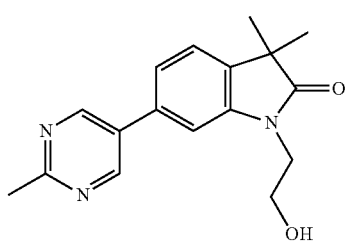 [SMILES: Cc1ncc(-c2ccc3c(c2)N(CCO)C(=O)C3(C)C)cn1]

Prepared in analogy to example 56 employing (2-bromoethoxy)(tert-butyl)dimethylsilane. The title compound was obtained as white solid.

MS ESI (m/z): 298.6 [(M+H)+].

¹H NMR (CDCl₃, 300 MHz): δ=8.83 (s, 2H), 7.33 (d, J=7.5 Hz, 1H), 7.23 (dd, J=1.4, 7.7 Hz, 1H), 7.11 (d, J=1.4 Hz, 1H), 3.96 (s, 4H), 2.79 (s, 3H), 1.43 (s, 6H).

Example 56

1-(3-Hydroxypropyl)-3,3-dimethyl-6-(2-methylpyrimidin-5-yl)indolin-2-one

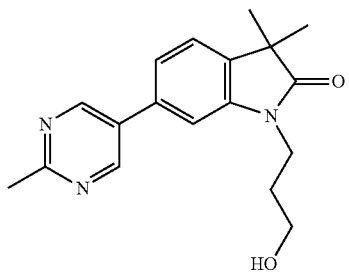 [SMILES: Cc1ncc(-c2ccc3c(c2)N(CCCO)C(=O)C3(C)C)cn1]

a) 1-(3-(tert-Butyldimethylsilyloxy)propyl)-3,3-dimethyl-6-(2-methylpyrimidin-5-yl)indolin-2-one To a solution of 3,3-dimethyl-6-(2-methylpyrimidin-5-yl)indolin-2-one (example 21, 140 mg, 553 μmol) in DMF (2.5 ml) under an argon atmosphere was added (3-bromopropoxy)(tert-butyl)dimethylsilane (280 mg, 256 μl, 1.11 mmol) and cesium carbonate (360 mg, 1.11 mmol). The reaction mixture was heated to 80° C. for 3 hours. The reaction mixture was poured into water and the aqueous phase was extracted with EtOAc. The combined organic layers were dried over Na₂SO₄ and the solvent was evaporated. The residue was purified by flash chromatography on silica gel using EtOAc/heptane as eluent. The title compound was obtained as light brown liquid (250 mg).

MS ESI (m/z): 426.6 [(M+H)+].

¹H NMR (CDCl₃, 300 MHz): δ=8.82 (s, 2H), 7.31 (d, J=7.5 Hz, 1H), 7.19 (dd, J=1.6, 7.5 Hz, 1H), 7.06 (d, J=1.4 Hz, 1H), 3.87 (t, J=7.2 Hz, 2H), 3.68 (t, J=5.9 Hz, 2H), 2.80 (s, 3H), 1.97-1.83 (m, 2H), 1.40 (s, 6H), 0.88 (s, 9H), 0.04 (s, 6H).

b) 1-(3-Hydroxypropyl)-3,3-dimethyl-6-(2-methylpyrimidin-5-yl)indolin-2-one

A solution of 1-(3-(tert-butyldimethylsilyloxy)propyl)-3,3-dimethyl-6-(2-methylpyrimidin-5-yl)indolin-2-one (250 mg, 587 μmol) in THF (10 ml) was cooled to 0° C. and a solution of TBAF in THF (1M, 587 μl, 587 μmol) was added. The reaction mixture was warmed to room temperature and stirred for 3 hours. The reaction mixture was treated with water and the aqueous phase was extracted with ethyl acetate. The combined organic layers were dried over sodium sulfate and the solvent was evaporated. The residue was purified by flash chromatography on silica gel using dichloromethane/methanol with 10% concentrated aqueous ammonia as eluent.

The title compound was obtained as off-white waxy solid (140 mg).

MS ESI (m/z): 312.5 [(M+H)+].

¹H NMR (CDCl₃, 300 MHz): δ=8.84 (s, 2H), 7.35 (d, J=7.7 Hz, 1H), 7.26-7.23 (m, 1H), 7.04 (d, J=1.2 Hz, 1H), 4.00-3.90 (m, 2H), 3.62-3.51 (m, 2H), 3.02 (t, J=6.8 Hz, 1H), 2.80 (s, 3H), 1.96-1.85 (m, 2H), 1.44 (s, 6H).

Example 57

3,3-Dimethyl-6-(2-methylpyrimidin-5-yl)-1-(2-(methylsulfonyl)(ethyl)indolin-2-one

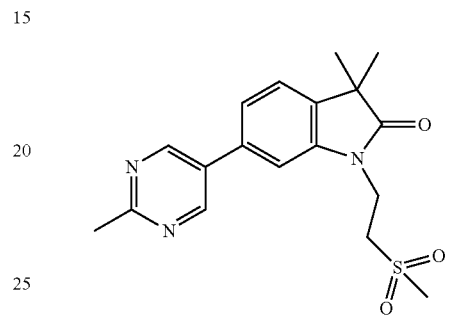

To a solution of 3,3-dimethyl-6-(2-methylpyrimidin-5-yl)indolin-2-one (example 21, 100 mg, 395 μmol) in DMF (2 ml) was added methylsulfonylethene (50.3 mg, 44.9 μl, 474 μmol) and cesium carbonate (154 mg, 474 μmol) and the reaction mixture was stirred at room temperature for 12 hours. Water was added and the aqueous phase was extracted with ethyl acetate. The combined organic layers were dried over Na₂SO₄ and the solvent was evaporated. The residue was purified by flash chromatography on silica gel using dichloromethane/methanol with 10% ammonia as eluent. The title compound was obtained as white solid (126 mg).

MS ESI (m/z): 360.6 [(M+H)+].

¹H NMR (CDCl₃, 300 MHz): δ=8.85 (s, 2H), 7.34 (d, J=7.9 Hz, 1H), 7.26 (dd, J=1.5, 7.6 Hz, 1H), 7.14 (d, J=1.2 Hz, 1H), 4.28 (t, J=6.8 Hz, 2H), 3.44 (t, J=6.7 Hz, 2H), 2.98 (s, 3H), 2.80 (s, 3H), 1.43 (s, 6H).

Example 58

6-Imidazol-1-yl-3,3-dimethyl-1,3-dihydro-indol-2-one

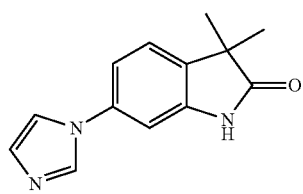 [SMILES: CC1(C)C(=O)Nc2cc(-n3ccnc3)ccc21]

Prepared in analogy to example 63 employing 1H-imidazole. The title compound was obtained as off-white solid.

MS ESI (m/z): 228.2 [(M+H)+].

¹H NMR (CDCl₃, 300 MHz): δ=8.46 (br s, 1H), 7.86 (s, 1H), 7.29-7.26 (m, 1H), 7.22 (s, 1H), 7.07 (dd, J=2.0, 7.9 Hz, 1H), 6.97 (d, J=1.8 Hz, 1H), 1.44 (s, 6H).

Example 59

1,3,3-Trimethyl-6-(3-methyl-1,2,4-oxadiazol-5-yl)indolin-2-one

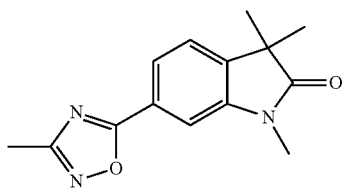 [SMILES: Cc1noc(-c2ccc3c(c2)N(C)C(=O)C3(C)C)n1]

a) 1,3,3-Trimethyl-2-oxoindoline-6-carboxylic acid

To a suspension of NaH (60% on mineral oil, 12.6 g, 314 mmol) in dry THF (260 ml) was added methyl 2-oxoindoline-6-carboxylate (15 g, 78.5 mmol) portionwise during 30 minutes. After gas-evolution ceased MeI (44.5 g, 19.6 ml, 314 mmol) was added dropwise with a syringe-pump during 80 minutes while carefully keeping the temperature between 24° C. and 28° C. The reaction mixture was stirred for 2 hours at room temperature and then quenched by adding water (5.65 ml, 314 mmol) and then 32% aqueous NaOH solution (19.6 g, 14.5 ml, 157 mmol) very carefully. The resulting mixture was poured into 100 mL TBME, the layers were separated and the organic layer was extracted with water. The combined aqueous layers were acidified with 25% aqueous HCl solution (20 ml). The resulting suspension was filtered. The aqueous layer was back-extracted with dichloromethane, the combined organic layers were dried with sodium sulfate and concentrated in vacuo. The obtained solid was combined with the filtered solid to give the title compound as light red solid (17.7 g).

MS ESI (m/z): 220.2 [(M+H)$^+$].

$^1$H NMR (DMSO-d$_6$, 300 MHz) δ=12.98 (br. s, 1H), 7.69 (dd, J=1.0, 7.7 Hz, 1H), 7.55-7.41 (m, 2H), 3.18 (s, 3H), 1.29 (s, 6H).

b) 1,3,3-Trimethyl-6-(3-methyl-1,2,4-oxadiazol-5-yl)indolin-2-one

A suspension of 1,3,3-trimethyl-2-oxoindoline-6-carboxylic acid (200 mg, 912 µmol) and CDI (229 mg, 1.37 mmol) in dry THF (9.03 ml) was heated to reflux under argon for 2 hours. The mixture was then cooled to room temperature, (Z)—N'-hydroxyacetimidamide (67.6 mg, 912 µmol) was added and the reaction was stirred for 24 hours at room temperature under argon. The mixture was concentrated in vacuo and the obtained residue was dissolved in acetic acid (13.4 g, 12.7 ml, 223 mmol). The reaction was then heated to reflux for 3 hours. The mixture was concentrated in vacuo and the resulting residue was dissolved in ethyl acetate and 1M aqueous sodium carbonate solution. The mixture was extracted with ethyl acetate and washed with 1M aqueous sodium carbonate solution. The combined organic layers were dried over sodium sulfate, filtered and the obtained solution was concentrated in vacuo. The obtained material was purified by silica gel chromatography using heptane/ethyl acetate as eluent.

MS ESI (m/z): 258.2 [(M+H)$^+$].

$^1$H NMR (CDCl$_3$, 300 MHz): δ=7.86 (dd, J=1.4, 7.7 Hz, 1H), 7.55 (d, J=1.2 Hz, 1H), 7.35 (d, J=7.7 Hz, 1H), 3.29 (s, 3H), 2.49 (s, 3H), 1.42 (s, 6H).

Example 60

3,3-Dimethyl-6-(3-methyl-1,2,4-oxadiazol-5-yl)indolin-2-one

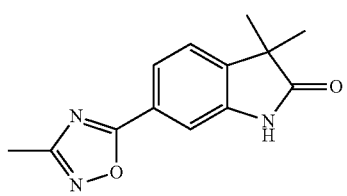 [SMILES: Cc1noc(-c2ccc3c(c2)NC(=O)C3(C)C)n1]

a) Methyl 3,3-dimethyl-2-oxoindoline-6-carboxylate

To a solution of MeI (7.42 g, 3.27 ml, 52.3 mmol) in DMF (75.0 ml) was added methyl 2-oxoindoline-6-carboxylate (5 g, 26.2 mmol). Once everything was dissolved NaH (60% in mineral oil, 1.05 g, 26.2 mmol) was added and the reaction mixture was stirred for 30 minutes at room temperature. Then again NaH (60% on mineral oil, 523 mg, 13.1 mmol) was added and stirring was continued for another hour. Again NaH (60% on mineral oil, 523 mg, 13.1 mmol) was added and stirring was continued for 15 hours. The reaction was quenched with 1M aqueous HCl solution, the mixture was extracted with ethyl acetate and the organic layers were washed with water. The combined organic layers were dried with sodium sulfate, filtered and the obtained solution was concentrated in vacuo. The resulting solid was triturated with diisopropyl ether, filtered and the collected solid was dried. The title compound was obtained as red solid (4.61 g)

MS ESI (m/z): 220.3 [(M+H)$^+$].

$^1$H NMR (CDCl$_3$, 300 MHz): δ=7.98 (br s, 1H), 7.78 (dd, J=1.3, 7.8 Hz, 1H), 7.58 (d, J=1.0 Hz, 1H), 7.26 (d, J=7.7 Hz, 1H), 3.92 (s, 3H), 1.42 (s, 6H).

b) 3,3-Dimethyl-2-oxoindoline-6-carboxylic acid

A suspension of methyl 3,3-dimethyl-2-oxoindoline-6-carboxylate (2 g, 9.12 mmol) in 25% aqueous HCl solution (55.1 ml, 423 mmol) was heated to 100° C. for 18 hours. The mixture was cooled to room temperature and diluted with water. The resulting suspension was filtered, washed with water and heptane and the collected solid was dried. The title compound was obtained as red solid (1.51 g).

MS ESI (m/z): 204.1 [(M-H)$^+$].

$^1$H NMR (DMSO-d$_6$, 300 MHz) δ=12.90 (br s, 1H), 10.49 (s, 1H), 7.60 (dd, =1.2, 7.7 Hz, 1H), 7.47-7.32 (m, 2H), 1.27 (s, 6H).

c) 3,3-Dimethyl-6-(3-methyl-1,2,4-oxadiazol-5-yl)indolin-2-one

Prepared in analogy to example 59b using 3,3-dimethyl-2-oxoindoline-6-carboxylic acid. The title compound was obtained as purple solid.

MS ESI (m/z): 244.3 [(M+H)$^+$].

$^1$H NMR (CDCl$_3$, 300 MHz): δ=7.85 (d, J=7.9 Hz, 1H), 7.67-7.56 (m, 2H), 7.34 (d, =7.7 Hz, 1H), 2.48 (s, 3H), 1.45 (s, 6H).

Example 61

6-(1H-Imidazol-1-yl)-1,3,3-trimethylindolin-2-one

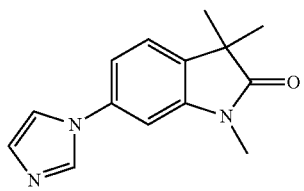 [SMILES: CN1C(=O)C(C)(C)c2ccc(-n3ccnc3)cc21]

To a solution of glyoxal (40% in water, 458 mg, 360 µl, 3.15 mmol) and formaldehyde (36% in water, 658 mg, 603 µl, 7.88 mmol) in methanol (1.58 ml) were added a solution of 6-amino-1,3,3-trimethyl-2-oxoindoline (300 mg, 1.58 mmol) in methanol (1.58 ml) and ammonium acetate (248 mg, 3.15 mmol) and the reaction mixture was heated to reflux. After 3 hours the mixture was quenched with 10 ml saturated aqueous NaHCO₃ solution. The mixture was extracted with TBME and the organic layers were washed with saturated aqueous NaHCO₃ solution. The combined organic layers were dried with sodium sulfate, filtered and concentrated in vacuo. The obtained material was purified by silica gel chromatography using dichloromethane/methanol as eluent. The obtained material was further purified by preparative reverse phase HPLC using a Gemini C18 5µ column and methanol/water/triethylamine as eluent. The title compound was obtained as white solid (169 mg).

MS ESI (m/z): 242.3 [(M+H)⁺].

¹H NMR (CDCl₃, 300 MHz): δ=7.85 (s, 1H), 7.33-7.20 (m, 3H), 7.07 (dd, J=1.9, 7.8 Hz, 1H), 6.84 (d, J=1.8 Hz, 1H), 3.30-3.22 (m, 3H), 1.41 (s, 6H).

Example 62

1,3,3-Trimethyl-6-(3-(trifluoromethyl)-1,2,4-oxadiazol-5-yl)indolin-2-one

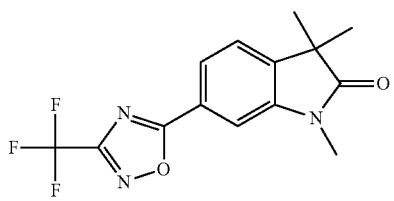 [SMILES: CN1C(=O)C(C)(C)c2ccc(-c3nc(C(F)(F)F)no3)cc21]

Prepared in analogy to example 59b using 1,3,3-trimethyl-2-oxoindoline-6-carboxylic acid (example 59a) and 2,2,2-trifluoro-N-hydroxy-acetamidine. The title compound was obtained as white solid.

MS ESI (m/z): 311 [M⁺]

¹H NMR (CDCl₃, 300 MHz): δ=7.94 (dd, J=1.6, 7.7 Hz, 1H), 7.60 (d, J=1.4 Hz, 1H), 7.40 (d, J=7.7 Hz, 1H), 3.31 (s, 3H), 1.43 (s, 6H).

Example 63

3,3-Dimethyl-6-(4-methyl-1H-imidazol-1-yl)indolin-2-one

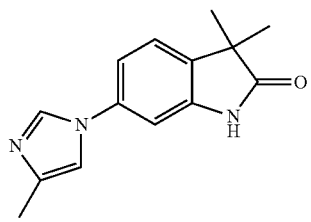 [SMILES: Cc1cn(-c2ccc3c(c2)NC(=O)C3(C)C)cn1]

Through a suspension of 6-bromo-3,3-dimethylindolin-2-one (example 24a, 200 mg, 833 µmol), 4-methyl-1H-imidazole (342 mg, 4.16 mmol), potassium carbonate (121 mg, 875 µmol) and 2-acetylcyclohexanone (29.2 mg, 27.1 µl, 208 µmol) in NMP (1.6 ml) argon was bubbled for 5 minutes, copper(I) chloride (8.25 mg, 83.3 µmol) was added and argon was bubbled through the suspension again for 5 minutes. The reaction mixture was heated to 130° C. for 16 hours. To the reaction mixture 4-methyl-1H-imidazole (342 mg, 4.16 mmol), potassium carbonate (121 mg, 875 µmol), 2-acetylcyclohexanone (29.2 mg, 27.1 µl, 208 µmol) and copper(I) chloride (8.25 mg, 83.3 µmol) were added and heated to 130° C. for another 24 hours. The mixture was diluted with EtOAc and saturated aqueous NaHCO₃ solution. The aqueous phase was extracted with EtOAc, the organic layers were combined and dried with Na₂SO₄. The solvent was evaporated and the residue was purified by silica gel chromatography using heptane/ethyl acetate as eluent, followed by preparative HPLC and by NH₂-silica gel chromatography using heptane/ethyl acetate as eluent. The title compound was obtained as white solid (56 mg).

MS ESI (m/z): 242.3 [(M+H)⁺].

¹H NMR (CDCl₃, 300 MHz): δ=7.72 (d, J=1.4 Hz, 1H), 7.70 (bs, 1H), 7.26-7.23 (m, 1H), 7.03 (dd, J=1.9, 8.0 Hz, 1H), 6.97 (t, J=1.2 Hz, 1H), 6.90 (d, J=1.8 Hz, 1H), 2.30 (s, 3H), 1.43 (s, 6H).

Example 64

1,3,3-Trimethyl-6-(4-methyl-1H-imidazol-1-yl)indolin-2-one

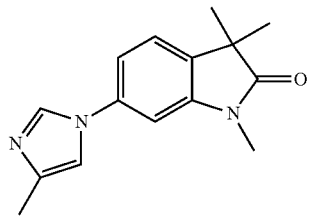 [SMILES: Cc1cn(-c2ccc3c(c2)N(C)C(=O)C3(C)C)cn1]

Prepared in analogy to example 63 using 6-bromo-1,3,3-trimethylindolin-2-one (example 1a). The title compound was obtained as off-white solid.

MS ESI (m/z): 256.3 [(M+H)⁺].

¹H NMR (CDCl₃, 300 MHz): δ=7.75 (d, =1.4 Hz, 1H), 7.25-7.24 (m, 1H), 7.04 (dd, J=2.0, 7.9 Hz, 1H), 7.01 (t, J=1.2 Hz, 1H), 6.81 (d, J=1.8 Hz, 1H), 3.25 (s, 3H), 2.31 (d, J=0.8 Hz, 3H), 1.40 (s, 6H).

Example 65

1,3,3-Trimethyl-6-(5-methyl-1H-imidazol-1-yl)indolin-2-one

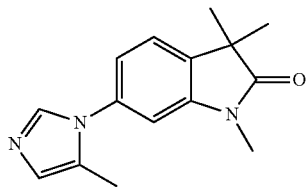 [SMILES: Cc1cncn1-c1ccc2c(c1)N(C)C(=O)C2(C)C]

Formed as minor isomer in example 64. The title compound was obtained as orange oil.

MS ESI (m/z): 256.3 [(M+H)$^+$].

$^1$H NMR (CDCl$_3$, 300 MHz): δ=7.59 (s, 1H), 7.29 (d, J=7.9 Hz, 1H), 6.96 (dd, J=1.9, 7.8 Hz, 1H), 6.92 (s, 1H), 6.75 (d, J=1.8 Hz, 1H), 3.24 (s, 3H), 2.20 (d, J=1.0 Hz, 3H), 1.43 (s, 6H).

Example 66

6-(1,5-Dimethyl-1H-imidazol-2-yl)-1,3,3-trimethylindolin-2-one

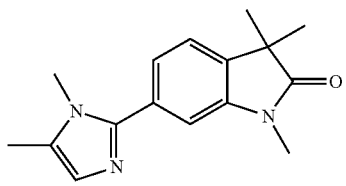 [SMILES: Cc1cnc(-c2ccc3c(c2)N(C)C(=O)C3(C)C)n1C]

a) 1,3,3-Trimethyl-2-oxoindoline-6-carbonitrile

A suspension of 6-bromo-1,3,3-trimethylindolin-2-one (example 1a, 500 mg, 1.97 mmol), zinc cyanide (277 mg, 2.36 mmol) and tetrakis(triphenylphosphine)palladium(0) (227 mg, 197 µmol) in DMF (13.0 ml) was heated to 80° C. for 17 hours under an argon atmosphere. The reaction mixture was treated with water and the aqueous phase was extracted with EtOAc. The combined organic layers were dried over Na$_2$SO$_4$ and the solvent was evaporated. The crude material was purified by silica gel flash chromatography using heptane/ethyl acetate as eluent. The title compound was obtained as white solid (371 mg).

ESI (m/z): 201.2 [(M+H)$^+$].

$^1$H NMR (CDCl$_3$, 300 MHz): δ=7.40 (dd, J=1.4, 7.5 Hz, 1H), 7.29 (d, J=8.1 Hz, 1H), 7.07 (d, J=1.2 Hz, 1H), 3.24 (s, 3H), 1.39 (s, 6H)

b) 1,3,3-Trimethyl-2-oxoindoline-6-carboximidamide

To a solution of lithium bis(trimethylsilyl)amide (1M in THF) (3.21 ml, 3.21 mmol) in dry diethylether (6 ml) at 0° C. under an argon atmosphere was added 1,3,3-trimethyl-2-oxoindoline-6-carbonitrile (314 mg, 1.57 mmol) in three portions. After 5 minutes the cooling bath was removed and stirring was continued at room temperature for 12 hours. The reaction mixture was cooled to 0° C. and aqueous HCl (6M, 1.57 ml, 9.41 mmol) was added slowly. The reaction mixture was stirred at 0° C. for 1 hour, then warmed to room temperature and stirred for 12 hours. The reaction mixture was diluted with diethyl ether and water and carefully basified to pH 14 with solid NaOH. The aqueous phase was extracted with dichloromethane. The combined organic layers were dried over Na$_2$SO$_4$ and the solvent was evaporated. The title compound was obtained as white solid (325 mg).

ESI (m/z): 218.3 [(M+H)].

c) 1,3,3-Trimethyl-6-(5-methyl-1H-imidazol-2-yl)indolin-2-one

To a solution of 1,3,3-trimethyl-2-oxoindoline-6-carboximidamide (550 mg, 2.53 mmol) in THF (10 ml) was added an aqueous solution of 1M sodium bicarbonate (5.06 ml, 5.06 mmol) followed by chloroacetone (234 mg, 202 µl, 2.53 mmol). The reaction mixture was heated to reflux and stirred for 5 hours. Further chloroacetone (20 µl) and aqueous sodium bicarbonate solution (500 µl) were added and stirring at reflux continued for further 3 hours. The reaction mixture was extracted with ethyl acetate and water, the combined organic layers were dried over Na$_2$SO$_4$ and the solvents were evaporated. The crude material was purified by silica gel chromatography using dichloromethane/methanol (with 10% concentrated ammonia solution), followed by preparative HPLC. The title compound was obtained as white solid (200 mg).

ESI (m/z): 256.3 [(M+H)$^+$].

$^1$H NMR (CDCl$_3$, 300 MHz): δ=7.46 (d, J=1.2 Hz, 1H), 7.39 (d, J=7.7 Hz, 1H), 7.20 (d, J=7.5 Hz, 1H), 6.86 (d, J=1.0 Hz, 1H), 3.19 (s, 3H), 2.33 (s, 3H), 1.37 (s, 6H).

d) 6-(1,5-Dimethyl-1H-imidazol-2-yl)-1,3,3-trimethylindolin-2-one

To a suspension of 1,3,3-trimethyl-6-(5-methyl-1H-imidazol-2-yl)indolin-2-one (195 mg, 764 µmol) and cesium carbonate (249 mg, 764 µmol) in dry DMF (4 ml) was added slowly a solution of iodomethane (97.6 mg, 43.0 µl, 687 µmol) in dry DMF (4 ml) and stirred at room temperature for 16 hours. The reaction mixture was quenched with water and the aqueous phase was extracted with ethyl acetate. The combined organic layers were dried over Na$_2$SO$_4$ and the solvents were evaporated. The crude material was purified by SFC (supercritical fluid chromatography with CO$_2$) to yield 60 mg 6-(1,4-dimethyl-1H-imidazol-2-yl)-1,3,3-trimethylindolin-2-one as light yellow solid. Mixed fractions were purified again by amino silicagel chromatography using dichloromethane/methanol (with 10% concentrated aqueous ammonia) as eluent. The title compound was obtained as light yellow solid (33 mg).

ESI (m/z): 270.5 [(M+H)$^+$].

$^1$H NMR (CDCl$_3$, 300 MHz): δ=7.24 (d, J=0.8 Hz, 1H), 7.20 (d, J=1.4 Hz, 1H), 7.19-7.16 (m, 1H), 6.92-6.85 (m, J=1.0 Hz, 1H), 3.63 (s, 3H), 3.24 (s, 3H), 2.28 (d, J=1.0 Hz, 3H), 1.40 (s, 6H).

Example 67

1,3,3-Trimethyl-6-(2-methyl-1H-imidazol-5-yl)indolin-2-one

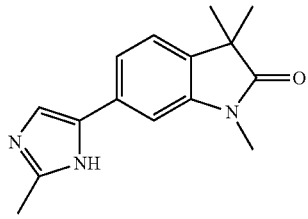

To a suspension of acetimidamide hydrochloride (757 mg, 7.77 mmol) in THF (324 ml) was added 1M aqueous sodium bicarbonate solution (14.0 ml, 14.0 mmol). After 20 minutes a solution of 6-(2-bromoacetyl)-1,3,3-trimethylindolin-2-one (example 70c, 460 mg, 1.55 mmol) in THF (23 ml) was added slowly. The reaction mixture was heated to 80° C. for 18 hours. The solvent was evaporated and water was added. The aqueous phase was extracted with EtOAc. The combined organic layers were dried over $Na_2SO_4$ and the solvent was evaporated. The crude material was purified by flash chromatography on $NH_2$-silica gel using dichloromethane/methanol (with 10% concentrated aqueous ammonia) as eluent followed by preparative reversed phase HPLC. The title compound was obtained as white foam (143 mg).

ESI (m/z): 256.5 [(M+H)$^+$].

$^1$H NMR (CDCl$_3$, 300 MHz): δ=7.42-7.27 (m, 2H), 7.21 (s, 1H), 7.18 (d, J=7.7 Hz, 1H), 3.26 (s, 3H), 2.51 (s, 3H), 1.73-1.48 (m, 1H), 1.38 (s, 6H).

Example 68

6-(1H-Imidazol-4-yl)-1,3,3-trimethylindolin-2-one

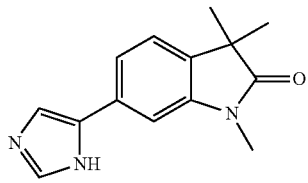 [SMILES: CN1C(=O)C(C)(C)c2ccc(-c3cnc[nH]3)cc21]

A solution of 1,3,3-trimethyl-6-(oxazol-5-yl)indolin-2-one (example 69c, 300 mg, 1.24 mmol) in formamide (11 ml) was heated to 180° C. in a sealed tube and stirred at this temperature for 3 hours. The reaction mixture was poured into water and extracted with ethyl acetate. The organic layers were dried with sodium sulfate, filtered and concentrated in vacuo. The crude material was purified by silica gel chromatography using dichloromethane/methanol as eluent. The title compound was isolated as brown viscous oil (268 mg).

MS ESI (m/z): 242.5 [(M+H)$^+$].

$^1$H NMR (CDCl$_3$, 300 MHz): δ=7.73 (d, J=0.8 Hz, 1H), 7.46-7.31 (m, 3H), 7.20 (d, J=7.7 Hz, 1H), 3.27 (s, 3H), 1.39 (s, 6H).

Example 69

1,3,3-Trimethyl-6-(oxazol-5-yl)indolin-2-one

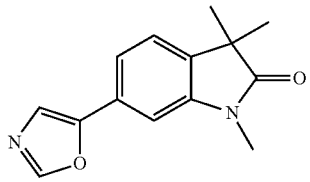 [SMILES: CN1C(=O)C(C)(C)c2ccc(-c3cnco3)cc21]

a) 6-(Hydroxymethyl)-1,3,3-trimethylindolin-2-one

To a suspension of 1,3,3-trimethyl-2-oxoindoline-6-carboxylic acid (example 59a, 150 mg, 684 μmol) in tetrahydrofuran (1 ml) was added dropwise borane tetrahydrofuran complex (1M in THF, 1 ml, 1.00 mmol) at 0° C. The cooling bath was removed and the reaction mixture stirred 2 hours at room temperature. The mixture was poured into 10 mL saturated aqueous sodium bicarbonate solution and extracted with ethyl acetate. The organic layers were dried with sodium sulfate, filtered and concentrated in vacuo. The title compound was obtained as light yellow foam (140 mg) and was used without further purification.

MS ESI (m/z): 206.5 [(M+H)$^+$].

$^1$H NMR (CDCl$_3$, 300 MHz): δ=7.18 (d, J=7.5 Hz, 1H), 7.08-7.00 (m, 1H), 6.91 (d, J=0.8 Hz, 1H), 4.72 (s, 2H), 3.23 (s, 3H), 1.37 (s, 6H).

b) 1,3,3-Trimethyl-2-oxoindoline-6-carbaldehyde

A suspension of 6-(hydroxymethyl)-1,3,3-trimethylindolin-2-one (140 mg, 682 μmol) and manganese dioxide (296 mg, 3.41 mmol) in dichloromethane (2 ml) was stirred at 30° C. for 15 hours. Again manganese dioxide (296 mg, 3.41 mmol) was added and the reaction mixture stirred 2 hours at reflux. The reaction mixture was filtered through a glass fiber filter, washed with dichloromethane and the obtained solution concentrated in vacuo. The title compound was obtained as light brown solid (110 mg) and was used without further purification.

MS ESI (m/z): 204.5 [(M+H)$^+$].

$^1$H NMR (CDCl$_3$, 300 MHz): δ=9.99 (s, 1H), 7.63-7.55 (m, 1H), 7.41-7.34 (m, 2H), 3.31-3.24 (m, 3H), 1.41 (s, 6H).

c) 1,3,3-Trimethyl-6-(oxazol-5-yl)indolin-2-one

To a suspension of 1,3,3-trimethyl-2-oxoindoline-6-carbaldehyde (110 mg, 541 μmol) and potassium carbonate (97.2 mg, 704 μmol) in methanol (2 ml) was added tosylmethyl isocyanide (106 mg, 541 μmol) and the reaction mixture was heated to 80° C. for 1.5 hours. The reaction mixture was poured into water and extracted with dichloromethane. The organic layers were dried with sodium sulfate, filtered and concentrated in vacuo. The title compound was obtained as brown foam (123 mg).

MS ESI (m/z): 243.6 [(M+H)$^+$].

$^1$H NMR (CDCl$_3$, 300 MHz): δ=7.93 (s, 1H), 7.42-7.34 (m, 2H), 7.26-7.23 (m, 1H), 7.10 (d, J=1.4 Hz, 1H), 3.27 (s, 3H), 1.40 (s, 6H)

Example 70

1,3,3-Trimethyl-6-(oxazol-4-yl)indolin-2-one

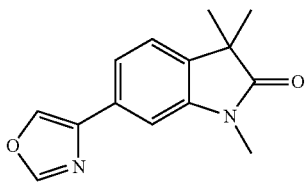 [SMILES: CN1C(=O)C(C)(C)c2ccc(-c3cocn3)cc21]

a) N-Methoxy-N,1,3,3-tetramethyl-2-oxoindoline-6-carboxamide

To a solution of 1,3,3-trimethyl-2-oxoindoline-6-carboxylic acid (example 59a, 0.2 g, 912 µmol) in dry N,N-dimethylformamide (4.56 ml) was added DIPEA (650 µl, 3.65 mmol) and the mixture stirred for 2 minutes. Then HATU (347 mg, 912 µmol) was added and stirring was continued for another 15 minutes. N,O-dimethylhydroxylamine hydrochloride (182 mg, 1.82 mmol) was added and stirring was continued for another 15 hours. The reaction mixture was diluted with ethyl acetate, water and 1M aqueous HCl solution. The mixture was extracted with ethyl acetate and the organic layers were washed with 1M aqueous HCl solution and 1M aqueous sodium carbonate solution. The combined organic layers were dried with sodium sulfate, filtered and concentrated in vacuo. The obtained material was purified by silica gel chromatography using heptane/ethyl acetate as eluent. The title compound was obtained as light brown viscous oil (237 mg).

MS ESI (m/z): 263.1 [(M+H)$^+$].
$^1$H NMR (CDCl$_3$, 300 MHz): δ=7.40 (dd, J=1.4, 7.7 Hz, 1H), 7.22 (d, J=7.7 Hz, 1H), 7.16 (d, J=1.2 Hz, 1H), 3.60 (s, 3H), 3.38 (s, 3H), 3.23 (s, 3H), 1.38 (s, 6H).

b) 6-Acetyl-1,3,3-trimethylindolin-2-one

A suspension of N-methoxy-N,1,3,3-tetramethyl-2-oxoindoline-6-carboxamide (5.8 g, 21.0 mmol) in tetrahydrofurane (23.5 ml) was cooled to 0° C. Methylmagnesium bromide (3.2M in 2-methyltetrahydrofurane, 13.1 ml, 42.0 mmol) was added dropwise keeping temperature below 8° C. The reaction mixture was stirred for 1 hour at 0° C. The reaction was carefully quenched with 1.25M ethanolic HCl (47 ml) and diluted with ethyl acetate and water. The aqueous phase was extracted with ethyl acetate and the organic layers were washed with water. The combined organic layers were dried with sodium sulfate, filtered and concentrated in vacuo. The obtained solid was again treated with ethyl acetate and 1M aqueous HCl solution, extracted with ethyl acetate and washed with 1M aqueous HCl solution. The combined organic layers were dried with sodium sulfate, filtered and concentrated in vacuo. The title compound was obtained as red solid (2.85 g).

MS ESI (m/z): 218.5 [(M+H)$^+$].
$^1$H NMR (CDCl$_3$, 300 MHz): δ=7.69 (dd, J=1.4, 7.7 Hz, 1H), 7.45 (d, J=1.2 Hz, 1H), 7.29 (d, J=7.7 Hz, 1H), 3.27 (s, 3H), 2.63 (s, 3H), 1.40 (s, 6H).

c) 6-(2-Bromoacetyl)-1,3,3-trimethylindolin-2-one

To a solution of 6-acetyl-1,3,3-trimethylindolin-2-one (1 g, 4.6 mmol) in THF (33.3 ml) and methanol (22.2 ml) was added tetra-N-butylammonium tribromide (2.26 g, 4.6 mmol) in THF (11.1 ml). The reaction mixture was heated to 50° C. for 3 hours and then concentrated in vacuo. The obtained material was purified by silica gel chromatography using heptane/ethyl acetate as eluent. The title compound was obtained as off white solid (1.08 g).

MS ESI (m/z): 296.4, 298.4 [(M+H)$^+$].
$^1$H NMR (CDCl$_3$, 300 MHz): δ=7.71 (dd, J=1.4, 7.7 Hz, 1H), 7.46 (d, J=1.4 Hz, 1H), 7.31 (d, J=7.7 Hz, 1H), 4.45 (s, 2H), 3.27 (s, 3H), 1.40 (s, 6H).

d) 1,3,3-Trimethyl-6-(oxazol-4-yl)indolin-2-one

In a pressure tube 6-(2-bromoacetyl)-1,3,3-trimethylindolin-2-one (1.05 g, 3.55 mmol) was treated with formamide (12.7 ml, 319 mmol), the tube was sealed and the reaction mixture was heated to 110° C. After 2 hours the reaction mixture was diluted with ethyl acetate, water and saturated aqueous sodium bicarbonate solution. The mixture was extracted with ethyl acetate and the organic layers were washed with saturated aqueous sodium bicarbonate solution. The combined organic layers were dried with sodium sulfate, filtered and concentrated in vacuo. The obtained material was purified by silica gel chromatography using heptane/ethyl acetate as eluent.

MS ESI (m/z): 243.6 [(M+H)$^+$].
$^1$H NMR (CDCl$_3$, 300 MHz): δ=7.97 (d, J=1.0 Hz, 1H), 7.96 (d, J=0.8 Hz, 1H), 7.42 (dd, J=1.4, 7.7 Hz, 1H), 7.28 (d, J=1.2 Hz, 1H), 7.23 (d, J=7.7 Hz, 1H), 3.27 (s, 3H), 1.39 (s, 6H).

Example 71

1,3,3-Trimethyl-6-(2-methyloxazol-5-yl)indolin-2-one

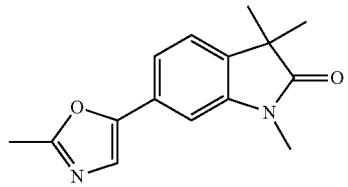 [SMILES: Cc1ncc(-c2ccc3c(c2)N(C)C(=O)C3(C)C)o1]

A solution of thallic acetate (263 mg, 690 µmol) and trifluoromethanesulfonic acid (184 µl, 2.07 mmol) in acetonitrile (2 ml) was stirred for 10 minutes. Then 6-acetyl-1,3,3-trimethylindolin-2-one (example 70b, 100 mg, 460 µmol) was added and the reaction mixture heated to 90° C. for 4 hours. Again thallic acetate (263 mg, 690 µmol) and trifluoromethanesulfonic acid (184 µl, 2.07 mmol) were added and stirring at 90° C. was continued for 15 hours. The reaction mixture was poured into 2M aqueous sodium carbonate solution and extracted with ethyl acetate. The organic layers were dried with sodium sulfate, filtered and concentrated in vacuo. The obtained material was purified by silica gel chromatography using heptane/ethyl acetate as eluent. The title compound was obtained as light brown solid (50 mg).

MS ESI (m/z): 257.6 [(M+H)$^+$].
$^1$H NMR (CDCl$_3$, 300 MHz): δ=7.32 (dd, J=1.6, 7.7 Hz, 1H), 7.25-7.19 (m, 2H), 7.05 (d, J=1.2 Hz, 1H), 3.27 (s, 3H), 2.55 (s, 3H), 1.39 (s, 6H).

Example 72

1,3,3-Trimethyl-6-(5-methyl-1,3,4-thiadiazol-2-yl)indolin-2-one

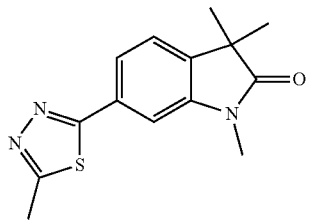 [SMILES: Cc1nnc(-c2ccc3c(c2)N(C)C(=O)C3(C)C)s1]

In a pressure tube 1,3,3-trimethyl-6-(4,4,5,5-tetramethyl-1,3,2-dioxaborolan-2-yl)indolin-2-one (example 29a, 0.1 g, 332 μmol) and 2-bromo-5-methyl-1,3,4-thiadiazole (71.3 mg, 398 μmol) were suspended in dioxane (2.66 ml) and a 2M aqueous sodium carbonate solution (664 μl) was added. Argon was bubbled through the mixture for 5 minutes, then bis(triphenylphosphine)palladium(II) chloride (23.8 mg, 33.2 μmol) was added, the tube was sealed and the reaction mixture was heated to 115° C. for 2.5 hours. The reaction mixture was diluted with ethyl acetate and methanol, 2 spoons silica gel were added and the mixture was concentrated in vacuo. The material was purified by silica gel chromatography using heptane/ethyl acetate as eluent. The title compound was obtained as light brown solid (87 mg).

MS ESI (m/z): 247.5 [(M+H)+].

$^1$H NMR (CDCl$_3$, 300 MHz): δ=7.56 (d, J=1.4 Hz, 1H), 7.50 (dd, J=1.6, 7.7 Hz, 1H), 7.29-7.26 (m, 1H), 3.29 (s, 3H), 2.83 (s, 3H), 1.41 (s, 6H).

Example 73

1,3,3-Trimethyl-6-(1,3,4-thiadiazol-2-yl)indolin-2-one

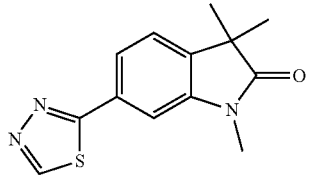 [SMILES: CN1C(=O)C(C)(C)c2ccc(-c3nncs3)cc21]

Prepared in analogy to example 72 using 2-bromo-1,3,4-thiadiazole. The title compound was obtained as off white solid.

MS ESI (m/z): 260.5 [(M+H)+].

$^1$H NMR (CDCl$_3$, 300 MHz): δ=9.12 (s, 1H), 7.65-7.56 (m, 2H), 7.30 (d, J=7.5 Hz, 1H), 3.30 (s, 3H), 1.42 (s, 6H).

Example 74

6-(2-Cyclopropyloxazol-5-yl)-1,3,3-trimethylindolin-2-one

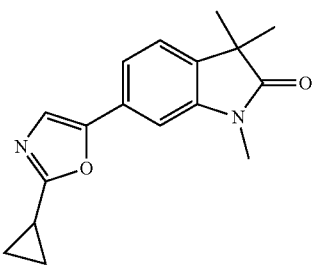 [SMILES: CN1C(=O)C(C)(C)c2ccc(-c3cnc(C4CC4)o3)cc21]

a) 6-(2-Azidoacetyl)-1,3,3-trimethylindolin-2-one

A suspension of 6-(2-bromoacetyl)-1,3,3-trimethylindolin-2-one (example 70c, 200 mg, 675 μmol) and sodium azide (87.8 mg, 1.35 mmol) in acetone (2 ml) was stirred for 2 hours at room temperature. The reaction mixture was poured into 50 mL water and extracted with dichloromethane. The organic layers were dried with sodium sulfate and concentrated in vacuo. The title compound was obtained as light brown solid (169 mg) and was used without further purification.

MS ESI (m/z): 259.5 [(M+H)+].

$^1$H NMR (CDCl$_3$, 300 MHz): δ=7.58 (dd, J=1.6, 7.7 Hz, 1H), 7.42 (d, J=1.2 Hz, 1H), 7.30 (d, J=7.7 Hz, 1H), 4.56 (s, 2H), 3.27 (s, 3H), 1.40 (s, 6H).

b) 6-(2-Cyclopropyloxazol-5-yl)-1,3,3-trimethylindolin-2-one

To a suspension of 6-(2-azidoacetyl)-1,3,3-trimethylindolin-2-one (165 mg, 639 μmol) and cyclopropanecarbonyl chloride (58.0 μl, 639 μmol) in toluene (2 ml) was added triphenylphosphine (285 mg, 1.09 mmol) and the mixture stirred for 5 hours at room temperature. The reaction mixture was filtered and washed with toluene. The obtained solution was concentrated in vacuo. The crude material was purified by silica gel chromatography using heptane/ethyl acetate as eluent. The title compound was obtained as light yellow solid (57 mg).

MS ESI (m/z): 283.5 [(M+H)+].

$^1$H NMR (CDCl$_3$, 300 MHz): δ=7.29 (dd, J=1.6, 7.9 Hz, 1H), 7.21 (d, J=7.7 Hz, 1H), 7.18 (s, 1H), 7.01 (d, J=1.2 Hz, 1H), 3.27 (s, 3H), 2.20-2.07 (m, 1H), 1.38 (s, 6H), 1.18-1.06 (m, 4H).

Example 75

1,3,3-Trimethyl-6-(2-(4-methylpiperazin-1-yl)oxazol-5-yl)indolin-2-one

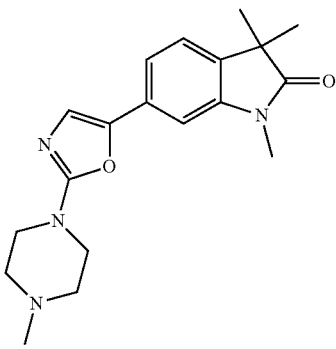 [SMILES: CN1CCN(c2ncc(-c3ccc4c(c3)N(C)C(=O)C4(C)C)o2)CC1]

a) 6-(2-Chlorooxazol-5-yl)-1,3,3-trimethylindolin-2-one

To a suspension of 1,3,3-trimethyl-6-(oxazol-5-yl)indolin-2-one (example 69, 310 mg, 1.28 mmol) in tetrahydrofuran (4.5 ml) at −70° C. to −68° C. was added dropwise LiHMDS (1.54 ml, 1.54 mmol). After warming to 0° C. for 10 minutes the reaction mixture was cooled to −70° C. to −64° C. and hexachloroethane (321 mg, 1.34 mmol) was added. The reaction mixture was warmed to room temperature and kept at this temperature for 5 hours. The reaction mixture was poured into 50 mL saturated aqueous NH$_4$Cl solution. The aqueous phase was extracted with TBME. The combined organic layers were washed with H$_2$O and dried over Na$_2$SO$_4$. The solvent was evaporated and the crude material was purified by flash chromatography on silica gel using heptane/ethyl acetate as eluent. The title compound was obtained as light yellow crystals (271 mg).

MS ESI (m/z): 277.4/279.4 [(M+H)$^+$].

$^1$H NMR (CDCl$_3$, 300 MHz): δ=7.32-7.23 (m, 3H), 7.03 (d, J=1.2 Hz, 1H), 3.27 (s, 3H), 1.39 (s, 6H).

b) 1,3,3-Trimethyl-6-(2-(4-methylpiperazin-1-yl)oxazol-5-yl)indolin-2-one

To a solution of 6-(2-chlorooxazol-5-yl)-1,3,3-trimethylindolin-2-one (0.062 g, 224 μmol) in DMF (2.2 ml) were added 1-methylpiperazine (24.9 mg, 27.6 μl, 246 μmol) and DIPEA (57.9 mg, 78.3 μl, 448 μmol). The reaction mixture was heated to 150° C. for 30 minutes under microwave irradiation. The reaction mixture was concentrated and then diluted with EtOAc, H$_2$O and 1M aqueous Na$_2$CO$_3$ solution. The aqueous phase was extracted with EtOAc, the combined organic layers were washed with brine, dried with Na$_2$SO$_4$ and the solvent was evaporated. The crude material was purified by silica gel chromatography using dichloromethane/methanol as eluent. The title compound was obtained as off-white foam (67 mg).

MS ESI (m/z): 341.5 [(M+H)$^+$].

$^1$H NMR (CDCl$_3$, 300 MHz): δ=7.21-7.15 (m, 2H), 7.07 (s, 1H), 6.90 (s, 1H), 3.64-3.61 (m, 4H), 3.25 (s, 3H), 2.55-2.52 (m, 4H), 2.36 (s, 3H), 1.37 (s, 6H).

Example 76

1,3,3-Trimethyl-6-(2-methyloxazol-4-yl)indolin-2-one

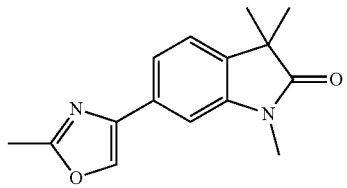 [SMILES: Cc1nc(-c2ccc3c(c2)N(C)C(=O)C3(C)C)co1]

A mixture of 6-(2-bromoacetyl)-1,3,3-trimethylindolin-2-one (example 70c, 100 mg, 338 μmol) and acetamide (300 mg, 259 μl, 5.08 mmol) was heated to 174° C. in a sealed tube for 16 hours. The reaction mixture was poured into 20 mL H$_2$O and the aqueous phase was extracted with EtOAc. The combined organic layers were washed with H$_2$O, dried over Na$_2$SO$_4$ and the solvent was evaporated. The crude material was purified by flash chromatography on silica gel using heptane/ethyl acetate as eluent. The title compound was obtained as white crystals (26 mg).

MS ESI (m/z): 257.1 [(M+H)$^+$].

$^1$H NMR (CDCl$_3$, 600 MHz): δ=7.83 (s, 1H), 7.37 (dd, J=1.5, 7.6 Hz, 1H), 7.24 (d, J=1.4 Hz, 1H), 7.21 (d, J=7.6 Hz, 1H), 3.26 (s, 3H), 2.54 (s, 3H), 1.38 (s, 6H).

Example 77

6-(2-Cyclopropylpyrimidin-5-yl)-1,3,3-trimethylindolin-2-one

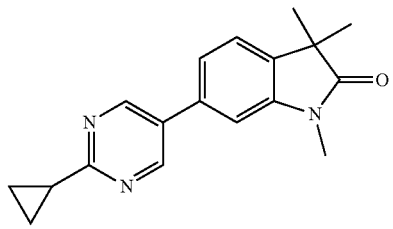 [SMILES: CN1C(=O)C(C)(C)c2ccc(-c3cnc(C4CC4)nc3)cc21]

Prepared in analogy to example 29b using 5-bromo-2-cyclopropyl-pyrimidine and a reaction time of 4 hours. The title compound was obtained as off white solid.

MS ESI (m/z): 294.2 [(M+H)$^+$].

Example 78

1-Cyclopropyl-6-(2-Cyclopropylpyrimidin-5-yl)-3,3-dimethyl-indolin-2-one

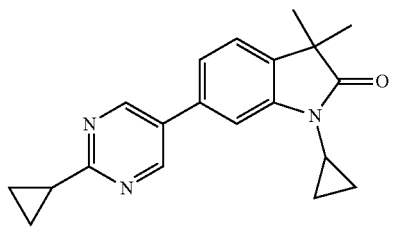 [SMILES: CC1(C)C(=O)N(C2CC2)c2cc(-c3cnc(C4CC4)nc3)ccc21]

a)
6-Bromo-1-cyclopropyl-3,3-dimethyl-indolin-2-one

To a suspension of 6-bromo-3,3-dimethylindolin-2-one (example 24a, 10 g, 41.6 mmol), cyclopropylboronic acid (7.16 g, 83.3 mmol), DMAP (15.6 g, 125 mmol) and copper (II) acetate (7.94 g, 43.7 mmol) in dry toluene (555 ml) was added 2 M sodium bis(trimethylsilyl)amide in THF (21.9 ml, 43.7 mmol). While bubbling dry air through the reaction mixture it was heated to 95° C. for 15 hours. After cooling to room temperature the mixture was diluted with TBME, quenched with water and acidified with 2 M aqueous HCl solution (~150 ml). The mixture was extracted with TBME and the organic layers were washed with 1 M aqueous HCl solution and brine. The combined organic layers were dried with sodium sulfate, filtered and the obtained solution concentrated in vacuo. The crude material was purified by silica gel chromatography using heptane/ethyl acetate as eluent. The title compound was obtained as light brown solid (10.322 g).

MS ESI (m/z): 280.3, 282.3 [(M+H)$^+$].

$^1$H NMR (300 MHz, CHLOROFORM-d) δ=7.24 (d, J=1.8 Hz, 1H), 7.19 (dd, J=1.6, 7.7 Hz, 1H), 7.03 (d, J=7.9 Hz, 1H), 2.67-2.57 (m, 1H), 1.32 (s, 6H), 1.13-0.98 (m, 2H), 0.98-0.84 (m, 2H)

b) 1-Cyclopropyl-3,3-dimethyl-6-(4,4,5,5-tetramethyl-1,3,2-dioxaborolan-2-yl)indolin-2-one repaired in analogy to example 29a using 6-bromo-1-cyclopropyl-3,3-dimethyl-indolin-2-one. The title compound was obtained as off white solid.

MS ESI (m/z): 328.2 [(M+H)$^+$].

c) 1-Cyclopropyl-6-(2-cyclopropylpyrimidin-5-yl)-3,3-dimethyl-indolin-2-one

Prepared in analogy to example 29b using 1-cyclopropyl-3,3-dimethyl-6-(4,4,5,5-tetramethyl-1,3,2-dioxaborolan-2-yl)indolin-2-one and 5-bromo-2-cyclopropyl-pyrimidine and a reaction time of 4 hours. The title compound was obtained as colorless viscous oil.

MS ESI (m/z): 320.3 [(M+H)$^+$].

Example 79

6-(6-Cyclopropylpyridazin-3-yl)-1,3,3-trimethyl-indolin-2-one

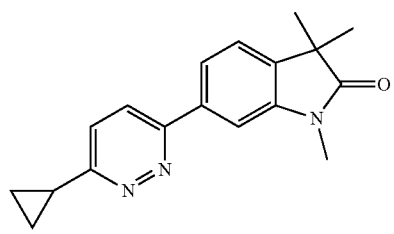 [SMILES: CN1C(=O)C(C)(C)c2ccc(-c3ccc(C4CC4)nn3)cc21]

Prepared in analogy to example 29b using 3-bromo-6-cyclopropyl-pyridazine and a reaction time of 4 hours. The title compound was obtained as off white solid.

MS ESI (m/z): 294.0 [(M+H)*].

Example 80

1-Cyclopropyl-6-(6-cyclopropylpyridazin-3-yl)-3,3-dimethyl-indolin-2-one

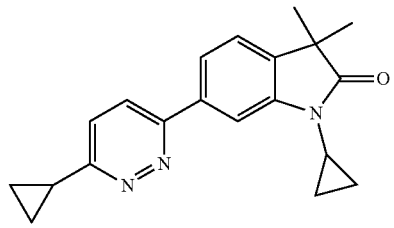 [SMILES: CC1(C)C(=O)N(C2CC2)c2cc(-c3ccc(C4CC4)nn3)ccc21]

Prepared in analogy to example 78c using 3-bromo-6-cyclopropyl-pyridazine and a reaction time of 4 hours. The title compound was obtained as light pink solid.

MS ESI (m/z): 320.0 [(M+H)$^+$].

Example 81

6-(6-Cyclopropylpyridazin-3-yl)-3,3-dimethyl-1-(oxetan-3-yl)indolin-2-one

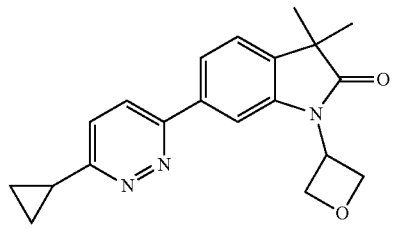 [SMILES: CC1(C)C(=O)N(C2COC2)c2cc(-c3ccc(C4CC4)nn3)ccc21]

a) 6-Bromo-3,3-dimethyl-1-(oxetan-3-yl)indolin-2-one

To a solution of 6-bromo-3,3-dimethylindolin-2-one (example 24a, 1.5 g, 6.25 mmol) in DMF (20.0 ml) under argon were added 3-bromooxetane (1.6 g, 895 µl, 11.2 mmol) and cesium carbonate (4.07 g, 12.5 mmol) and the reaction mixture heated to 60° C. for 17.5 hours. Again 3-bromooxetane (250 µl) and cesium carbonate (2 g) were added and stirring at 60° C. continued for 3.5 hours. The reaction mixture was treated with 50 mL 1 M aqueous HCl solution and extracted with EtOAc. The combined organic layers were dried over sodium sulfate and concentrated in vacuo. The crude material purified by silica gel chromatography using heptane/ethyl acetate as eluent. The title compound was obtained as white solid (1.49 g)

MS ESI (m/z): 296.3, 298.3 [(M+H)$^+$].

$^1$H NMR (300 MHz, CHLOROFORM-d) δ=7.71 (d, J=1.6 Hz, 1H), 7.30-7.23 (m, 1H), 7.12 (d, J=7.9 Hz, 1H), 5.63-5.50 (m, 1H), 5.16-4.98 (m, 4H), 1.36 (s, 6H)

b) 3,3-Dimethyl-1-(oxetan-3-yl)-6-(4,4,5,5-tetramethyl-1,3,2-dioxaborolan-2-yl)indolin-2-one Prepared in analogy to example 29a using 6-bromo-3,3-dimethyl-1-(oxetan-3-yl)indolin-2-one. The title compound was obtained as pale white solid.

MS ESI (m/z): 344.2 [(M+H)$^+$].

c) 6-(6-Cyclopropylpyridazin-3-yl)-3,3-dimethyl-1-(oxetan-3-yl)indolin-2-one Prepared in analogy to example 29b using 3-bromo-6-cyclopropyl-pyridazine and a reaction time of 4 hours. The title compound was obtained off white solid.

MS ESI (m/z): 335.8 [(M+H)$^+$].

Example 82

3,3-Dimethyl-6-(2-methylpyrimidin-4-yl)indolin-2-one

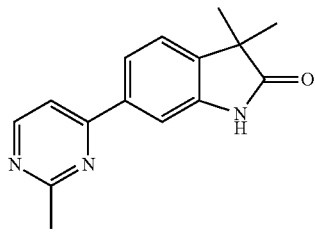 [SMILES: Cc1nccc(-c2ccc3c(c2)NC(=O)C3(C)C)n1]

Prepared in analogy to example 29b using 3,3-dimethyl-6-(2-methylpyridin-4-yl)indolin-2-one (example 24a) and a reaction time of 2.5 hours. The title compound was obtained as white solid.

MS ESI (m/z): 254.1 [(M+H)$^+$].

Example 83

1,3,3-Trimethyl-6-(2-methyl-4-pyridyl)pyrrolo[3,2-c]pyridin-2-one

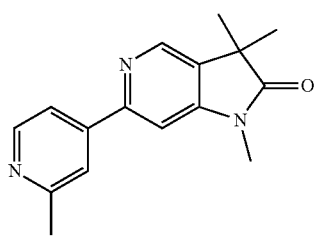 [SMILES: Cc1cc(-c2cc3c(cn2)C(C)(C)C(=O)N3C)ccn1]

a) 6-Chloro-1,3,3-trimethyl-1,3-dihydro-pyrrolo[3,2-c]pyridin-2-one

To a stirred solution of 6-chloro-1,3-dihydro-pyrrolo[3,2-c]pyridin-2-one (2.0 g, 11.86 mmol) in THF (15 ml), was added NaH (60%, 1.9 g, 47.45 mmol) portion wise at 0° C. The reaction mixture was stirred at this temperature for 10 minutes then at 25° C. for 20 minutes. Then MeI (3.0 ml, 47.45 mmol) was added slowly to the reaction mixture at 0° C. and then stirred at 25° C. for 2 hours. The reaction was quenched by the addition of saturated aqueous ammonium chloride solution (10 ml) at 0° C. The mixture was extracted with ethyl acetate and washed with water. The combined organic layers were dried with sodium sulfate, filtered and the obtained solution concentrated in vacuo. The crude material was purified by silicagel chromatography using hexane/ethyl acetate as eluent. The title compound was obtained as white solid (1.5 g) MS ESI (m/z): 210.9 [(M+H)$^+$].

b) 1,3,3-Trimethyl-6-(2-methyl-4-pyridyl)pyrrolo[3,2-c]pyridin-2-one

In a pressure tube 6-chloro-1,3,3-trimethyl-1,3-dihydro-pyrrolo[3,2-c]pyridin-2-one (0.12 g, 0.57 mmol) and 2-methylpyridine-4-boronic acid (0.093 g, 0.68 mmol) were suspended in 2M aqueous sodium carbonate solution (0.5 ml) and dioxane (4 ml). The reaction mixture was purged with argon for 15 minutes. Then Pd(dppf)Cl$_2$ (0.042 g, 0.057 mmol) was added and purging was continued for 15 minutes. The tube was sealed and the reaction mixture was heated to 110° C. for 12 hours. The reaction mixture was diluted with ethyl acetate and water. The reaction mixture was extracted with ethyl acetate and washed with water and brine. The combined organic layers were dried with sodium sulfate, filtered and the obtained solution concentrated in vacuo. The crude material was purified by silica gel chromatography using hexane/ethyl acetate as eluent. The title compound was obtained as off white solid (55 mg).

MS ESI (m/z): 267.8 [(M+H)$^+$].

Example 84

3,3-Dimethyl-6-(2-methyl-4-pyridyl)-1H-pyrrolo[3,2-c]pyridin-2-one

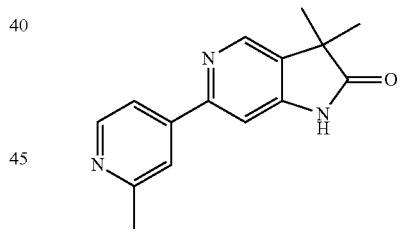

a) 6-Chloro-3,3-dimethyl-1,3-dihydro-pyrrolo[3,2-c]pyridin-2-one

Prepared in analogy to example 24a from 6-chloro-1,3-dihydro-pyrrolo[3,2-c]pyridin-2-one. The title compound was obtained as yellow solid.

MS ESI (m/z): 197.0 [(M+H)$^+$].

b) 3,3-Dimethyl-6-(2-methyl-4-pyridyl)-1H-pyrrolo[3,2-c]pyridin-2-one

This compound was prepared in analogy to 83b from 6-chloro-3,3-dimethyl-1,3-dihydro-pyrrolo[3,2-c]pyridin-2-one. The title compound was obtained as off white solid.

MS ESI (m/z): 253.8 [(M+H)$^+$].

Example 85

1,3,3-Trimethyl-6-(1-methyl-1H-pyrazol-4-yl)indolin-2-one

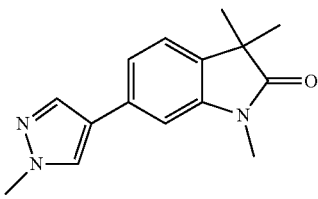 [SMILES: CN1C(=O)C(C)(C)c2ccc(-c3cnn(C)c3)cc21]

To a solution of 6-bromo-1,3,3-trimethylindolin-2-one (example 1a, 75 mg, 295 µmol) and 1-methyl-4-(4,4,5,5-tetramethyl-1,3,2-dioxaborolan-2-yl)-1H-pyrazole (95.0 mg, 443 µmol) in 1,2-Dimethoxyethane (3.4 ml) in a pressure tube was added 2 M aqueous sodium carbonate solution (0.7 ml) and triphenylphosphine (18.6 mg, 70.8 µmol). Argon was bubbled through the mixture during 5 minutes. Then palladium(II)acetate (9.54 mg, 42.5 µmol) was added and again argon bubbled through the reaction mixture during 5 minutes. The tube was sealed and the reaction mixture stirred 16 hours at 90° C. The reaction mixture was concentrated in vacuo. The residue was diluted with dichloromethane, silica gel was added and the mixture again concentrated in vacuo. The crude material was purified by silica gel chromatography using heptane/ethyl acetate as eluent. The obtained material was again purified by amine silica gel chromatography using heptane/ethyl acetate as eluent. The title compound was obtained as white solid (43 mg) MS ESI (m/z): 256.5 [(M+H)+].

Example 86

1-Cyclopropyl-3,3-dimethyl-6-(1-methyl-1H-pyrazol-4-yl)indolin-2-one

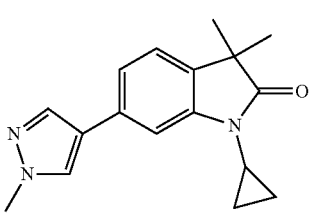 [SMILES: Cn1cc(-c2ccc3c(c2)N(C2CC2)C(=O)C3(C)C)cn1]

Prepared in analogy to example 85 using 6-bromo-1-cyclopropyl-3,3-dimethyl-indolin-2-one (example 78a). The title compound was obtained as light yellow foam.
MS ESI (m/z): 282.6 [(M+H)+].

Example 87

3,3-Dimethyl-6-(1-methyl-1H-pyrazol-4-yl)indolin-2-one

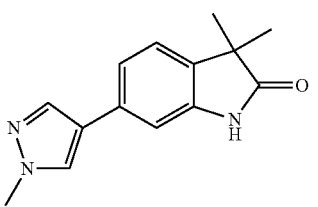 [SMILES: Cn1cc(-c2ccc3c(c2)NC(=O)C3(C)C)cn1]

Prepared in analogy to example 85 using 6-bromo-3,3-dimethyl-1,3-dihydro-indol-2-one (example 24a). The title compound was obtained as white solid.
MS ESI (m/z): 242.6 [(M+H)+].

Example 88

6-(2-Cyclopropylpyrimidin-5-yl)-3,3-dimethyl-indolin-2-one

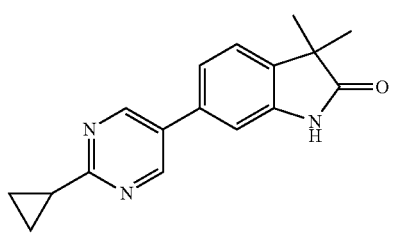

Prepared in analogy to example 24b using 5-bromo-2-cyclopropyl-pyrimidine with a reaction time of 4 hours. The title compound was obtained as off white solid.
MS ESI (m/z): 280.3 [(M+H)+].

Example 89

1-Cyclopropyl-3,3-dimethyl-6-(2-methyl-4-pyridyl)pyrrolo[3,2-c]pyridin-2-one

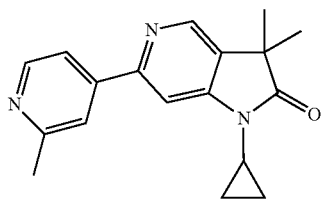 [SMILES: Cc1cc(-c2cc3c(cn2)C(C)(C)C(=O)N3C2CC2)ccn1]

a) 6-Chloro-1-cyclopropyl-3,3-dimethyl-1,3-dihydro-pyrrolo[3,2-c]pyridin-2-one

Prepared in analogy to example 78a from 6-chloro-3,3-dimethyl-1,3-dihydro-pyrrolo[3,2-c]pyridin-2-one (example 84a). The title compound was obtained as white solid.
MS ESI (m/z): 237.1 [(M+H)+].

b) 1-Cyclopropyl-3,3-dimethyl-6-(2-methyl-4-pyridyl)pyrrolo[3,2-c]pyridin-2-one

Prepared in analogy to example 83b from 6-chloro-1-cyclopropyl-3,3-dimethyl-1,3-dihydro-pyrrolo[3,2-c]pyridin-2-one. The title compound was obtained as light brown solid.
MS ESI (m/z): 294.6 [(M+H)+].

Example 90

1-Cyclopropyl-3,3-dimethyl-6-(4-methyl-1H-imidazol-1-yl)indolin-2-one

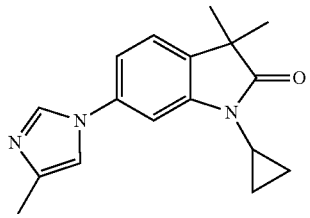 [SMILES: Cc1cn(-c2ccc3c(c2)N(C2CC2)C(=O)C3(C)C)cn1]

Prepared in analogy to example 63 from 6-bromo-1-cyclopropyl-3,3-dimethyl-indolin-2-one (example 78a). The title compound was obtained as off white foam.

MS ESI (m/z): 282.1 [(M+H)$^+$].

Example 91

1-Cyclopropyl-3,3-dimethyl-6-(5-methyl-1H-imidazol-1-yl)indolin-2-one

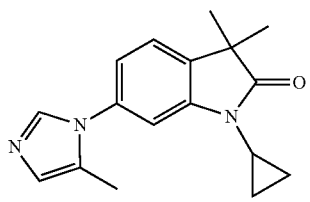 [SMILES: Cc1cncn1-c1ccc2c(c1)N(C1CC1)C(=O)C2(C)C]

The title compound was isolated as off white foam in the reaction to example 90.

MS ESI (m/z): 282.1 [(M+H)$^+$].

Example 92

3,3-Dimethyl-6-(2-methylpyrimidin-5-yl)-1H-pyrrolo[3,2-c]pyridin-2-one

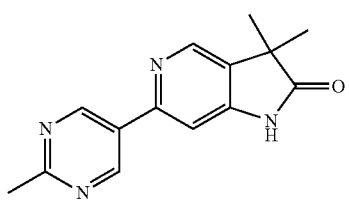 [SMILES: Cc1ncc(-c2cc3c(cn2)C(C)(C)C(=O)N3)cn1]

Prepared in analogy to example 84b using 2-methylpyrimidine-5-boronic acid and a reaction time of 6 hours. The title compound was obtained as off white solid.

MS ESI (m/z): 255.0 [(M+H)$^+$].

Example 93

1,3,3-Trimethyl-6-(5-methyl-1,3,4-oxadiazol-2-yl)indolin-2-one

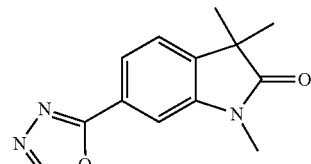

a) N'-Acetyl-1,3,3-trimethyl-2-oxoindoline-6-carbohydrazide

To a solution of 1,3,3-trimethyl-2-oxoindoline-6-carboxylic acid (example 59a, 120 mg, 547 µmol) in dichloromethane (6 ml) under argon were added 1H-benzo[d][1,2,3]triazol-1-ol (HOBt, 118 mg, 876 µmol), N1-((ethylimino)methylene)-N3,N3-dimethylpropane-1,3-diamine hydrochloride (EDCI, 168 mg, 876 µmol), triethylamine (138 mg, 191 µl, 1.37 mmol) and DMF (1 ml). Then acetohydrazide (40.5 mg, 547 µmol) was added. The reaction mixture was stirred in a sealed tube at room temperature for 16 hours. Then the reaction mixture was concentrated in vacuo. The residue was diluted with dichloromethane, silica gel was added and the mixture concentrated in vacuo. The crude material was purified by silica gel chromatography using dichloromethane/methanol as eluent. The title compound was obtained as white foam (135 mg), still containing HOBt. This material was used without further purification.

MS ESI (m/z): 276.1 [(M+H)$^+$].

b) 1,3,3-Trimethyl-6-(5-methyl-1,3,4-oxadiazol-2-yl)indolin-2-one

To a solution of N'-acetyl-1,3,3-trimethyl-2-oxoindoline-6-carbohydrazide (129.5 mg, 470 µmol) in acetonitrile (6 ml) were added triethylamine (143 mg, 197 µl, 1.41 mmol) and p-toluenesulfonyl chloride (137 mg, 706 µmol). The reaction mixture was stirred room temperature for 16 hours. The reaction mixture was treated with 15 ml saturated aqueous sodium bicarbonate solution and extracted ethylacetate. The organic layers were dried with sodium sulfate, filtered and the obtained solution concentrated in vacuo. The residue was diluted with dichloromethane, silica gel was added and the mixture concentrated in vacuo. The crude material was purified by silica gel chromatography using heptane/ethyl acetate as eluent. The title compound was obtained as light yellow solid (88 mg).

MS ESI (m/z): 258.2 [(M+H)$^+$].

Example 94

6-(5-Cyclopropyl-1,3,4-oxadiazol-2-yl)-1,3,3-trimethylindolin-2-one

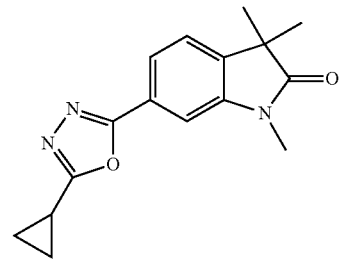 [SMILES: CN1C(=O)C(C)(C)c2ccc(-c3nnc(C4CC4)o3)cc21]

Prepared in analogy to example 93 using cyclopropanecarbohydrazide. The title compound was obtained as light yellow solid.
MS ESI (m/z): 284.2 [(M+H)$^+$].

Example 95

6-(5-Cyclopropyl-1,3,4-oxadiazol-2-yl)-3,3-dimethylindolin-2-one

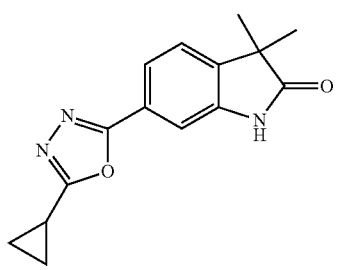 [SMILES: CC1(C)C(=O)Nc2cc(-c3nnc(C4CC4)o3)ccc21]

Prepared in analogy to example 93 from 3,3-dimethyl-2-oxoindoline-6-carboxylic acid (example 60b) using cyclopropanecarbohydrazide. The title compound was obtained as light red solid.
MS ESI (m/z): 270.2 [(M+H)$^+$].

Example 96

6-(4-Cyclopropyl-1H-imidazol-1-yl)-1,3,3-trimethylindolin-2-one

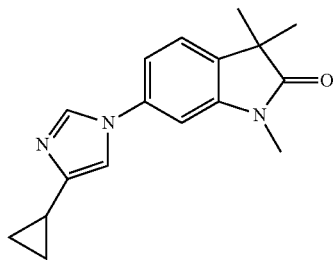 [SMILES: CN1C(=O)C(C)(C)c2ccc(-n3cnc(C4CC4)c3)cc21]

Prepared in analogy to example 63 from 6-bromo-1,3,3-trimethylindolin-2-one (example 1a) using 4-cyclopropyl-1H-imidazole. The title compound was obtained as yellow oil.
MS ESI (m/z): 282.2 [(M+H)$^+$].

Example 97

6-(5-Cyclopropyl-1H-imidazol-1-yl)-1,3,3-trimethylindolin-2-one

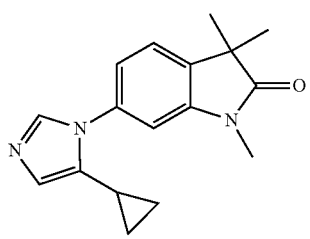 [SMILES: CN1C(=O)C(C)(C)c2ccc(-n3cncc3C3CC3)cc21]

The title compound was obtained as white foam in the reaction to example 96.
MS ESI (m/z): 282.2 [(M+H)$^+$].

Example 98

1-Cyclopropyl-6-(4-cyclopropyl-1H-imidazol-yl)-3,3-dimethylindolin-2-one

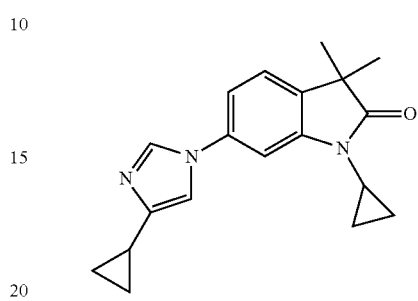

Prepared in analogy to example 96 from 6-bromo-1-cyclopropyl-3,3-dimethyl-indolin-2-one (example 78a). The title compound was obtained as light yellow viscous oil.
MS ESI (m/z): 308.3 [(M+H)$^+$].

Example 99

1-Cyclopropyl-6-(5-cyclopropyl-1H-imidazol-yl)-3,3-dimethylindolin-2-one

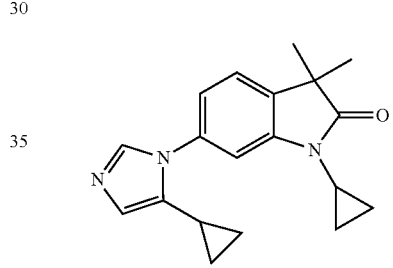

The title compound was obtained as light yellow solid in the reaction to example 98.
MS ESI (m/z): 308.3 [(M+H)$^+$].

Example 100

6-(1-Cyclopropyl-1H-pyrazol-4-yl)-1,3,3-trimethylindolin-2-one

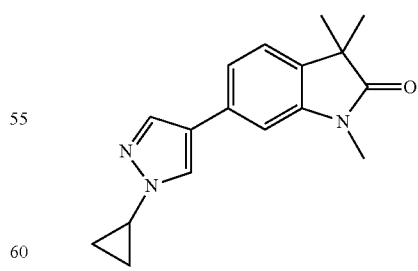

a) 1,3,3-Trimethyl-6-(1H-pyrazol-4-yl)indolin-2-one

In a microwave vial 6-bromo-1,3,3-trimethylindolin-2-one (example 1a, 200 mg, 787 μmol) and tert-butyl 4-(4,4,5,5-tetramethyl-1,3,2-dioxaborolan-2-yl)-1H-pyrazole-1- carboxylate (232 mg, 787 μmol) were combined with dioxane (4.5 ml) and 2 M aqueous sodium carbonate solution (787 μl, 1.57 mmol). The mixture was sparged with argon for 5 minutes. Then [1,1'-bis(diphenylphosphino)ferrocene]dichloropalladium(II) (32.1 mg, 39.4 μmol) was added and sparging with argon continued for another 5 minutes. The vial was then sealed and heated to 120° C. for 30 minutes under microwave irradiation. The reaction mixture was diluted with ethyl acetate and saturated aqueous sodium bicarbonate solution. The resulting mixture was extracted with ethyl acetate, the combined organic layers dried with sodium sulfate, filtered, and the obtained solution concentrated in vacuo. The crude material was purified by silica gel chromatography using heptane/ethyl acetate as eluent. The title compound was obtained as brown viscous oil (115 mg).
MS ESI (m/z): 242.5 [(M+H)+].

b) 6-(1-Cyclopropyl-1H-pyrazol-4-yl)-1,3,3-trimethylindolin-2-one

Prepared in analogy to example 104 from 1,3,3-trimethyl-6-(1H-pyrazol-4-yl)indolin-2-one. The title compound was obtained as light yellow oil.
MS ESI (m/z): 282.2 [(M+H)+].

Example 101

6-(4-Cyclopropyl-1H-imidazol-yl)-3,3-dimethylindolin-2-one

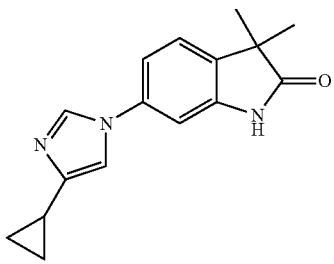 [SMILES: CC1(C)C(=O)Nc2cc(-n3cnc(C4CC4)c3)ccc21]

Prepared in analogy to example 63 using 4-cyclopropyl-1H-imidazole. The title compound was obtained as off white solid.
MS ESI (m/z): 268.1 [(M+H)+].

Example 102

1-Cyclopropyl-6-(5-cyclopropyl-1,3,4-oxadiazol-2-yl)-3,3-dimethylindolin-2-one

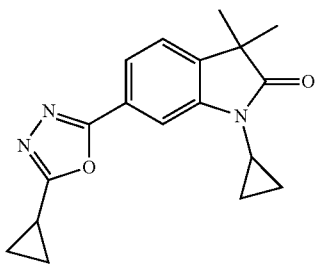 [SMILES: CC1(C)C(=O)N(C2CC2)c2cc(-c3nnc(C4CC4)o3)ccc21]

a) Methyl 1-cyclopropyl-3,3-dimethyl-2-oxoindoline-6-carboxylate

In a reactor were placed 6-bromo-1-cyclopropyl-3,3-dimethylindolin-2-one (example 78a, 4 g, 14.3 mmol) and triethylamine (4.00 ml, 28.6 mmol), then ethyl acetate (50 ml) and methanol (50 ml) were added and the reactor put under argon. Then 1,1'-bis(diphenylphosphino)ferrocene-palladium(II) dichloride dichlormethane adduct (1.17 g, 1.43 mmol) was added and the reactor flushed with CO and pressure adjusted to 50 bars. The reaction mixture was heated to 100° C. and stirred at this temperature under CO for 48 hours. The reaction mixture was cooled to room temperature, diluted with methanol and concentrated in vacuo. The crude material was purified by silica gel chromatography using heptane/ethyl acetate as eluent. The title compound was obtained as off white solid (3.6 g).
MS ESI (m/z): 260.5 [(M+H)+].
$^1$H NMR (300 MHz, CHLOROFORM-d) δ=7.79 (dd, J=1.5, 7.8 Hz, 1H), 7.73 (d, J=1.0 Hz, 1H), 7.24 (d, J=7.7 Hz, 1H), 3.94 (s, 3H), 2.74-2.64 (m, 1H), 1.35 (s, 6H), 1.17-1.02 (m, 2H), 1.00-0.88 (m, 2H)

b) 1-Cyclopropyl-3,3-dimethyl-2-oxoindoline-6-carboxylic acid

To a suspension of methyl 1-cyclopropyl-3,3-dimethyl-2-oxoindoline-6-carboxylate (3.6 g, 13.9 mmol) in methanol (55.5 ml) was added 1 M aqueous NaOH solution (55.5 ml, 55.5 mmol) and the reaction mixture stirred at room temperature for 5 hours. The reaction mixture was diluted with TBME and water. The layers were separated and the organic layer extracted 0.1 M aqueous NaOH solution and the aqueous layers washed with TBME. The combined aqueous layers were acidified with 25% aqueous HCl solution. The mixture was extracted with dichloromethane and the organic layers washed with brine. The combined organic layers were dried with sodium sulfate, filtered and concentrated in vacuo. The title compound was obtained as light yellow solid (3.33 g)
MS ESI (m/z): 246.5 [(M+H)+].
$^1$H NMR (300 MHz, CHLOROFORM-d) δ=7.89 (dd, J=1.4, 7.7 Hz, 1H), 7.81 (d, J=1.2 Hz, 1H), 7.29 (d, J=7.7 Hz, 1H), 2.78-2.62 (m, 1H), 1.38 (s, 6H), 1.19-1.03 (m, 2H), 1.03-0.88 (m, 2H)

c) 1-Cyclopropyl-6-(5-cyclopropyl-1,3,4-oxadiazol-2-yl)-3,3-dimethylindolin-2-one Prepared in analogy to example 93 with 1-cyclopropyl-3,3-dimethyl-2-oxoindoline-6-carboxylic acid using cyclopropanecarbohydrazide. The title compound was obtained as light yellow solid.
MS ESI (m/z): 310.1 [(M+H)+].

Example 103

1,3,3-Trimethyl-6-(6-morpholinopyridin-3-yl)indolin-2-one

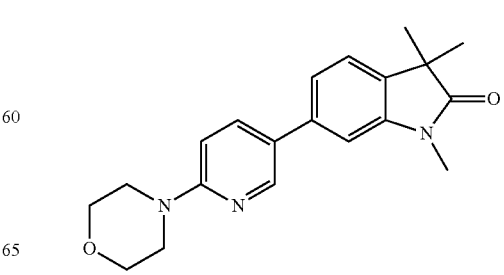

Prepared in analogy to example 1 using 6-morpholinopyridin-3-ylboronic acid and a reaction time of 3 hours. The title compound was obtained as light brown solid.

MS ESI (m/z): 338.2 [(M+H)$^+$]

$^1$H NMR (300 MHz, CHLOROFORM-d) δ=8.46 (d, J=2.6 Hz, 1H), 7.74 (dd, J=2.5, 8.8 Hz, 1H), 7.25-7.17 (m, 2H), 6.95 (s, 1H), 6.96 (s, 1H), 6.72 (d, J=8.7 Hz, 1H), 3.92-3.79 (m, 4H), 3.63-3.49 (m, 4H), 3.26 (s, 3H), 1.40 (s, 6H)

Example 104

6-(1-Cyclopropyl-1H-imidazol-4-yl)-1,3,3-trimethyl-indolin-2-one

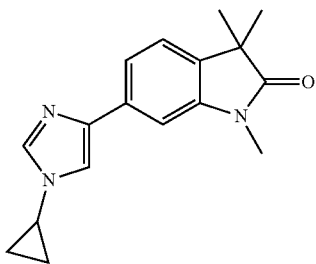 [SMILES: CN1C(=O)C(C)(C)c2ccc(-c3cn(C4CC4)cn3)cc21]

To a suspension of 6-(1H-imidazol-4-yl)-1,3,3-trimethyl-indolin-2-one (example 68, 120 mg, 497 μmol), cyclopropylboronic acid (107 mg, 1.24 mmol) and sodium carbonate (132 mg, 1.24 mmol) in 1,2-dichloroethane (6 ml) was added dropwise a solution of copper(II) acetate (111 mg, 597 μmol) and 2,2 dipyridyl (94.2 mg, 597 μmol) in 1,2-dichloroethane (9 ml) (which was prepared at 70° C.) during 4 minutes. The reaction mixture was stirred 2.5 hours at 70° C., then 16 hours at room temperature. The reaction mixture was diluted with dichloromethane and washed with saturated aqueous ammonium chloride solution and with brine. The organic layer was dried with sodium sulfate, filtered and the obtained solution concentrated in vacuo. The residue was diluted with dichloromethane, amine silica gel was added and the mixture concentrated in vacuo. The crude material was purified by amine silica gel chromatography using heptane/ethyl acetate as eluent. The title compound was obtained as white foam (97 mg).

MS ESI (m/z): 282.2 [(M+H)$^+$].

Example 105

1-Cyclopropyl-3,3-dimethyl-6-(5-methyl-1,3,4-oxadiazol-2-yl)indolin-2-one

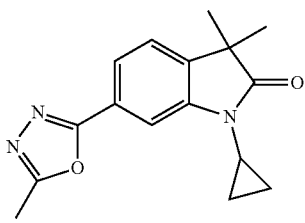 [SMILES: Cc1nnc(-c2ccc3c(c2)N(C2CC2)C(=O)C3(C)C)o1]

Prepared in analogy to example 93 from 1-cyclopropyl-3,3-dimethyl-2-oxoindoline-6-carboxylic acid (example 102b). The title compound was obtained as an off white solid.

MS ESI (m/z): 284.1 [(M+H)$^+$].

Example 106

3,3-Dimethyl-6-(5-methyl-1,3,4-oxadiazol-2-yl)indolin-2-one

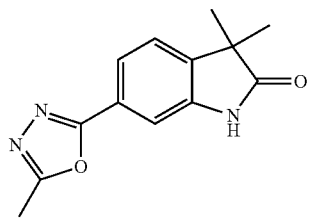 [SMILES: Cc1nnc(-c2ccc3c(c2)NC(=O)C3(C)C)o1]

Prepared in analogy to example 93 from 3,3-dimethyl-2-oxoindoline-6-carboxylic acid (example 60b). The title compound was obtained as light red foam.

MS ESI (m/z): 262.1 [(M+H)$^+$].

Example 107

1-Cyclopropyl-6-(1-cyclopropyl-1H-pyrazol-4-yl)-3,3-dimethylindolin-2-one

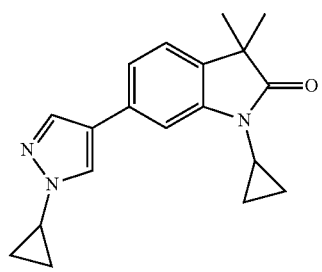 [SMILES: CC1(C)C(=O)N(C2CC2)c2cc(-c3cnn(C4CC4)c3)ccc21]

Prepared in analogy to example 100 from 6-bromo-1-cyclopropyl-3,3-dimethyl-indolin-2-one (example 78a). The title compound was obtained as white solid.

MS ESI (m/z): 308.6 [(M+H)$^+$].

Example 108

1,3,3-Trimethyl-6-(2-methylpyrimidin-5-yl)pyrrolo[3,2-c]pyridin-2-one

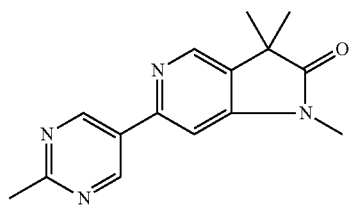

A mixture of 6-chloro-1,3,3-trimethyl-1,3-dihydro-pyrrolo[3,2-c]pyridin-2-one (example 83a) (0.1 g, 0.475 mmol), 2-methylpyrimidine-5-boronic acid (0.078 g, 0.57 mmol) and NaOtBu (0.068 g, 0.712 mmol) in dioxane (2.0 ml) in a microwave vessel was sparged with argon for 15 minutes.

Then Brettphos (0.019, 0.024 mmol) was added to the reaction mixture and sparging was continued for 15 minutes. The vial was sealed and the reaction mixture was irradiated to 110° C. for 1 hour. The reaction mixture was filtered through celite and the filtrate was concentrated in vacuo. The crude material was purified by preparative reversed phase HPLC over a X Terra Prep RPC18 250×19 mm 10μ column using acetonitrile/5 mM aqueous ammonium acetate solution as eluent. The title compound was obtained as off white solid (30 mg)

MS ESI (m/z): 268.8 [(M+H)⁺].

Example 109

1-Cyclopropyl-3,3-dimethyl-6-(1-methyl-1H-imidazol-4-yl)indolin-2-one

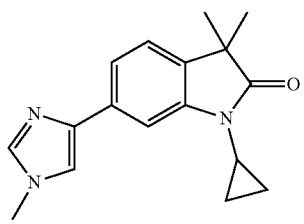 [SMILES: Cn1cnc(-c2ccc3c(c2)N(C2CC2)C(=O)C3(C)C)c1]

a) 1-Cyclopropyl-3,3-dimethyl-6-(oxazol-5-yl)indolin-2-one

Prepared in analogy to example 69 from 1-cyclopropyl-3,3-dimethyl-2-oxoindoline-6-carboxylic acid (example 102b). The title compound was obtained as brown viscous oil.

MS ESI (m/z): 269.5 [(M+H)⁺].

b) 1-Cyclopropyl-6-(1H-imidazol-4-yl)-3,3-dimethylindolin-2-one

Prepared in analogy to example 68 from 1-cyclopropyl-3,3-dimethyl-6-(oxazol-5-yl)indolin-2-one and a reaction time of 15 hours. The title compound was obtained as light brown foam.

MS ESI (m/z): 268.5 [(M+H)⁺].

c) 1-Cyclopropyl-3,3-dimethyl-6-(1-methyl-1H-imidazol-4-yl)indolin-2-one

Prepared in analogy to example 110 from 1-cyclopropyl-6-(1H-imidazol-4-yl)-3,3-dimethylindolin-2-one. The title compound was obtained as white solid.

MS ESI (m/z): 282.16 [(M+H)⁺].

Example 110

1,3,3-Trimethyl-6-(1-methyl-1H-imidazol-4-yl)indolin-2-one

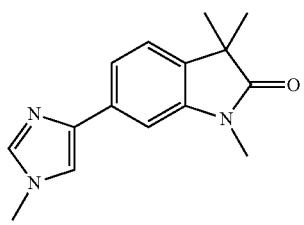 [SMILES: CN1C(=O)C(C)(C)c2ccc(-c3cn(C)cn3)cc21]

To a solution of 6-(1H-imidazol-4-yl)-1,3,3-trimethylindolin-2-one (example 68, 100 mg, 414 μmol) in DMF (5 ml) at 0° C. NaH (60% on mineral oil, 67.8 mg, 1.7 mmol) was added. After stirring for 15 minutes iodomethane (88.2 mg, 38.7 μl, 622 μmol) was added at 0° C. The reaction mixture was stirred 2 hours at 0° C. At 0° C. water was added dropwise, then the mixture was diluted with brine and extracted with ethyl acetate. The organic layers were combined and dried with sodium sulfate, filtered and the obtained solution concentrated in vacuo. The obtained material was purified by preparative supercritical fluid chromatography over a AD-H 20×250 mm 5 μm column using carbon dioxide/methanol/diethylamine as eluent. The title compound was obtained as off white solid (47 mg)

MS ESI (m/z): 256.2 [(M+H)⁺].

Example 111

1-Cyclopropyl-6-(1 H-imidazol-4-yl)-3,3-dimethyl-1H-pyrrolo[3,2-c]pyridin-2(3H)-one

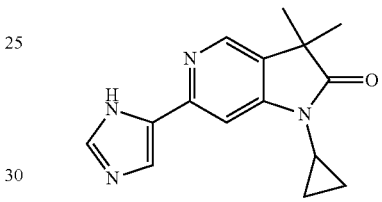

Prepared in analogy to J. Med. Chem. 2008, vol 51, no 20, pp 6571-6580, supporting information page S24/25 from 6-chloro-1-cyclopropyl-3,3-dimethyl-1,3-dihydro-pyrrolo[3,2-c]pyridin-2-one (example 89a) using N,N-dimethyl-4-(tributylstannyl)-1H-imidazole-1-sulfonamide. The title compound was obtained as white foam.

MS ESI (m/z): 269.2 [(M+H)⁺].

Example 112

6-(1-Cyclopropyl-1H-pyrazol-4-yl)-3,3-dimethylindolin-2-one

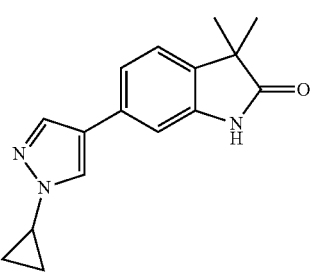 [SMILES: CC1(C)C(=O)Nc2cc(-c3cnn(C4CC4)c3)ccc21]

a) 6-Bromo-1-(4-methoxybenzyl)-3,3-dimethylindolin-2-one

A solution of 6-bromo-3,3-dimethylindolin-2-one (example 24a, 250 mg, 1.04 mmol) in DMF (8 ml) in a pressure tube was sparged with argon for 5 minutes. Then 1-(bromomethyl)-4-methoxybenzene (209 mg, 1.04 mmol) and cesium carbonate (679 mg, 2.08 mmol) were added and sparging with argon continued for 5 minutes. The vial was sealed and the reaction mixture heated to 80° C. After 1 hour the reaction mixture was treated with water and extracted with ethyl acetate. The organic layers were combined, dried with sodium sulfate, filtered and the obtained solution concentrated in vacuo. The crude material was purified by silica gel chromatography using heptane/ethyl acetate as eluent. The title compound was obtained as red liquid (340 mg).

MS ESI (m/z): 360.5, 362.5 [(M+H)].

$^1$H NMR (300 MHz, CHLOROFORM-d) δ=7.23-7.17 (m, 2H), 7.15 (dd, J=1.6, 7.9 Hz, 1H), 7.05 (d, J=7.9 Hz, 1H), 6.89-6.82 (m, 3H), 4.81 (s, 2H), 3.78 (s, 3H), 1.40 (s, 6H)

b) 1-(4-Methoxybenzyl)-3,3-dimethyl-6-(1H-pyrazol-4-yl)indolin-2-one

To a mixture of 6-bromo-1-(4-methoxybenzyl)-3,3-dimethylindolin-2-one (750 mg, 2.08 mmol) and tert-butyl 4-(4,4,5,5-tetramethyl-1,3,2-dioxaborolan-2-yl)-1H-pyrazole-1-carboxylate (947 mg, 3.12 mmol) in 1,2-dimethoxyethane (20 ml) and 2 M aqueous sodium carbonate solution (4 ml) in a pressure tube was added triphenylphosphine (135 mg, 500 μmol). The mixture was sparged with argon for 5 minutes, then palladium(II)acetate (67.3 mg, 300 μmol) was added and sparging with argon continued for another 5 minutes. The vial was sealed and the reaction heated to 100° C. for 16 hours. To the reaction mixture silica gel was added and the mixture concentrated in vacuo. The crude material was purified by silica gel chromatography using heptane/ethyl acetate as eluent. The title compound was obtained as light yellow foam (573 mg)

MS ESI (m/z): 348.2 [(M+H)$^+$].

c) 6-(1-Cyclopropyl-1H-pyrazol-4-yl)-1-(4-methoxybenzyl)-3,3-dimethylindolin-2-one Prepared in analogy to example 104 from 1-(4-methoxybenzyl)-3,3-dimethyl-6-(1H-pyrazol-4-yl)indolin-2-one. The title compound was obtained as light yellow viscous oil.

MS ESI (m/z): 388.3 [(M+H)*].

d) 6-(1-Cyclopropyl-1H-pyrazol-4-yl)-3,3-dimethylindolin-2-one

A solution of 6-(1-cyclopropyl-1H-pyrazol-4-yl)-1-(4-methoxybenzyl)-3,3-dimethylindolin-2-one (117 mg, 302 μmol) in TFA (2 ml) in a sealed tube was stirred 17 hours at 110° C. Again TFA (0.5 ml) was added and the reaction mixture was stirred another 22 hours at 110° C. The reaction mixture was poured into 2 M aqueous sodium carbonate solution and extracted with ethyl acetate. The combined organic layers were dried over sodium sulfate, filtered and concentrated in vacuo. The residue was diluted with dichloromethane, amine silica gel was added and the mixture concentrated in vacuo. The crude material was purified by preparative silica gel chromatography using heptane/ethyl acetate as eluent. The title compound was obtained as light yellow foam (75 mg).

MS ESI (m/z): 268.2 [(M+H)$^+$].

Example 113

6-(1-Cyclopropyl-1H-imidazol-yl)-3,3-dimethylindolin-2-one

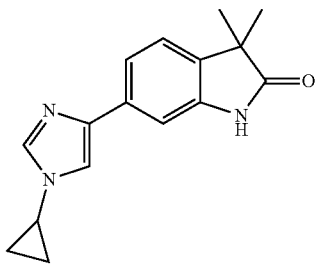 [SMILES: CC1(C)C(=O)Nc2cc(-c3cn(C4CC4)cn3)ccc21]

a) Methyl 1-(4-methoxybenzyl)-3,3-dimethyl-2-oxoindoline-6-carboxylate

Prepared in analogy to example 102a using 6-bromo-1-(4-methoxybenzyl)-3,3-dimethylindolin-2-one (example 112a). The title compound was obtained as yellow viscous oil.

MS ESI (m/z): 340.5 [(M+H)$^+$].

b) 1-(4-Methoxybenzyl)-3,3-dimethyl-2-oxoindoline-6-carboxylic acid

Prepared in analogy to example 102b using methyl 1-(4-methoxybenzyl)-3,3-dimethyl-2-oxoindoline-6-carboxylate at 50° C. for 16 hours. The title compound was obtained as white solid.

MS ESI (m/z): 326.6 [(M+H)$^+$].

c) N-Methoxy-1-(4-methoxybenzyl)-N,3,3-tri methyl-2-oxoindoline-6-carboxamide

Prepared in analogy to example 70a using 1-(4-methoxybenzyl)-3,3-dimethyl-2-oxoindoline-6-carboxylic acid. The title compound was obtained as light yellow solid.

MS ESI (m/z): 369.5 [(M+H)$^+$].

d) 6-Acetyl-1-(4-methoxybenzyl)-3,3-dimethylindolin-2-one

Prepared in analogy to example 70b using N-methoxy-1-(4-methoxybenzyl)-N,3,3-trimethyl-2-oxoindoline-6-carboxamide. The title compound was obtained as orange solid.

MS ESI (m/z): 324.5 [(M+H)$^+$].

e) 6-(2-Bromoacetyl)-1-(4-methoxybenzyl)-3,3-dimethylindolin-2-one

Prepared in analogy to example 70c using 6-acetyl-1-(4-methoxybenzyl)-3,3-dimethylindolin-2-one. The title compound was obtained as light yellow foam.

MS ESI (m/z): 402.2, 404.2 [(M+H)$^+$].

f) 6-(1H-Imidazol-4-yl)-1-(4-methoxybenzyl)-3,3-dimethylindolin-2-one

A suspension of 6-(2-bromoacetyl)-1-(4-methoxybenzyl)-3,3-dimethylindolin-2-one (718 mg, 1.78 mmol) in formamide (15 ml) in a sealed pressure tube was heated to 180° C.

for 3.5 hours. Heating was removed and the reaction mixture stirred at room temperature for 16 hours. Then the reaction mixture was concentrated in vacuo. The residue was diluted with dichloromethane, amine silica gel was added and the mixture concentrated in vacuo. The crude material was purified by silica gel chromatography using ethyl acetate as eluent. The title compound was obtained as brown viscous oil (613 mg) still containing formamide. The material was used without further purification.

MS ESI (m/z): 348.2 [(M+H)+].

g) 6-(1-Cyclopropyl-1H-imidazol-4-yl)-1-(4-methoxybenzyl)-3,3-dimethylindolin-2-one Prepared in analogy to example 104 using 6-(1H-imidazol-4-yl)-1-(4-methoxybenzyl)-3,3-dimethylindolin-2-one and a reaction time of 4.5 hours. The title compound was obtained as light red foam.

MS ESI (m/z): 388.3 [(M+H)+].

h) 6-(1-Cyclopropyl-1H-imidazol-yl)-3,3-dimethylindolin-2-one

Prepared in analogy to example 112d using 6-(1-cyclopropyl-1H-imidazol-4-yl)-1-(4-methoxybenzyl)-3,3-dimethylindolin-2-one. The title compound was obtained as orange solid.

MS ESI (m/z): 268.2 [(M+H)+].

Example 114

7-Cyclopropyl-5,5-dimethyl-2-(2-methylpyridin-4-yl)-5H-pyrrolo[2,3-d]pyrimidin-6(7H)-one

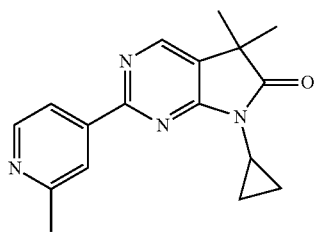

a) Ethyl 2-(2,4-dichloro-6-(cyclopropylamino)pyrimidin-5-yl)acetate

In a pressure tube ethyl 2-(2,4,6-trichloropyrimidin-5-yl) acetate (1.6 g, 5.94 mmol) was dissolved in N,N-dimethylformamide (39.6 ml). Then cyclopropylamine (380 mg, 462 µl, 6.53 mmol) and DIPEA (921 mg, 1.24 ml, 7.12 mmol) were added, the tube sealed and the mixture heated to 50° C. for 1.5 hours. The reaction mixture was diluted with ethyl acetate, water and brine. The mixture was extracted with ethyl acetate and the organic layers were washed with brine, with 1 M aqueous HCl solution and with brine. The combined organic layers were dried with sodium sulfate, filtered and the obtained solution concentrated in vacuo. The crude material was purified by silica gel chromatography using heptane/ethyl acetate as eluent. The title compound was obtained as light brown solid (1.363 g).

MS ESI (m/z): 290.0, 292.0, 294.0 [(M+H)+].

$^1$H NMR (300 MHz, CHLOROFORM-d) δ=6.14 (br. s., 1H), 4.18 (q, J=7.2 Hz, 2H), 3.58 (s, 2H), 3.01-2.88 (m, 1H), 1.27 (t, J=7.1 Hz, 3H), 0.97-0.83 (m, 2H), 0.62-0.50 (m, 2H)

b) 2,4-Dichloro-7-cyclopropyl-5,5-dimethyl-5H-pyrrolo[2,3-d]pyrimidin-6(7H)-one In a pressure tube MeI (1.24 g, 548 µl, 8.76 mmol) was added to a suspension of ethyl 2-(2,4-dichloro-6-(cyclopropylamino)pyrimidin-5-yl)acetate (1.24 g, 4.27 mmol) and cesium carbonate (6.96 g, 21.4 mmol) in dry DMF (42.7 ml). The tube was sealed and the reaction mixture heated to 60° C. for 2 hours. Again MeI (121 mg, 53.4 µl, 855 µmol) was added and stirring at 60° C. continued for another 1.5 hours. The reaction mixture was diluted with ethyl acetate, saturated aqueous sodium bicarbonate solution and brine. The mixture was extracted with ethyl acetate and the organic layers were washed with saturate aqueous sodium carbonate solution and with brine. The combined organic layers were dried with sodium sulfate, filtered and concentrated in vacuo. The crude material was purified by silica gel chromatography using heptane/ethyl acetate as eluent. The title compound was obtained as white solid (725 mg)

MS ESI (m/z): 272.1, 274.1, 276.1 [(M+H)+]

$^1$H NMR (300 MHz, CHLOROFORM-d) δ=2.90-2.77 (m, 1H), 1.48 (s, 6H), 1.13-1.02 (m, 4H)

c) 4-Chloro-7-cyclopropyl-5,5-dimethyl-2-(2-methylpyridin-4-yl)-5H-pyrrolo[2,3-d]pyrimidin-6(7H)-one Prepared in analogy to example 1b from 2,4-dichloro-7-cyclopropyl-5,5-dimethyl-5H-pyrrolo[2,3-d]pyrimidin-6 (7H)-one using 2-methylpyridine-4-boronic acid and a reaction time of 2.5 hours. The title compound was obtained as white solid.

MS ESI (m/z): 329.2, 331.2 [(M+H)+]

$^1$H NMR (300 MHz, CHLOROFORM-d) δ=8.66 (d, J=5.2 Hz, 1H), 8.12 (s, 1H), 8.07 (dd, J=1.1, 5.1 Hz, 1H), 3.03-2.91 (m, 1H), 2.68 (s, 3H), 1.53 (s, 6H), 1.21-1.10 (m, 4H)

d) 7-Cyclopropyl-5,5-dimethyl-2-(2-methylpyridin-4-yl)-5H-pyrrolo[2,3-d]pyrimidin-6(7H)-one A flask containing a suspension of 4-chloro-7-cyclopropyl-5,5-dimethyl-2-(2-methylpyridin-4-yl)-5H-pyrrolo[2,3-d]pyrimidin-6(7H)-one (0.073 g, 222 µmol) in methanol (2.22 ml) was evacuated 4 times (frothing) and flushed with argon. Then 10% Pd/C (23.6 mg, 22.2 µmol) was added and degassing was repeated. Then the apparatus was again 4 times evacuated (frothing) and flushed with hydrogen. The reaction mixture was stirred at room temperature und hydrogen atmosphere for 2 hours. Again methanol (2.22 ml) and 10% Pd/C (23.6 mg, 22.2 mol) were added, degassing and flushing with hydrogen repeated and the reaction mixture stirred at room temperature for 16 hours. The reaction mixture was diluted with ethyl acetate, water and saturated aqueous sodium bicarbonate solution. The mixture was filtered through dicalite and washed with water and ethyl acetate. The obtained mixture was extracted with ethyl acetate and the organic layers were washed with brine. The combined organic layers were dried with sodium sulfate, filtered and concentrated in vacuo. The crude material was purified by silica gel chromatography using heptane/ethyl acetate as eluent. The title compound was obtained as white solid (41 mg).

MS ESI (m/z): 295.2 [(M+H)⁺]

¹H NMR (300 MHz, CHLOROFORM-d) δ=8.66 (dd, J=0.6, 5.2 Hz, 1H), 8.37 (s, 1H), 8.13 (s, 1H), 8.08 (dd, J=1.1, 5.1 Hz, 1H), 3.02-2.92 (m, 1H), 2.68 (s, 3H), 1.45 (s, 6H), 1.23-1.11 (m, 4H)

Example 115

3,3-Dimethyl-6-(6-methylpyrimidin-4-yl)indolin-2-one

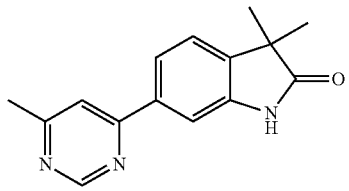 [SMILES: Cc1cc(-c2ccc3c(c2)NC(=O)C3(C)C)ncn1]

Prepared in analogy to example 17 using 4-bromo-6-methylpyrimidine. The title compound was obtained as brown solid.

MS ESI (m/z): 254.2 [(M+H)⁺]

Example 116

3,3-Dimethyl-6-(3-methylpyridin-4-yl)-1H-pyrrolo[3,2-c]pyridin-2(3H)-one

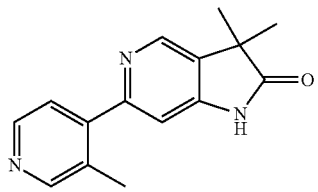 [SMILES: Cc1cnccc1-c1cc2c(cn1)C(C)(C)C(=O)N2]

Prepared in analogy to example 83b from 6-chloro-3,3-dimethyl-1,3-dihydro-pyrrolo[3,2-c]pyridin-2-one (example 84a) using 2-methyl-pyridine-4-boronic acid. The title compound was obtained as colorless oil.

MS ESI (m/z): 254.2 [(M+H)⁺]

¹H NMR (300 MHz, CHLOROFORM-d) δ=8.55 (s, 1H), 8.53 (d, J=5.0 Hz, 1H), 8.44 (s, 1H), 7.60 (d, J=5.7 Hz, 1H), 7.29 (d, J=5.0 Hz, 1H), 6.97 (s, 1H), 2.39 (s, 3H), 1.52 (s, 6H)

Example 117

1-Cyclopropyl-3,3-dimethyl-6-(6-methyl-3-pyridyl)pyrrolo[3,2-c]pyridin-2-one

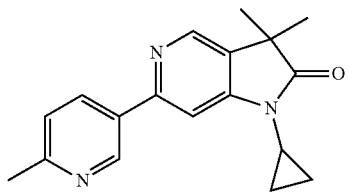 [SMILES: Cc1ccc(-c2cc3c(cn2)C(C)(C)C(=O)N3C2CC2)cn1]

In a pressure tube a suspension of 6-chloro-1-cyclopropyl-3,3-dimethyl-1,3-dihydro-pyrrolo[3,2-c]pyridin-2-one (example 89a, 0.20 g, 0.845 mmol) and 2-methylpyridine-5-boronic acid (0.139 g, 1.014 mmol) and cesium carbonate (0.55 g, 1.69 mmol) in dioxane (4 ml) was purged with argon for 15 minutes. Then Pd₂(dba)₃·CHCl₃ (0.085 g, 0.084 mmol) and xantphos (0.098 g, 0.17 mmol) were added and purging was continued for 15 minutes. The tube was sealed and the reaction mixture was heated to 110° C. for 12 hours. The reaction mixture was diluted with ethyl acetate and water. The mixture was extracted with ethyl acetate and the organic layers were washed with water followed by brine. The combined organic layers were dried with sodium sulfate, filtered and concentrated in vacuo. The crude material was purified by silica gel chromatography using hexane/ethyl acetate as eluent. The title compound was obtained as yellow solid (40 mg).

MS ESI (m/z): 294.0 [(M+H)⁺]

Example 118

3,3-Dimethyl-6-(6-methyl-3-pyridyl)-1H-pyrrolo[3,2-c]pyridin-2-one

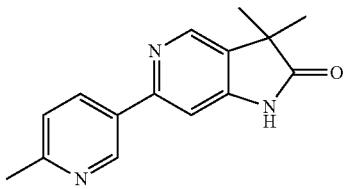 [SMILES: Cc1ccc(-c2cc3c(cn2)C(C)(C)C(=O)N3)cn1]

Prepared in analogy to example 117 from 6-chloro-3,3-dimethyl-1,3-dihydro-pyrrolo[3,2-c]pyridin-2-one (example 84a). The title compound was obtained as white solid.

MS ESI (m/z): 253.8 [(M+H)⁺]

Example 119

6-(4-Isopropyl-1H-imidazol-yl)-3,3-dimethylindolin-2-one

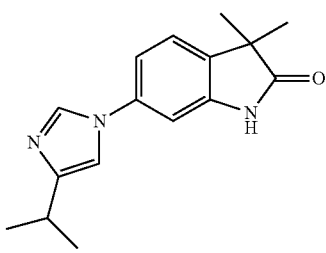 [SMILES: CC(C)c1cn(-c2ccc3c(c2)NC(=O)C3(C)C)cn1]

Prepared in analogy to example 63 using 4-isopropyl-1H-imidazole. The title compound was obtained as off white solid.

MS ESI (m/z): 270.3 [(M+H)⁺]

Example 120

6-(4-Isopropyl-1H-imidazol-1-yl)-1,3,3-trimethylindolin-2-one

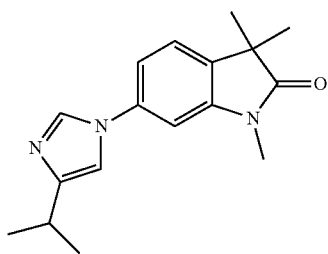 [SMILES: CC(C)c1cn(-c2ccc3c(c2)N(C)C(=O)C3(C)C)cn1]

Prepared in analogy to example 63 from 6-bromo-1,3,3-trimethylindolin-2-one (example 1a) using 4-isopropyl-1H-imidazole. The title compound was obtained as light brown oil.

MS ESI (m/z): 284.2 [(M+H)$^+$]

Example 121

1-Ethyl-3,3-dimethyl-6-(2-methylpyrimidin-5-yl)indolin-2-one

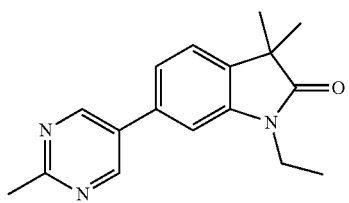 [SMILES: CCN1C(=O)C(C)(C)c2ccc(-c3cnc(C)nc3)cc21]

A suspension of 3,3-dimethyl-6-(2-methylpyrimidin-5-yl)indolin-2-one (example 21, 100 mg, 395 µmol) and cesium carbonate (257 mg, 790 µmol) in DMF (1.5 ml) was treated with bromoethane (64.5 mg, 592 µmol) and the suspension was heated at 60° C. for 20 minutes. The reaction mixture was diluted with water and ethyl acetate. The mixture was extracted with ethyl acetate and the organic layers were washed with water. The combined organic layers were dried with sodium sulfate, filtered and concentrated in vacuo. The residue was crystallized from ethyl acetate/heptane 1:5 at −20° C. The title compound was obtained as off white solid (88 mg).

MS ESI (m/z): 282.2 [(M+H)$^+$]

Example 122

1-Cyclopropyl-3,3-dimethyl-6-(3-methyl-4-pyridyl)pyrrolo[3,2-c]pyridin-2-one

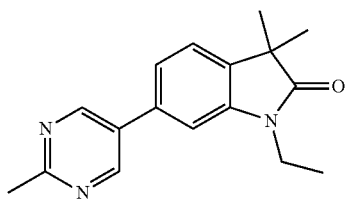 [SMILES: CCN1C(=O)C(C)(C)c2ccc(-c3cnc(C)nc3)cc21]

Prepared in analogy to example 83b from 6-chloro-1-cyclopropyl-3,3-dimethyl-1,3-dihydro-pyrrolo[3,2-c]pyridin-2-one (example 89a) using 3-methylpyridine-4-boronic acid. The title compound was obtained as off white solid.

MS ESI (m/z): 294.0 [(M+H)$^+$]

Example 123

1,3,3-Trimethyl-6-(3-methyl-4-pyridyl)pyrrolo[3,2-c]pyridin-2-one

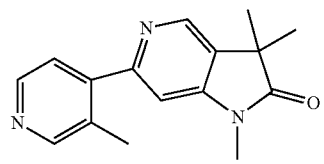 [SMILES: Cc1cnccc1-c1cc2c(cn1)C(C)(C)C(=O)N2C]

Prepared in analogy to example 83 using 3-methylpyridine-4-boronic acid. The title compound was obtained as off white solid.

MS ESI (m/z): 267.8 [(M+H)$^+$]

Example 124

1,3,3-Trimethyl-6-(6-methyl-3-pyridyl)pyrrolo[3,2-c]pyridin-2-one

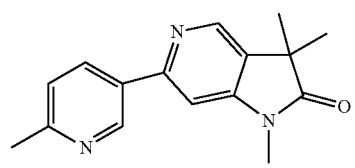 [SMILES: Cc1ccc(-c2cc3c(cn2)C(C)(C)C(=O)N3C)cn1]

Prepared in analogy to example 83 using 2-methylpyridine-5-boronic acid. The title compound was obtained as off white solid.

MS ESI (m/z): 267.8 [(M+H)$^+$]

Example 125

1-Cyclopropyl-3,3-dimethyl-6-(2-methylpyrimidin-5-yl)-1H-pyrrolo[3,2-c]pyridin-2(3H)-one

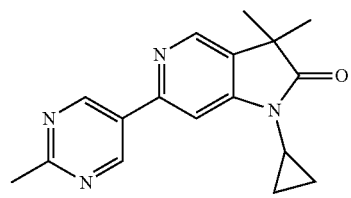 [SMILES: Cc1ncc(-c2cc3c(cn2)C(C)(C)C(=O)N3C2CC2)cn1]

a) 2-Methyl-5-(trimethylstannyl)pyrimidine

In pressure tube 5-bromo-2-methylpyrimidine (500 mg, 2.89 mmol) and hexamethylditin (2.9 g, 1.85 ml, 8.67 mmol) were combined with dioxane (24 ml). The mixture was sparged with argon for 2 minutes, then bis(triphenylphosphine)palladium(II) dichloride (203 mg, 289 μmol) was added and the tube sealed. The reaction mixture was heated to 90° C. for 5 hours. The reaction mixture was poured into 1 M aqueous potassium fluoride solution and extracted with ethyl acetate. The organic layers were washed with 1 M aqueous potassium fluoride solution, combined, dried with sodium sulfate and concentrated in vacuo. The crude material was purified by silica gel chromatography using heptane/ethyl acetate as eluent. The title compound was obtained as yellow viscous oil (590 mg).

MS ESI (m/z): 259.0 [(M+H)$^+$](main peak, Sn specific isotopic pattern)

b) 1-Cyclopropyl-3,3-dimethyl-6-(2-methylpyrimidin-5-yl)-1H-pyrrolo[3,2-c]pyridin-2(3H)-one In a pressure tube 6-chloro-1-cyclopropyl-3,3-dimethyl-1H-pyrrolo[3,2-c]pyridin-2(3H)-one (example 89a, 100 mg, 422 μmol) and 2-methyl-5-(trimethylstannyl)pyrimidine (130 mg, 507 μmol) were combined with dry DMF (2 ml). The mixture was sparged 5 minutes with argon. Then tetrakis(triphenylphosphine)palladium (0) (48.8 mg, 42.2 μmol) was added, the tube sealed and the reaction mixture heated to 80° C. for 16 hours. The reaction mixture was diluted with ethyl acetate, water and saturated aqueous sodium bicarbonate solution. The mixture was extracted with ethyl acetate and the organic layers were washed with saturated aqueous sodium bicarbonate solution. The combined organic layers were dried with sodium sulfate, filtered and concentrated in vacuo. The crude material was purified by silica gel chromatography using dichloromethane/methanol as eluent. The obtained material was triturated with diisopropylether. The title compound was obtained as yellow solid (75 mg).

MS ESI (m/z): 295.2 [(M+H)$^+$]

Example 126

1-(2-Methoxyethyl)-3,3-dimethyl-6-(2-methylpyrimidin-5-yl)indolin-2-one

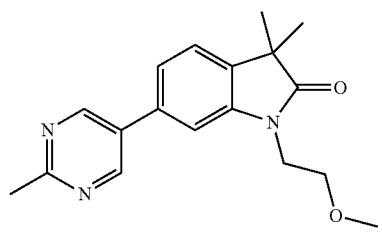

To a solution of 3,3-dimethyl-6-(2-methylpyrimidin-5-yl)indolin-2-one (example 21, 100 mg, 395 μmol) in DMF (3 ml) was added sodium hydride (55% on mineral oil, 20.7 mg, 474 mol) at 0° C. The reaction was stirred at 0° C. for 5 minutes and then room temperature. After 30 minutes at room temperature 1-bromo-2-methoxyethane (71.3 mg, 48.2 μl, 513 μmol) was added dropwise and the reaction was stirred at room temperature for further 3 hours. The mixture was partitioned between water and ethyl acetate. The mixture was extracted with ethyl acetate, the combined organic layers were dried with sodium sulfate, filtered and the obtained solution concentrated in vacuo. The crude material was purified by silica gel chromatography using heptane/ethyl acetate as eluent. The obtained material was crystallized from Diethylether/heptane 1:2 at −20° C.). The title compound was obtained as white solid (58 mg).

MS ESI (m/z): 312.2 [(M+H)$^+$].

Example 127

3,3-Dimethyl-6-(2-methylpyrimidin-5-yl)-1-(2,2,2-trifluoroethyl)indolin-2-one

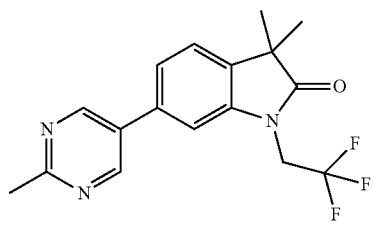 [SMILES: Cc1ncc(-c2ccc3c(c2)N(CC(F)(F)F)C(=O)C3(C)C)cn1]

Prepared in analogy to example 121 using 2-bromo-1,1,1-trifluoroethane and a reaction time of 4 hours. The title compound was obtained as off white solid.

MS ESI (m/z): 336.2 [(M+H)$^+$].

Example 128

3,3-Dimethyl-6-(2-methylpyrimidin-5-yl)-1(2-(trifluoromethoxy)ethyl)indolin-2-one

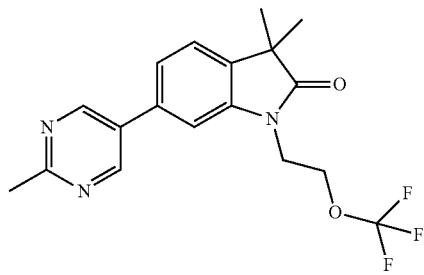 [SMILES: Cc1ncc(-c2ccc3c(c2)N(CCOC(F)(F)F)C(=O)C3(C)C)cn1]

Prepared in analogy to example 121 using 1-bromo-2-(trifluoromethoxy)ethane with a reaction time of 3 hours at room temperature. The title compound was obtained as off white solid.

MS ESI (m/z): 366.2 [(M+H)$^+$].

Example 129

3,3-Dimethyl-6-(2-methylpyrimidin-5-yl)-1-(oxetan-3-ylmethyl)indolin-2-one

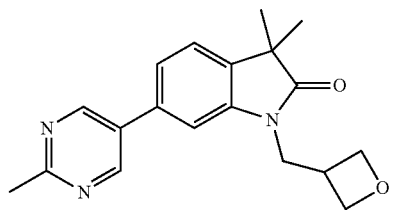 [SMILES: Cc1ncc(-c2ccc3c(c2)N(CC2COC2)C(=O)C3(C)C)cn1]

Prepared in analogy to example 126 using 3-(bromomethyl)oxetane. The title compound was obtained as white solid.
MS ESI (m/z): 324.3 [(M+H)⁺].

Example 130

3,3-Dimethyl-6-(2-methylpyrimidin-5-yl)-1-(3,3,3-trifluoro-2-hydroxypropyl)indolin-2-one

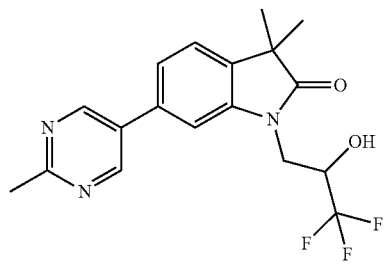 [SMILES: Cc1ncc(-c2ccc3c(c2)N(CC(O)C(F)(F)F)C(=O)C3(C)C)cn1]

Prepared in analogy to example 121 using 3-bromo-1,1,1-trifluoropropan-2-ol with a reaction time of 2 hours at 100° C. The title compound was obtained as white solid.
MS ESI (m/z): 366.2 [(M+H)⁺].

Example 131

1-(3-Fluoropropyl)-3,3-dimethyl-6-(2-methylpyrimidin-5-yl)indolin-2-one

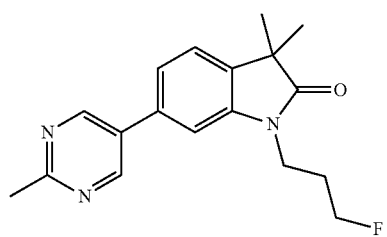 [SMILES: Cc1ncc(-c2ccc3c(c2)N(CCCF)C(=O)C3(C)C)cn1]

Prepared in analogy to example 126 using 1-bromo-3-fluoropropane. The title compound was obtained as white solid.
MS ESI (m/z): 314.2 [(M+H)⁺].

Example 132

1-(2-Fluoroethyl)-3,3-dimethyl-6-(2-methylpyrimidin-5-yl)indolin-2-one

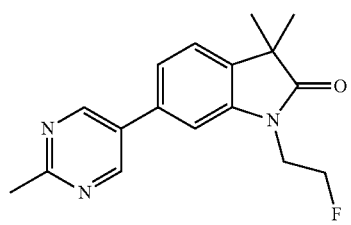 [SMILES: Cc1ncc(-c2ccc3c(c2)N(CCF)C(=O)C3(C)C)cn1]

Prepared in analogy to example 126 using 1-bromo-2-fluoroethane. The title compound was obtained as white solid.
MS ESI (m/z): 300.2 [(M+H)⁺].

Example 133

6-(1-Ethyl-1H-imidazol-4-yl)-1,3,3-trimethylindolin-2-one

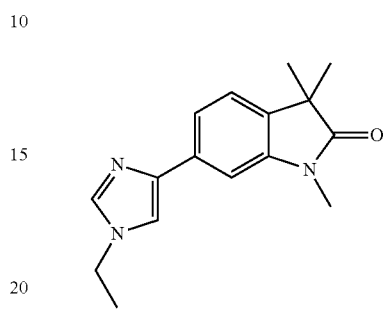

Prepared in analogy to example 126 from 6-(1H-imidazol-4-yl)-1,3,3-trimethylindolin-2-one (example 68) using ethyl bromide and a reaction time of 20 hours. The title compound was obtained as light brown oil.
MS ESI (m/z): 270.2 [(M+H)+].

Example 134

1,3,3-Trimethyl-6-(1-(2,2,2-trifluoroethyl)-1H-imidazol-4-yl)indolin-2-one

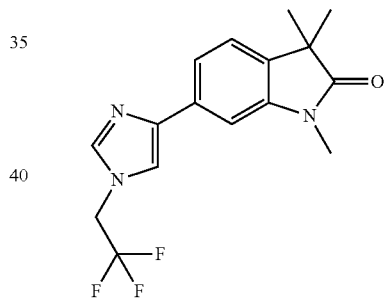

Prepared in analogy to example 126 from 6-(1H-imidazol-4-yl)-1,3,3-trimethylindolin-2-one (example 68) using 2,2,2-trifluoroethyl trifluoromethanesulfonate. The title compound was obtained as light brown foam.
MS ESI (m/z): 324.2 [(M+H)+].

Example 135

6-(2-Fluoro-4-pyridyl)-1,3,3-trimethyl-pyrrolo[3,2-c]pyridin-2-one

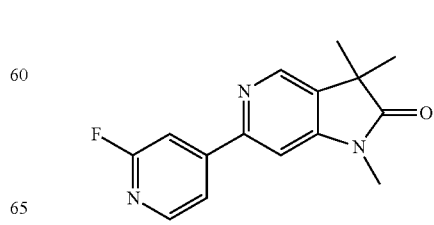

To a solution of 6-chloro-1,3,3-trimethyl-1,3-dihydro-pyrrolo[3,2-c]pyridin-2-one (example 83a, 200 mg, 0.950 mmol) in dioxane (10 ml) and water (2.5 ml) were added sodium carbonate (179.6 mg, 1.695 mmol) and 2-fluoro-4-(4,4,5,5-tetramethyl-[1,3,2]dioxaborolan-2-yl)-pyridine (318 mg, 1.429 mmol). The apparatus was 3 times evacuated and flushed with nitrogen. The mixture was sparged with nitrogen for 10 minutes, then Pd(PPh$_3$)$_4$ (11.1 mg, 0.01 mmol) was added and sparging with nitrogen continued for 10 minutes. The reaction mixture was heated to 110° C. for 16 hours with vigorous stirring. The reaction mixture was diluted with ice-water and extracted with ethyl acetate, and the organic layers were washed with brine. The combined organic layers were dried with sodium sulfate, filtered and concentrated in vacuo. The crude material was purified by silica gel chromatography using ethyl acetate as eluent. The title compound was obtained as off white solid (50 mg).

MS ESI (m/z): 271.7 [(M+H)$^+$].

Example 136

1'-Methyl-6'-(2-methylpyridin-4-yl)spiro[cyclopropane-1,3'-pyrrolo[3,2-c]pyridin]-2'(1'H)-one

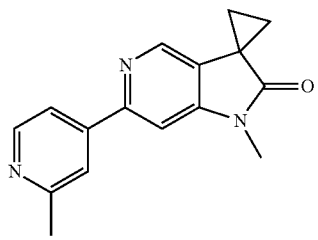 [SMILES: Cc1cc(-c2cc3c(cn2)C2(CC2)C(=O)N3C)ccn1]

a) 6-Chlorospiro[1H-pyrrolo[3,2-c]pyridine-3,1'-cyclopropane]-2-one

To a stirred solution of 6-chloro-1,3-dihydro-pyrrolo[3,2-c]pyridin-2-one (2.0 g, 11.905 mmol) and diisopropylamine (3.553 ml, 25.0 mmol) in THF (60.0 ml) was added n-BuLi (2.1 M in Toluene, 22.7 ml, 47.619 mmol) at −30° C. under argon. Then the reaction mixture was stirred for minutes in which temperature reached 0° C. At this temperature was added ethylenedibromide (3.092 ml, 35.714) in THF (5.0 ml). After the addition the cooling bath was removed and the reaction mixture stirred at 25° C. for 16 hours. The reaction mixture was quenched with 30 ml saturated aqueous ammonium chloride solution and extracted with ethyl acetate. The organic layers were dried with sodium sulfate, filtered and the obtained solution concentrated in vacuo. The crude material was triturated with hexane, filtered and dried. The title compound was obtained as brown solid (1.7 g) and was used without further purification.

MS ESI (m/z): 195.6 [(M+H)$^+$].

b) 6'-Chloro-1'-methyl-spiro[cyclopropane-1,3'-pyrrolo[3,2-c]pyridine]-2'-one

To a stirred solution of 6-chlorospiro[1H-pyrrolo[3,2-c]pyridine-3,1'-cyclopropane]-2-one (3.8 g, 19.522 mmol) in dry THF (120 ml) was added NaH (60%, 0.936 g, 23.427 mmol) portion wise at 0° C. under argon. The reaction mixture was then stirred at 0° C. for 10 minutes, then the temperature was increased to 25° C. for 20 minutes. Then MeI (1.465 ml, 23.427 mmol) was added slowly at 0° C. to the reaction mixture and stirring was continued for another 4 hours at 25° C. Then the reaction was quenched with saturated aqueous ammonium chloride solution at 0° C., extracted with ethyl acetate and the organic layers were washed with water. The combined organic layers were dried with sodium sulfate, filtered and the obtained solution concentrated in vacuo. The crude material was purified by silica gel chromatography using hexane/ethyl acetate as eluent. The title compound was obtained as light yellow solid (1.85 g).

MS ESI (m/z): 209.6 [(M+H)$^+$].

c) 1'-Methyl-6'-(2-methylpyridin-4-yl)spiro[cyclopropane-1,3'-pyrrolo[3,2-c]pyridin]-2'(1'H)-one Prepared in analogy to example 1b from 6'-chloro-1'-methyl-spiro[cyclopropane-1,3'-pyrrolo[3,2-c]pyridine]-2'-one using 2-methylpyridine-4-boronic acid. The title compound was obtained as off white solid.

MS ESI (m/z): 266.2 [(M+H)$^+$].

Example 137

6-(5-Ethyl-1,3,4-oxadiazol-2-yl)-1,3,3-trimethyl-indolin-2-one

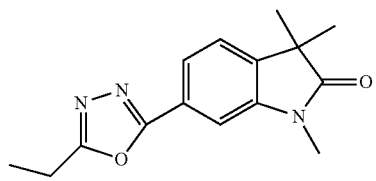 [SMILES: CCc1nnc(-c2ccc3c(c2)N(C)C(=O)C3(C)C)o1]

Prepared in analogy to example 93 using propanehydrazide. The title compound was obtained as white solid.

MS ESI (m/z): 272.1 [(M+H)$^+$].

Example 138

1'-Methyl-6'-(pyridin-3-yl)spiro[cyclopropane-1,3'-pyrrolo[3,2-c]pyridin]-2'(1'H)-one

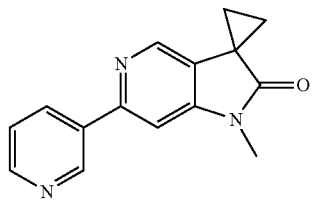 [SMILES: CN1C(=O)C2(CC2)c2cnc(-c3cccnc3)cc21]

Prepared in analogy to example 1b from 6'-chloro-1'-methyl-spiro[cyclopropane-1,3'-pyrrolo[3,2-c]pyridine]-2'-one (example 136b) using pyridine-3-boronic acid. The title compound was obtained as off white solid.

MS ESI (m/z): 252.1 [(M+H)$^+$].

Example 139

1'-Cyclopropyl-6'-(2-methylpyridin-4-yl)spiro[cyclopropane-1,3'-pyrrolo[3,2-c]pyridin]-2'(1'H)-one

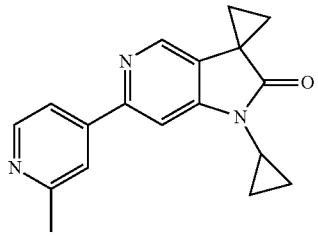 [SMILES: Cc1cc(-c2cc3c(cn2)C2(CC2)C(=O)N3C2CC2)ccn1]

a) 6'-Chloro-1'-cyclopropyl-spiro[cyclopropane-1,3'-pyrrolo[3,2-c]pyridine]-2'-one Prepared in analogy to example 78a from 6-chlorospiro[1H-pyrrolo[3,2-c]pyridine-3,1'-cyclopropane]-2-one (example 136a). The title compound was obtained as pale yellow solid.
MS ESI (m/z): 234.7 [(M+H)$^+$].

b) 1'-Cyclopropyl-6'-(2-methylpyridin-4-yl)spiro[cyclopropane-1,3'-pyrrolo[3,2-c]pyridin]-2'(1'H)-one Prepared in analogy to example 1b from 6'-chloro-1'-cyclopropyl-spiro[cyclopropane-1,3'-pyrrolo[3,2-c]pyridine]-2'-one) using 2-methylpyridine-4-boronic acid. The title compound was obtained as white solid.
MS ESI (m/z): 292.1 [(M+H)$^+$].

Example 140

1'-Cyclopropyl-6'-(pyridin-3-yl)spiro[cyclopropane-1,3'-pyrrolo[3,2-c]pyridin]-2'(1'H)-one

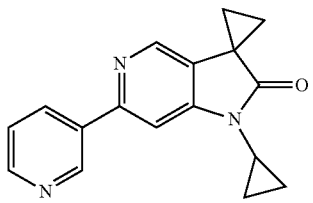 [SMILES: O=C1N(C2CC2)c2cc(-c3cccnc3)ncc2C12CC2]

Prepared in analogy to example 1b from 6'-chloro-1'-cyclopropyl-spiro[cyclopropane-1,3'-pyrrolo[3,2-c]pyridine]-2'-one) (example 139a) using pyridine-3-boronic acid. The title compound was obtained as off white solid.
MS ESI (m/z): 278.1 [(M+H)$^+$].

Example 141

3,3-Dimethyl-6-[5-[1-(trifluoromethyl)cyclopropyl]-1,3,4-oxadiazol-2-yl]indolin-2-one

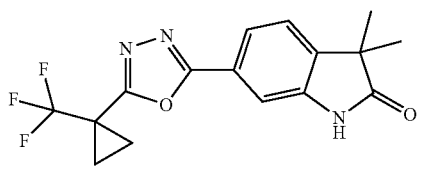 [SMILES: CC1(C)C(=O)Nc2cc(-c3nnc(C4(C(F)(F)F)CC4)o3)ccc21]

a) Methyl 3,3-dimethyl-2-oxo-2,3-dihydro-1H-indole-6-carboxylate

A solution of compound 6-bromo-3,3-dimethyl-1,3-dihydro-indol-2-one (example 24a, 4 g, 16.66 mmol) in MeOH (40 ml) and DMF (4 ml) was sparged with argon for 10 minutes. Then DIPEA (29.5 ml, 166.6 mmol) and Pd(dppf)Cl$_2$ (1.36 g, 1.67 mmol) were added and sparging was continued for another 15 minutes. The reaction mixture was then stirred at 100° C. at 10.3 bar for 16 hours under CO gas. The reaction mixture was cooled to 25° C. and concentrated in vacuo. The residue was dissolved in ethyl acetate and the organic phase was washed with water followed by brine. The organic layer was dried with sodium sulfate, filtered and concentrated in vacuo. The crude material was purified by silica gel chromatography using hexane/ethyl acetate as eluent. The title compound was obtained as yellow solid (2.8 g).
MS ESI (m/z): 220.2 [(M+H)$^+$].

b) 3,3-Dimethyl-2-oxo-2,3-dihydro-1H-indole-6-carbohydrazide

To a stirred solution of methyl 3,3-dimethyl-2-oxo-2,3-dihydro-1H-indole-6-carboxylate (0.5 g, 2.28 mmol) in methanol (7 ml) was added hydrazine hydrate (1.1 ml, 22.8 mmol) and the reaction mixture was stirred at room temperature for 16 hours. Then the mixture was concentrated in vacuo. Three times toluene was added and the mixture concentrated in vacuo. The title compound was obtained as brown solid (0.48 g) and was used without further purification.
MS ESI (m/z): 220.2 [(M+H)$^+$].

c) N'-[(3,3-Dimethyl-2-oxo-2,3-dihydro-1H-indol-6-yl)carbonyl]-1-(trifluoromethyl)cyclopropane-1-carbohydrazide To a stirred solution of 1-(trifluoromethyl)cyclopropane-1-carboxylic acid (0.07 g, 0.45 mmol) in DMF (2 ml) was added TBTU (022 g, 0.68 mmol) followed by N-methyl morpholine (0.15 ml, 1.3 mmol) and the reaction mixture was stirred at 25° C. for 15 minutes. Then 3,3-dimethyl-2-oxo-2,3-dihydro-1H-indole-6-carbohydrazide (0.1 g, 0.73 mmol) was added and the reaction mixture stirred at 25° C. for 16 hours. The reaction mixture was concentrated in vacuo. The residue was diluted with dichloromethane and washed with saturated aqueous sodium bicarbonate solution followed by water. The organic layer was dried with sodium sulfate and concentrated in vacuo. The crude material was purified by silica gel chromatography ethyl acetate as eluent. The title compound was obtained as off white solid (90 mg) and was used without further purification.
MS ESI (m/z): 356.2 [(M+H)$^+$].

d) 3,3-Dimethyl-6-[5-[1-(trifluoromethyl)cyclopropyl]-1,3,4-oxadiazol-2-yl]indolin-2-one Prepared in analogy to example 93b from N'-[(3,3-dimethyl-2-oxo-2,3-dihydro-1H-indol-6-yl)carbonyl]-1-(trifluoromethyl)cyclopropane-1-carbohydrazide. The title compound was obtained as pale yellow solid.
MS ESI (m/z): 337.8 [(M+H)$^+$].

Example 142

6-(3-Cyclopropylisoxazol-5-yl)-1,3,3-trimethylindolin-2-one

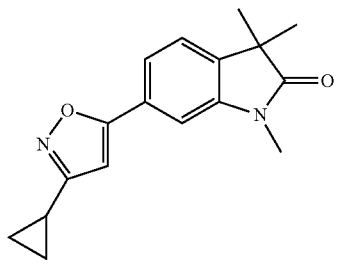 [SMILES: CN1C(=O)C(C)(C)c2ccc(-c3cc(C4CC4)no3)cc21]

a) 1-Cyclopropyl-3-(1,3,3-trimethyl-2-oxoindolin-6-yl)propane-1,3-dione

To a solution of 6-acetyl-1,3,3-trimethylindolin-2-one (example 70b, 326 mg, 1.5 mmol) and methyl cyclopropanecarboxylate (150 mg, 153 µl, 1.5 mmol) in THF (8 ml) was added at 22° C. under inert atmosphere sodium hydride (55% on mineral oil, 137 mg, 3.15 mmol) in one portion. The suspension was stirred at 22° C. for 39 hours. The mixture was partitioned between 1 M aqueous HCl solution and ethyl acetate and the aqueous layer was extracted with ethyl acetate. The combined organic layers were dried with sodium sulfate, filtered and the obtained solution concentrated in vacuo. The crude material was purified by silica gel chromatography using heptane/ethyl acetate as eluent. The title compound was obtained as colorless solid (243 mg).

MS ESI (m/z): 286.1 [(M+H)$^+$]

b) 6-(3-Cyclopropylisoxazol-5-yl)-1,3,3-trimethylindolin-2-one

To a solution of 1-cyclopropyl-3-(1,3,3-trimethyl-2-oxoindolin-6-yl)propane-1,3-dione (220 mg, 771 µmol) in ethanol (4.6 ml) in a pressure tube was added at 22° C. under argon hydroxylamine hydrochloride (53.6 mg, 771 µmol). The tube was sealed and the reaction mixture heated 85° C. for 15 hours. The mixture was diluted with saturated aqueous sodium bicarbonate solution and ethyl acetate. The mixture was extracted with ethyl acetate, the combined organic layers were dried with sodium sulfate, filtered and the obtained solution concentrated in vacuo. The crude material was purified by preparative supercritical fluid chromatography over a AD-H 20×250 mm 5 µm column using carbon dioxide/methanol as eluent. The title compound was obtained as light red oil (65 mg).

MS ESI (m/z): 283.1 [(M+H)$^+$]

Example 143

1,3,3-Trimethyl-6-(3-methylisoxazol-5-yl)indolin-2-one

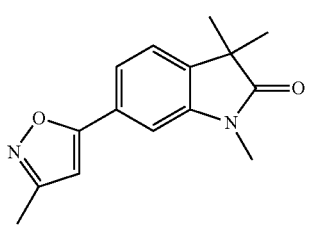 [SMILES: Cc1cc(-c2ccc3c(c2)N(C)C(=O)C3(C)C)on1]

Prepared in analogy to example 142 using methyl acetate. The title compound was obtained as light yellow solid.

MS ESI (m/z): 257.1 [(M+H)$^+$]

Example 144

6-(Methoxymethyl)isoxazol-5-yl)-1,3,3-trimethylindolin-2-one

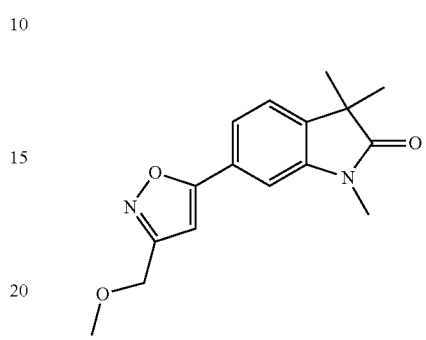

Prepared in analogy to example 142 using methyl 2-methoxyacetate. The title compound was obtained as colorless oil.

MS ESI (m/z): 290.1 [(M+H)$^+$]

Example 145

1,3,3-Trimethyl-6-(2-(tetrahydro-2H-pyran-4-yl)oxazol-5-yl)indolin-2-one

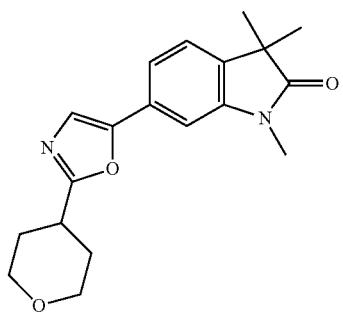 [SMILES: CN1C(=O)C(C)(C)c2ccc(-c3cnc(C4CCOCC4)o3)cc21]

a) 6-(2-Azidoacetyl)-1,3,3-trimethylindolin-2-one

To a solution of 6-(2-bromoacetyl)-1,3,3-trimethylindolin-2-one (example 70c, 1.75 g, 5.9 mmol) in acetone (17.5 ml) was added at 22° C. under inert atmosphere sodium azide (767 mg, 11.8 mmol) and stirred at 22° C. for 6 hours. The reaction mixture was poured into water and extracted with dichloromethane, the combined organic layers were dried with sodium sulfate, filtered and the obtained solution concentrated in vacuo. The title compound was obtained as light yellow solid (1.51 g).

MS ESI (m/z): 259.1 [(M+H)$^+$]

b) 1,3,3-Trimethyl-6-(2-(tetrahydro-2H-pyran-4-yl)oxazol-5-yl)indolin-2-one To a colorless solution of triphenylphosphine (345 mg, 1.32 mmol) in toluene (2.5 ml) was added at 22° C. under inert atmosphere 6-(2-azidoacetyl)-1,3,3-trimethylindolin-2-one (200 mg, 774 µmol) followed after 2 minutes by tetrahydro-2H-pyran-4-chloride (115 mg, 774 µmol). The reaction mixture was stirred at 22° C. for 18 hours. Then the reaction mixture concentrated in vacuo and the residue was purified by silica gel chromatography using heptane/ethyl acetate as eluent. The obtained material was again purified by preparative reversed phase HPLC over a YMC Actus Triart C18 100×30 mm 5 µm 12 nm column using water/acetonitrile/formic acid as eluent. The title compound was obtained as colorless oil (45 mg).

MS ESI (m/z): 327.2 [(M+H)$^+$]

Example 146

1,3,3-Trimethyl-6-pyridazin-4-yl-pyrrolo[3,2-c]pyridin-2-one

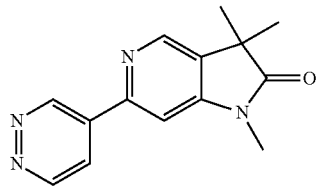 [SMILES: CN1C(=O)C(C)(C)c2cnc(-c3ccnnc3)cc21]

To a solution of 6-chloro-1,3,3-trimethyl-1,3-dihydro-pyrrolo[3,2-c]pyridin-2-one (example 83a, 250 mg, 1.19 mmol) in dioxane (12.5 ml) and water (3.1 ml) were added potassium carbonate (329 mg, 2.381 mmol) and 4-(4,4,5,5-tetramethyl-[1,3,2]dioxaborolan-2-yl)-pyridazine (367 mg, 1.786 mmol). The apparatus was evacuated and backfilled with nitrogen three times. Then the mixture was sparged with nitrogen for 10 minutes. Then Pd(dppf)Cl$_2$ was added and the mixture again sparged with nitrogen for 10 minutes. The reaction mixture was heated to 110° C. for 16 hours with vigorous stirring. The reaction mixture was diluted with ice-water, extracted with ethyl acetate and the organic layers washed with brine. The combined organic layer were dried with sodium sulfate, filtered and the obtained solution concentrated in vacuo. The crude material was purified silica gel chromatography using ethyl acetate as eluent. The title compound was obtained as off white solid (30 mg).

MS ESI (m/z): 254.8 [(M+H)$^+$]

Example 147

1-Cyclopropyl-3,3-dimethyl-6-[5-(trifluoromethyl)-1,3,4-oxadiazol-2-yl]indolin-2-one

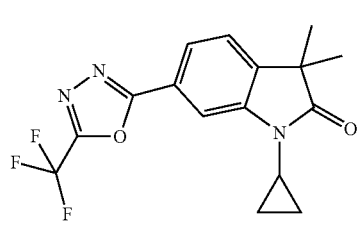 [SMILES: CC1(C)C(=O)N(C2CC2)c2cc(-c3nnc(C(F)(F)F)o3)ccc21]

a) 1-Cyclopropyl-3,3-dimethyl-2-oxo-2,3-dihydro-1H-indole-6-carbohydrazide

Prepared in analogy to example 141a-b from 6-bromo-1-cyclopropyl-3,3-dimethyl-indolin-2-one (example 78a). The title compound was obtained as white solid.

MS ESI (m/z): 260.2 [(M+H)$^+$]

b) 1-Cyclopropyl-3,3-dimethyl-2-oxo-N'-(trifluoroacetyl)-2,3-dihydro-1H-indole-6-carbohydrazide To a stirred solution of 1-cyclopropyl-3,3-dimethyl-2-oxo-2,3-dihydro-1H-indole-6-carbohydrazide (0.2 g, 0.77 mmol) in THF (5 ml) was added trifluoroaceticanhydride (0.33 ml, 2.31 mmol) at 0° C. The reaction mixture was then stirred at 25° C. for 2 hours. The reaction mixture was concentrated in vacuo. The title compound was obtained as white foam (0.22 g) which was used without further purification. LC-MS: 356.2 (M+H).

MS ESI (m/z): 356.2 [(M+H)$^+$]

c) 1-Cyclopropyl-3,3-dimethyl-6-[5-(trifluoromethyl)-1,3,4-oxadiazol-2-yl]indolin-2-one Prepared in analogy to example 93b from 1-cyclopropyl-3,3-dimethyl-2-oxo-N'-(trifluoroacetyl)-2,3-dihydro-1H-indole-6-carbohydrazide. The title compound was obtained as white solid.

MS ESI (m/z): 338.3 [(M+H)$^+$]

Example 148

3,3-Dimethyl-6-(6-methylpyridin-3-yl)indolin-2-one

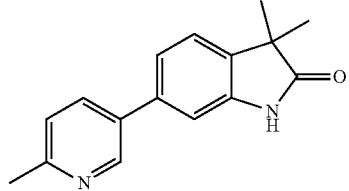 [SMILES: Cc1ccc(-c2ccc3c(c2)NC(=O)C3(C)C)cn1]

Prepared in analogy to example 1b from 6-bromo-3,3-dimethyl-1,3-dihydro-indol-2-one (example 24a) using 6-methylpyridine-3-boronic acid. The title compound was obtained as off white solid.

MS ESI (m/z): 253.3 [(M+H)$^+$]

Example 149

6-(4-Fluoropyridin-3-yl)-3,3-dimethylindolin-2-one

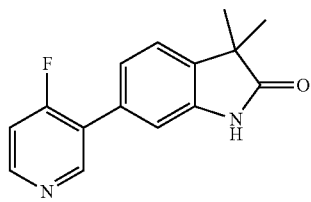 [SMILES: CC1(C)C(=O)Nc2cc(-c3cnccc3F)ccc21]

Prepared in analogy to example 1b from 6-bromo-3,3-dimethyl-1,3-dihydro-indol-2-one (example 24a) using 4-fluoropyridine-3-boronic acid pinacol ester. The title compound was obtained as light brown solid.

MS ESI (m/z): 257.2 [(M+H)+]

Example 150

6-(5-Ethyl-1,3,4-oxadiazol-2-yl)-3,3-dimethyl-indolin-2-one

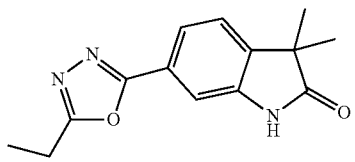 [SMILES: CCc1nnc(-c2ccc3c(c2)NC(=O)C3(C)C)o1]

a) N'-[(3,3-Dimethyl-2-oxo-2,3-dihydro-1H-indol-6-yl)carbonyl]propanehydrazide

To a stirred solution of 3,3-dimethyl-2-oxo-2,3-dihydro-1H-indole-6-carbohydrazide (example 141b, 0.3 g, 1.37 mmol) in DMF/dichloromethane 1:3 (4 ml) was added triethyl amine (0.47 ml, 3.42 mmol) followed by propionyl chloride (0.15 ml, 1.64 mmol). The reaction mixture was stirred at 25° C. for 2 hours. Then the reaction mixture was concentrated in vacuo. The residue was dissolved in ethyl acetate and the organic layer was washed with saturated aqueous sodium bicarbonate solution followed by water. The organic layer was dried with sodium sulfate, filtered and the obtained solution concentrated in vacuo. The title compound was obtained as light brown solid (195 mg) and was used without further purification.

MS ESI (m/z): 276.2 [(M+H)+]

b) 6-(5-Ethyl-1,3,4-oxadiazol-2-yl-3,3-dimethyl-indolin-2-one

Prepared in analogy to example 93b using acetonitrile/DMF 4:1 as solvent. The title compound was obtained as white solid.

MS ESI (m/z): 258.2 [(M+H)+]

Example 151

3,3-Dimethyl-6-(1-methyl-1H-imidazol-4-yl)indolin-2-one

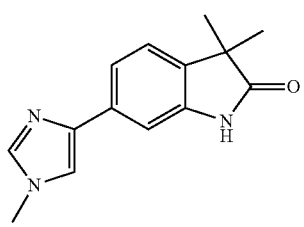 [SMILES: Cn1cnc(-c2ccc3c(c2)NC(=O)C3(C)C)c1]

Prepared in analogy to example 17 using 4-bromo-1-methyl-1H-imidazole. The title compound was obtained as light brown solid.

MS ESI (m/z): 242.2 [(M+H)+]

Example 152

1,3,3-Trimethyl-6-[5-(oxetan-3-yl)-1,3,4-oxadiazol-2-yl]indolin-2-one

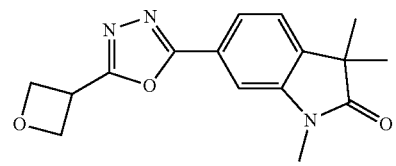 [SMILES: CN1C(=O)C(C)(C)c2ccc(-c3nnc(C4COC4)o3)cc21]

a) Methyl 1,3,3-trimethyl-2-oxoindoline-6-carboxylate

Prepared in analogy to example 141a from 6-bromo-1,3,3-trimethylindolin-2-one (example 1a). The title compound was obtained as yellow solid.

MS ESI (m/z): 234.1 [(M+H)+]

b) 1,3,3-Trimethyl-6-[5-(oxetan-3-yl)-1,3,4-oxadiazol-2-yl]indolin-2-one

Prepared in analogy to example 141 from methyl 1,3,3-trimethyl-2-oxoindoline-6-carboxylate using oxetane-3-carboxylic acid. The title compound was obtained as white solid.

MS ESI (m/z): 300.2 [(M+H)+]

Example 153

1,3,3-Trimethyl-6-[4-(trifluoromethyl)imidazol-1-yl]indolin-2-one

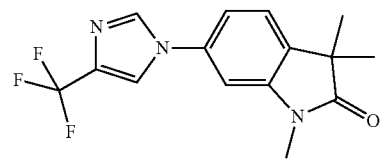 [SMILES: CN1C(=O)C(C)(C)c2ccc(-n3cnc(C(F)(F)F)c3)cc21]

A suspension of 6-bromo-1,3,3-trimethylindolin-2-one (example 1a, 25.0 mg, 0.098 mmol), 4-(trifluoromethyl)-1H-imidazole (20.094 mg, 0.148 mmol) and potassium carbonate (40.8 mg, 0.295 mmol) in acetonitrile (2.0 ml) in a microwave tube was sparged with argon for 5 minutes. Then CuI (3.749 mg, 0.02 mmol) and N,N'-dimethylethane-1,2-diamine (0.0040 ml, 0.034 mmol) were added and degassing was repeated. The tube was sealed and the reaction mixture was heated to 90° C. under microwave irradiation. The reaction mixture was concentrated in vacuo. The residue was diluted with ethyl acetate and washed with 1 M aqueous HCl solution. The organic layer was dried with sodium sulfate, filtered and the obtained solution concentrated in vacuo. The crude material was purified by silica gel chromatography using hexane/ethyl acetate as eluent. The title compound was obtained as off-white solid (10 mg).

MS ESI (m/z): 310.2 [(M+H)+]

Example 154

1-Cyclopropyl-3,3-dimethyl-6-[4-(trifluoromethyl) imidazol-1-yl]indolin-2-one

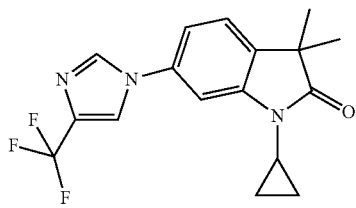 [SMILES: CC1(C)C(=O)N(C2CC2)c2cc(-n3cnc(C(F)(F)F)c3)ccc21]

Prepared in analogy to example 153 from 6-bromo-1-cyclopropyl-3,3-dimethyl-indolin-2-one (example 78a). The title compound was obtained as off white solid.

MS ESI (m/z): 336.0 [(M+H)$^+$]

Example 155

3,3-Dimethyl-6-(5-methylpyrazin-2-yl)indolin-2-one

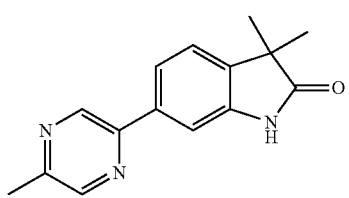 [SMILES: Cc1cnc(-c2ccc3c(c2)NC(=O)C3(C)C)cn1]

Prepared in analogy to example 17 using 2-bromo-5-methylpyrazine. The title compound was obtained as light yellow solid.

MS ESI (m/z): 254.1 [(M+H)$^+$]

Example 156

6-(2,6-Dimethylpyrimidin-4-yl)-3,3-dimethylindolin-2-one

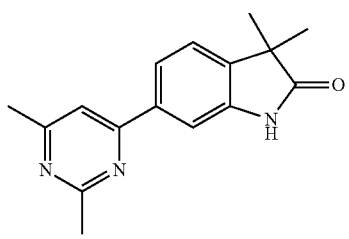 [SMILES: Cc1cc(-c2ccc3c(c2)NC(=O)C3(C)C)nc(C)n1]

Prepared in analogy to example 17 using 4-bromo-2,6-dimethylpyrimidine. The title compound was obtained as light yellow solid.

MS ESI (m/z): 268.2 [(M+H)$^+$]

Example 157

3,3-Dimethyl-6-(6-methylpyridazin-3-yl)indolin-2-one

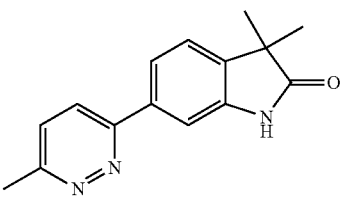

Prepared in analogy to example 17 using 3-bromo-6-methylpyridazine. The title compound was obtained as light yellow solid.

MS ESI (m/z): 254.1 [(M+H)$^+$]

Example 158

1-Cyclopropyl-3,3-dimethyl-6-[5-(oxetan-3-yl)-1,3,4-oxadiazol-2-yl]indolin-2-one

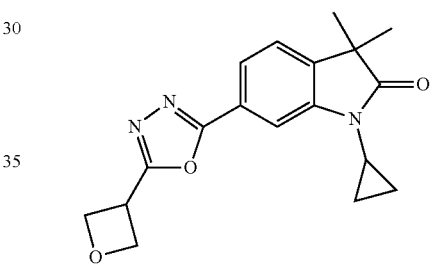

Prepared in analogy to example 141 from 1-cyclopropyl-3,3-dimethyl-2-oxo-2,3-dihydro-1H-indole-6-carbohydrazide (example 147a) using oxetane-3-carboxylic acid. The title compound was obtained as off white solid.

MS ESI (m/z): 326.3 [(M+H)$^+$]

Example 159

6-(4-Ethyl-1H-imidazol-1-yl)-1,3,3-trimethylindolin-2-one

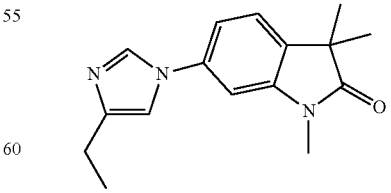

Prepared in analogy to example 63 from 6-bromo-1,3,3-trimethylindolin-2-one (example 1a) using 4-ethyl-1H-imidazole. The title compound was obtained as colorless oil.

MS ESI (m/z): 270.1 [(M+H)$^+$]

Example 160

3,3-Dimethyl-6-[5-(oxetan-3-yl)-1,3,4-oxadiazol-2-yl]indolin-2-one

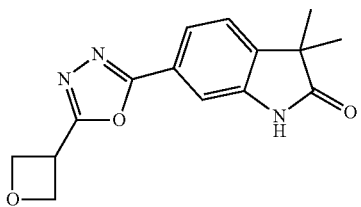 [SMILES: CC1(C)C(=O)Nc2cc(-c3nnc(C4COC4)o3)ccc21]

Prepared in analogy to example 141 using oxetane-3-carboxylic acid. The title compound was obtained as white solid.

MS ESI (m/z): 286.2 [(M+H)+]

Example 161

3,3-Dimethyl-6-(2-methyloxazol-5-yl)indolin-2-one

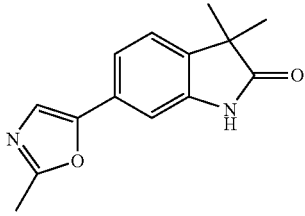

a) 1-(4-Methoxybenzyl)-3,3-dimethyl-6-(oxazol-5-yl)indolin-2-one

In a reaction tube were placed 6-bromo-1-(4-methoxybenzyl)-3,3-dimethylindolin-2-one (example 112a, 144 mg, 400 μmol), palladium (II) acetate (4.49 mg, 20.0 μmol), 2-di-t-butylphosphino-3,4,5,6-tetramethyl-2',4',6'-tri-i-propylbiphenyl (19.2 mg, 40.0 μmol), pivalic acid (16.3 mg, 18.6 μl, 160 μmol) and potassium carbonate (166 mg, 1.2 mmol). The vial was capped, evacuated and backfilled with nitrogen three times. Dry DMA (1.5 ml) was added by syringe followed by oxazole (55.2 mg, 800 μmol) and the reaction mixture heated to 110° C. for 24 hours. After cooling to room temperature the reaction mixture was directly purified by silica gel chromatography using heptane/ethyl acetate as eluent. The obtained material was dissolved in dichloromethane and washed with water. The organic layers were dried with sodium sulfate, filtered and the obtained solution concentrated in vacuo. The title compound was obtained as light yellow oil (57 mg).

MS ESI (m/z): 349.2 [(M+H)+]

b) 1-(4-Methoxybenzyl)-3,3-dimethyl-6-(2-methyloxazol-5-yl)indolin-2-one

To a solution of 1-(4-methoxybenzyl)-3,3-dimethyl-6-(oxazol-5-yl)indolin-2-one (200 mg, 574 μmol) in THF (4 ml) was added at 22° C. 1 M borane tetrahydrofuran complex in THF (689 dl, 689 μmol) while some gas evolution was remarked. After 30 minutes the solution was cooled to −78° C. followed by addition of 1.6 M n-butyllithium in hexane (431 μl, 689 μmol). After 15 minutes at −78° C. iodomethane (97.8 mg, 43.0 μl, 689 μmol) was added by syringe and the mixture was allowed to warm to −20° C. and stirred at this temperature for 4 hours. The mixture was quenched with 5% acetic acid in ethanol (v/v) (10.3 g, 9.86 ml, 8.61 mmol) and stirred at 22° C. for 16 hours. The mixture was poured into saturated aqueous sodium bicarbonate solution and extracted with ether. The organic layers were washed with brine, combined, dried with sodium sulfate, filtered and the obtained solution concentrated in vacuo. The residue was purified by silica gel chromatography using heptane/ethyl acetate as eluent. The title compound was obtained as light yellow oil (36 mg).

MS ESI (m/z): 363.2 [(M+H)+]

c) 3,3-Dimethyl-6-(2-methyloxazol-5-yl)indolin-2-one

In a tube 1-(4-methoxybenzyl)-3,3-dimethyl-6-(2-methyloxazol-5-yl)indolin-2-one (35 mg, 96.6 μmol) was dissolved in trifluoroacetic acid (661 mg, 446 μl, 5.79 mmol). The tube was set under argon, sealed and the reaction mixture was heated to 140° C. for 1 hour under microwave irradiation. The mixture was concentrated in vacuo. The residue was purified by silica gel chromatography using heptane/ethyl acetate as eluent. The title compound was obtained as light brown solid (15.9 mg).

MS ESI (m/z): 243.1 [(M+H)+]

Example 162

6-(4-Ethylimidazol-1-yl)-3,3-dimethyl-indolin-2-one

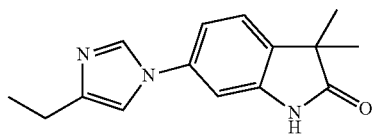 [SMILES: CCc1cn(-c2ccc3c(c2)NC(=O)C3(C)C)cn1]

a) 6-Bromo-3,3-dimethyl-1-(2-trimethylsilylethoxymethyl)indolin-2-one

To a suspension of NaH (60%, 0.18 g, 4.58 mmol) in THF (5 ml) was added a solution of 6-bromo-3,3-dimethyl-2,3-dihydro-1H-indol-2-one (example 24a, 1.0 g, 4.16 mmol) in THF (5 ml) at 0° C. and the reaction mixture was stirred at this temperature for 30 minutes. Then [2-(chloromethoxy)ethyl]trimethylsilane (0.82 ml, 4.58 mmol) was added to this mixture and stirring was continued at 25° C. for 16 hours. The reaction mixture was concentrated in vacuo. The residue was dissolved in ethyl acetate (50 ml) and the organic layer was washed with water. The separated organic layer was dried with sodium sulfate, filtered and the obtained solution concentrated in vacuo. The crude material was purified by silica gel chromatography using hexane/ethyl acetate as eluent. The title compound was obtained as red liquid (1.3 g).

MS ESI (m/z): 370.2 [(M+H)+]

b) 6-(4-Ethylimidazol-1-yl)-3,3-dimethyl-1-(2-trimethylsilylethoxymethyl)indolin-2-one Prepared in analogy to example 63 from 6-bromo-3,3-dimethyl-1-(2-trimethylsilylethoxymethyl)indolin-2-one using 4-ethyl-1H-imidazole. The title compound was obtained as yellow gum.

MS ESI (m/z): 385.9 [(M+H)$^+$]

c) 6-(4-Ethylimidazol-1-yl)-3,3-dimethyl-indolin-2-one

To a stirred solution of 6-(4-ethyl-1H-imidazol-yl)-3,3-dimethyl-1-{[2-(trimethylsilyl)ethoxy]methyl}-2,3-dihydro-1H-indol-2-one (0.16 g, 0.42 mmol) in dichloromethane (5 ml) was added TFA (2.8 ml, 37.34 mmol) at 0° C. and the reaction mixture was stirred at 25° C. for 4 hours. The reaction mixture was concentrated in vacuo and the residue was dissolved in a mixture of dichloromethane/methanol 4:1 (5 ml). Then ethylene diamine (2.8 ml, 41.49 mmol) was added to the mixture and it was stirred at 25° C. for 16 hours. The reaction mixture was concentrated in vacuo and the residue was dissolved in ethyl acetate. The organic layer was washed with water, separated, dried with sodium sulfate, filtered and the obtained solution concentrated in vacuo. The crude material was purified by silica gel chromatography using hexane/ethyl acetate as eluent. The title compound was obtained as yellow sticky solid (30 mg).

MS ESI (m/z): 256.0 [(M+H)$^+$]

Example 163

6-(1,3-Dimethyl-1H-pyrazol-5-yl)-3,3-dimethylindolin-2-one

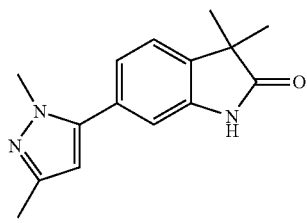 [SMILES: Cc1cc(-c2ccc3c(c2)NC(=O)C3(C)C)n(C)n1]

a) 1-(1-(4-Methoxybenzyl)-3,3-dimethyl-2-oxoindolin-6-yl)butane-1,3-dione

Prepared in analogy to example 142a from 6-acetyl-1-(4-methoxybenzyl)-3,3-dimethylindolin-2-one (example 113d) using methyl acetate. The title compound was obtained as yellow oil.

MS ESI (m/z): 366.2 [(M+H)$^+$]

b) 6-(1,3-Dimethyl-1H-pyrazol-5-yl)-1-(4-methoxybenzyl)-3,3-dimethylindolin-2-one In a reaction tube to a solution of 1-(1-(4-methoxybenzyl)-3,3-dimethyl-2-oxoindolin-6-yl)butane-1,3-dione (135 mg, 369 µmol) in THF (1.4 ml) was added at 22° C. methylhydrazine (85.1 mg, 97.3 µl, 1.85 mmol) and p-toluenesulfonic acid monohydrate (3.51 mg, 18.5 µmol). The tube was flushed with argon, sealed and the reaction mixture was stirred at 80° C. for 2 hours. The mixture was adsorbed on silica gel, evaporated and purified by silica gel chromatography using dichloromethane/methanol as eluent. The obtained material was further purified by preparative normal phase HPLC using a Reprosil Chiral-NR column and heptane/ethanol 60:40 as eluent. The title compound was obtained as colorless oil (73 mg).

MS ESI (m/z): 376.2 [(M+H)$^+$]

c) 6-(1,3-Dimethyl-1H-pyrazol-5-yl)-3,3-dimethyl-indolin-2-one

Prepared in analogy to example 161c from 6-(1,3-dimethyl-1H-pyrazol-3-yl)-1-(4-methoxybenzyl)-3,3-dimethyl-indolin-2-one. The title compound was obtained as colorless solid.

MS ESI (m/z): 256.1 [(M+H)$^+$]

Example 164

3,3-Dimethyl-6-(1-methyl-1H-pyrazol-3-yl)indolin-2-one

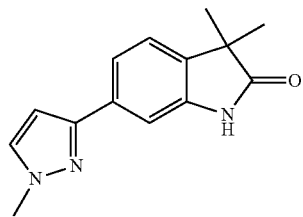 [SMILES: Cn1ccc(-c2ccc3c(c2)NC(=O)C3(C)C)n1]

Prepared in analogy to example 17 using 3-iodo-1-methyl-1H-pyrazole. The title compound was obtained as off white solid.

MS ESI (m/z): 242.1 [(M+H)$^+$]

Example 165

6-(2-(Hydroxymethyl)oxazol-5-yl)-1,3,3-trimethyl-indolin-2-one

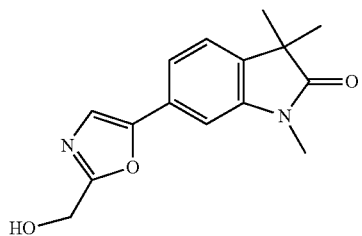 [SMILES: CN1C(=O)C(C)(C)c2ccc(-c3cnc(CO)o3)cc21]

a) (5-(1,3,3-Trimethyl-2-oxoindolin-6-yl)oxazol-2-yl)methyl acetate

Prepared in analogy to example 145 using 2-chloro-2-oxoethyl acetate. The title compound was obtained as yellow oil.

MS ESI (m/z): 315.2 [(M+H)$^+$]

b) 6-(2-(Hydroxymethyl)oxazol-5-yl)-1,3,3-trimethylindolin-2-one

To a solution of (5-(1,3,3-trimethyl-2-oxoindolin-6-yl)oxazol-2-yl)methyl acetate (34 mg, 108 µmol) in MeOH (0.7 ml) was added potassium carbonate (17.9 mg, 130 µmol) and mixture was stirred at 22° C. for 2 hours. The reaction mixture was concentrated in vacuo and the residue was purified by silica gel chromatography using heptane/ethyl acetate as eluent. The obtained material was further purified by preparative reversed phase HPLC over a YMC Actus Triart C18 100×30 mm 5 µm 12 nm column using water/acetonitrile/formic acid as eluent. The title compound was obtained as colorless oil (12 mg).
MS ESI (m/z): 273.1 [(M+H)⁺]

Example 166

6-(5-(Hydroxymethyl)-1,3,4-oxadiazol-2-yl)-3,3-dimethylindolin-2-one

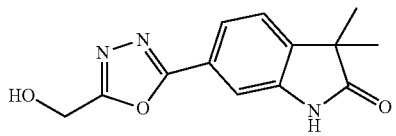 [SMILES: CC1(C)C(=O)Nc2cc(-c3nnc(CO)o3)ccc21]

a) Ethyl 2-[2-(3,3-dimethyl-2-oxo-indoline-6-carbonyl)hydrazino]-2-oxo-acetate To a stirred solution of 3,3-dimethyl-2-oxo-2,3-dihydro-1H-indole-6-carbohydrazide (example 141b, 0.2 g, 0.91 mmol) in DMF:dichloromethane 1:3 (4 ml) was added triethyl amine (0.32 ml, 2.28 mmol) followed by ethyloxalyl chloride (0.12 ml, 1.09 mmol). The reaction mixture was stirred at 25° C. for 12 hours. After completion mixture was concentrated in vacuo and the residue was dissolved in EtOAc. The organic layer was washed with saturated aqueous sodium bicarbonate solution followed by water, dried with sodium sulfate, filtered and the obtained solution concentrated in vacuo. The crude material was purified by silica gel chromatography using hexane/ethyl acetate as eluent. The title compound was obtained as white solid (70 mg).
MS ESI (m/z): 318.2 [(M+H)⁺]

b) Ethyl 5-(3,3-dimethyl-2-oxo-indolin-6-yl)-1,3,4-oxadiazole-2-carboxylate Prepared in analogy to example 93b from ethyl 2-[2-(3,3-dimethyl-2-oxo-indoline-6-carbonyl)hydrazino]-2-oxo-acetate using acetonitrile/DMF 4:1 as solvent. The title compound was obtained as white solid.
MS ESI (m/z): 302.0 [(M+H)⁺]

c) 6-(5-(Hydroxymethyl)-1,3,4-oxadiazol-2-yl)-3,3-dimethylindolin-2-one

To a stirred solution of ethyl 5-(3,3-dimethyl-2-oxo-indolin-6-yl)-1,3,4-oxadiazole-2-carboxylate (0.35 g, 1.16 mmol) in THF (5 ml) was added LiBH₄ (0.127 g, 5.81 mmol) at 25° C. and the reaction mixture was stirred at this temperature for 30 minutes. The reaction was quenched with 20% aqueous KOH solution and the residue was filtered off and washed with dichloromethane/methanol 9:1. The filtrate was concentrated in vacuo and the crude material was purified by silica gel chromatography using hexane/ethyl acetate as eluent. The obtained material was further purified by preparative reversed phase HPLC, using a Synergi 4µ Max-RP 80A° column and acetonitrile/water/formic acid as eluent. The title compound was obtained as colorless solid (29 mg).
MS ESI (m/z): 260.1 [(M+H)⁺]

Example 167

3,3-Dimethyl-6-[4-(trifluoromethyl)imidazol-1-yl]indolin-2-one

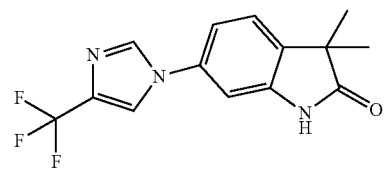 [SMILES: CC1(C)C(=O)Nc2cc(-n3cnc(C(F)(F)F)c3)ccc21]

a) 1-[(4-Methoxyphenyl)methyl]-3,3-dimethyl-6-[4-(trifluoromethyl)imidazol-1-yl]indolin-2-one Prepared in analogy to example 153 from 6-bromo-1-(4-methoxybenzyl)-3,3-dimethylindolin-2-one (example 112a) using 4-trifluoromethyl-1H-imidazole. The title compound was obtained as white solid.
MS ESI (m/z): 416.3 [(M+H)⁺]

b) 3,3-Dimethyl-6-[4-(trifluoromethyl)imidazol-1-yl]indolin-2-one

In a sealed tube a mixture of 1-[(4-methoxyphenyl)methyl]-3,3-dimethyl-6-[4-(trifluoromethyl)imidazol-1-yl]indolin-2-one (0.15 g, 0.36 mmol) and TFA (5 ml) was heated to 120° C. for 72 hours. The reaction mixture was concentrated in vacuo and the residue was dissolved in EtOAc. The mixture was washed with saturated aqueous sodium bicarbonate solution, the organic layer dried with sodium sulfate, filtered and the obtained solution concentrated in vacuo. The crude material was purified by silica gel chromatography using hexane/ethyl acetate as eluent. The title compound was obtained as brown solid (77 mg).
MS ESI (m/z): 296.0 [(M+H)⁺]

Example 168

3,3-Dimethyl-6-[4-(2,2,2-trifluoro-1-hydroxy-ethyl)imidazol-1-yl]indolin-2-one

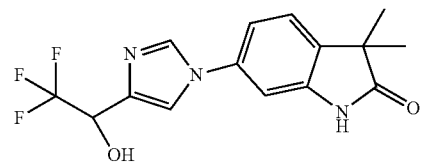 [SMILES: CC1(C)C(=O)Nc2cc(-n3cnc(C(O)C(F)(F)F)c3)ccc21]

a) 2,2,2-Trifluoro-1-(1H-imidazol-5-yl)ethanol

A mixture of imidazole (4.0 g, 58.75 mmol) and trifluoroacetaldehyde methyl hemiacetal (3.82 g, 29.37 mmol) was heated to reflux under argon for 2 hours at 150° C., the mixture became homogeneous and the generated methanol refluxed. The reaction mixture was concentrated in vacuo. The crude material was purified by silica gel column chromatography using hexane/ethyl acetate as eluent. The title compound was obtained as white semisolid (1.5 g).

MS ESI (m/z): 166.8 [(M+H)+]

b) tert-Butyl-dimethyl-[2,2,2-trifluoro-1-(1H-imidazol-5-yl)ethoxy]silane

To a solution of 2,2,2-trifluoro-1-(1H-imidazol-5-yl)ethanol (300.0 mg, 1.807 mmol) in dichloromethane (6 ml) was added triethylamine (2.507 ml, 18.072 mmol) drop wise at 0° C. The reaction mixture was stirred at 0° C. for 15 minutes, then TBDMS-C (817.048 mg, 5.422 mmol) was added and stirring continued for 16 hours. The reaction mixture was diluted with water and the mixture extracted with dichloromethane. The combined organic layers were dried with sodium sulfate, filtered and the obtained solution concentrated in vacuo. The crude material was purified by silica gel chromatography using hexane/ethyl acetate as eluent. The title compound was obtained as white semisolid (150.0 mg).

MS ESI (m/z): 280.8 [(M+H)+]

c) 6-[4-[1-[tert-Butyl(dimethyl)silyl]oxy-2,2,2-trifluoro-ethyl]imidazol-1-yl]-1-[(4-methoxyphenyl)methyl]-3,3-dimethyl-indolin-2-one Prepared in analogy to example 153 from 6-bromo-1-(4-methoxybenzyl)-3,3-dimethylindolin-2-one (example 112a) and tert-butyl-dimethyl-[2,2,2-trifluoro-1-(1H-imidazol-5-yl)ethoxy]silane. The title compound was obtained as off white solid.

MS ESI (m/z): 559.6 [(M+H)+]

d) 3,3-Dimethyl-6-[4-(2,2,2-trifluoro-1-hydroxy-ethyl)imidazol-1-yl]indolin-2-one Prepared in analogy to example 167b from 6-[4-[1-[tert-butyl(dimethyl)silyl]oxy-2,2,2-trifluoro-ethyl]imidazol-1-yl]-1-[(4-methoxyphenyl)methyl]-3,3-dimethyl-indolin-2-one. The title compound was obtained as off white solid.

MS ESI (m/z): 326.1 [(M+H)+]

Example 169

1-Cyclopropyl-6-[4-(1-hydroxyethyl)imidazol-1-yl]-3,3-dimethyl-indolin-2-one

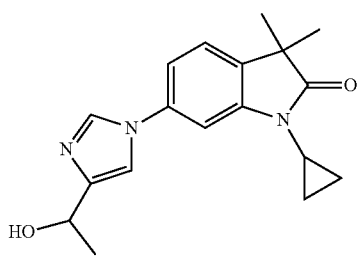 [SMILES: CC(O)c1cn(-c2ccc3c(c2)N(C2CC2)C(=O)C3(C)C)cn1]

a) tert-Butyl-[1-(1H-imidazol-5-yl)ethoxy]-dimethyl-silane

Prepared in analogy to example 168b using 1-(3H-Imidazol-4-yl)-ethanol. The title compound was obtained as colourless liquid.

MS ESI (m/z): 227.0 [(M+H)+]

b) 6-[4-[1-[tert-Butyl(dimethyl)silyl]oxyethyl]imidazol-1-yl]-cyclopropyl-3,3-dimethyl-indolin-2-one Prepared in analogy to example 153 from 6-bromo-1-cyclopropyl-3,3-dimethyl-indolin-2-one (example 78a) and tert-butyl-[1-(1H-imidazol-5-yl)ethoxy]-dimethyl-silane. The title compound was obtained as light brown semisolid.

MS ESI (m/z): 426.6 [(M+H)+]

c) 1-Cyclopropyl-6-[4-(1-hydroxyethyl)imidazol-1-yl]-3,3-dimethyl-indolin-2-one

To a solution of 6-[4-[1-[tert-butyl(dimethyl)silyl]oxyethyl]imidazol-1-yl]-1-cyclopropyl-3,3-dimethyl-indolin-2-one (0.09 g, 0.212 mmol) in methanol (8 ml) was added 12 M aqueous HCl solution (0.5 ml) at 0° C. and the mixture stirred at 25° C. for 24 hours. The reaction mixture was concentrated in vacuo. The residue was diluted with dichloromethane and washed with 10% aqueous sodium bicarbonate solution. The organic layers were dried with sodium sulfate, filtered and concentrated in vacuo. The crude material was purified by silica gel chromatography using hexane/ethyl acetate as eluent. The title compound was obtained as off white semisolid (40 mg).

MS ESI (m/z): 312.2 [(M+H)+]

Example 170

1-Cyclopropyl-3,3-dimethyl-6-[4-(2,2,2-trifluoro-1-hydroxy-ethyl)imidazol-1-yl]indolin-2-one

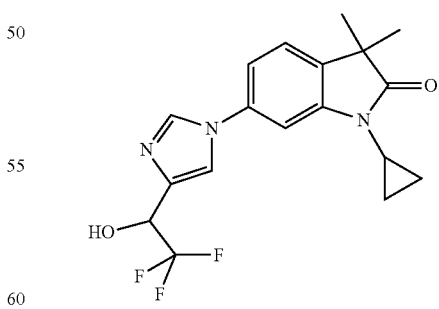

Prepared in analogy to example 169b-c using tert-butyl-dimethyl-[2,2,2-trifluoro-1-(1H-imidazol-5-yl)ethoxy]silane (example 168b). The title compound was obtained as off white solid.

MS ESI (m/z): 366.0 [(M+H)+]

Example 171

6-[4-(1-Hydroxyethyl)imidazol-1-yl]-1,3,3-trimethyl-indolin-2-one

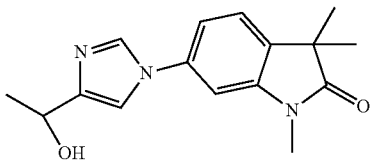 [SMILES: CC(O)c1cn(-c2ccc3c(c2)N(C)C(=O)C3(C)C)cn1]

Prepared in analogy to example 169 from 6-bromo-1,3,3-trimethylindolin-2-one (example 1a). The title compound was obtained as off white solid.
MS ESI (m/z): 286.2 [(M+H)+]

Example 172

6-[4-(1-Hydroxyethyl)imidazol-1-yl]-3,3-dimethyl-indolin-2-one

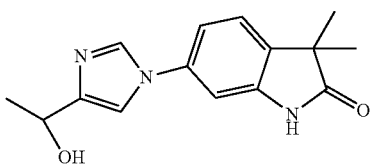 [SMILES: CC(O)c1cn(-c2ccc3c(c2)NC(=O)C3(C)C)cn1]

a) 6-[4-[1-[tert-Butyl(dimethyl)silyl]oxyethyl]imidazol-1-yl]-3,3-dimethyl-1-(2-trimethylsilylethoxymethyl)indolin-2-one Prepared in analogy to example 153 from 6-bromo-3,3-dimethyl-1-(2-trimethylsilylethoxymethyl)indolin-2-one (example 162a) and tert-butyl-[1-(1 H-imidazol-5-yl)ethoxy]-dimethyl-silane (example 169a). The title compound was obtained as yellow sticky solid.
MS ESI (m/z): 516.1 [(M+H)+]

b) 6-[4-(1-Hydroxyethyl)imidazol-1-yl]-3,3-dimethyl-indolin-2-one

Prepared in analogy to example 162c from 6-[4-[1-[tert-butyl(dimethyl)silyl]oxyethyl]imidazol-1-yl]-3,3-dimethyl-1-(2-trimethylsilylethoxymethyl)indolin-2-one. The title compound was obtained as light yellow solid.
MS ESI (m/z): 272.0 [(M+H)+]

Example 173

1-(2,3-Dihydroxypropyl)-3,3-dimethyl-6-(2-methylpyrimidin-5-yl)indolin-2-one

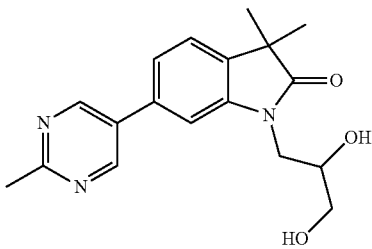 [SMILES: Cc1ncc(-c2ccc3c(c2)N(CC(O)CO)C(=O)C3(C)C)cn1]

a) 1-Allyl-3,3-dimethyl-6-(2-methylpyrimidin-5-yl)indolin-2-one

Prepared in analogy to example 126 from 3,3-dimethyl-6-(2-methylpyrimidin-5-yl)indolin-2-one (example 21) using allyl bromide. The title compound was obtained as colorless viscous oil.
MS ESI (m/z): 294.1 [(M+H)+]

b) 1-(2,3-Dihydroxypropyl)-3,3-dimethyl-6-(2-methylpyrimidin-5-yl)indolin-2-one In a pressure tube 1-allyl-3,3-dimethyl-6-(2-methylpyrimidin-5-yl)indolin-2-one (110 mg, 375 µmol), 4-methylmorpholine n-oxide monohydrate (76.0 mg, 562 µmol) and osmium tetroxide (596 mg, 596 µl, 93.7 µmol) were combined with THF (2 ml) and t-BuOH (200 µl). The tube was sealed and the reaction mixture stirred at 60° C. for 6 hours. The reaction mixture was poured into saturated aqueous sodium sulfite solution and extracted with ethyl acetate. The organic layers were washed with saturated aqueous sodium sulfite solution, dried with sodium sulfate, filtered and the obtained solution concentrated in vacuo. The crude material was purified by amine silica gel chromatography using dichloromethane/methanol as eluent. The title compound was obtained as white foam (94 mg).
MS ESI (m/z): 328.2 [(M+H)+]

Example 174

1-((4S,5R)-4-(hydroxymethyl)tetrahydrofuran-2-yl)-3,3-dimethyl-6-(2-methylpyrimidin-5-yl)indolin-2-one

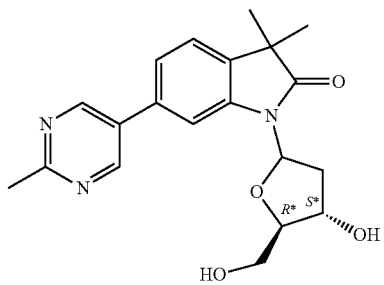 [SMILES: Cc1ncc(-c2ccc3c(c2)N(C2C[C@H](O)[C@@H](CO)O2)C(=O)C3(C)C)cn1]

a) (2R,3S)-5-(3,3-Dimethyl-6-(2-methylpyrimidin-5-yl)-2-oxoindolin-1-yl)-2-((4-methylbenzoyloxy)methyl)tetrahydrofuran-3-yl 4-methylbenzoate To a suspension of 3,3-dimethyl-6-(2-methylpyrimidin-5-yl)indolin-2-one (example 21, 0.1 g, 395 µmol) in acetonitrile (10.5 ml) under argon was added NaH on mineral oil (60%, 19.7 mg, 493 µmol) and the reaction mixture stirred 1 hour at room temperature. Then a suspension of 3,5-di-o-(p-toluyl)-2-deoxy-d-ribofuranosyl chloride (256 mg, 592 µmol) in dry THF (2.63 ml) was added and stirring at room temperature continued for 16 hours. Then 2 spoons silicagel were added to the reaction and the suspension concentrated in vacuo. The crude material purified by silica gel chromatography using heptane/ethyl acetate as eluent. The title compound was obtained as yellow amorphous solid (132 mg).
MS ESI (m/z): 606.3 [(M+H)+]

b) 1-((4S,5R)(hydroxymethyl)tetrahydrofuran-2-yl)-3,3-dimethyl-6-(2-methylpyrimidin-5-yl)indolin-2-one To (2R,3S)-5-(3,3-dimethyl-6-(2-methylpyrimidin-5-yl)-2-oxoindolin-1-yl)-2-((4-methylbenzoyloxy)methyl)tetrahydrofuran-3-yl 4-methylbenzoate (0.13 g, 215 µmol) was added 7 M ammonia in methanol (1.3 ml, 9.1 mmol) and the reaction mixture stirred at room temperature for 19 hours. Again 7 M ammonia in methanol (1.3 ml, 9.1 mmol) was added and stirring at room temperature continued for another 22 hours. Then the reaction was heated to 40° C. for 3 hours and then 50° C. for 3 hours. Then heating was removed and the reaction mixture stirred at room temperature for 72 hours. The reaction mixture was concentrated in vacuo. The crude material was purified by silica gel chromatography using dichloromethane/methanol as eluent. The title compound was obtained as white foam being a mixture of α and β form 2:1.

MS ESI (m/z): 370.2 [(M+H)$^+$]

Example 175

1-(2,3-dimethoxypropyl)-3,3-dimethyl-6-(2-methylpyrimidin-5-yl)indolin-2-one

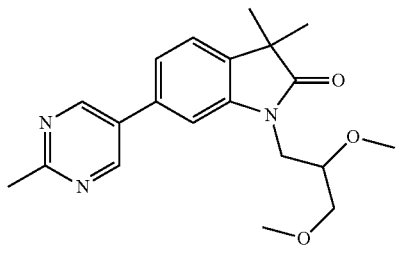

To a mixture of 1-(2,3-dihydroxypropyl)-3,3-dimethyl-6-(2-methylpyrimidin-5-yl)indolin-2-one (example 173, 72 mg, 220 µmol) in DMF (2.5 ml) was added NaH (60% on mineral oil, 19.4 mg, 484 µmol) and the mixture stirred 15 minutes at room temperature. Then MeI (78.0 mg, 34.4 µl, 550 µmol) was added and stirring at room temperature continued for 16 hours. Then again NaH (60% on mineral oil, 19.4 mg, 484 µmol) and MeI (78.0 mg, 34.4 µl, 550 µmol) were added and stirring continued for 1.5 hours. The reaction was quenched with water, extracted with ethyl acetate and the organic layers washed with water. The combined organic layers were dried with sodium sulfate, filtered and the obtained solution concentrated in vacuo. The crude material was purified by silica gel chromatography using dichloromethane/methanol as eluent. The title compound was obtained as light yellow viscous oil (52 mg).

MS ESI (m/z): 356.2 [(M+H)$^+$]

Example 176

3,3-dimethyl-6-(2-methylpyrimidin-5-yl)-1-(tetrahydrofuran-3-yl)indolin-2-one

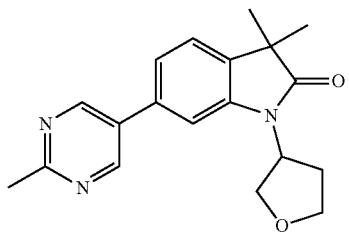 [SMILES: Cc1ncc(-c2ccc3c(c2)N(C2CCOC2)C(=O)C3(C)C)cn1]

A suspension of 3,3-dimethyl-6-(2-methylpyrimidin-5-yl)indolin-2-one (example 21, 50 mg, 197 µmol), 3-chlorotetrahydrofuran (42.1 mg, 37.1 µl, 395 µmol) and cesium carbonate (129 mg, 395 µmol) in DMF (800 µl) was stirred at room temperature for 64 hours. Then the reaction mixture was cooled to 0° C. and NaH (60% on mineral oil, 9.47 mg, 237 µmol) was added, cooling bath removed and stirred for 10 minutes. Then at room temperature again 3-chlorotetrahydrofuran (42.1 mg, 37.1 µl, 395 µmol) was added and stirring continued for 2 hours. Then the reaction was heated to 85° C. and stirred at this temperature for 16 hours. Again NaH (60% on mineral oil, 9.47 mg, 237 µmol) and 3-chlorotetrahydrofuran (42.1 mg, 37.1 µl, 395 µmol) were added and stirring at 85° C. continued for 24 hours. Again NaH (60% on mineral oil, 9.47 mg, 237 µmol) and 3-chlorotetrahydrofuran (42.1 mg, 37.1 µl, 395 µmol) were added and stirring continued for 24 hours. The reaction mixture was directly purified by silica gel chromatography using heptane/ethyl acetate as eluent. The obtained material was further purified by preparative reversed phase HPLC over a Phenomenex Gemini NX 5µ C18 110A column using acetonitrile/water/formic acid as eluent. The title compound was obtained as white solid (22 mg).

MS ESI (m/z): 324.2 [(M+H)$^+$]

Biological Assays and Data

Now it has been found that the compounds of formula I may be used for the treatment of CNS diseases.

The described compounds of formula I reduce L-687,414-induced hyperlocomotion. This was assessed by using a computerized Digiscan 16 Animal Activity Monitoring System (Omnitech Electronics, Columbus, Ohio) to quantify locomotor activity. Animals were kept under a 12 h light/dark cycle and experiments were performed during the light period. Each activity monitoring chamber consisted of a Plexiglas box (41×41×28 cm; W×L×H) with sawdust bedding on the floor surrounded by invisible horizontal and vertical infrared sensor beams. The test boxes were divided by a Plexiglas cross providing each mouse with 20×20 cm of moving space. Cages were connected to a Digiscan Analyzer linked to a computer that constantly collected the beam status information. Records of photocell beam interruptions for individual animals were taken every 5 min over the duration of the experimental session and the sum of the first 6 periods was used as the final parameter. Compounds were administered either p.o. 15 min before a s.c. injection of 50 mg/kg of L-687,414, or i.p. at the same time as a s.c. injection of 50 mg/kg of L-687,414. Mice were then transferred from their home cage to the recording chambers for a 15-min habituation phase allowing free exploration of the new environment. Horizontal activity was then recorded for a 30-min time period. The % inhibition of L-687,414-induced hyperlocomotion was calculated according to the equation:

$$((Veh+L\text{-}687{,}414 \text{ horizontal activity} - drug+L\text{-}687{,}414 \text{ horizontal activity})Veh+L\text{-}687{,}414 \text{ horizontal activity}) \times 100$$

ID$_{50}$ values, defined as doses of each compound producing 50% inhibition of L-687,414-induced hyperlocomotion, were calculated by linear regression analysis of a dose-response data using an Excel-based computer-fitting program.

As data was not presupposed to be normally distributed, groups treated with test compounds were statistically compared with the control (vehicle-treated) group using one-tailed Mann Whitney U tests. In statistics, the Mann-Whitney Utest (also called the Mann-Whitney-Wilcoxon (MWW) or Wilcoxon rank-sum test) is a non-parametric statistical hypothesis test for assessing whether one of two samples of independent observations tends to have larger values than the other. It is one of the most well-known non-parametric significance tests. A p value gives the probability that two groups are significantly different from each other and the value of <0.05 is generally accepted as a criterion, it implies that there is >95% chance that two groups are really different from each other. P values given in table 1 are one-tailed since only decreases in locomotion were expected and tested for (Mann, H. B., Whitney, D. R. (1947), "On a Test of Whether one of Two Random Variables is Stochastically Larger than the Other", Annals of Mathematical Statistics, 18 (1), 50-60).

TABLE 1

Effects of compounds of formula I on L-687,414-induced hyperlocomotion

| Expl. | structure | Doses po [mg/kg] | $ID_{50}$ po [mg/kg] | Lowest P value | Dose ip [mg/kg] | Inhibition, ip [%] | P value |
|---|---|---|---|---|---|---|---|
| 3 | 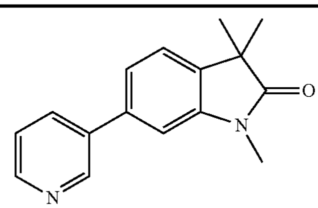 | | | | 30 | 53.4 | 0.0074 |
| 4 | 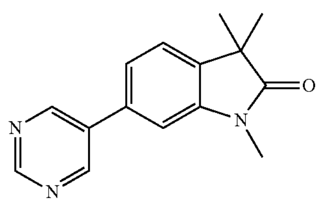 [SMILES: CN1C(=O)C(C)(C)c2ccc(-c3cncnc3)cc21] | | | | 30 | 74.6 | 0.032 |
| 7 | 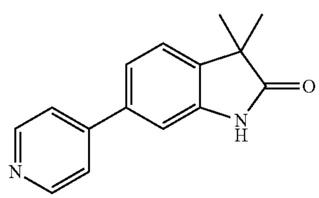 [SMILES: CC1(C)C(=O)Nc2cc(-c3ccncc3)ccc21] | 10-30-50 | 29.2 | 0.0059 | | | |
| 8 | 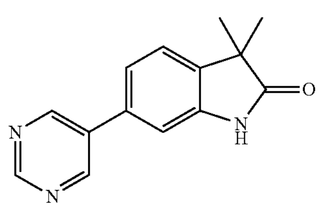 [SMILES: CC1(C)C(=O)Nc2cc(-c3cncnc3)ccc21] | | | | 30 | 52.5 | 0.0052 |
| 10 | 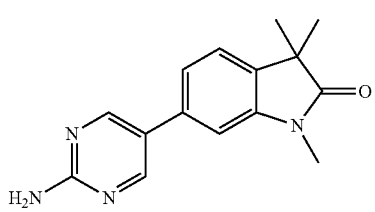 [SMILES: CN1C(=O)C(C)(C)c2ccc(-c3cnc(N)nc3)cc21] | | | | 30 | 97.1 | 0.000078 |
| 11 | 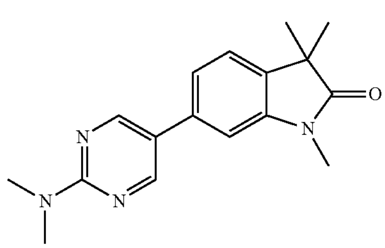 [SMILES: CN(C)c1ncc(-c2ccc3c(c2)N(C)C(=O)C3(C)C)cn1] | | | | 30 | 72.2 | 0.014 |

TABLE 1-continued

Effects of compounds of formula I on L-687,414-induced hyperlocomotion

| Expl. | structure | Doses po [mg/kg] | ID$_{50}$ po [mg/kg] | Lowest P value | Dose ip [mg/kg] | Inhibition, ip [%] | P value |
|---|---|---|---|---|---|---|---|
| 12 | 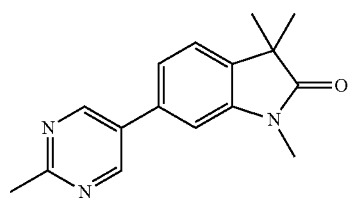 [SMILES: Cc1ncc(-c2ccc3c(c2)N(C)C(=O)C3(C)C)cn1] | | | | 30 | 93.7 | 0.000078 |
| 13 | 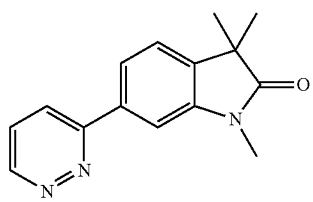 [SMILES: CN1C(=O)C(C)(C)c2ccc(-c3cccnn3)cc21] | | | | 30 | 76.9 | 0.025 |
| 14 | 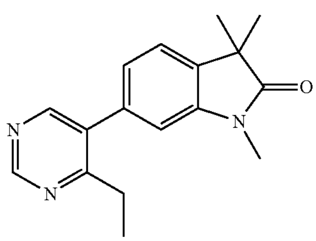 [SMILES: CCc1ncncc1-c1ccc2c(c1)N(C)C(=O)C2(C)C] | | | | 30 | 66.4 | 0.00093 |
| 16 | 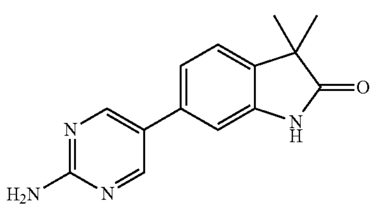 [SMILES: CC1(C)C(=O)Nc2cc(-c3cnc(N)nc3)ccc21] | | | | 30 | 89.4 | 0.00054 |
| 17 | 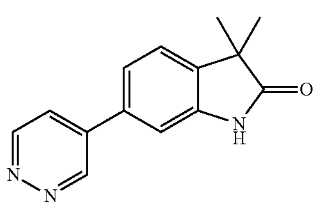 [SMILES: CC1(C)C(=O)Nc2cc(-c3ccnnc3)ccc21] | | | | 30 | 66.7 | 0.041 |
| 19 | 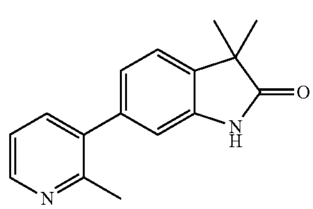 [SMILES: Cc1ncccc1-c1ccc2c(c1)NC(=O)C2(C)C] | | | | 30 | 61.6 | 0.00054 |
| 20 | 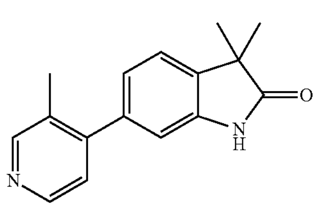 [SMILES: Cc1cnccc1-c1ccc2c(c1)NC(=O)C2(C)C] | | | | 30 | 47.5 | 0.0074 |

TABLE 1-continued

Effects of compounds of formula I on L-687,414-induced hyperlocomotion

| Expl. | structure | Doses po [mg/kg] | ID$_{50}$ po [mg/kg] | Lowest P value | Dose ip [mg/kg] | Inhibition, ip [%] | P value |
|---|---|---|---|---|---|---|---|
| 21 | 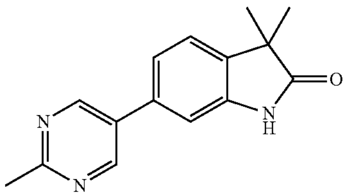 [SMILES: Cc1ncc(-c2ccc3c(c2)NC(=O)C3(C)C)cn1] | 1-3-10 | 1.62 | 0.0075 | | | |
| 23 | 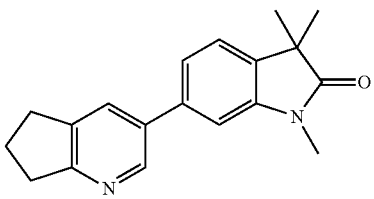 [SMILES: CN1C(=O)C(C)(C)c2ccc(-c3cnc4c(c3)CCC4)cc21] | | | | 30 | 81.6 | 0.000078 |
| 25 | 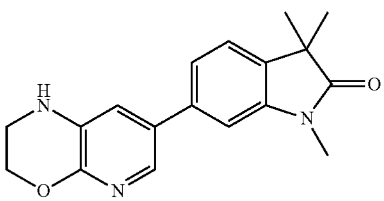 [SMILES: CN1C(=O)C(C)(C)c2ccc(-c3cnc4c(c3)NCCO4)cc21] | 1-3-10 | 3.03 | 0.023 | | | |
| 28 | 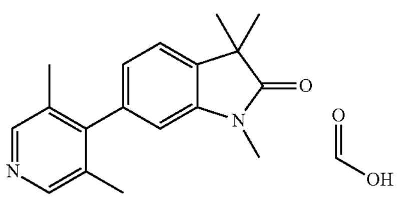 | | | | 30 | 68.4 | 0.032 |
| 30 | 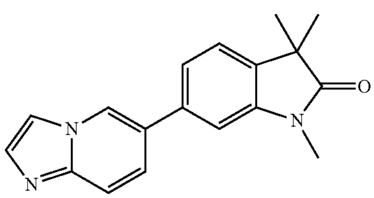 [SMILES: CN1C(=O)C(C)(C)c2ccc(-c3ccc4nccn4c3)cc21] | | | | 30 | 49.1 | 0.014 |
| 31 | 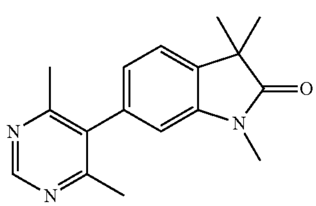 [SMILES: Cc1ncnc(C)c1-c1ccc2c(c1)N(C)C(=O)C2(C)C] | | | | 30 | 81.2 | 0.00054 |
| 34 | 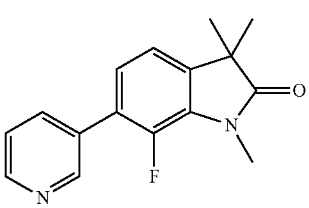 [SMILES: CN1C(=O)C(C)(C)c2ccc(-c3cccnc3)c(F)c21] | | | | 30 | 56.9 | 0.0015 |

TABLE 1-continued

Effects of compounds of formula I on L-687,414-induced hyperlocomotion

| Expl. | structure | Doses po [mg/kg] | ID$_{50}$ po [mg/kg] | Lowest P value | Dose ip [mg/kg] | Inhibition, ip [%] | P value |
|---|---|---|---|---|---|---|---|
| 36 | 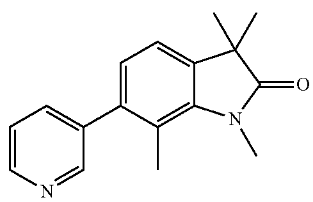 [SMILES: Cc1c(-c2cccnc2)ccc2c1N(C)C(=O)C2(C)C] | | | | 30 | 79.3 | 0.00093 |
| 38 | 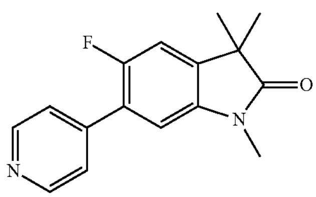 [SMILES: CN1C(=O)C(C)(C)c2cc(F)c(-c3ccncc3)cc21] | | | | 30 | 57.3 | 0.0074 |
| 39 | 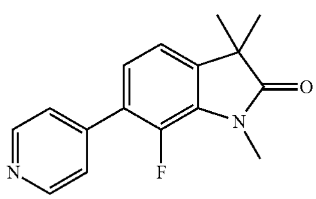 [SMILES: CN1C(=O)C(C)(C)c2ccc(-c3ccncc3)c(F)c21] | | | | 30 | 77.6 | 0.00093 |
| 43 | 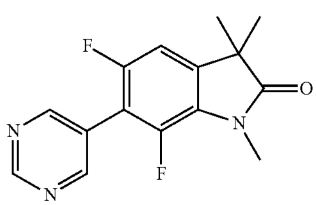 [SMILES: CN1C(=O)C(C)(C)c2cc(F)c(-c3cncnc3)c(F)c21] | | | | 30 | 60.5 | 0.0052 |
| 48 | 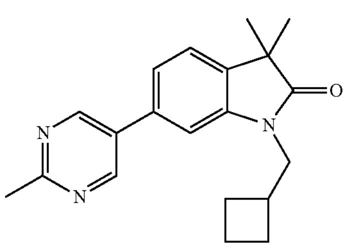 [SMILES: Cc1ncc(-c2ccc3c(c2)N(CC2CCC2)C(=O)C3(C)C)cn1] | | | | 30 | 68.6 | 0.0015 |
| 50 | 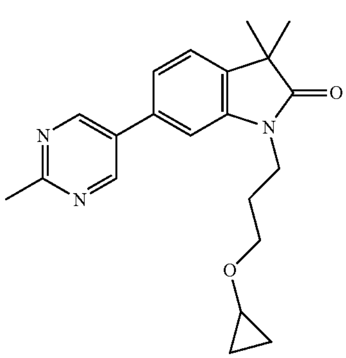 [SMILES: Cc1ncc(-c2ccc3c(c2)N(CCCOC2CC2)C(=O)C3(C)C)cn1] | | | | 30 | 86.3 | 0.000078 |

TABLE 1-continued

Effects of compounds of formula I on L-687,414-induced hyperlocomotion

| Expl. | structure | Doses po [mg/kg] | ID$_{50}$ po [mg/kg] | Lowest P value | Dose ip [mg/kg] | Inhibition, ip [%] | P value |
|---|---|---|---|---|---|---|---|
| 55 | 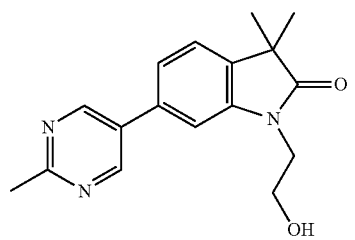 [SMILES: Cc1ncc(-c2ccc3c(c2)N(CCO)C(=O)C3(C)C)cn1] | 1-3-10 | 0.88 | 0.021 | | | |
| 56 | 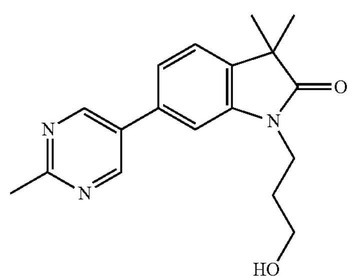 [SMILES: Cc1ncc(-c2ccc3c(c2)N(CCCO)C(=O)C3(C)C)cn1] | | | | 30 | 93.9 | 0.00016 |
| 57 | 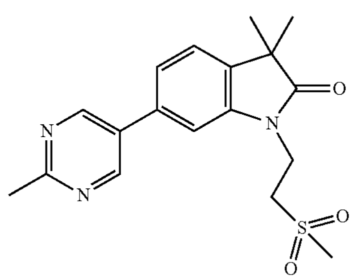 [SMILES: Cc1ncc(-c2ccc3c(c2)N(CCS(C)(=O)=O)C(=O)C3(C)C)cn1] | | | | 30 | 79.9 | 0.00031 |
| 59 | 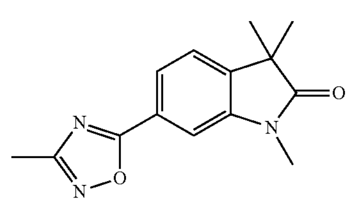 [SMILES: Cc1noc(-c2ccc3c(c2)N(C)C(=O)C3(C)C)n1] | | | | 30 | 45.2 | 0.0015 |
| 60 | 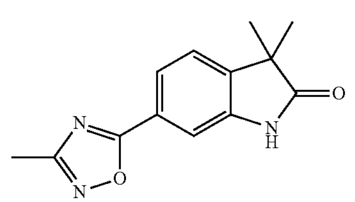 [SMILES: Cc1noc(-c2ccc3c(c2)NC(=O)C3(C)C)n1] | | | | 30 | 24 | 0.014 |
| 61 | 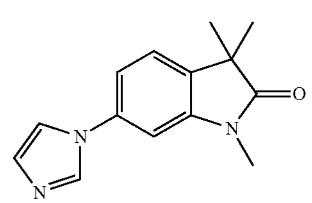 [SMILES: CN1C(=O)C(C)(C)c2ccc(-n3ccnc3)cc21] | 3-10-30 | 10.71 | 0.0016 | | | |

TABLE 1-continued
Effects of compounds of formula I on L-687,414-induced hyperlocomotion
| Expl. | structure | Doses po [mg/kg] | ID$_{50}$ po [mg/kg] | Lowest P value | Dose ip [mg/kg] | Inhibition, ip [%] | P value |
|---|---|---|---|---|---|---|---|
| 63 | 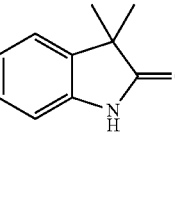 | | | | 30 | 68.9 | 0.000078 |
| 67 | 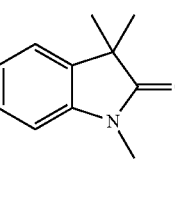 | | | | 30 | 42.6 | 0.014 |
| 71 | 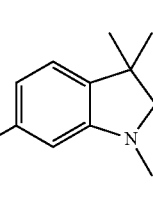 | | | | 30 | 68.5 | 0.000078 |
| 72 | 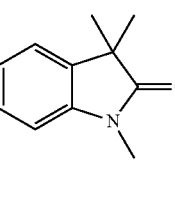 | | | | 30 | 67.4 | 0.000078 |
| 79 | 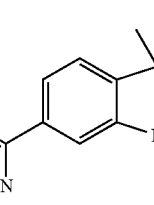 | | | | 20 | 62.5 | 0.00521 |
| 83 | 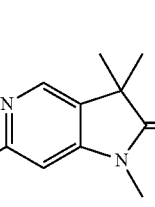 | | | | 30 | 53 | 0.01033 |

TABLE 1-continued

Effects of compounds of formula I on L-687,414-induced hyperlocomotion

| Expl. | structure | Doses po [mg/kg] | ID$_{50}$ po [mg/kg] | Lowest P value | Dose ip [mg/kg] | Inhibition, ip [%] | P value |
|---|---|---|---|---|---|---|---|
| 87 | 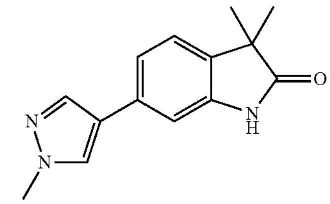 [SMILES: Cn1cc(-c2ccc3c(c2)NC(=O)C3(C)C)cn1] | | | | 30 | 82.8 | 0.00521 |
| 92 | 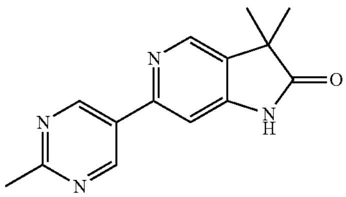 [SMILES: Cc1ncc(-c2cc3c(cn2)C(C)(C)C(=O)N3)cn1] | | | | 30 | 80.9 | 0.00054 |
| 93 | 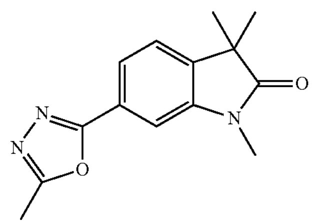 [SMILES: Cc1nnc(-c2ccc3c(c2)N(C)C(=O)C3(C)C)o1] | | | | 30 | 68.6 | 0.0035 |
| 106 | 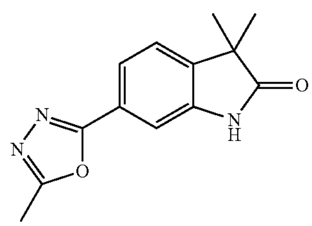 [SMILES: Cc1nnc(-c2ccc3c(c2)NC(=O)C3(C)C)o1] | | | | 30 | 75.7 | 0.00008 |
| 113 | 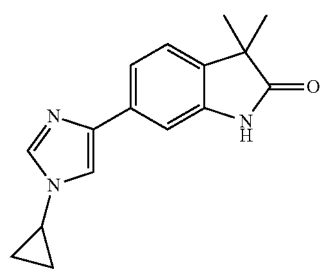 [SMILES: CC1(C)C(=O)Nc2cc(-c3cn(C4CC4)cn3)ccc21] | | | | 30 | 83.9 | 0.00008 |
| 114 | 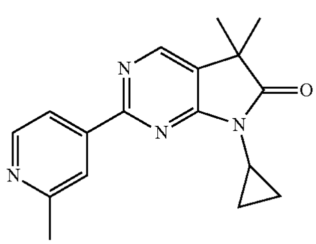 [SMILES: Cc1cc(-c2ncc3c(n2)N(C2CC2)C(=O)C3(C)C)ccn1] | | | | 20 | 42 | 0.0419 |

TABLE 1-continued
Effects of compounds of formula I on L-687,414-induced hyperlocomotion
| Expl. | structure | Doses po [mg/kg] | ID$_{50}$ po [mg/kg] | Lowest P value | Dose ip [mg/kg] | Inhibition, ip [%] | P value |
|---|---|---|---|---|---|---|---|
| 128 | 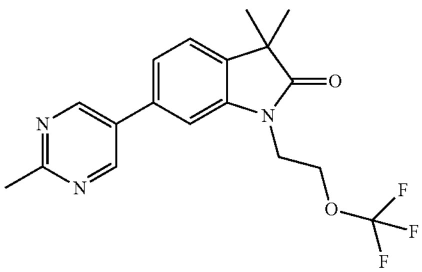 [SMILES: Cc1ncc(-c2ccc3c(c2)N(CCOC(F)(F)F)C(=O)C3(C)C)cn1] | | | | 30 | 66.1 | 0.03248 |
| 129 | 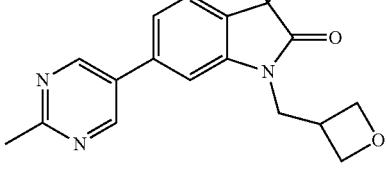 | | | | 30 | 95.5 | 0.00054 |
| 130 | 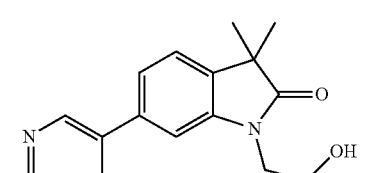 | | | | 30 | 89.4 | 0.0035 |
| 131 | 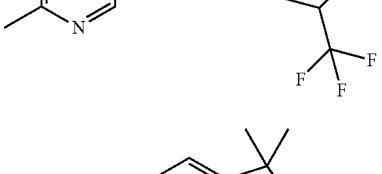 | | | | 30 | 95.3 | 0.00031 |
| 132 | 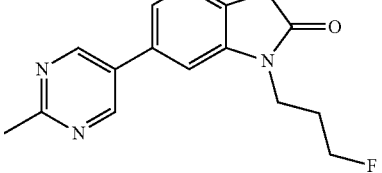 | | | | 30 | 95.3 | 0.00031 |
| 133 | 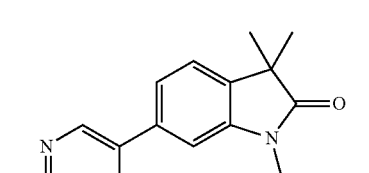 | | | | 30 | 44 | 0.03248 |

TABLE 1-continued

Effects of compounds of formula I on L-687,414-induced hyperlocomotion

| Expl. | structure | Doses po [mg/kg] | ID$_{50}$ po [mg/kg] | Lowest P value | Dose ip [mg/kg] | Inhibition, ip [%] | P value |
|---|---|---|---|---|---|---|---|
| 134 | | | | | 30 | 79.8 | 0.00008 |
| 136 | | | | | 30 | 89.7 | 0.00016 |
| 140 | | | | | 30 | 69.3 | 0.00093 |
| 143 | | | | | 30 | 65.7 | 0.00093 |
| 168 | | | | | 30 | 77 | 0.00031 |
| 175 | | | | | 30 | 95.3 | 0.00008 |

As mentioned above, some compounds have been tested in SmartCube®, an analytical system developed by PsychoGenics Inc.

SmartCube® was used to compare the behavioral signature of a test compound to a database of behavioral signatures obtained from a large set of clinically approved reference drugs, grouped per indications. In this way, the neuropharmacological effects of a test compound can be predicted by similarity to major classes of compounds, such as antipsychotics, anxiolytics and antidepressants. This approach is ideally suited to screen collections of existing drugs or drug candidates with previously unknown neuropharmacology, which could expedite the development of new and unexpected treatments for psychiatric disorders.

Some compounds of the present invention were injected i.p. at different doses 15 minutes before the test. At least 8 mice were used in each treatment group. Digital videos of the subjects were processed with computer vision algorithms to extract over 2000 dependent measures including frequency and duration of many different behavioral states. The results of the classifications are presented as bar charts for each compound and dose (mg/kg), the Y-axis indicates the relative probability that the test compound will show efficacy in the specific CNS indication.

Figure 2:
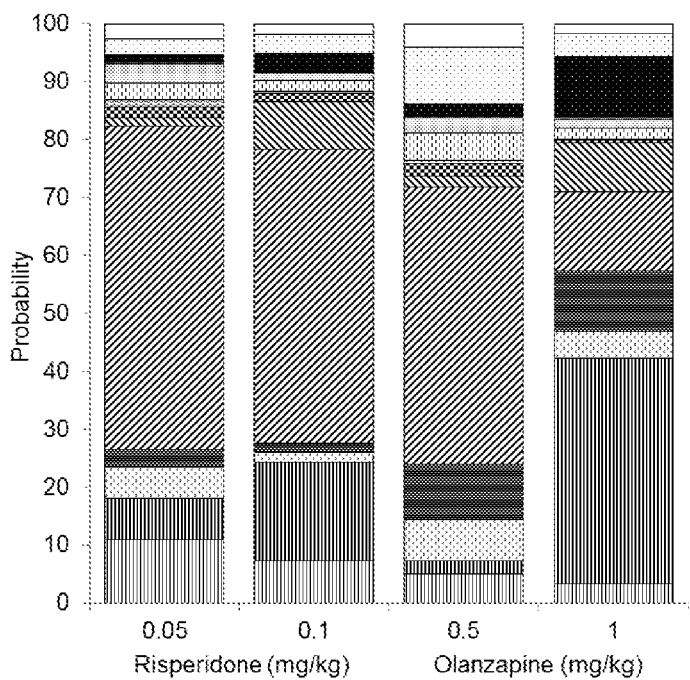
FIG. 2 is a bar chart exhibiting the SmartCube® behavioral signatures of the atypical antipsychotics olanzapine and risperidone are shown.

The bar charts of example compounds 13, 54, 58 and 71 at a dose of 25 mg/kg are shown in FIG. 1. For comparison, the behavioral signatures of the atypical antipsychotics olanzapine and risperidone are shown in FIG. 2. Compounds of the present invention show similar signatures to those of atypical antipsychotics. An independent analysis was performed on the unclassified data to determine the similarity of the example compounds to active doses of known atypical antipsychotics. For this analysis, we use discrimination rate as the measure of separability between the two drugs, i.e. one drug's "distinguishability" from another. A rate equal to 50% (or 0.5) corresponds to zero distinguishability. Empirical data has shown that a threshold rate for reliable separation lies above 70% i.e., two drugs showing a discrimination rate of 70% or lower are considered similar, whereas a discrimination rate higher than 70% indicates that two drugs are dissimilar. The table below shows the similarity analysis of selected compounds of the present invention to several atypical antipsychotics. In most cases, the example compounds show a similarity to risperidone, clozapine and olanzapine with a discrimination rate of ≤0.70.

TABLE 2

Similarity analysis of compounds of formula I (at 25 mg/kg) showing effects in SmartCube ®

|  | Clozapine | Olanzapine | Risperidone |
| --- | --- | --- | --- |
| Example 13 | 0.69 | 0.70 | 0.72 |
| Example 54 | 0.69 | 0.61 | 0.63 |
| Example 58 | 0.63 | 0.69 | 0.66 |
| Example 71 | 0.79 | 0.66 | 0.63 |

Therefore, it can be assumed that the present compounds have similar efficacies as known atypical antipsychotics.

FIG. 1: SmartCube® signatures of compounds 13, 54, 58 and 71 (at 25 mg/kg)—similar to those of atypical antipsychotics.

FIG. 2: SmartCube® signatures of atypical antipsychotics olanzapine and risperidone (each at two doses).

The compounds of formula (I) and pharmaceutically acceptable salts thereof can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. However, the administration can also be effected rectally, e.g. in the form of suppositories, or parenterally, e.g. in the form of injection solutions.

The compounds of formula (I) and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula (I), but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, medicaments containing a compound of formula (I) or pharmaceutically acceptable salts thereof and a therapeutically inert excipient are also an object of the present invention, as is a process for the production of such medicaments which comprises bringing one or more compounds of formula I or pharmaceutically acceptable salts thereof and, if desired, one or more other therapeutically valuable substances into a galenical dosage form together with one or more therapeutically inert carriers. The active compounds may also be used in form of their prodrugs.

As further mentioned earlier, the use of the compounds of formula (I) for the preparation of medicaments useful in the prevention and/or the treatment of the above recited diseases is also an object of the present invention.

The dosage can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult person weighing 70 kg accordingly lies between 0.7-1400 mg per day, preferably between 7 and 700 mg per day.

Preparation of Pharmaceutical Compositions Comprising Compounds of the Invention Tablets of the following composition are manufactured in the usual manner:

| ingredient | mg/tablet | | | |
|---|---|---|---|---|
| | 5 | 25 | 100 | 500 |
| Compound of formula I | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure

1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Capsules of the following composition are manufactured:

| ingredient | mg/capsule | | | |
|---|---|---|---|---|
| | 5 | 25 | 100 | 500 |
| Compound of formula I | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure

1. Mix ingredients 1, 2 and 3 in a suitable mixer for 30 minutes.
2. Add ingredients 4 and 5 and mix for 3 minutes.
3. Fill into a suitable capsule.

A compound of formula I lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

Injection solutions of the following composition are manufactured:

| ingredient | mg/injection solution. |
|---|---|
| Compound of formula I | 3 |
| Polyethylene Glycol 400 | 150 |
| acetic acid | q.s. ad pH 5.0 |
| water for injection solutions | ad 1.0 ml |

Manufacturing Procedure

A compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

We claim:

1. A compound of formula

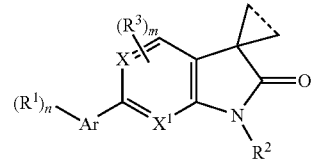

I wherein

Ar is a 6 membered heteroaryl group, containing one or two N-atoms, which are the groups pyridinyl, pyrimidinyl, pyridazinyl;

$R^1$ is hydrogen, $C_{1-7}$-alkyl, halogen, amino, dimethylamino, cyano, $C_{1-7}$-alkyl substituted by halogen, $C_{1-7}$-alkyl substituted by hydroxy, $CH(OH)CF_3$, $(CH_2)_o$—$C_{1-7}$-alkoxy, cycloalkyl optionally substituted by $CF_3$, or heterocycloalkyl selected from pyrrolidinyl, morpholinyl, thiomorpholinyl, piperidinyl, piperazinyl, tetrahydropyran-4-yl, tetrahydrofuran-3-yl or oxetanyl, optionally substituted by $C_{1-7}$-alkyl;

$R^2$ is hydrogen, $C_{1-7}$-alkyl, $(CH_2)_o$-cycloalkyl, $(CH_2)_o$—O-cycloalkyl, $(CH_2)_o$—$C_{1-7}$-alkoxy, $(CH_2)_o$—$C_{1-7}$-alkoxy substituted by halogen, $(CH_2)_o$-heterocycloalkyl selected from pyrrolidinyl, morpholinyl, thiomorpholinyl, piperidinyl, piperazinyl, tetrahydropyran-4-yl, tetrahydrofuran-3-yl or oxetanyl, optionally substituted by $C_{1-7}$-alkyl, $(CH_2)_o$—$S(O)_2$-cycloalkyl, $C_{1-7}$-alkyl substituted by one or two hydroxy, $C_{1-7}$-alkyl substituted by one or two $C_{1-7}$-alkoxy, $(CH_2)_o$—$S(O)_2$—$C_{1-7}$-alkyl substituted by halogen or $CH_2CH(OH)CF_3$;

$R^3$ is halogen or $C_{1-7}$-alkyl;

X is CH;

$X^1$ is CH;

n is 1 or 2;

o is 0, 1, 2 or 3;

m is 0, 1 or 2;

and the dotted line indicates a bond may or may not be present; and, pharmaceutically acceptable salts thereof, with a racemic mixture, or with its corresponding enantiomer and/or optical isomer and/or stereoisomer thereof.

2. A compound of formula I according to claim 1, which compounds are selected from:

3,3-Dimethyl-6-(pyridin-3-yl)indolin-2-one;
3,3-Dimethyl-6-(pyridin-4-yl)indolin-2-one;
3,3-Dimethyl-6-(pyrimidin-5-yl)indolin-2-one;
6-(2-Aminopyrimidin-5-yl)-3,3-dimethylindolin-2-one;
3,3-Dimethyl-6-(pyridazin-4-yl)indolin-2-one;
6-(6-Aminopyridin-3-yl)-3,3-dimethylindolin-2-one;
3,3-Dimethyl-6-(2-methylpyridin-3-yl)indolin-2-one;
3,3-Dimethyl-6-(3-methylpyridin-4-yl)indolin-2-one;
3,3-Dimethyl-6-(2-methylpyrimidin-5-yl)indolin-2-one;
3,3-Dimethyl-6-(2-methylpyridin-4-yl)indolin-2-one;
5-(3,3-Dimethyl-2-oxoindolin-6-yl)nicotinonitrile;
6-(2,4-Dimethyl-pyridin-3-yl)-3,3-dimethyl-1,3-dihydroindol-2-one;
3,3-Dimethyl-6-(2-methylpyrimidin-4-yl)indolin-2-one;
6-(2-Cyclopropylpyrimidin-5-yl)-3,3-dimethyl-indolin-2-one;
3,3-Dimethyl-6-(6-methylpyrimidin-4-yl)indolin-2-one;
3,3-Dimethyl-6-(6-methylpyridin-3-yl)indolin-2-one;

6-(4-Fluoropyridin-3-yl)-3,3-dimethylindolin-2-one;
6-(2,6-Dimethylpyrimidin-4-yl)-3,3-dimethylindolin-2-one; or
3,3-Dimethyl-6-(6-methylpyridazin-3-yl)indolin-2-one; or,
a pharmaceutically acceptable salt thereof.

3. A compound of formula I according to claim 1, wherein Ar is a six membered heteroaryl group, containing one or two N-atoms and $R^2$ is $C_{1-7}$-alkyl.

4. A compound of formula I according to claim 3, wherein the compounds are selected from:
1,3,3-Trimethyl-6-(pyridin-4-yl)indolin-2-one;
1,3,3-Trimethyl-6-(2-methylpyridin-4-yl)indolin-2-one;
1,3,3-Trimethyl-6-(pyridin-3-yl)indolin-2-one;
1,3,3-Trimethyl-6-(pyrimidin-5-yl)indolin-2-one;
1,3,3-Trimethyl-6-(pyridin-2-yl)indolin-2-one;
1,3,3-Trimethyl-6-(2-(pyrrolidin-1-yl)pyrimidin-5-yl)indolin-2-one;
6-(2-Aminopyrimidin-5-yl)-1,3,3-trimethylindolin-2-one;
6-(2-(Dimethylamino)pyrimidin-5-yl)-1,3,3-trimethylindolin-2-one;
1,3,3-Trimethyl-6-(2-methylpyrimidin-5-yl)indolin-2-one;
1,3,3-Trimethyl-6-(pyridazin-3-yl)indolin-2-one;
6-(4-Ethylpyrimidin-5-yl)-1,3,3-trimethylindolin-2-one;
6-(6-Aminopyridin-3-yl)-1,3,3-trimethylindolin-2-one;
1,3,3-Trimethyl-6-(6-methylpyridazin-3-yl)indolin-2-one;
6-(5-Aminopyridin-3-yl)-1,3,3-trimethylindolin-2-one;
6-(3,5-Dimethyl-pyridin-4-yl)-1,3,3-trimethyl-1,3-dihydro-indol-2-one;
6-(4,6-Dimethyl-pyrimidin-5-yl)-1,3,3-trimethyl-1,3-dihydro-indol-2-one;
6-(2,4-Dimethyl-pyridin-3-yl)-1,3,3-trimethyl-1,3-dihydro-indol-2-one;
7-Fluoro-1,3,3-trimethyl-6-(pyridin-3-yl)indolin-2-one;
1,3,3,7-Tetramethyl-6-(pyridin-3-yl)indolin-2-one;
5-Fluoro-1,3,3-trimethyl-6-(pyridin-3-yl)indolin-2-one;
5-Fluoro-1,3,3-trimethyl-6-(pyridin-4-yl)indolin-2-one;
7-Fluoro-1,3,3-trimethyl-6-pyridin-4-yl-1,3-dihydro-indol-2-one;
5-Fluoro-1,3,3-trimethyl-6-(2-methylpyridin-4-yl)indolin-2-one;
1-Isopropyl-3,3-dimethyl-6-(2-methylpyrimidin-5-yl)indolin-2-one;
5,7-Difluoro-1,3,3-trimethyl-6-pyridin-3-yl-1,3-dihydro-indol-2-one;
5,7-Difluoro-1,3,3-trimethyl-6-pyrimidin-5-yl-1,3-dihydro-indol-2-one;
1,3,3,5-Tetramethyl-6-(2-methyl-pyridin-4-yl)-1,3-dihydro-indol-2-one;
5,7-Difluoro-1,3,3-trimethyl-6-(2-methyl-pyrimidin-5-yl)-1,3-dihydro-indol-2-one;
6-(2-Cyclopropylpyrimidin-5-yl)-1,3,3-trimethyl-indolin-2-one;
6-(6-Cyclopropylpyridazin-3-yl)-1,3,3-trimethyl-indolin-2-one;
1,3,3-Trimethyl-6-(6-morpholinopyridin-3-yl)indolin-2-one;
1-Ethyl-3,3-dimethyl-6-(2-methylpyrimidin-5-yl)indolin-2-one;
a pharmaceutically acceptable salt thereof.

5. A compound of formula I according to claim 1, wherein Ar is a 6 membered heteroaryl group, containing one or two N-atoms and $R^2$ is $(CH_2)_o$-cycloalkyl, $(CH_2)_o$—O-cycloalkyl, $(CH_2)_o$—$C_{1-7}$-alkoxy, $(CH_2)_o$—$C_{1-7}$-alkoxy substituted by halogen, $(CH_2)_o$-heterocycloalkyl selected from pyrrolidinyl, morpholinyl, thiomorpholinyl, piperidinyl, piperazinyl, tetrahydropyran-4-yl, tetrahydrofuran-3-yl or oxetanyl optionally substituted by $C_{1-7}$-alkyl, $(CH_2)_o$—$S(O)_2$-cycloalkyl, $C_{1-7}$-alkyl substituted by one or two hydroxy, $C_{1-7}$-alkyl substituted by one or two $C_{1-7}$-alkoxy, $(CH_2)_oS(O)_2$—$C_{1-7}$-alkyl, $C_{1-7}$-alkyl substituted by halogen $CH_2CH(OH)CF_3$.

6. A pharmaceutical composition comprising a compound according to claim 1 and at least one pharmaceutically acceptable excipient, carrier or diluent.

7. A process for preparation of a compound according to claim 1 comprising
(a) reacting a compound of formula (2)

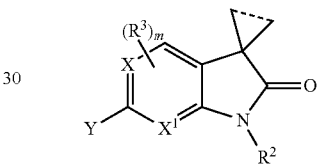

2 with a boronic acid derivative of formula (3)

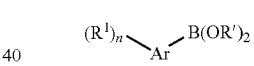

3 to a afford a compound of formula (I)

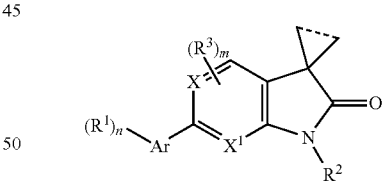

I wherein Y is bromine or iodine, R' is hydrogen or $C_{1-7}$-alkyl, and,
(b) if desired, converting the compounds obtained into pharmaceutically acceptable acid addition salts.

* * * * *